US009493747B2

(12) United States Patent
Getmanova et al.

(10) Patent No.: US 9,493,747 B2
(45) Date of Patent: Nov. 15, 2016

(54) ENGINEERED TRANSGLUTAMINASE BARREL PROTEINS

(75) Inventors: Elena V. Getmanova, Lexington, MA (US); Alexander Kovtun, Stow, MA (US); Lin Sun, West Roxbury, MA (US); Edward Fritsch, Concord, MA (US); Brian Seed, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 792 days.

(21) Appl. No.: 12/811,483

(22) PCT Filed: Jan. 5, 2009

(86) PCT No.: PCT/US2009/000016
§ 371 (c)(1),
(2), (4) Date: Oct. 4, 2010

(87) PCT Pub. No.: WO2009/088968
PCT Pub. Date: Jul. 16, 2009

(65) Prior Publication Data

US 2011/0059504 A1 Mar. 10, 2011

Related U.S. Application Data

(60) Provisional application No. 61/009,890, filed on Jan. 3, 2008.

(51) Int. Cl.
*C12N 9/10* (2006.01)

(52) U.S. Cl.
CPC .................................. *C12N 9/1044* (2013.01)

(58) Field of Classification Search
None
See application file for complete search history.

(56) References Cited

U.S. PATENT DOCUMENTS 7,745,391 B2 * 6/2010 Mintz et al. ................ 514/19.3

FOREIGN PATENT DOCUMENTS

WO WO-01/42432 A2 6/2001
WO WO-02/32925 A2 4/2002

OTHER PUBLICATIONS

Yee et al. (PNAS vol. 91, pp. 7296-7300, Jul. 1994) Huber et al. (JBC, vol. 272, No. 34, 1997, pp. 21018-21026)).*
Komaromi et al. (J. Thromb Haemost., vol. 9 (1), pp. 1538-7836).*
Takahashi et al. (Blood, vol. 91, pp. 2830-2838, 1998).*
Wells ( Biochemistry, vol. 29, pp. 8509-8517, 1990).*
Yee et al. (PNAS, vol. 91, pp. 7296-7300, 1994).*
Ariens et al. ( Blood, vol. 100, No. 3, 2002, pp. 743-754).*
Becker et al., "Identification of two novel nonsense mutations in the transglutaminase 1 gene in a Hungarian patient with congenital ichthyosiform erythroderma," *Exp. Dermatol.* 12:324-329, 2003.
Begg et al., "Mechanism of allosteric regulation of transglutaminase 2 by GTP," *Proc. Natl. Acad. Sci. U.S.A.* 103:19683-19688, 2006.
Extended European Search Report for European Application No. 09700780, mailed Mar. 27, 2012 (10 pages).
Fesus et al., "Transglutaminase 2: an enigmatic enzyme with diverse functions," *Trends Biochem. Sci.* 27:534-539, 2002.
Hang, "Identification of a Novel Recognition Sequence for Fibronectin within the $NH_2$-terminal β-Sandwich Domain of Tissue Transglutaminase," *Journal of Biological Chemistry* 280:23675-23683, 2005.
International Search Report for International Application No. PCT/US2009/000016, mailed Aug. 20, 2009 (3 pages).
Lai et al., "Purification and Characterization of Recombinant Human Coagulation Factor XIII A-Chains Expressed in *E. coli*," *Protein Expression and Purification* 5:125-132, 1994.
Sabo et al., "Perturbations in factor XIII resulting from activation and inhibition examined by solution based methods and detected by MALDI-TOF MS," *Biochemistry* 46:10089-10101, 2007.
Shi et al., "Expression in *Escherichia coli* and Purification of Hexahistidine-Tagged Human Tissue Transglutaminase," *Protein Expression and Purification* 24:366-373, 2002.

* cited by examiner

*Primary Examiner* — Hope Robinson
(74) *Attorney, Agent, or Firm* — Fish & Richardson P.C.

(57) ABSTRACT

Disclosed herein are methods and compositions related to engineered fragments of the human transglutaminase-related protein family, described herein as engineered transglutaminase barrel proteins (ETBPs), that have utility as high affinity, high selectivity target-binding proteins offering advantages as antibody equivalents for therapeutic, analytical, manufacturing and research purposes. ETBPs differ from naturally occurring human transglutaminase fragments by the addition, deletion, replacement and/or substitution of the naturally occurring amino acid sequence. ETBPs can be easily expressed in prokaryotic cells and in many cases can be purified by a simple solubilization and precipitation method.

10 Claims, 41 Drawing Sheets

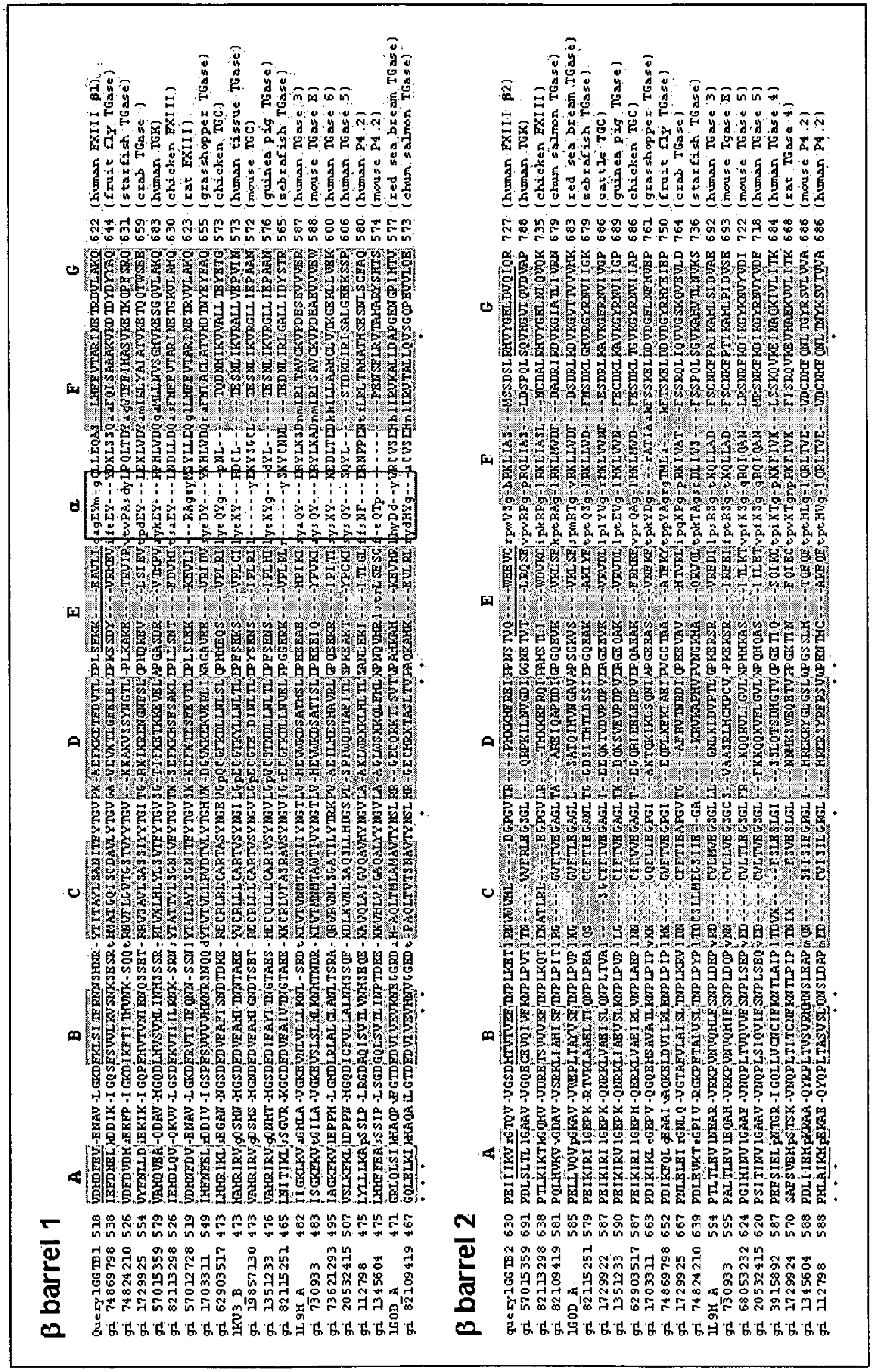

Fig. 1B

[Figure: Multiple sequence alignment showing β barrel 1 and β barrel 2 domains across various transglutaminase sequences from different organisms including human FXIII, fruit fly TGase, starfish TGase, crab TGase, human TGK, chicken FXIII, rat FXIII, grasshopper TGase, chicken TGC, human tissue TGase, mouse TGC, guinea pig TGase, zebrafish TGase, human TGase 3, mouse TGase B, human TGase 6, human TGase 5, human P4.2, mouse P4.2, red sea bream TGase, and chum salmon TGase. Alignment columns are labeled A, B, C, D, E, α, F, G.]

Fig. 4

```
             M  T  I  P  E  I  I  I  K  V  R  G  T  Q  V  V  G  S  D  M  T  V  I  V  E  F  T
F13β2        ATGACCATCCCTGAGATCATCATCAAGGTCCGTGGCACTCAGGTAGTTGGTTCTGACATGACTGTGATAGTTGAGTTTACC
F13β2opt     ATGACCATCCCTGAGATCATCATCAAGGTCCGCGGCACTCAGGTCGTGGGTTCTGACATGACTGTGATCGTGGAGTTTACC

             N  P  L  K  E  T  L  R  N  V  W  V  H  L  D  G  P  G  V  T  R  P  M  K  K  M  F
F13β2        AATCCTTTAAAAGAAACCCTGCGAAATGTCTGGGTACACCTGGATGGTCCTGGAGTAACAAGACCAATGAAGAAGATGTTC
F13β2opt     AATCCTCTGAAAGAAACCCTGCGCAATGTCTGGGTGCACCTGGATGGTCCTGGAGTCACACGCCCAATGAAGAAGATGTTC

             R  E  I  R  P  N  S  T  V  Q  W  E  E  V  C  R  P  W  V  S  G  H  R  K  L  I  A
F13β2        CGTGAAATCCGGCCCAACTCCACCGTGCAGTGGGAAGAAGTGTGCCGGCCCTGGGTCTCTGGGCATCGGAAGCTGATAGCC
F13β2opt     CGCGAAATCCGCCCAAACTCCACCGTGCAGTGGGAAGAAGTGTGCCGCCCATGGGTCTCTGGGCATCGCAAGCTGATCGCC

             S  M  S  S  D  S  L  R  H  V  Y  G  E  L  D  V  Q  I  Q  R  R
F13β2        AGCATGAGCAGTGACTCCCTGAGACATGTGTATGGCGAGCTGGACGTGCAGATTCAAAGACGA
F13β2opt     AGCATGAGCAGTGACTCCCTGCGCCATGTGTATGGCGAGCTGGACGTGCAGATTCAACGCCGC
```

| Myostatin Binders | BC loop | DE loop | FG loop | Scaffold mutation | In vitro construct | Clone ID | Kd, nM | B max, % |
|---|---|---|---|---|---|---|---|---|
| Group M1-A50 | TNPFKETLRS | REIPPKTT | RTQYLI | V91L | 39633-C1 (■) | M17 | 39.9 | 74.8 |
| | TNPFKETLRS | SEIRPNST | RTQYLI | V91L | 39633-G5 (▲) | | 33.6 | 64.1 |
| | SNPFKETLRN | REIPPKTT | RTQYLI | V91L | 39633-G1 (▼) | | 38.9 | 52.0 |
| | TNPLSQTLSA | REIPPKTT | RTQYLI | V91L | 39633-B3 (◆) | | 9.9 | 6.1 |
| Group M2-A50 | SNPFKETLRN | SEIRPNST | PSLLHL | | 39908-G4 (■) | M7 | 28.4 | 49.0 |
| | TNPFKETLRS | REIPPKTT | PSLLHL | | 39908-H10 (▲) | M4 | 29.7 | 47.3 |
| | TNPFKETLRS | SEIRPNST | PSLLHL | | 39908-G12 (▼) | M10 | 25.6 | 34.1 |
| | TNLHKETLRN | SEIRPNST | PSLLHL | | 39633-D2 (●) | | 11.2 | 6.8 |
| Group M3-A50 | TNPFKETLRN | CEIRPNSI | CSLSPW | ΔS82, M83R | 39633-D6 (■) | M020 | 20.3 | 79.6 |
| | SNPFKETLRN | SEIRPNST | CSLSPW | ΔS82, M83R | 39908-E5 (▲) | M56 | 21.9 | 77.9 |
| | TNPFKETLRS | REIPPKTT | CSLSPW | ΔS82, M83R | 39908-D2 (▼) | M29 | 23.3 | 68.8 |
| | TNPFKETLRS | REIPPKTT | CQLLPW | ΔS82, M83R | 39908-B2 (◆) | M07 | 27.1 | 75.9 |
| | TNPFKETLRS | REIPPKTT | -TLRPW | | 39633-G6 (✱) | M18 | 19.7 | 75.1 |
| | TNLWKEALRN | REIATHST | -TLRPW | V39H | 39908-E1 (●) | M04 | 14.9 | 40.2 |
| Group M1-A | TNPLKETLRN | PAIPHNHK | PQLFHI | | 39885-A1 (■) | M1-1 | 21.8 | 67.3 |
| | TNPLKETLRN | PTISRFKR | PQLQHL | | 39973-C10 (▲) | | 22.8 | 72.0 |
| | TNPLKETLRN | ATIPPYLP | PQLIHL | | 39973-F10 (▼) | | 28.7 | 68.0 |
| Group M2-A | TNPLKETLRN | PAIPHNHK | INYFYK | | 39885-C11 (◆) | | 41.6 | 18.8 |
| Group M3-A | TNPLKETLRN | PAIPHNHK | NSSSNQ | | 39888-B7 (●) | | 7.1 | 1.2 |

B

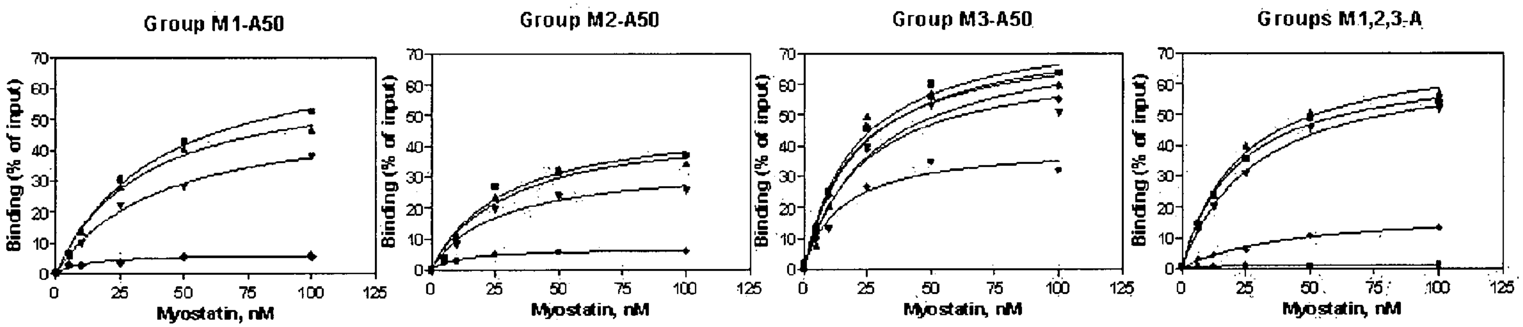

Fig. 18
B
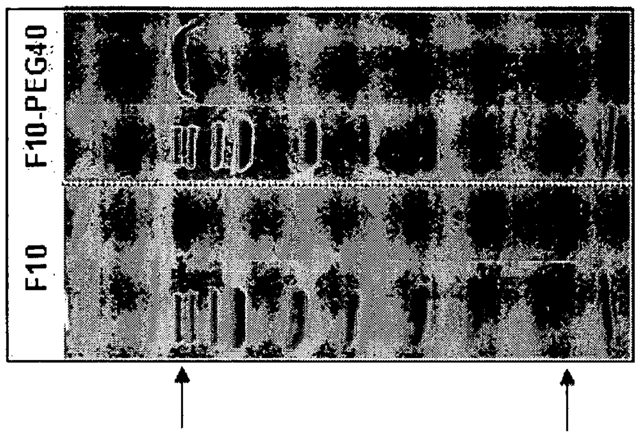
A
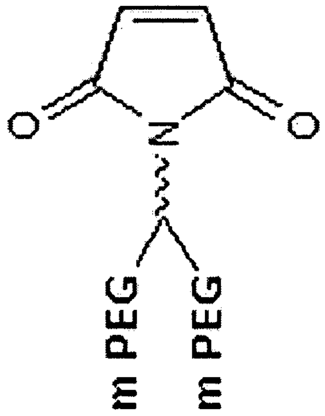

Fig. 19
A
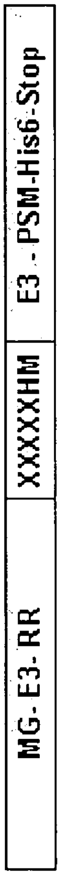
B
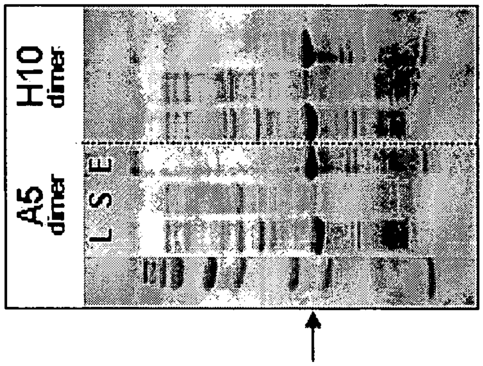

A

| β-NGF binders | BC loop | DE loop | FG loop | Scaffold mutation | *In vitro* construct | Kd, nM | B max, % |
|---|---|---|---|---|---|---|---|
| Group N1 | TNPLHEPLLF | RIISPHAT | SIGFQA | | 61362-C6 (■) | 24.0 | 5.5 |
| Group N2 | INTSHETLPS | PEIPPNSS | IRDSSR | Δ67-70, P71A | 61362-F2 (▲) | 62.0 | 35.4 |
| Group N3 | TDTVLEILRT | PHIRPKVT | LIASLR | G17D | 61363-C1 (▼) | 2.8 | 1.8 |
| Group N4 | TNPLEENLYN | YQISTNIP | GAHTKD | G45E | 61363-C12 (◆) | 36.0 | 33.6 |
| | TNPLKETLYN | WEIRTNHP | SSNSRD | V15A | 61363-H1 (●) | 22.9 | 8.4 |
| | TIPLQDIL-N | FSIRMTPA | SFHTHR | I23L | 61362-B8 (□) | 3.8 | 2.1 |

B

| FcεRI binder pools | Kd, nM | B max, % |
|---|---|---|
| PR7-16 nM (■) | 6.5 | 32.3 |
| PR7-1.6 nM (▲) | 7.1 | 40.4 |
| PR8-0.1 nM (▼) | 5.1 | 40.8 |

Fig. 25

M S N V D M D F E V E N A V L G K D
F K L S I T F R N
F13β1
ATGTCCAACGTTGACATGGACTTTGAAGTGGAAAATGCTGTGCTGGGAAAAGACTTCAAGCTCTCCATC
ACCTTCCGGAAC

N S H N R Y T I T A Y L S A N I T F
Y T G V P K A E F
F13β1
AACAGCCACAACCGTTACACCATCACAGCTTATCTCTCAGCCAACATCACCTTCTACACCGGGGTCCCG
AAGGCAGAATTC

K K E T F D V T L E P L S F K K E A
V L I Q A G E Y M
F13β1
AAGAAGGAGACGTTCGACGTGACGCTGGAGCCCTTGTCCTTCAAGAAAGAGGCGGTGCTGATCCAAGCC
GGCGAGTACATG

G Q L L E Q A S L H F F V T A R I N
E T R D V L A K Q
F13β1
GGTCAGCTGCTGGAACAAGCGTCCCTGCACTTCTTTGTCACAGCTCGCATCAATGAGACCAGGGATGTT
CTGGCCAAGCAA

K S T V L
F13β1 AAGTCCACCGTGCTA

ATGACCATCCCTGAGATCATCATCAAGGTCCGCGGCACTCAGGTCGTGGGTTCTGACATGACTGTGATCGTGGAGTTTAC

TACTGGTAGGGACTCTAGTAGTAGTTCCAGGCGCCGTGAGTCCAGCACCCAAGACTGTACTGACACTAGCACCTCAAATG

N P L K E T L R N V W V H L D G P G V T R P M K K M

CAATCCTCTGAAAGAAACCCTGCGCAATGTCTGGGTGCACCTGGATGGTCCTGGAGTCACACGCCCAATGAAGAAGATGT

GTTAGGAGACTTTCTTTGGGACGCGTTACAGACCCACGTGGACCTACCAGGACCTCAGTGTGCGGGTTACTTCTTCTACA

BC

F R E I R P N S T V Q W E E V V R P W V S G H R K L I

TCCGCGAAATCCGCCCAAACTCCACCGTGCAGTGGGAAGAAGTGGTCCGCCCATGGGTCTCTGGGCATCGCAAGCTGATC

AGGCGCTTTAGGCGGGTTTGAGGTGGCACGTCACCCTTCTTCACCAGGCGGGTACCCAGAGACCCGTAGCGTTCGACTAG

DE

A S M S S D S L R H V Y G E L D V Q I Q R R

GCCAGCATGAGCAGTGACTCCCTGCGCCATGTGTATGGCGAGCTGGACGTGCAGATTCAACGCCGC

CGGTCGTACTCGTCACTGAGGGACGCGGTACACATACCGCTCGACCTGCACGTCTAAGTTGCGGCG

FG

Oligonucleotides for FG6 and FG6+6 libraries:

| | |
|---|---|
| F13BC: | ACTGTGATCGTGGAGTTT577558CCT786555655577CTGCGCAATGTCTGGGTG |
| F13DE: | AAGATGTTCCGCGAAATC767CCA557877577GTGCAGTGGGAAGAAGTG |
| F13FG6: | CTGATCGCCAGCATGAGC568657877786767758GTGTATGGCGAGCTGGAC |
| F13FG6+6: | CTGATCGCCAGCATGAGC568657877NNSNNSNNSNNSNNSNNS786767758GTGTATGGCGAGCTGGAC |

Randomization phosphoamidite mixes:

| | | | | |
|---|---|---|---|---|
| 5: | 50.00%A, | 16.67%G, | 16.67%C, | 16.67%T |
| 6: | 16.67%A, | 50.00%G, | 16.67%C, | 16.67%T |
| 7: | 16.67%A, | 16.67%G, | 50.00%C, | 16.67%T |
| 8: | 16.67%A, | 16.67%G, | 16.67%C, | 50.00%T |
| N: | 25%A, | 25%G, | 25%C, | 25%T |
| S: | 50%G, | 50%C | | |

ENGINEERED TRANSGLUTAMINASE BARREL PROTEINS

CROSS-REFERENCE TO RELATED APPLICATIONS

This application is the U.S. National Stage filing under 35 U.S.C. §371 of International Application No. PCT/US2009/000016, filed Jan. 5, 2009, which claims benefit of U.S. Provisional Application No. 61/009,890, filed Jan. 3, 2008, each of which is incorporated by reference.

SEQUENCE LISTING

The instant application contains a Sequence Listing which has been submitted in ASCII format via EFS-Web and is hereby incorporated by reference in its entirety. Said ASCII copy, created on Oct. 1, 2010, is named 00786543.txt and is 266,477 bytes in size.

BACKGROUND OF THE INVENTION

In general, the present invention relates to engineered transglutaminase polypeptides, methods for their production as well as for their use for binding or for recognizing given ligands.

The adaptive immune system is a highly evolved, flexible system for the recognition and neutralization of foreign organisms and macromolecules. At the core of adaptive immunity is an engine for the creation of a vast variety of different similar structures that have been diversified by combinatorial assembly of varied building blocks with highly random linker segments. The two principle recognition complexes of the higher vertebrate adaptive immune system, antibodies and the T cell antigen receptor, are similarly assembled, and function through their cognate cell types, B cells and T cells, to effect a coordinated resistance to pathogens. Although all elements of the adaptive recognition system of higher vertebrates are based on assemblies of monomer domains of the immunoglobulin fold, in cyclostomes, convergent evolution has created an adaptive immune system that is constructed by the assembly of recognition elements derived from leucine rich repeats.

The effector proteins of the B cell arm of the adaptive immune system, particularly antibodies of the IgG subtype, have many attractive properties as candidate therapeutic agents. IgG antibodies are stable highly soluble proteins with a long in vivo half life that have weak immunogenicity within a given species. They often can be selected to have high affinities for their targets and are known to have few intrinsic safety liabilities. IgG antibodies as a class have relatively predictable behavior in vitro and in vivo, but are large, heterodimeric, disulfide-stabilized, glycosylated proteins that are difficult to make in prokaryotic cells. It has been hypothesized that antibodies may be effectively replaced for a variety of purposes by artificial antibody-like proteins, derived by the diversification of natural or unnatural scaffolds. Such antibody equivalents might be more readily manufactured and might have favorable tissue penetration and biodistribution properties compared with antibodies themselves.

In recent years recombinant antibodies of substantially human sequence have played a major role in therapeutic medicine as universal recognition moieties for a number of targets in different diseases. Human monospecific antibodies of the IgG subtype provide high specificity, bivalency, fully human composition, and long plasma half-life. The known limitations of antibodies relate largely to their biophysical properties (high molecular weight, multidomain assemblage, disulfide bonds, glycosylation), which require eukaryotic manufacturing processes that are more complex and more expensive than their prokaryotic counterparts. Fragments of antibodies, such as scFv domains, Fab domains and multivalent miniantibodies have been produced in bacteria, and offer some opportunities for the realization of low cost, highly effective therapeutic agents.

Scaffolds based on different human or non-human proteins or protein domains have emerged as an independent class of alternative therapeutic molecules. The status of alternative scaffolds and selection procedures used to identify high affinity binding proteins based on those scaffolds have been recently reviewed. Different proteins have been investigated as frameworks for bringing the diversified sequences to targets, including affibodies, lipocalins, ankyrin-repeat proteins, natural peptide binding domains, enzymes, GFP, small disulfide-bonded peptides, protease inhibitors, and others. Approximately 50 protein scaffolds have been proposed so far but only a few have been developed extensively for medical applications (Adnectins (Bristol-Myers Squibb Co), Anticalins (Pieris AG), Microbodies (Nascacell Technologies AG), Nanobodies (Ablynx), Kunitz domains (Dyax), Peptide aptamers (Aptanomics), Affibodies (Affibody AB), DARPins (Molecular Partners AG), Affilins (Scil Proteins GmbH), Tetranectins (Borean) and Avimers (Amgen)). Several are in preclinical development and a few examples are undergoing clinical trials (anti-VEGFR2 AdNectin (phase I), anti-IL6 Avimer (phase I) and engineered Kunitz-type protease inhibitor anti-kallikrein DX-88 (phase II-III)).

Although for prospective therapeutic applications to date, alternative scaffolds have largely been employed as neutralizing agents for ligand-receptor interaction, cytokine, toxin, or Fc-fusions are being investigated to confer on the binding protein a cytostatic or cytotoxic effect similar to that achieved through antibody-dependent cellular cytotoxicity (ADCC). The potential role of alternative scaffolds in diagnosis is important since large arrays of specific small reagents could be produced to many different targets. Compared to antibodies, small scaffolds should have better tissue penetration which could be advantageous for solid tumor targets.

Criteria for choosing an appropriate alternative scaffold for therapeutic purposes have been disclosed by several sources. Preferable alternative scaffolds have small size (for stability, ease of manufacturing, convenience of selection in some display methods, and tissue penetration in solid tumor applications); high thermodynamic stability and high solubility (for optimal prolonged performance in human plasma) and compatibility with therapeutic use in humans. The latter has been interpreted by some to mean that the scaffold is preferably of human origin (to avoid unwanted immunogenic effects), but scaffolds based on non-human mammalian proteins, bacterial proteins, or synthetic proteins have been proposed. Preferable scaffolds often have few disulfide bonds and free cysteines (which can lead to non-specific target binding during selection), but if the scaffold fold is stable and self-associates well in prokaryotes, as described for the type A repeats disclosed by WO 06/055689, the incorporation of cysteines may not be problematic. If the scaffold is chosen to be of human origin to minimize the adverse consequences of the generation of antibodies against the scaffold, the protein to be used as an alternative scaffold should preferably already exist in human plasma, preferably at a high concentration, and the introduction of a low titer of autoreactive antibodies to the scaffold should preferably have minimal adverse physiological consequences.

The presence of a structurally rigid core that is able to tolerate changes of surface residues without losing stability or correct folding of the protein is also desirable. Alternative scaffolds preferably exhibit protease resistance in addition to their other properties. Protease resistance can be useful for manufacturing, stability, and compatibility with biological samples or environments.

SUMMARY OF THE INVENTION

In one aspect, the invention features an optionally substituted loop-diversified and/or extension-diversified engineered transglutaminase barrel protein with at least one barrel domain derived from a Transglut-C domain of a terrestrial vertebrate (e.g., a mammalian or human Transglut-C domain).

In another aspect, the invention features a method for preparing an enriched composition of target-binding, loop-diversified or extension-diversified engineered transglutaminase barrel proteins from a terrestrial vertebrate by (i) providing a collection of nucleic acids encoding the loop-diversified or extension-diversified engineered transglutaminase barrel proteins in a display-conducive context, (ii) expressing the collection of nucleic acids in vivo or in vitro to provide a collection of loop-diversified or extension-diversified engineered transglutaminase barrel proteins operably linked to the nucleic acid that encodes them, (iii) contacting the expressed engineered transglutaminase barrel proteins with a target; (iv) removing expressed engineered transglutaminase barrel proteins that do not bind to the target; and (v) recovering the engineered transglutaminase barrel proteins enriched for binding to the target.

In another aspect, the invention features another method for preparing an enriched composition of target-binding, loop-diversified or extension-diversified engineered transglutaminase barrel proteins by: (i) providing a collection of nucleic acids encoding the loop-diversified or extension-diversified engineered transglutaminase barrel proteins, (ii) expressing the collection of nucleic acids in vivo or in vitro to provide a collection of loop-diversified or extension-diversified engineered transglutaminase barrel proteins, (iii), contacting the expressed engineered transglutaminase barrel proteins with a target; and (iv) identifying collections of expressed engineered transglutaminase barrel proteins that bind to the target.

The invention also features a method for identifying individual target-binding, loop-diversified or extension-diversified engineered transglutaminase barrel proteins by: (i) providing a collection of nucleic acids encoding the loop-diversified or extension-diversified engineered transglutaminase barrel proteins, (ii) expressing the collection of nucleic acids in vivo or in vitro to provide a collection of optionally individually indexed, loop-diversified or extension-diversified engineered transglutaminase barrel proteins, (iii) contacting the optionally individually indexed engineered transglutaminase barrel proteins with a target; and (iv) identifying collections or individual engineered transglutaminase barrel proteins that bind to the target.

In yet another aspect, the invention features an isolated nucleic acid encoding an engineered transglutaminase barrel protein or a loop-diversified and/or extension-diversified engineered transglutaminase barrel protein in an expression-conducive context.

In yet another aspect, the invention features a method for expressing and purifying a protein including at least one optionally engineered transglutaminase barrel protein domain from a prokaryotic host by: (i) expressing the protein by fermentation in the prokaryotic host; (ii) collecting the insoluble pellet resulting from lysis or disruption of the prokaryotic host under neutral to alkaline conditions; (iii) optionally washing the resulting pellet by resuspension and sedimentation; and (iv) dissolving the pellet under acidic conditions.

The invention also features a method for chemically modifying and purifying a protein including at least one optionally engineered transglutaminase barrel protein domain to achieve optimal in vivo pharmacokinetic properties of the protein by: (i) modifying the protein with a single cystein near the c-terminus that is then modified with polyethelene glycol, and (ii) purifying the modified protein by anion exchange chromatography.

In any of the foregoing aspects, the engineered transglutaminase barrel protein can be an engineered Factor XIII barrel protein.

By "branched polyalkylene glycol" is meant a branched polymer created by the joining of one or more optionally substituted oligomers or polymers of units of the form $-(O-CR_1R_2-CR_3R_4)_n-O-R_5$, where $R_1$, $R_2$, $R_3$, $R_4$, and $R_5$, are the same or different and selected from H, F, or lower alkyl optionally substituted with one or more F; and n is 3 or greater. A branched polyalkylene glycol contains one or more linker structures (branches) of the form A-Y-linker-($X_1X_2$) where $X_1{=}-(O-CR_1R_2-CR_3R_4)_n-O-R_5$ and Y may be a bond or a linear polyalkylene glycol and A is a group selected to provide covalent or stable noncovalent linkage to a protein. As used, the term branched polyalkylene glycol includes block or random copolymers of units corresponding to the formula above, wherein the substituents $R_1$, $R_2$, $R_3$, $R_4$, and $R_5$, may vary from block to block or from monomer to monomer, for example as in a block or random copolymer of polyethylene and polypropylene glycols.

By "coding sequence" is meant the sequence of nucleic acid residues that upon translation give rise to a polypeptide.

By "display" is meant any system that permits the enrichment or identification of a target-binding protein by (i) contacting a mixture of target-binding and target-nonbinding proteins each operably linked to a nucleic acid encoding said target-binding or target-nonbinding protein and (ii) separating said target-binding proteins from said target-nonbinding proteins to provide a composition enriched in the target-binding proteins compared to the initial composition.

By "display-conducive context" means any form in which a target-binding protein can be expressed such that it is available to both bind to a target and retain an operable linkage or physical relationship (for example, by association with the same host cell, phage, or fusion construct) to a nucleic acid encoding said target-binding protein.

By "engineered Factor XIII barrel protein" is meant a protein comprising one or more domains derived from the C terminal beta barrel domains of a blood-borne transglutaminase that have been modified by addition, deletion, replacement, or substitution of one or more amino acid residues.

By "engineered transglutaminase barrel protein" is meant a protein comprising one or more domains derived from the beta barrel domains of the Transglut-C family that have been modified by addition, deletion, replacement or substitution of one or more amino acid residues.

By "expressible clone" is meant a recombinant nucleic acid construct bearing an open reading frame that can be translated from N-terminus to C-terminus without termination. A "non-expressible clone" is a recombinant nucleic acid construct bearing an open reading frame that contains either frameshift or termination mutations that prevent complete translation of the coding sequence.

By "expression-conducive context" is meant the appropriate combination of flanking sequences, vector elements, regulatory sequences, or other nucleic acid sequences empirically determined to support, improve, or regulate the production of a polypeptide chain from the sequence that encodes it. The production of the polypeptide chain can be either in vitro or in vivo. For example, an expression-conducive context for a prokaryotic expression system might comprise an optionally regulated promoter of bacterial or bacteriophage origin, a ribosome binding sequence, the coding sequence of the protein to be expressed, and an optional transcriptional termination sequence. An expression-conducive context for prokaryotic in vitro expression might comprise an RNA or translatable nucleic acid comprising a ribosome binding sequence and the coding sequence of the protein to be expressed, or such expression-conducive context for prokaryotic in vitro expression might comprise a DNA or transcribable nucleic acid encoding such RNA or translatable nucleic acid as well as regulatory sequences permitting the transcription of said DNA or transcribable nucleic acid to afford said RNA or translatable nucleic acid. An expression-conducive context for eukaryotic in vitro expression might comprise an RNA or translatable nucleic acid bearing the coding sequence of the protein to be expressed and optionally bearing 5' and 3' flanking sequences that provide RNA stability or improve the efficiency of translation.

By "extension-diversified" as applied to a transglutaminase barrel protein is meant a transglutaminase barrel protein wherein at least one terminus, either the N-terminus or the C-terminus, of a beta barrel has been replaced and/or extended with an amino acid sequence of no greater than 30% (e.g., less than 25%, 20%, 15%, 10%, 5%, 1%, 0.1%, or less) identity to the original sequence. An extension-diversified engineered transglutaminase barrel protein may have one or both termini extended or modified.

By "Factor XIII barrel protein" is meant a protein comprising one or more domains derived from the Transglut-C family beta barrel domains of a blood-borne transglutaminase.

By "individually indexed collection" is meant any collection of species constituted as mixtures or not, so composed that the activity of any individual member can be inferred from the analysis of the activities of all mixtures.

By "isolated nucleic acid encoding a Factor XIII barrel protein in an expression-conducive context" is meant a nucleic acid composition that can be replicated in vivo or in vitro and that comprises the coding sequence for a polypeptide in an expression-conducive context, wherein said polypeptide comprises a Factor XIII barrel protein not in the native context of Factor XIII. The phrase "not in the native context of Factor XIII" means that, at minimum, the sequences encoding the catalytic domain of Factor XIII are not present.

By "isolated nucleic acid encoding a transglutaminase barrel protein in an expression-conducive context" is meant a nucleic acid composition that can be replicated in vivo or in vitro and that comprises the coding sequence for a polypeptide in an expression-conducive context, wherein said polypeptide comprises a transglutaminase barrel protein not in the native context of the transglutaminase. The phrase "not in the native context of the transglutaminase" means that, at minimum, the sequences homologous to the catalytic domain of a transglutaminase are not present.

By "loop-diversified" as applied to a transglutaminase barrel protein is meant a transglutaminase barrel protein wherein at least one loop connecting beta strands of a barrel has been replaced with an amino acid sequence of no greater than 30% identity (e.g., less than 25%, 20%, 15%, 10%, 5%, 1%, 0.1%, or less identity) to the original sequence.

By "linear polyalkylene glycol" is meant an optionally substituted oligomer or polymer of units of the form $A\text{-}(O—CR_1R_2—CR_3R_4)_n—O—R_5$, where $R_1$, $R_2$, $R_3$, $R_4$, and $R_5$, are the same or different and selected from H, F, or lower alkyl optionally substituted with one or more F; A is a group selected to provide covalent or stable noncovalent linkage to a protein; and n is 3 or greater. As used the term linear polyalkylene glycol includes linear block or random copolymers of units corresponding to the formula above, wherein the substituents $R_1$, $R_2$, $R_3$, $R_4$, and $R_5$, may vary from block to block or from monomer to monomer.

By "library" or "pool" is meant a collection of two or more species constituted as a single mixed entity. Preferably, a "library" or "pool" includes at least $10^2$, $10^5$, $10^{10}$, $10^{13}$, or $10^{15}$ members or some range within these numbers.

By "nucleic acid" is meant an optionally substituted deoxyribonucleic acid or ribonucleic acid or homologous polymer of nucleic acid bases or base analogs that can be either copied to provide an image or replica of itself or that can be translated to form a peptide, polypeptide, or protein.

By "operably linked" or "operable linkage" is meant a stable, covalent or noncovalent attachment of two or more species so described that is capable of providing a statistical association of the operably linked species sufficiently powerful that the identification or extraction of one element permits the identification or recovery of the other element in at least 10% (e.g., at least 20%, 30%, 40%, 50%, 75%, 90%, 95%, 99%, or more) of attempts.

By "peptide" is meant an optionally substituted oligomer or polymer of naturally occurring or unnatural amino acids covalently linked by one or more amide bonds.

By "stable noncovalent linkage" is meant a noncovalent association that permits the continued proximity of the two or more elements such that after a period of time encompassing the expected duration of use of the two more associated elements, no more than 50% (e.g., less than 40%, 30%, 25%, 20%, 15%, 10%, 5%, 1%, 0.1%, or less) of the elements have disassociated. For example, a stable noncovalent linkage for a complex intended to persist for 3 hours at 37° C. will have a half life of at least 3 hours at 37° C.

The term "substitution" in the context of an amino acid sequence is taken to mean the chemical or enzymatic modification of one or more amino acid residues of a polypeptide to afford a substituted polypeptide. Common forms of substitution include attachment of prosthetic groups, polymers, nucleic acids, linkers, small natural or synthetic molecules or fragments thereof, such as modifying radicals, for example methyl or other lower alkyl, formyl, acetyl, or other lower acyl, phosphoryl, or sulfonyl.

By "terrestrial vertebrate" is meant any species belonging to the taxonomic classes phylogenetically more recent than pisces, whether extant or not, including without limitation the classes mammalia, ayes, reptilia and amphibian (e.g., human).

By "Transglut-C family" is meant the family of beta barrels identified by databases of conserved protein domains, such as Pfam, family PF00927, InterPro, family IPR008958, or SuperFamily, family SSF49309.

By "transglutaminase barrel protein" is meant a protein comprising one or more domains derived from the beta barrel domains of the Transglut-C family.

BRIEF DESCRIPTION OF THE DRAWINGS

FIG. 1A discloses SEQ ID NO: 521.

FIG. 1B is an alignment of the β-barrel 1 (SEQ ID NOS: 522-542, respectively, in order of appearance) and β-barrel 2 (SEQ ID NOS: 543-563, respectively, in order of appearance) of the protein sequences from the indicated Transglutaminase family, C-terminal domains. Seven beta sheets (A, B, C, D, E, F, and G) are underlined and highlighted in gray, α-helix is marked with a box, conserved residues are in bold, and the most conserved domain residues are marked with stars.

FIG. 3B discloses "His6" as SEQ ID NO: 29.

FIG. 4 is an alignment showing the nucleotide and protein sequences (SEQ ID NOS: 585, 584, and 586, respectively, in order of appearance) for wild type and optimized F13β2 scaffold. Codons optimized for *E. coli* and in vitro expression are highlighted in gray; single cysteine residue and T650I polymorphism are underlined.

FIG. 9A is the C-NNS library, FIG. 9B is the 50% NNS library, and FIG. 9C is the A-NNS library. Myostatin concentrations used in the selections were as follows: R1 (250 nM), R2-R5 (100 nM), R6 (C-NNS and A-NNS: 100 nM; A-50% NNS: 100 and 10 nM); R7 (C-NNS and A-NNS: 100 nM and 10 nM; A-50% NNS: 10 and 1 nM), R8 (C-NNS and A-NNS: 10 nM and 1 nM; A-50% NNS: 1 nM), R9 (C-NNS: 1 nM; A-NNS: 1 and 0.1 nM). Selection pools used for further fusion production after target concentration drop are marked with an arrow.

FIG. 11A is a table showing the results of a radioactive binding assay for the indicated selected molecules to human myostatin. FIG. 11A discloses the "BC loop" sequences as SEQ ID NOS: 599, 599-601, 600, 599, 599, 602-603, 600, 599, 599, 599, 604, 605, 605, 605, 605, and 605, respectively, in order of appearance, the "DE loop" sequences as SEQ ID NOS: 606-607, 606, 606-607, 606-607, 607-608, 607, 606, 606, 606, 609-612, 610, and 610, respectively, in order of appearance, and the "FG loop" sequences as SEQ ID NOS: 613, 613, 613, 613-614, 614, 614, 614, 615, 615, 615-617, 617-622, respectively, in order of appearance.

FIG. 11B is a series of graphs showing binding of the indicated molecules to myostatin.

FIG. 18A is a schematic showing the structure of Y-Mal-40K (Y-Shape PEG Maleimide, MW 40 kDa; JenKem Technology USA Inc., Allen, Tex.).

FIG. 18B is an image of an SDS-PAGE gel showing three pegylated forms of F13β2 myostatin binder F10. Tagless myostatin binding protein F10 (PCM) was expressed in *E. coli* at 37° C., purified from insoluble fraction and pegylated with Y-MAL-40K.

FIG. 19A is a schematic showing the configuration of E3 homodimer molecule for expression. FIG. 19A discloses "His6" as SEQ ID NO: 29.

FIG. 19B is an image of SDS-PAGE gels showing expression of E3 homodimers in *E. coli*. Proteins were purified from the insoluble fraction. Lanes were loaded as described above.

FIG. 21A discloses the "BC loop" sequences as SEQ ID NOS: 623-628, the "DE loop" sequences as SEQ ID NOS: 629-634 and the "FG loop" sequences as SEQ ID NOS: 635-640, all respectively, in order of appearance.

FIGS. 24A and B disclose "His6" as SEQ ID NO: 29.

FIG. 25 is an alignment showing the nucleic acid (SEQ ID NO: 641) and protein (SEQ ID NO: 642) sequences of wild type F13β1 scaffold.

FIGS. 26A and B disclose "His6" as SEQ ID NO: 29.

FIG. 29 discloses "His6" as SEQ ID NO: 29.

FIG. 30A discloses "His6" as SEQ ID NO: 29.

FIG. 36 discloses SEQ ID NOS: 29 and 649-651, respectively, in order of appearance.

FIG. 37 is a schematic showing the randomization strategy for FG6 and FG6+6 libraries. Randomized positions are underlined in larger font. Oligonucleotides used for randomization are shown. For each position, 50% of wildtype residues are preserved. Exact composition of each randomized position is shown. FIG. 37 discloses SEQ ID NOS: 653, 652, and 654-657, respectively, in order of appearance.

DETAILED DESCRIPTION OF THE INVENTION

Members of the transglutaminase family of proteins share a common four domain structure consisting of a β-sandwich domain, core domain, and β-barrel 1 and β-barrel 2 domains, first identified in the structure of the coagulation factor XIII A1 polypeptide (Yee et al. Proc. Natl. Acad. Sci. USA 1994, 91:7296). The transglutaminase family of proteins falls within a larger transglutaminase superfamily that includes proteins that share homology to the core domain but often lack the C-terminal barrel structures, and can act as proteases or peptide N-glycanases instead of transglutaminases. In the PFAM conserved domain database, the individual β-barrels of the transglutaminase family are classified as comprising the Transglut-C domain family (pfam000927). Human proteins that include β-barrel domains belonging to the Transglut-C domain family presently comprise Factor XIII A1 chain, seven proteins identified as transglutaminase-1 through transglutaminase-7, the erythrocyte membrane protein band 4.2, the protein identified by GenPept/SwissProt record Q6ZTL3, and the protein identified by GenPept/SwissProt record Q9H035.

Figure 1A:
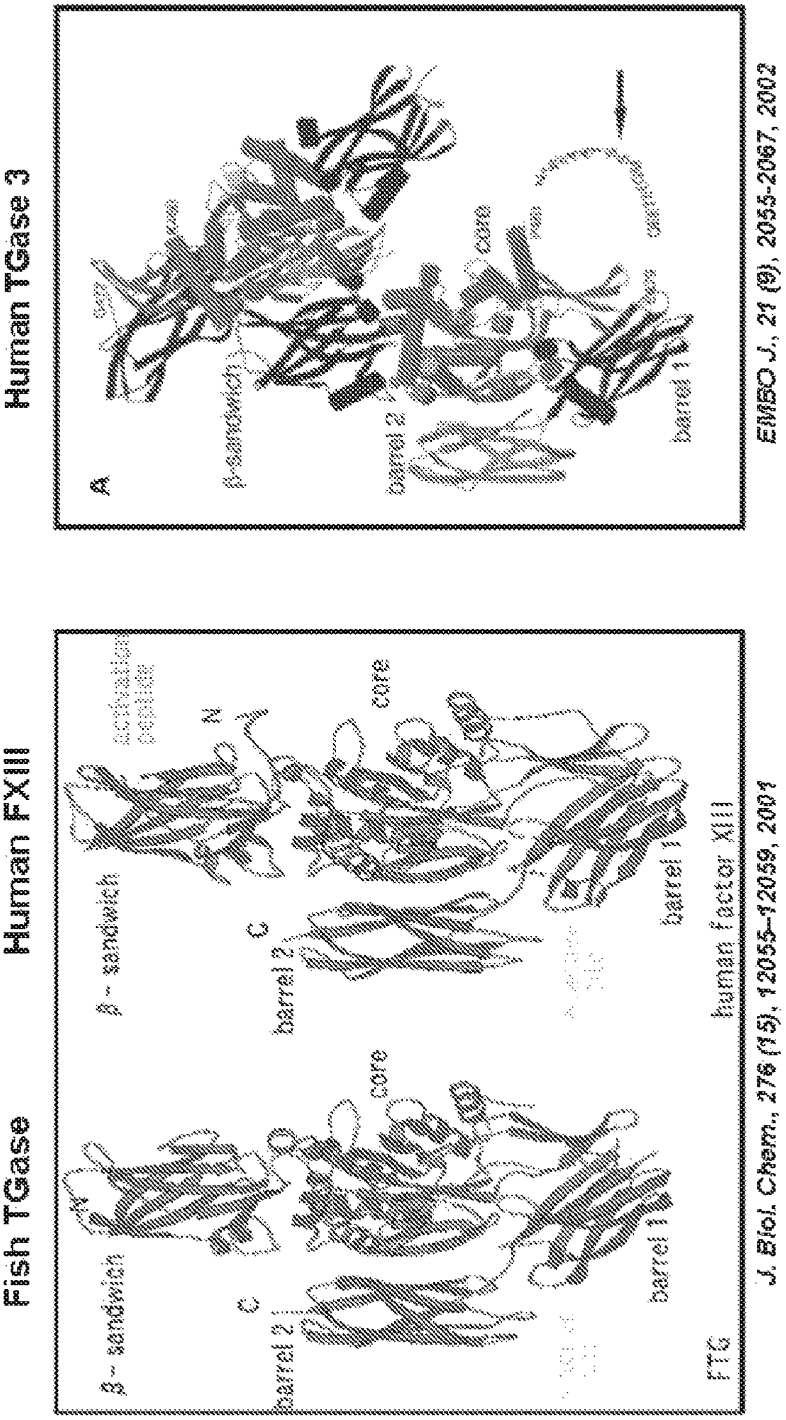
FIG. 1A is a series of schematics showing the three dimensional structures of the indicated proteins.

Transglutaminases vary greatly in sequence between and within species, but share the conserved structural domains, including the beta barrels (FIGS. 1A and 1B). For example, the fish TGase has only 29% sequence identity with human FXIII in the barrel 2 domain, but has a structure very similar to human FXIII, including all four sequential domains in a conserved spatial orientation (Noguchi et al. J. Biol. Chem. 2001, 276:12055) (FIG. 1A).

The two C-terminal domains have a seven-stranded β-barrel fold and "3+4" sheet structure (FIG. 1B). They each contain approximately 100 residues, are 50 Å long and 25 Å wide. In Factor XIII, the β-barrel 1 sequence extends from Ser517 to Leu628 and the β-barrel 2 sequence extends from Thr629 to Met732. The choice of starting point for the numbering of the beta barrel sequences is to some extent arbitrary, and from the crystallographic coordinates the core sequences that comprise the termini of the strands of the second barrel spans Ile633 to Arg728. The residues from Leu628 to Ile633, exclusive, can be considered linker sequences.

The 7 beta strands of barrels of the family are designated strands A through G (FIG. 1B). The A, C, E and G strands extend in the same approximate direction and the B, D, and F strands in the opposite direction. The overall organization of the barrel, with the N-terminus prior to the beginning of the A strand and the C-terminus at the end of the G strand, establishes a natural polarity of the barrel in the direction of the A, C, E and G strands. The strands are connected to one another by loops, of which AB, CD, and EF are located at the end proximate to the C terminus of the barrel, and BC, DE, and FG are located at the end proximate to the N-terminus of the barrel.

Alternative scaffolds drafted as domains from larger proteins preferably have a compact, autonomous structure that is stable in the absence of the remaining domains of the protein. The Transglut-C domains that have been studied to date appear to possess this attribute. For example, both C-terminal domains of the human FXIII-A molecule have been reported to be stable at extremely high temperatures (Tm=90-110° C.) and to exhibit independent folding, as demonstrated by spectroscopic methods.

Although the two barrel domains of transglutaminases are structurally related, there is usually no significant primary sequence similarity between them, nor is their similarity in sequence to fibronectin type III domains. An examination of the two barrel domains reveals that their conserved and diverse sequence segments are similarly arranged, with most variations between BC and CD loops, CD and DE loops, and EF and FG loops (FIG. 1B). Several nearly invariant residues, including Asn541, Asn672, Gly562, Gly671, Pro579, and Pro685, are spatially located in the loop regions: Asn541 and Asn672 in BC loop, Gly562 and Gly671 in CD loop, and Pro579 and Pro685 in DE loop.

Among human transglutaminases that might be used as a source for diversified β-barrel proteins, coagulation factor XIII is of particular interest because it is naturally found in plasma. Proteins that are naturally found in plasma may be better templates for diversification of proteins that are intended to be used therapeutically. For example, autoimmune reactions against plasma proteins induced by crossreactivity to a therapeutically administered protein may have less severe consequences than auto-immune reactions directed against intracellular proteins as the latter reactions might destroy cells, tissues or organs, or have other deleterious consequences. For example, the autoimmune diseases dermatitis herpetiformis and celiac sprue are known to be accompanied by autoantibodies against epidermal transglutaminase (transglutaminase 3) and tissue transglutaminase (transglutaminase 2). β-barrel domains from transglutaminase family proteins expressed only or predominantly in immunologically privileged cells may also have reduced capacity to induce autoimmune syndromes if administered therapeutically. An example of such a transglutaminase family protein is erythrocyte band 4.2 protein.

Factor XIII (FXIII) is the final zymogen of the blood coagulation cascade of higher vertebrates, and is responsible for the crosslinking of fibrin peptides to form mechanically and enzymatically stable clots. In blood platelets, megakaryocytes, monocytes, macrophages, spleen, chondrocytes and placenta FXIII is found as a dimer of identical catalytic A subunits (83 kDa), and in plasma as a heterotetramer of two A and two noncatalytic B subunits (90 kDa) noncovalently linked together and bound to fibrinogen. The carrier B subunit, normally present in excess in plasma, stabilizes the A subunit and protects it from proteolysis. FXIII is not secreted by the classical secretory leader-dependent pathway, but exits the cell by a poorly understood mechanism.

The A subunit of FXIII is activated by thrombin cleavage C-terminal to residue 37 of the protein (Takagi and Doolittle Biochemistry 1974, 13:750). In the presence of $Ca^{2+}$, activated plasma FXIII dissociates from its noncatalytic B subunits; the A subunits undergo a conformational change to assume the enzymatically active form FXIIIa, which exercises its transglutaminase activity on fibrin provided by the action of thrombin (Factor II) on fibrinogen. Fibrin itself promotes the activation of FXIII by serving as a cofactor for the calcium-dependent conformational change of FXIII-A, which in turn allows the thrombin catalyzed activation of FXIII to FXIIIa. In the absence of $Ca^{2+}$ and at high thrombin concentrations a second thrombin cleavage can also occur on the 79-kDa enzyme leading to the formation of 25- and 54-kDa fragments. FXIIIa forms intermolecular γ-glutamyl-ϵ-lysylamide crosslinks between noncovalently polymerized fibrin macromolecular complexes, fibrin monomers, α-2 antiplasmin, fibrinogen, fibronectin, collagen, and other proteins to enhance the mechanical strength of the fibrin clot, protect it from proteolytic degradation, and provide stability to the extracellular matrix.

The average concentration of FXIII in human plasma is approximately 150 nM. Rare cases of factor XIII A chain deficiency result in inefficient wound and bone healing, severe bleeding, high risk for spontaneous abortion and intracranial hemorrhage, and are treated by substitution therapy. Exogenously administered FXIII has a half-life of 9-10 days.

Although there is no direct evidence of involvement of β-barrels in the enzymatic function of transglutaminase family proteins, the movement of the β-barrel region upon activation has been proposed and/or demonstrated. For example upon binding to an active site inhibitor, transglutaminase 2 undergoes a profound change in conformation in which the β-barrels are rotated away from the catalytic core, forming a highly extended structure (Pinkas et al., PLoS Biol. 2007, 5:e327). Similarly, in Factor XIII, Tyr560, positioned on a loop of β-barrel 1, is involved in hydrogen-bonding with the active site cysteine of FXIII (Cys314) and is probably displaced by the glutamine donor substrate which approaches the active site from the direction of the two β-barrel domains. Hydrogen/deuterium exchange (HDX) studies have shown that $Ca^{2+}$ binding could potentially direct β barrel 1 to roll away from the catalytic core to allow glutamine substrate access (Sabo et al, Biochemistry 2007, 46:10089). Within β-barrel 2, chemical modification and proteolysis studies have provided evidence for C695 exposure upon activation. It has been shown that glutamine-bearing substrates create a more solvent accessible region within β-barrel 2, which in turn is potentially involved in lysine substrate recognition. This hypothesis is supported by the observation that antibody 5A2, which targets the FXIIIa epitope 646-658, displays uncompetitive inhibition toward the glutamine substrate and competitive inhibition against the lysine substrate.

Figure 2:
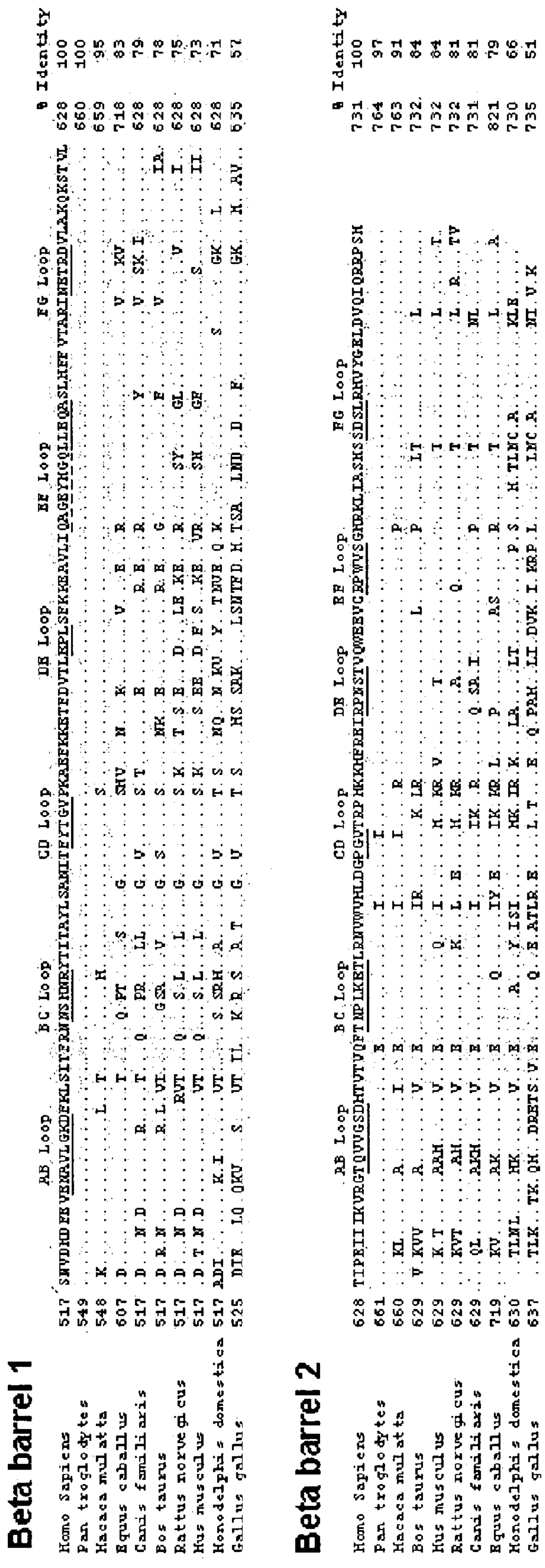
FIG. 2 is an alignment showing phylogeny of coagulation factor XIII beta barrel 1 and 2. The alignment of A subunit of factor XIII beta barrel domains from human (NP_000120 FXIII A) (SEQ ID NOS: 564 and 574, respectively); chimpanzee (XP_518220 FXIII) (SEQ ID NOS 565 and 575, respectively); monkey (XP_001096669 FXIII A1) (SEQ ID NOS: 566 and 576, respectively); bovine (XP_588122 FXIII A1) (SEQ ID NOS: 569 and 577, respectively); mouse (NP_083060 FXIII A1) (SEQ ID NOS: 571 and 578, respectively); rat (NP_067730 FXIII A1) (SEQ ID NOS: 570 and 579, respectively); dog (XP_857147 FXIII A) (SEQ ID NOS: 568 and 580, respectively); horse (XP_001492734 FXIII) (SEQ ID NOS: 567 and 581, respectively); opossum (XP 001368010 FXIII) (SEQ ID NOS: 572 and 582, respectively); and chicken (NP_990016 FXIII A1) (SEQ ID NOS: 573 and 583, respectively). Residues identical to human FXIII sequence are replaced with dots.

Factor XIII-related proteins found in different species appear to be highly conserved in length and sequence. The beta barrel domains within these proteins are highly conserved (FIG. 2). For example, the chicken factor XIII polypeptide has 55% sequence identity to the human polypeptide in the beta barrel region (from Asn518 to the Arg728) whereas the rhesus macaque factor XIII polypeptide shares 94% sequence identity from Val519 to Met732.

Functional recombinant A subunit of FXIII has been produced in yeast and the recombinant product has entered clinical studies for treatment of FXIII-A deficiency conditions. Conflicting data have been disclosed regarding *E. coli* expression of FXIII-A: one study reported only non-functional recombinant FXIII-A, while another reported expression of fully functional FXIII-A with properties similar to native plasma or yeast-produced FXIII-A chains. To date the production of individual beta barrel domains of FXIII by recombinant methods has not been disclosed, although highly stable 24 kDa and 12 kDa C-terminal fragments, corresponding to β1β2 and β2 barrels have been obtained by elastase digestion from recombinant FXIII-A.

The present invention provides compositions based on beta barrel domains of transglutaminases, described herein as engineered transglutaminase barrel proteins (ETBPs). ETBPs comprise one or more artificially diversified transglutaminase beta barrel domains. An ETBP may be solely comprised of barrel one domains or solely comprised of barrel two domains or may be comprised of mixtures of the two barrel types. In particular an ETBP may contain diversified examples of both barrels in the native organization in which they are found in Factor XIII, erythrocyte band 4.2 protein, or the tissue transglutaminases 1-7, in which barrel one lies N terminal to barrel two. ETBPs are derived from naturally occurring barrel sequences by the addition, deletion, or substitution of residues in the naturally occurring barrel sequences. Of particular interest are the ETBPs that have been derived by substitution of one or more loops of a naturally occurring barrel sequence, or that have been derived by the addition of one or more peptide extensions at the N-terminus and/or the C-terminus. ETBPs derived by modification of loop sequences are called loop-diversified ETBPs whereas ETBPs derived by extension are called extension-diversified ETBPs. A given ETBP may be both loop-diversified and extension-diversified, and may contain additional sequence variation, for example improving affinity, stability, selectivity, or solubility, that have been introduced at any location in the molecule. In addition an ETBP may be optionally substituted with prosthetic groups, polymers, proteins, nucleic acids, carbohydrates, metals, or natural or synthetic small molecules.

Diversity of loop or extension regions in ETBPs is introduced through the incorporation of diversity in nucleic acids encoding ETBPs. For this purpose random or indexed collections of nucleic acids encoding different sequences can be prepared according to any of several methods known in the art. Such collections can be prepared in ways that favor specific sequences or residues, or disfavor specific sequences or residues, by altering the probability of appearance of specific nucleotides in a site-specific or site-non-specific manner, or by specifying triplets of nucleic acid residues corresponding to individual codons and varying the relative abundance of said triplets in a site-specific or site-non-specific manner. For example, to reduce the abundance of cysteine residues, encoded in DNA by TGY, the relative abundance of T in the first position, G in the second position, or a pyrimidine in the third position, can be reduced in the template nucleic acid, illustrated here as DNA. Alternatively a mix of triplet precursors corresponding to each of the individual amino acids could be prepared, from which the triplets TGT and TGC are excluded. To reduce the frequency of termination codons a common strategy is to randomize loops or extensions in the form $(NNS)_n$, where n denotes the number of random triplets to be included, N represents any nucleotide, and S represents C or G in the standard IUPAC nucleotide nomenclature. Since two of three stop codons (TGA and TAA) have an A in the third position, an NNS strategy is expected to reduce the frequency of stop codons from 3/64 to 1/32 compared to an NNN strategy.

The preparation of loop-diversified ETBPs may be carried out by any of several different schemes well known in the art. For example, libraries of ETBPs containing loop regions replaced by random peptide sequences of the same or different length can be prepared by recombinant DNA methods. Such libraries can be prepared as variants of a single scaffold having up to six loops diversified in a single ETBP or can be prepared as separate libraries each having one diversified loop per ETBP, or by some combination of loop-diversified libraries, for example having two diversified loops at one end and one at the other. Schemes in which individual libraries of loops are provided are often coupled with a facility for the interchange of the individual libraries, for example by the placement of restriction enzyme cleavage sites in the non-diversified regions that permit shuffling and reassembly of the library templates by restriction enzyme digestion and ligation. Other methods for shuffling of existing sequences are well-known in the art, and include stimulated recombination in vitro or in vivo, and nucleic acid shuffling and rejoining by PCR or isothermal amplification. In some cases it may be useful to create sublibraries from existing libraries, or sublibraries that incorporate some previously selected candidate ETBP as a starting point for the generation of further diversity focused on a particular ETBP with desirable properties. For example, to further improve the affinity of a pool of candidate ETBPs that shows a predominance of one loop sequence, a new library can be created in which that loop sequence is taken as the starting point and further randomization is introduced by partial or complete randomization of the other loops and/or by partial randomization of the predominant loop.

Extension randomization can be similarly carried out at the N-terminus or C-terminus or both. The starting point for randomization can be either a naturally occurring transglutaminase barrel or a preselected candidate ETBP. The extension-diversified ETBP is created by the addition of one or more residues to the N-terminus or C-terminus or both. Very long extensions are likely to compromise the stability or solubility of the ETBP and hence practical extensions are in most cases likely to be less than fifty residues in length, more preferably less than forty residues in length, and most preferably less than 20 residues in length, although longer extensions can be formed by intermediate selection for ETBP starting points that have favorable stability or solubility. Further randomization of an initially preselected extension-diversified ETBP can be focused on a preselected sequence by introducing, through the use of diversified nucleic acid templates, a weighted probability of mutation at each residue that is provided to introduce a predetermined number of changes per extension. The weighting of the likelihood of change per residue can be varied by specifying the percentage of each nucleotide to be incorporated at a given location.

For either loop diversity or extension diversity many different strategies for retaining proximity in sequence space to a favored sequence are known in the art. By way of example and without limitation, to diversify around the codon for methionine, ATG, and retain hydrophobic character, the template could be specified to contain at the first position 40% A and 20% of each other residue (C or G or T), at the second position 70% T and 10% of each other residue, and at the third position 75% of G and 25% C. Such a mixture would weight the substituted residues toward hydrophobic amino acids (which often contain a T in the second position), consistent with the hydrophobic character of methionine. The most likely encoded amino acid would be methionine itself. Depending on practical limitations for the preparation of the template nucleic acids, it may be more or less convenient to randomize each position in a manner specific for that residue, and in practice randomization schemes are frequently chosen that introduce an invariant probability of retaining one dominant residue and a fixed proportion of alternate residues, for example 70% A, 30% B for A, 70% C, 30% D for C, 70% G, 30% H for G and 70% T, 30% V for T. B, D, H and V are respectively the IUPAC codes for “not A”=C, G, or T, “not C”=A, G, or T, “not G”=A, C or T, and “not T (and not U)”=A, C or G.

The engineered transglutaminase barrel proteins of the present invention are useful for the creation of binding proteins that adsorb with high affinity to selected targets. The potential uses of such binding proteins are broad, and include, without limitation, the analytical detection and measurement of molecules or complexes of molecules, the interruption or neutralization of cellular or humoral signaling events via the blockade of enzymes, receptors or ligands, the normalization of homeostatic balance by return of functionality compromised by age, disease, or trauma, the induction of receptor-mediated signaling by receptor agonism, the targeting of undesired cells for destruction, and the localization of binding targets, for example of tumors, microbes, thromboses, or sites of tissue damage. Targets of artificial binding proteins are often proteins or peptides but can also be carbohydrates, lipids, nucleic acids, small molecules such as drugs, metabolites, or toxins, or compositions formed from small molecules or inorganic species such as either natural or synthetic polymers, glasses, metals or alloys, semiconductors or insulators; targets can also comprise modifications or substitutions of proteins, carbohydrates, lipids, or nucleic acids, or combinations of one or more such agents, such as a carbohydrate-substituted proteins, carbohydrate-substituted lipid, RNA-protein complexes, etc. Methods for identifying binding proteins that display high-affinity and high specificity for their targets are known in the art.

ETBPs of the present invention can also be used to create novel activities, such as catalytic activity, or substrate activity, based on the incorporation of prosthetic groups or designed or randomly selected sequences that can be installed in the ETBP. For example ETBPs can be used to generate substrates or inhibitors of proteases, or to provide proximity enrichment for substrates for enzymatic activities. In keeping with their utility as antibody equivalents, genetic selections or designed modifications that introduce catalytic potential can be incorporated into ETBPs through methods well known in the art, such as selection for affinity to a transition state analog of an intermediate that is found in a reaction to be facilitated by an ETBP.

To achieve high affinity and selectivity, ETBPs can be endowed with a novel surface complementary to a target of interest. For this purpose random libraries of proteins can be created and screened for rare variants that have desired properties; alternatively, specific variants can be designed by computational analysis of the target binding surface and construction of a series of candidate binding proteins that may have the appropriate behavior. Random substitution schemes can be employed when the detailed molecular structure of the target is not known, or when the most appropriate site on a structurally well-characterized molecule cannot be determined in advance. Most contemporary scaffold diversification strategies are based on random substitution. The invention further provides for mixed computational and random strategies, for example in which random diversification leads to candidates that are further optimized by directed substitution, or the use of computational techniques to predict families of candidates that can be screened for an activity of interest.

Construction of Libraries and Designed Variants

Libraries of ETBPs can be prepared in various ways known to those skilled in the art. Disseminated random substitution, clustered substitution, and designed (targeted) alteration are strategies that have been employed to increase the affinity of a given diversified scaffold for a particular target protein. In general, the objective of such diversification is to increase affinity without compromising the overall stability or solubility of the protein. One of the most widely employed strategies is surface randomization, the replacement of endogenous sequences on one particular aspect or face of a protein in order to generate a highly diverse collection of surfaces. Two common subtypes of surface randomization are loop and pocket diversification, used for proteins that are naturally convex or concave respectively. Randomizations may conserve or alter length if the scaffold is appropriately stable. In addition the natural geometry of the scaffold may be altered by incorporation of structural elements that endow the randomized or grafted sequences with particular folds or shapes. Among the known elements that may be employed for such purposes are the placement of cysteine residues such that a disulfide-linked loop is formed, the introduction of helix or sheet-destabilizing residues, such as glycine or proline, the incorporation of beta turns or Trp cage motifs, or the formation of additional secondary structure elements, such as short alpha helical or beta strand sequences.

The affinity and stability of loop-substitution surface randomized ETBPs can be further improved by the inclusion of mutations in the beta strands that improve rigidity or alter the positioning of the loops. Such favorable non-contact site mutations are well-known in the art and can be discovered by random mutagenesis once an initial candidate has been identified. Typically mutagenesis of the entire ETBP is performed, with selection for variants that exhibit higher binding affinity.

The engineered transglutaminase barrel proteins of the present invention can be further adapted to include diverse polypeptides sequences at their amino or carboxyl termini. The additional diversity may enhance affinity by providing secondary binding sites to the target, or may enhance the functional properties of the protein by binding to proteins with enhanced plasma half-life, or proteins that are known to be enriched in the vicinity of the target, or that afford the possibility of concentration in an organ or tissue-specific manner by binding to organ or tissue-specific secondary targets. When additional diversity elements are incorporated at the amino or carboxyl termini, measures may have to be employed to protect those elements from naturally occurring exopeptidases, such as the peptidyl peptidases, aminopeptidases, carboxypeptidases, and related enzymes. Methods of predicting and defeating susceptibility to exopeptidases are well known in the art. Methods of blocking exopeptidase activity include amino and carboxyl-terminal modification, incorporation of additional residues that are not substrates for the exopeptidases, or chemical modifications that destroy susceptibility.

The identification of a high-affinity, high selectivity ETBP can be achieved by either screening methods or selection methods. A screening method typically requires two elements: a supply of candidate ETBPs to be tested for affinity to the target; and a systematic method for the enumeration of the candidates, such as an ordered array or systematically composed mixture that can be deconvolved to reveal the identity of the most active variants. Screening methods often require that large numbers of ETBPs be evaluated; in such cases it is common to use pooling schemes to mix candidates, allowing the presence or absence of a desired candidate to be determined with fewer measurements. Active pools are further subdivided to identify active unique species. Candidates derived from such screens can be subjected to further randomization and screening to progressively derive ETBPs of higher binding affinity.

Selection methods typically require a library of candidate ETBPs, each prepared in a form that provides a genetic linkage between the protein and a nucleic acid that encodes or identifies the protein. A mechanism must be provided to physically isolate and purify candidate binding proteins and their associated nucleic acids from the remaining library members that lack activity. In selection methods many fewer measurements are typically performed than in screening methods.

The present invention further provides methods for the identification of ETBPs having favorable affinity, selectivity, solubility, and thermal stability. Numerous selection methods for the enrichment of nucleic acids encoding proteins of interest that bind to a specific target are known in the art and are useful for the generation of the desired ETBPs. Among these are the so-called display technologies, including phage display, yeast display, bacterial display, viral display, mammalian cell display, ribosome display, RNA display and DNA display. For the application of a particular form of display, an appropriate vector must be provided that is suitable for the display of the ETBP in the context in which selection is to take place. For example for commonly practiced forms of bacteriophage display, a plasmid encoding a translational fusion between a solvent-exposed phage structural protein and the ETBP must be created. For cellular display, such as bacterial, yeast or mammalian cell display, a fusion or stable association is created between a surface protein and the ETBP. For ribosome or mRNA display, a fusion or stable association must be created between the diversified binding protein and the mRNA that encodes it. For DNA display a fusion or stable association must be created between the ETBP and a high affinity, typically site-selective, DNA-binding protein. For some types of selection method, physical association of the binding protein and the nucleic acid that encodes it is provided by physical compartmentalization. For example, in emulsion selection methods, a small aqueous droplet is provided in which the ETBP is synthesized from a template nucleic acid. In this case the physical association is provided by the compartmentalization afforded by the nonaqueous phase that separates the individual droplets.

Display-based selections consist of one or more cycles of enrichment, each of which comprises: (i) contacting the target of interest with a mixture of diversified proteins in display context, e.g. as phage particles, cells, or RNA fusions; (ii) physically separating those phage particles, cells or RNA fusions that bind the target from those that do not bind the target, or bind less avidly, and (iii) amplifying the resulting isolated binding population by in vivo or in vitro methods to generate a new, enriched collection of diversified proteins that can be subjected to additional rounds of contact and purification. For display-based selections it is a requirement that the target permit physical isolation of the complex of target and ETBP. For example the target may be labeled with an antibody domain, peptide tag, fluorophore, biotin, or other affinity or labeling moiety, allowing the complex of ETBP and target to be physically separated from ETBPs that do not interact with the target. Alternatively antibodies or binding reagents specific for the target can be employed to effect separation. Often it is necessary to exclude unwanted ETBPs, for example those that bind to extraneous portions of the target, or to components of the apparatus used to effect physical separation. Common separation strategies rely upon an affinity matrix for the antibody domain, peptide tag, biotin, epitope or affinity moiety, such as a bead or magnetic particle bearing the cognate binding element for such antibody domain, tag, biotin, epitope or affinity moiety. Examples of commonly encountered binding elements include protein A, streptavidin, monoclonal or polyclonal antibodies, and coordinated transition metal divalent cations. Alternatively, separations based on fluorescence detection and sorting can be used. Such separations typically distinguish the signal conveyed by a fluorescent moiety or fluorophore attached to the target, and permit the identification and selective separation of cells or particles bearing high concentrations of the target by fluorescence-activated cell sorting. The contributions of undesired ETBPs can be reduced by preabsorption steps that mimic target exposure and enrichment, but are conducted in the absence of target.

Affinity

Selections or screens for ETBPs having the desired binding can be carried out by the methods described above followed by methods to identify candidate ETBPs of particular interest according to their affinity, activity, selectivity, solubility, or thermostability. Many methods for the measurement of affinity are known in the art and include solid phase as well as solution phase measurements of association constant or reaction on and off rates for combination of the ETBP with a target, or for the measurement of the catalytic activity of a catalytic ETBP. From the analysis of such equilibrium or kinetic constants the affinity of the ETBP for its target can be measured. Some methods of measuring affinity include, solid phase assays, such as planar or bead format assays, solution phase assays, or cell-based assays. Detection in such assays can be based on the analysis of changes in a signal generated by a detectably labeled target or ETBP, such as a radiolabeled target or ETBP or targets or ETBPs conjugated to or associated with an enzymatic activity or a fluorophore or fluorescent protein, or an active prosthetic group that behaves as a catalyst for a reaction or a change in property that is easily monitored. Common methods for measuring affinity include radiolabel or enzyme-linked immunosorbent assays, or assays based on surface plasmon resonance, fluorescence resonance, fluorescence polarization, or fluorescence autocorrelation spectroscopy or microscopy. A common form of affinity measurement is one in which target is immobilized on the solid phase, and varying concentrations of a solution containing a detectable form of the ETBP is contacted with the immobilized target to measure the amount of ETBP bound as a function of ETBP concentration.

Activity

For therapeutic purposes it is often useful to determine the activity of a particular ETBP for its proposed utility. For example, if the ETBP is to exert a therapeutic action by inhibiting the binding of an enzyme to its substrate or a ligand to its receptor, candidate ETBPs with affinity for the enzyme, ligand or receptor can be tested for their ability to inhibit the functional association that should be compromised for the desired effect. A bioassay is often used to determine the activity of a candidate ETBP, in which a cellular process or an in vivo response is measured in the presence or absence of progressively greater amounts of the ETBP of interest.

Selectivity

ETBPs according to the present invention may bind to single members of families of targets, or multiple members of families of targets, to achieve the desired therapeutic, analytical, manufacturing, or research utility. For example, the neutralization of biological activity for therapeutic purposes may optimally require the antagonism of more than one target, or the quantitation of such biological activity for analytical purposes may require the recognition of more than one target, or the purification of some targets of interest may require the recognition of families of related molecules. The selectivity of candidate ETBPs can be manipulated during selection or screening by including comparator targets for which binding affinity is either desired or not desired. For example, to create a highly selective ETBP that recognizes one member of a multimember family of targets, such as family of closely related proteins, a preselection can be made with the undesired targets, discarding the so-selected ETBPs, followed by a selection with the desired target. Or the activity of the ETBP identified by selection or screening methods can be assessed by comparing the binding affinity to the desired target with that of unrelated targets or related targets for which affinity is either desired or not desired. Such screening methods need not provide precise information, but for convenience may convey simple approximate measures of relative affinity, for example based on signal strength in an assay format similar to that of an enzyme linked immunosorbent assay (ELISA).

Solubility and Stability

Candidate ETBPs of the present invention that have been identified by selection or screening can be further evaluated and modified if necessary for additional properties that are required for the field of use. For example, for the manufacturing of ETBPs intended for most uses, a candidate ETBP can be highly soluble and thermostable. Methods are provided by the present invention for the evaluation of the solubility and thermostability of ETBPs as well as their suitability for expression in properly folded form in *E. coli*. In general methods for the evaluation of thermostability are well known in the art, and consist of thermal stress testing or extended storage testing at defined temperatures, followed by measurement of binding activity. In some cases a test for relative thermostability can be as simple as the measurement of the fraction of ETBP remaining soluble following incubation of the ETBP for a defined time at a particular temperature. Another suitable method for measuring thermostability is differential scanning calorimetry. Methods for the indirect assessment of folded status of proteins in *E. coli* are also known in the art, and in the present invention comprise fusion of the candidate ETBP to an easily monitored protein whose activity is only apparent in its properly folded form, such as GFP or an antibiotic resistance. The relative degree of folding has been found by others to be a property shared by both domains of a fusion protein in *E. coli*, so that if the ETBP moiety is not properly folded, the likelihood that the GFP or antibiotic resistance moiety will be folded is commensurately low. In such cases cells expressing inactive or improperly folded ETBP fusion proteins will not show high green fluorescence or high antibiotic resistance.

Compositions

Compositions of nucleic acids and polypeptides, as well as substituted nucleic acids and substituted polypeptides, are included in the present invention.

Substituted ETBPs

Substituted ETBPs according to the present invention can be created by site-specific targeting methods that are either chemical or enzymatic in nature. Substitution may be provided either in vivo or in vitro, and can endow the nucleic acid or polypeptide with additional features useful for selection, purification, or therapeutic, analytical, manufacturing or research utility. Exemplary substitutions that are frequently encountered in the art include prosthetic groups, such as biotin and lipoic acid, N-terminal modifications, such as various amides and cyclic amides, alkylations of cysteine or selenocysteine residues, replacement of natural with unnatural amino acids, as for example may be practiced by proteolytic resection and replacement, the formation of isopeptide bonds such as are formed between glutamine and lysine residues, polymer substituents, such as polyalkylene glycols of varying lengths and/or branch structures, small organic molecule substituents, including receptor or ligand binding molecules or their fragments, and various other peptide or nonpeptide adducts that may be attached to the ETBP for a particular utility. The substitutions may aid in the detection, purification, or localization of the ETBPs and may confer favorable properties by virtue of such localization. For example substituted ETBPs may bind to plasma or cell surface proteins to extend the half life of the substituted barrel, or may be concentrated on the surface of particular cells, or in certain organs or tissues, by virtue of their affinity for cell-, organ- or tissue-selective secondary targets, such as receptors, carbohydrates, lipids or combinations of such secondary targets as may be presented by the organism to be treated or exposed to the substituted barrel.

The engineered transglutaminase barrel proteins of the present invention may be delivered as pure proteins or may be generated in situ, for example following delivery by a gene targeting or genetic therapy that may involve the in vitro or in vivo modification of the genetic complement of an existing cell to produce the polypeptides of the present invention.

Substitution or Modification to Achieve Extended In Vivo Half Life

Engineered transglutaminase barrel proteins may be modified to extend their plasma half life, for example by modification with polyethylene glycols, by translational fusion or post-translational crosslinking to naturally occurring plasma proteins having extended half life or by a combination of such methods. Suitable naturally occurring plasma proteins having extended half life include antibodies, albumin, apolipoproteins, serpins and some constituents of the complement and coagulation cascades. For example, translational fusion to human antibody Fc domains, particularly human IgG1 Fc domain, has been a widely used to improve plasma persistence of proteins. ETBPs may also be endowed with extended half life by dimerization or multimerization to produce polypeptides that are too large to be naturally subject to renal filtration. Suitable methods for dimerization or multimerization include disulfide bond formation, translational fusion, and chemical or enzymatic crosslinking that is either site-selective or site-nonselective. When translational fusion is employed it may be necessary to provide one or more flexible linkers connecting monomers of the diversified barrel. Such flexible linkers are well known in the art and may consist of a plurality of glycine residues in combination with chiral amino acids that provide favorable aqueous solubility, such as the charged or uncharged hydrophilic amino acids aspartic acid, glutamic acid, arginine, histidine lysine, serine, threonine, tyrosine, asparagine, or glutamine. Flexible linkers need not be confined to glycine and hydrophilic residues so long as the linker so constructed does not confer otherwise unfavorable biophysical properties on the ETBP, such as poor solubility, instability to aggregation, or susceptibility to proteolysis.

The formation of antibodies against ETBPs of the present invention can be minimized by the attachment of polymers, such as polyethylene glycols of varying size, branching morphology and attachment groups, to the barrels, their N terminal or C terminal extensions, or their prosthetic groups, using either site-selective or site-nonselective methods.

Additional Uses of ETBPs

Therapeutic Uses

The engineered transglutaminase barrel proteins of the present invention can be used as targeting principles to deliver other therapeutic or analytical elements to an organism in need of therapy or diagnosis. For example, they may be attached to highly active cytostatic or cytotoxic agents to effect the growth arrest or elimination of an undesired cell type, such as a neoplastic or pre-neoplastic cell, or for the reduction in mass of a hypertrophic tissue or organ such as a hypertrophic prostate, or for the elimination of populations of immune cells that are undesired, for example those promoting or causing autoimmune syndromes. Such cytostatic or cytotoxic agents may be synthetic or natural small molecules, for example, maytansine and its derivatives, anthraquinones, alkylating agents such as cyclophosphamide or its prodrug forms, tubulin-binding agents, geldanamycin or its derivatives, or enediyne antibiotics such as calicheamycin, among others. The cytostatic or cytotoxic agents may also be proteinaceous toxins or combinations of small molecules and proteinaceous toxins. Proteinaceous toxins that may be employed for the purposes of cytostatic or cytotoxic therapies include bacterial toxins, members of which can be drawn from the 339 or more species or families that have been identified to date, including their natural variants, serotypes, isoforms, and allelic forms from both Gram-positive and Gram-negative bacteria (Alouf and Popoff, Eds. "The Comprehensive Sourcebook of Bacterial Protein Toxins, 3rd Ed." Academic Press. 2006). Exemplary bacterial toxins widely used for selective ablation of target cells or tissues include diphtheria toxin, *Pseudomonas* exotoxin A, anthrax lethal factor, and aerolysin.

Bispecific ETBPs

Dimeric or higher multimeric ETBPs can be used to juxtapose cells or induce cellular actions by receptor crosslinking that may have a favorable therapeutic effect. For example, therapeutic strategies aimed at amplifying the cytotoxic action of macrophages, natural killer cells, or cytotoxic T cells have been described which rely upon the use of bispecific antibodies or related compositions. Such bispecific antibodies typically provide one antibody combining site that recognizes a target on the cell type to be ablated, and a second antibody combining site that recognizes a cell surface receptor on macrophages, natural killer cells, or T cells that, if engaged, induces the cytolytic effector program of those cells, leading to destruction of the target. Alternate forms of bispecific antibodies promote the selective disabling of responses by mast cells or B cells by producing crosslinks between activating receptors, such as the high affinity receptor for IgE on mast cells or the immunoglobulin receptor on B cells, and inactivating receptors, such as the inhibitory receptor for immunoglobulin FcγRIIB, also found on mast cells and B cells. The coordination of the activating receptor and the inhibitory receptor frustrates the signals emanating from the activating receptor, resulting in a favorable therapeutic effect. Similar bispecific compositions can be provided by the ETBPs of the present invention, which can be joined by a variety of methods to provide bi- or multi-specific binding principles for therapeutic treatments.

In addition ETBPs of the invention may be used to target prodrug activating enzymes to cells, tissues or organs that are desired to be made subject to the action of the drug of interest. Such uses of ETBPs follow closely the uses of antibodies in antibody directed enzyme prodrug therapies, which rely upon antibodies for the targeting of a prodrug metabolizing moiety which converts a circulating prodrug to an active form. Such local activation schemes have been developed to allow a more specific delivery of highly toxic chemotherapeutic agents to the vicinity of a neoplastic cell in vivo.

Engineered transglutaminase barrel proteins can also be used to deliver bioactive principles to a cell, organ, or tissue that is desired to be targeted. To produce interference with the function of a particular pathway that may be essential systemically but undesired in a specific organ, for example to block a hepatic action but not a central nervous system or renal or muscular action, an engineered transglutaminase barrel protein can be used to convey an antagonist of that pathway to a specific tissue, by (as in the example cited) binding to a liver-specific cell surface protein. A bioactive principle delivered by the ETBP can be attached to the ETBP by translational fusion or by chemical or enzymatic modification in a site-selective or site-nonselective manner.

Diagnostic Uses

ETBPs of the present invention can be used as antibody equivalents for many assay purposes. ETBPs can serve as the capture or detection reagent for ELISA-type assays or as the detection reagent for ELISpot assays or for the enumeration of protein abundance by flow cytometric measurement technologies. ETBPs can be conjugated to fluorophores, fluorescent proteins or enzymes to aid in the detection and/or quantitation of analytes of interest. Translational fusions of ETBPs to enzymes or other proteins that aid in the detection of analytes can be made and the resulting fusions can be expressed in prokaryotic or eukaryotic cells to provide a convenient renewable source of reagent. The favorable thermostability properties of ETBPs allow their use in arrays of analyte detector, for example in the planar format of protein binding arrays, or in the bead format of multiplexed fluorophore ratio indexed bead systems, such as the Luminex system. Detection of analyte binding with an ETBP can follow many of the assay format designs and detection schemes that have been disclosed for high sensitivity and selectivity detection by antibodies, such as light scattering, light surface plasmon scattering, fluorescence polarization, time resolved fluorescence, fluorescence autocorrelation, electroluminescence, chemiluminescence, fluorescence resonant energy transfer, fluorescence quenching or unmasking, coagulation or flocculation of beads, cells or other particles, or by providing nucleic acid or modified nucleic acid tags for detection by amplification methods including polymerase chain reaction, ligation-mediated probe amplification, branched nucleic acid assay, or isothermal amplification, with or without a ligation step; or by conveying enzymatic activities detectable by absorbance, fluorescence, evanescent field or surface potential perturbation. Monospecific or multispecific ETBPs can be prepared to identify unique analytes or families of analytes. In addition, monomeric, or multimeric ETBPs can be used as capture or detection reagents.

Labeled ETBPs can be used to image diseased cells, tissues or organs, either in vivo or in vitro. ETBPs can be conjugated to radionuclides, or to prosthetic groups incorporating or binding to other molecules comprising radionuclides. Common radionuclides used in imaging include F-18, I-131, I-123, Tc-99m, In-111 or Ga-67. Alternatively ETBPs can be conjugated to groups enclosing caged hyperpolarized xenon, or can be joined or attached to beads, nanoparticles or nanocrystals susceptible to detection by magnetic resonance imaging. Radionuclides can be detected by nuclear scintigraphy using equipment and methodology well known in the art, such as gamma cameras and positron emission tomography. In addition, images obtained by one modality, such as magnetic resonance imaging can be superimposed on images obtained by other modalities, such as nuclear scintigraphy, or two or more radionuclides of different spectral properties can be combined with different ETBPs, to permit better localization of images and more precise staging or diagnosis of disease conditions. Uses of such conjugated ETBPs include the in vivo imaging of tumors, infections, regions of ischemic damage or poor perfusion, clots, bone or eroded bone, sites of inflammation or degeneration, accumulations of amyloids, paraproteins or prion proteins, or to interrogate the status of prosthetic devices and/or their interfaces with normal or diseased tissue. ETBPs labeled with enzymes, fluorophores, fluorescent proteins, ferritin, gold or silver particles, or electron dense beads, can be used in conjunction with microscopic or ultramicroscopic techniques to diagnose pathological conditions or to identify, enumerate or quantitate the burden of relevant targets that signify the disease status of the cells, tissues, organs or organisms being studied.

The imaging of tissues using labeled or conjugated ETBPs can be used to guide diagnostic or therapeutic procedures, such as biopsies, resections, radioablations, radiotherapy, or locally delivered chemotherapy.

Manufacturing Uses

The favorable thermostability and solubility properties of the ETBPs of the present invention also permit their use as adsorption reagents for the purification of proteins and complex biological structures, such as vaccine components. The positive manufacturing economies of prokaryotic production allow ETBPs to be used in settings for which the routine use of antibody reagents or materials would be considered prohibitively expensive.

Typically, for a manufacturing use an ETBP having the desired selectivity, solubility, thermostability, and affinity for a target will be prepared in a form that allows its constitution into an adsorbent, which may comprise a column medium, bead, or coated surface to which a target stream is to be exposed. Following adsorption of the target to the solid support, the nonbound material will be removed by one or more washing steps and the desired target material will be eluted, typically by raising or lowering the pH, as is common in the elution of antibody-based affinity supports. Various hydrophilic matrices that are used as supports for such affinity media are well known in the art and includes various, typically porous and crosslinked, polymers, such as crosslinked agaroses, dextrans, acrylamides, hydrophilic acrylates, or inorganic matrices such as controlled pore glass, or nonporous but fine particles such as magnetic beads, and functionalized or surface passivated silica or cellulose particles. ETBPs can be attached to such media by methods such as electrophilic attack by aldehydes, oxiranes, activated carbonates, iminocarbonates, cyanate esters, haloacetamides, maleimides, or activated esters, including carbodiimide activated carboxylic acids. Many commercial suppliers of pre-activated media suitable for attachment of the ETBP are known. In addition the ETBP can be engineered by the incorporation of specific residues or sequences that favor the attachment of the ETBP to the media in an ETBP site-selective manner. For example, the incorporation of cysteine or selenocysteine residues, or substrate sequences for transglutaminases or sortases can be used to provide specific sites at which the ETBP can be linked to a solid support.

Research Uses

Research and analytical uses of ETBPs include the replacement of antibodies for detection and quantitation of analytes in various contexts, for example in immunoblotting, ELISA, ELISpot, flow cytometry, bead-based coagulation or detection systems, for detection of analytes by light scattering, surface plasmon scattering, chemiluminescent or electroluminescent detection, by fluorescence polarization, time-resolved fluorescence, fluorescence autocorrelation, fluorescence resonant energy transfer, or fluorescence quenching or unmasking. ETBPs can be conjugated with various fluorophores or fluorescent proteins to provide probes for the presence or absence of analytes. The analytes may include proteins, carbohydrates, nucleic acids, lipids, small molecules of natural, synthetic or semisynthetic origin, as well as polymers, glasses, metals and alloys, or combinations of these. ETBPs can be conjugated to enzymes, proteins, nucleic acids, carbohydrates, lipids, polymers, small molecules of natural, synthetic or semisynthetic origin, to provide an analyte detection method or additional functionality, or can be endowed with additional substituents having utility for detection or amplification of signal, such as by providing covalent or stable noncovalent attachment of nucleic acid or modified nucleic acid tags for detection by amplification methods including polymerase chain reaction, ligation-mediated probe amplification, branched nucleic acid assay, or isothermal amplification, with or without a ligation step. ETBPs can be adsorbed on solid surfaces, such as plates, trays, capillaries, fabrics, flexible or rigid sheets, beads, or particles, all of which may provide either surfaces for noncovalent absorption or chemically activated surfaces for covalent attachment. Such ETBP-substituted surfaces may be used to provide either capture reagents, or in the case of bead or particulate adsorbed material, detection reagents. Examples of uses of labeled ETBPs include, without limitation, microscopy, ultramicroscopy, flow cytometry, flow microscopy, immunoblotting, immunoprecipitation, spectroscopy, or in vivo imaging.

Methods of Preparation

ETBPs of the present invention are often easily prepared by expression in prokaryotic cells, such as *E. coli*. Moreover ETBPs often have unusual and favorable solubility properties that allow them to be readily purified using simple scalable steps amenable to high volume manufacturing. ETBPs according to the present invention frequently present a pH-dependent solubility profile that is opposite to that of many *E. coli* proteins. At neutral pH and in moderate ionic strength, ETBPs often have moderate to poor solubility, whereas ETBPs are very soluble and retain their structures under acidic conditions, for example in 10-100 mM HCl. Accordingly ETPBs can often be purified without recourse to chromatography by the simple expedient of alternating the pH of an aqueous solution or suspension of ETBPs. A few successive alternations suffice to afford highly pure ETBP in many cases. ETBPs can be further purified by conventional methods, for example to remove endotoxin or remaining contaminant proteins, if desired. Fusion proteins bearing ETBP moieties often behave with respect to alternations of pH as the ETBPs themselves, so that for example an ETBP-GFP fusion protein can frequently be easily prepared from *E. coli* by harvesting an insoluble pellet of ETBP-GFP fusion protein produced by fermentation and extracting soluble protein in dilute HCl. This property of ETBPs is not confined to engineered transglutaminase barrel proteins, but is often found among unmodified barrel proteins. The ability to form fusions that can be easily purified without recourse to chromatographic methods is highly attractive for numerous applications in biotechnology, particularly those that require inexpensive high volume production of pure materials. Accordingly the present invention also provides methods for the purification of fusion proteins comprising unmodified or native transglutaminase barrel proteins.

The invention will now be further illustrated by the following non-limiting examples.

EXAMPLES

Example 1

Characterization of Wild Type F13β2 Scaffold

Figure 3:
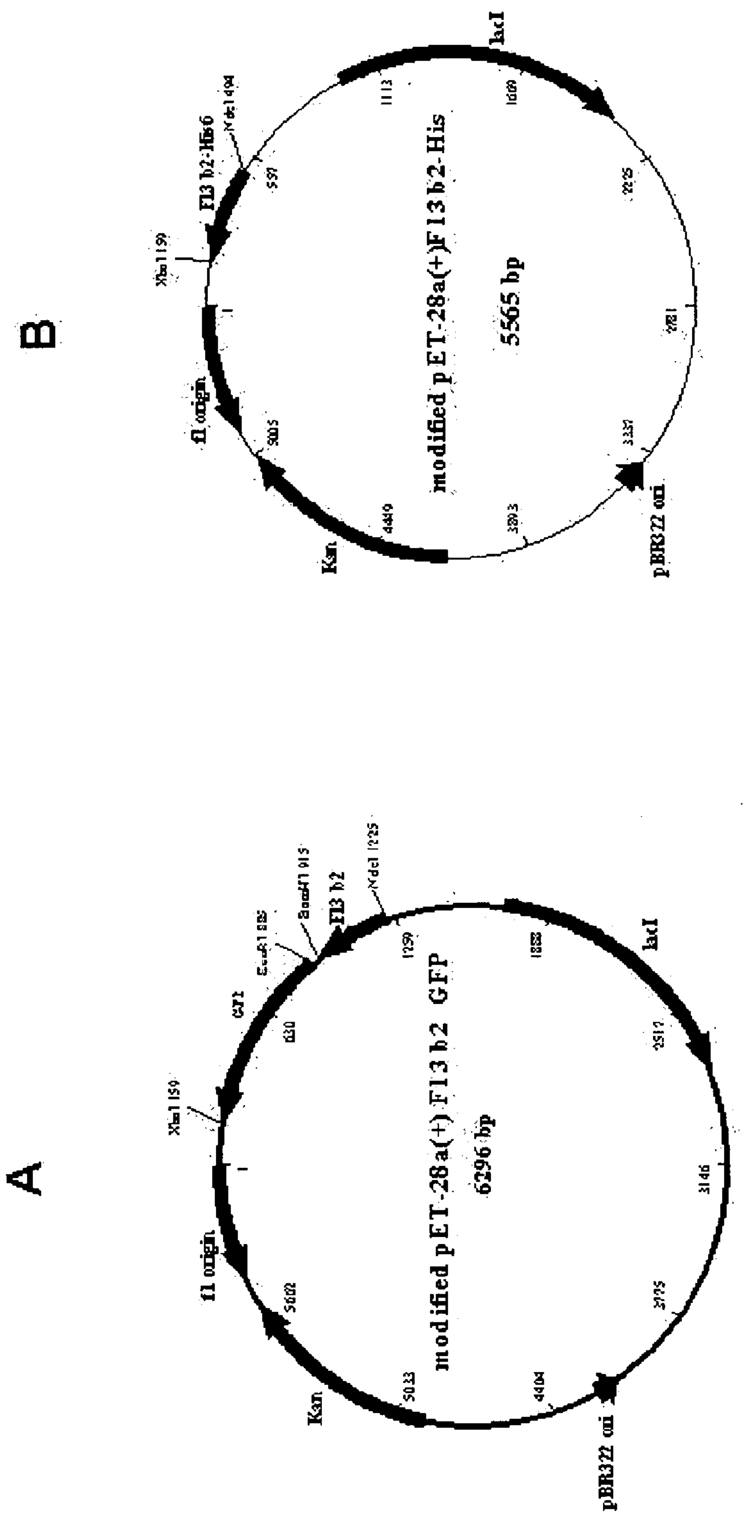
FIGS. 3A and 3B are schematic maps of the indicated expression plasmids for F13β2 scaffold.

Alternative scaffolds for therapeutic applications are preferably prepared in high yield and purity by prokaryotic fermentation. To characterize the ability of an isolated barrel domain to autonomously fold in *E. coli* a fusion of the human β-barrel 2 domain joined at its C-terminus to GFP was studied. For this purpose wild type human factor XIIIA β-barrel 2 domain (positions T629-R729) was amplified from full length FXIII-A cDNA clone (SC120099; OriGene Technologies, Inc., Rockville, Md.) by PCR with primers oligo17 and oligo 18rev (all primers used for cloning are presented in Table 10). An initiator methionine codon was introduced at the location corresponding to the N-terminus of the protein and the final fragment was cloned into Nde I and Bam HI cloning sites of modified pet28(a+) vector, containing GFP protein. The map of the plasmid (modified pet28(a+)-F13β2-GFP) is shown in FIG. 3A. The correct clone was confirmed by sequencing (FIG. 4). The sequence corresponded to the known sequence of factor XIII-A (accession number NP_000120) with one change (T650I) which is consistent with existing polymorphism reported within the FXIII-A (Gerhard et al, Genome Res. 2004, 14:2121). The three residues at the C-terminus (P730-M732) were not included in the F13β2 scaffold construct because they are not resolved in the crystal structure and hence can likely adopt multiple configurations in solution. Also, for selections involving C-terminal extensions the sharp turn at the proline residue (P730) could potentially bring the extended portion into close proximity with loops of the scaffold and interfere with binding to a target. Re-introduction of the P730-S731-M732 sequence into the C-terminus of selected binder proteins can be performed after selection (see below).

Figure 5:
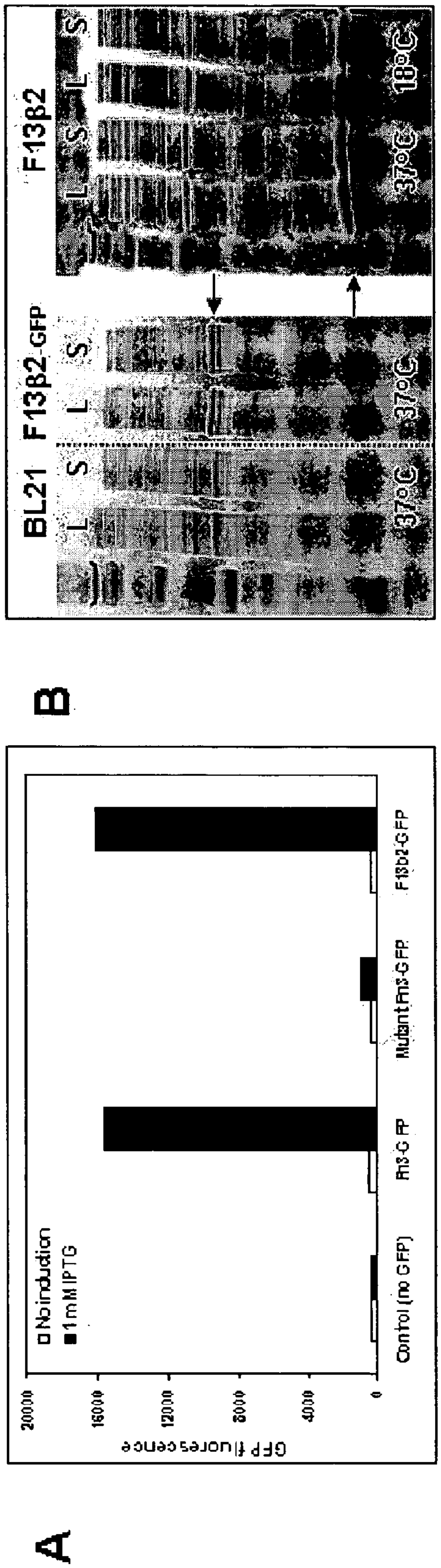
FIG. 5A is a graph showing GFP fluorescence measured of the indicated construct under the indicated conditions. F13β2, Fn3, and mutant Fn3 (L19D, I21A, W23S) were expressed as GFP fusions in *E. coli* at 37° C., and GFP fluorescence ws measured at an emission of 510 nm.
FIG. 5B is an image of SDS-PAGE gels showing F13β2-GFP and F13β2-His6 "His6" disclosed as SEQ ID NO: 29) expression in *E. coli* under different temperature conditions as total (L) and soluble in 1×PBS, pH 7.4 (S) fractions. Non-induced BL21 cells were used as a control.

The resulting isolated Factor XIII β2 barrel protein is a small domain of 102 amino acids with methionine at the first position and R102 (corresponding to R729 of FXIII-A) at the C-terminus. The wild type Factor XIII β2 barrel protein GFP fusion was expressed in *E. coli* BL21 (DE3) pLysS cells (Invitrogen). In brief, the cells were grown on a nitrocellulose filter placed on LB agar plate (containing 50 μg/mL kanamycin) overnight at 37° C. Protein expression was induced by transferring the nitrocellulose filter with cells onto a new plate containing 1 mM IPTG and incubation for additional 3 hours at 37° C. The level of folded protein expression was assessed visually under UV light. Alternatively, BL21 cells containing F1362-GFP construct were grown in LB culture (containing 50 μg/mL kanamycin) and induced at $A_{600}$~0.6 with 1 mM IPTG. After 3 hours incubation at 37° C. the cells were pelleted by centrifugation at 10000 rpm for 3 minutes at 4° C. and resuspended in 1×PBS buffer (137 mM NaCl, 2.7 mM KCl, 10 mM sodium phosphate, pH 7.4) to $A_{600}$=1.5. GFP fluorescence was measured using a Molecular Devices spectrofluorimeter ($A_{ex}$=490 nm; $A_{em}$=510 nm; 5 nm bandwidth). It has been shown that when various proteins are expressed in *E. coli* as an N-terminal fusion with GFP, folding and formation of the GFP chromophore is related to the correct folding of the upstream domain. When the isolated Factor XIII β2 barrel protein was expressed as a fusion to GFP, a high yield of green fluorescence was observed, indicating the scaffold is likely folded properly (FIG. 5A). The F1362 scaffold behaves similarly to another well characterized alternative scaffold, the wild type 10Fn3 domain (Koide et al, J. Mol. Biol. 1998, 284:1141), whereas a control mutant Fn3 with disrupted hydrophobic core was not folded.

The solubility of the expressed protein was also assessed by SDS-PAGE analysis of total and soluble fractions. The cell pellet from 1 ml culture was collected, and after freeze/thaw disruption, resuspended in 1×PBS (pH 7.4), containing Lysonase™ Bioprocessing Reagent (EMD Chemicals Inc., San Diego, Calif.). After incubation at room temperature for 20 minutes CHAPS was added to 0.4% final concentration. The solution was rotated for 20 minutes at 4° C., and the soluble fraction was separated by centrifugation. Aliquots of total and soluble fractions were collected before and after centrifugation for SDS-PAGE analysis. Additionally the fluorescence was monitored under UV light in cell pellet, insoluble pellet and soluble fraction. Characterization by SDS-PAGE showed that the F13β2-GFP fusion is soluble at 37° C. (FIG. 5B).

Optimal protein expression is required for in vitro protein production during selection and for *E. coli* expression in development stages of therapeutic product. Therefore, the F13β2 sequence was optimized for both mammalian and *E. coli* expression prior to further scaffold engineering. Changes were made based on Codon Usage Database developed by Yasukazu Nakamura (www.kazusa.or/jp/codon/readme_codon.html). During the first step of construction three fragments (ABC, CDE and EFG) were obtained by PCR using overlapping primers: oligo 19 and oligo 20rev; oligo 21 and oligo 22rev; oligo 23 and oligo 25rev, respectively. The fragments were mixed in equimolar ratio and PCR was performed with flanking primers oligo 53 and oligo 28rev to introduce NdeI at 5' end, and His6-tag-Stop sequence and Barn HI site at 3' end. The final fragment was cloned into modified pet28(a+) vector. The map of the plasmid (modified pet28(a+)-F13β2-His6 (XhoI) (sequence set forth in Table 14)) is shown in FIG. 3B. Codons for 20 amino acids were changed and the new sequence was used for further constructions (FIG. 4). The optimized single F13β2 domain, containing His6 sequence on the C-terminus was expressed for 3 hours at 37° C. or overnight at 18° C. in *E. coli* as described for F13β2-GFP fusion, and total and soluble fractions were analyzed by SDS-PAGE. For His-tag affinity purification the supernatant was rotated for 1 hr at 4° C. with Ni-NTA agarose (Qiagen) preequilibrated with buffer C (1×PBS [pH7.4], 0.5 M NaCl; 20 mM Imidazole, 0.3% CHAPS). The resin was washed with 50 column volumes of buffer C and 30 column volumes of buffer D (1×PBS [pH7.4], 20 mM Imidazole). The protein was eluted with 1×PBS, 200 mM Imidazole (pH 7.4) and was dialyzed against 1×PBS at 4° C. The protein concentration was measured using Coomassie (Bradford) protein assay reagent (Pierce Biotechnology, Inc., Rockford, Ill.). The F13β2 scaffold was soluble (FIG. 5B) when expressed at 37° C. and 18° C. yielding approximately 5-10 mg of pure protein from one liter culture by affinity chromatography via a His6 tag.

Example 2

Single Cysteine Mutagenesis of F13β2 Domain

Figure 6:
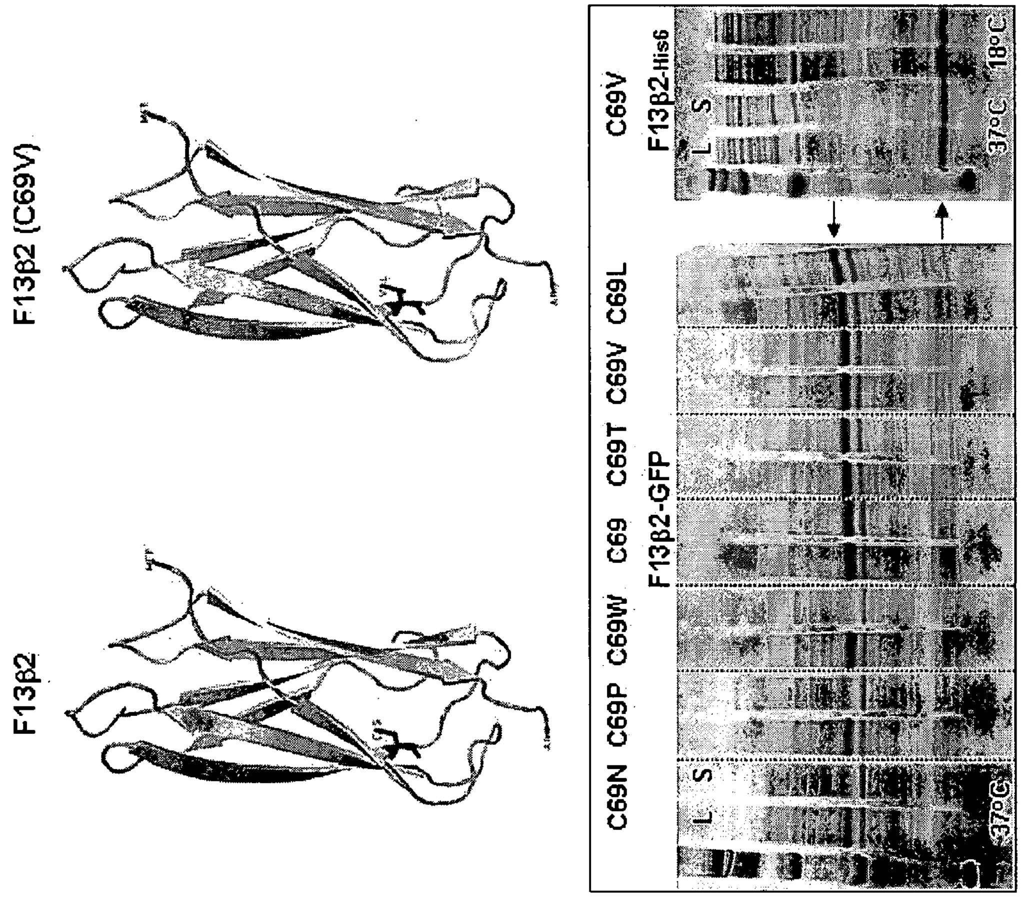
FIG. 6A is a schematic showing the structure of F13β2 scaffold as derived from the published crystal structure. Cys69 is facing toward the hydrophobic core to the domain and positioned in close proximity of other hydrophobic residues in the core (e.g., Met20). F13β2 C69V mutant was selected for construction of combinatorial libraries.
FIG. 6B is an image of SDS-PAGE gels showing expression of F13β2-C69X-GFP and F13β2-C69V-His6 ("His6" disclosed as SEQ ID NO: 29) mutant proteins as expressed in *E. coli* under the indicated temperature conditions.

The F13β2 scaffold has a single cysteine at position 69 with a side chain directed towards the hydrophobic core of the domain (FIG. 6A). Because free cysteines can sometimes pose challenges in selection, expression, or purification, we performed NNS randomization of C69. A two-step PCR was performed using the codon-optimized F13β2 clone as a template. During the first step, two fragments were obtained using two pairs of primers: oligo 17/oligo 22rev and oligo 51/oligo 52rev. The fragments were recombined in a second PCR with flanking primers oligo 17 and oligo 52rev and the final fragment was cloned into NdeI and BamHI sites of a modified pet28(a+) vector containing GFP (Waldo et al, 1999). F13β2 C69X mutants were expressed as N-terminal GFP-fusions in *E. coli* and the correct folding and solubility of the proteins at 37° C. in 1×PBS were assessed by GFP fluorescence of colonies growing on agar and by SDS-PAGE of total and soluble fractions as described above for wild type F13β2 scaffold (FIG. 6B). Substitutions with large or hydrophilic amino acids (tryptophan, asparagine) or the constrained amino acid proline resulted in a loss of solubility following expression at 37° C. A C69T mutant was completely soluble whereas a C69S substitution was only partially soluble at 37° C. The aliphatic hydrophobic amino acids valine, leucine and alanine were found to be useful to replace Cys69 without changing solubility. A single F13β2C69V-His6 ("His6 disclosed as SEQ ID NO: 29) domain was generated by PCR using primers oligo 53 and oligo 28rev (Barn HI), and was shown to be soluble when expressed at 37° C. and 18° C. (FIG. 6B). Subsequently, the Factor XIII β2 barrel protein bearing a C69V mutation was employed in F13β2 library construction.

Example 3

Point Mutagenesis of F13β2 Scaffold at W38 and Y92

Randomization of an alternative scaffold can be performed by diversification of the surface of a known ligand or receptor binding site or by diversification of surfaces not known to participate in ligand or receptor binding. Preferable randomization strategies minimize changes that destabilize the scaffold core. The data obtained with Cys69 substitutions illustrate that core substitutions of transglutaminase barrel proteins may have reduced solubility and/or stability if they result in energetically unfavorable structures. To test the utility of randomization of scaffold sequences not contributing to the integrity of the beta barrel, we randomized two hydrophobic residues in F13β2 domain that are predicted to have solvent-exposed side chains: W38 and Y92. These residues are positioned in close proximity to the rest of FXIII-A protein and could possibly be involved in hydrophobic interactions with other domains of FXIII. Changing bulky solvent-exposed hydrophobic residues could potentially produce a more stable, soluble scaffold. The codon-optimized F13β2 clone was used as a template for two-step PCR. Initially, two fragments were prepared for W38X randomization using two pair of primers (oligo 17/oligo 48rev and oligo 49/oligo 52rev). The fragments were recombined in second PCR with flanking primers oligo 17 and oligo 52 rev. To introduce Y92X randomization PCR product was produced with oligo 17 and oligo 50rev and extended with flanking primers oligo 17 and oligo 52 rev. The final fragments were cloned into NdeI and BamHI sites of modified pet28(a+) vector. The F13β2 mutants were expressed as N-terminal GFP-fusions in *E. coli* BL21 and the correct folding and solubility of the proteins at 37° C. in 1×PBS were assessed by GFP fluorescence of colonies growing on agar and by SDS-PAGE of total and soluble fractions as described above for wild type F13β2 scaffold. Most of the W38X (9) and Y92X (12) mutants were soluble, resembling the wild type F13β2 domain (Table 1). Only substitution with the structurally constrained amino acid proline resulted in a complete loss of solubility, possibly due to energetically unfavorable changes in the β-sheet in which W38 is positioned. It is possible that introduction of a sharp turn into β-strand via proline could disrupt the integrity of the domain. All other changes were well-tolerated by the scaffold which was a good indication for further randomization studies.

TABLE 1

Solubility profile of F13β2 mutants.

| Mutation (X) | W38X | Y92X |
|---|---|---|
| Ala | yes (partially) | yes |
| Arg | N.D. | yes |
| Asn | N.D. | yes |
| Asp | N.D. | yes |
| Cys | yes (partially) | N.D. |
| Gln | N.D. | N.D. |
| Glu | N.D. | N.D. |
| Gly | yes (partially) | yes |
| His | yes | yes |
| Ile | N.D. | yes |
| Leu | yes | yes |
| Lys | N.D. | yes |
| Met | N.D. | yes |
| Phe | yes (partially) | N.D. |
| Pro | no | N.D. |
| Ser | yes (partially) | yes |
| Thr | N.D. | yes |
| Trp | yes | N.D. |
| Tyr | N.D. | yes |
| Val | yes | N.D. |

F13β2-W38X and F13β2-Y92X mutant proteins were expressed as GFP fusions in *E. coli* at 37° C. and their solubility in 1xPBS, pH 7.4 was assessed by GFP fluorescence and SDS-PAGE (N.D.—not determined).

Example 4

Loop Diversification of the F13β2 Scaffold

Figure 7:
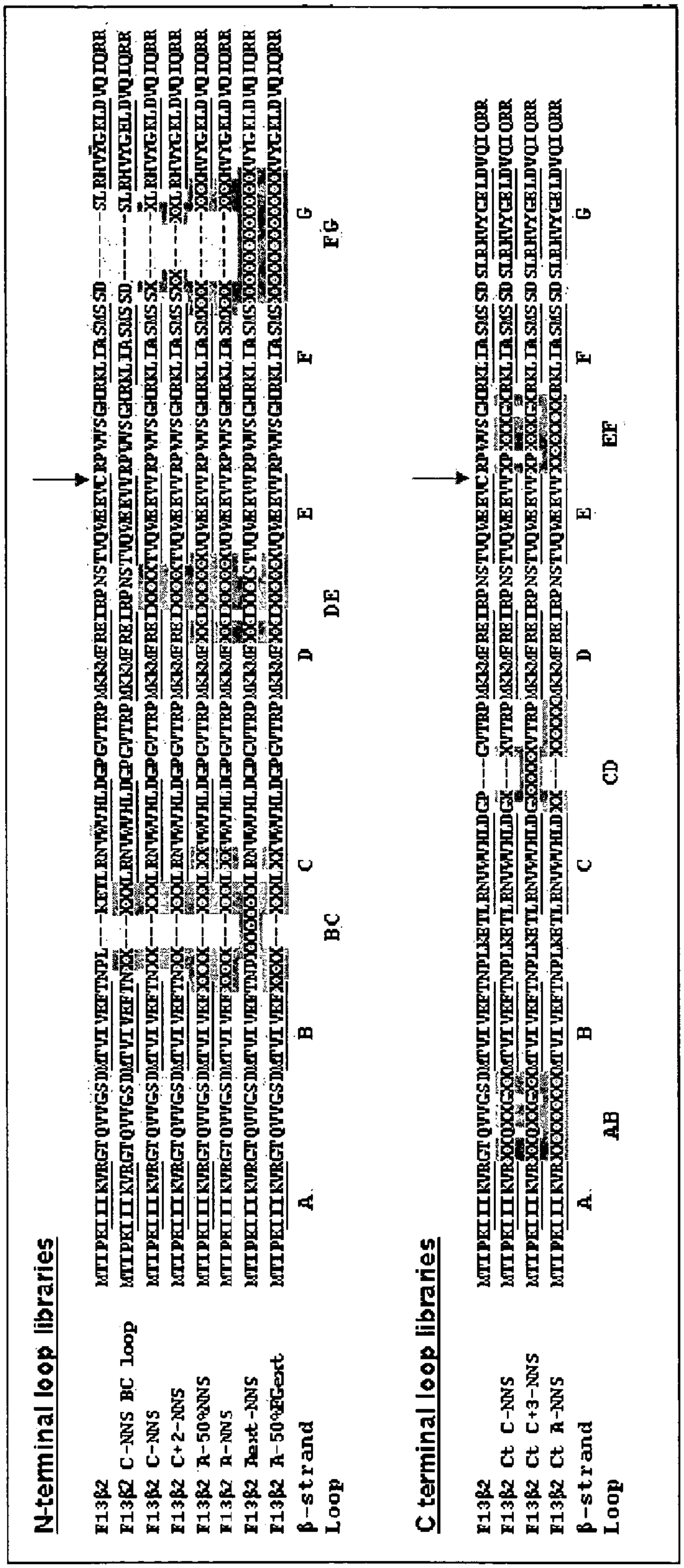
FIG. 7 is an alignment of protein sequences of F13β2 libraries. β-strands are underlined (SEQ ID NOs:658-664); single cysteine (C69) and C69V mutation are marked with arrows; W38, y72, and randomized residues are highlighted in gray; randomized (NNS) residues are substituted with X.
Figure 8:
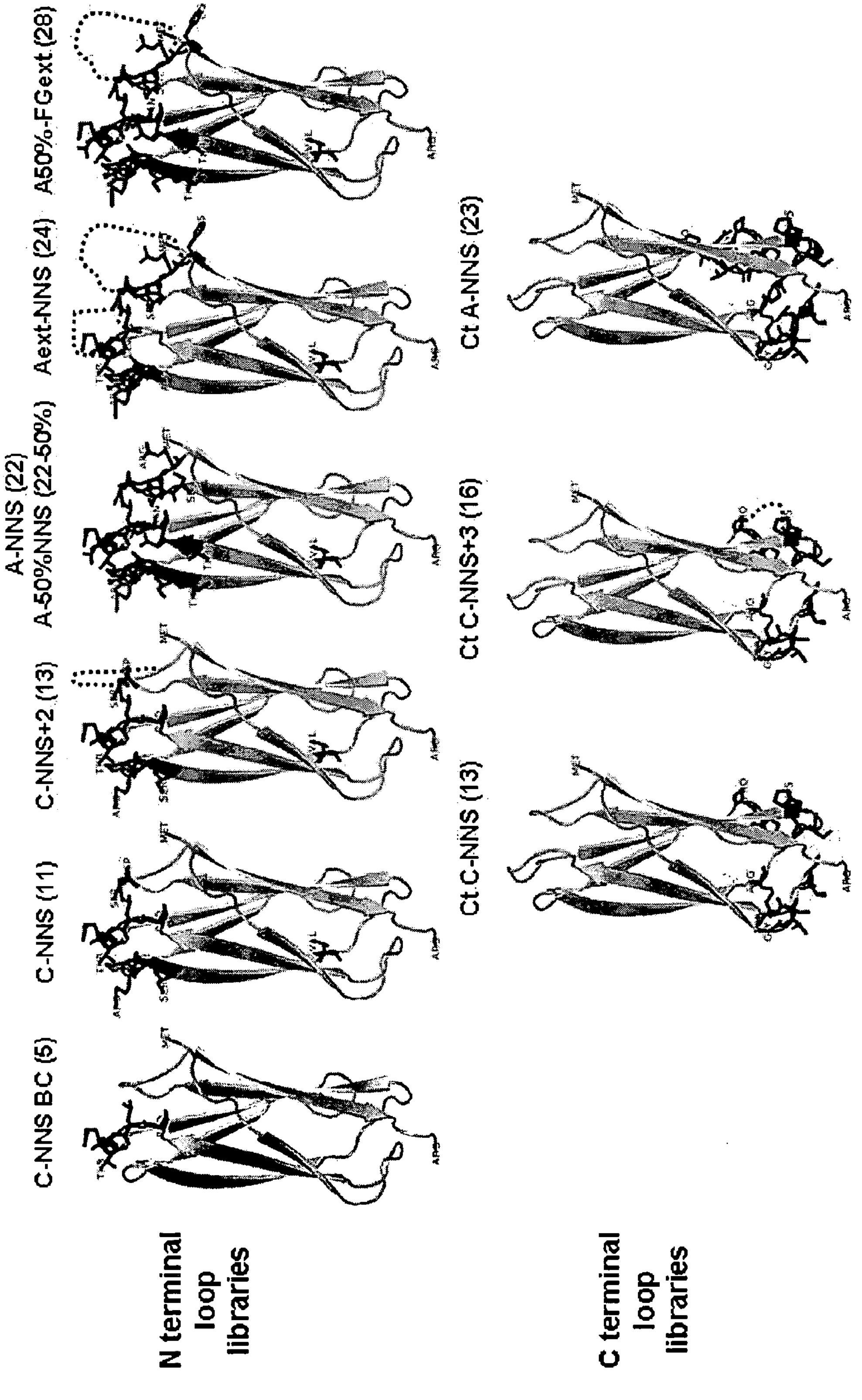
FIG. 8 is a series of schematics showing the structure of F13β2 libraries. Randomized BC, DE, FG and AB, CD, EF loops are shaded black; first (Met1) residue, last (Arg102) residue, C69V mutation, and first and last residues of the randomized loops are marked on the structure; the sites of loop extensions are marked with dotted lines.

Several loop diversification schemes were designed based on the crystal structure of the A subunit of factor XIII. Loop diversification can be carried out by complete randomization or by retention of specific residues that might play a structural role in the stability of the loop or protein fold, such as loop residues for which the side chains extend toward the core. Six potential randomization loops are present in F13β2 structure: three (BC, DE, and FG) at the N-terminus and three (AB, CD, and EF) at the C-terminus of the domain (FIG. 7 and FIG. 8).

All F13β2 libraries were based on the sequence of optimized F13β2C69V clone and constructed by two-step PCR using synthetic randomized oligonucleotides. For N-terminal loop libraries three loop regions—BC, DE, and FG, were randomized by using NNS (C-NNS BC loop, C-NNS, C+2-NNS, A-NNS and Aext-NNS libraries) or 50% NNS, containing 50% NNS and 50% wild type F13β2 nucleotide, which resulted in 55 to 71% of random amino acid changes (A-50% NNS and A-50% FGext libraries). For C-terminal loop libraries (Ct C-NNS, Ct C+3-NNS, Ct A-NNS libraries) three loop regions—AB, CD, and EF, were randomized using an NNS scheme. During the first step of construction three fragments (ABC, CDE and EFG) were obtained by PCR using overlapping primers (200 pmol/each): C-NNS library (oligo 19 and oligo 35rev (BC C-NNS); oligo 21 and oligo 41 rev (DE C-NNS); oligo 63 (C69V) and oligo 45rev (FG C-NNS)); C+2-NNS library (oligo 19 and oligo 35rev (BC C-NNS); oligo 21 and oligo 41rev (DE C-NNS); oligo 63 (C69V) and oligo 46rev (FG+2 C-NNS)); A-NNS library (oligo 19 and oligo 34rev (BC A-NNS); oligo 39 and oligo 40rev (DE A-NNS); oligo 63 (C69V) and oligo 44rev (FG A-NNS)); A-50% NNS library (oligo 19 and oligo 55revl (BC A-50% NNS); oligo 39 and oligo 56revl (DE A-50% NNS); oligo 63 (C69V) and oligo 57revl (FG A-50% NNS)); Aext NNS library (oligo 19 (671) and oligo 68revl (BC Aext-NNS); oligo 691 and oligo 70revl (DE Aext-NNS); oligo 63 (711) (C69V) and oligo 72revl (FG Aext-NNS)); A-50% FGext library (oligo 19 (671) and oligo 55revl (BC A-50% NNS); oligo 39 and oligo 56revl (DE A-50% NNS); oligo 63 (711) (C69V) and oligo 72revl (FG Aext-NNS)); Ct C-NNS library (oligo 33 (AB C-NNS) and oligo 20rev; oligo 37 (CD C-NNS) and oligo 22rev; oligo 43 (C69) (EF C-NNS) and oligo 25rev); Ct C+3-NNS library (oligo 33 (AB C-NNS) and oligo 20rev; oligo 38 (CD C+3-NNS) and oligo 22rev; oligo 43 (C69) (EF C-NNS) and oligo 25rev); Ct A-NNS library (oligo 32 (791) (AB A-NNS) and oligo 20rev (80revl); oligo 36 (811) (CD A-NNS) and oligo 22rev (82revl); oligo 831 (C69) (EF A-NNS) and oligo 84revl ($G_4S$ (SEQ ID NO: 32))). For C-NNS BC loop test library ABC (randomized BC loop) fragment was obtained using overlapping primers oligo 19 and oligo 35rev, and CDEFG fragment was amplified with primers oligo 21 and oligo 52rev using F13β2C69V clone as a template. For solubility characterization the loop fragments of each library were mixed in equal molar ratio and PCR was performed with flanking primers oligo 53 and oligo 52rev to introduce NdeI at 5' end, and Barn HI site at 3' end. F13β2 library proteins were expressed as N-terminal GFP fusions by using a modified pet28(a+) vector, in *E. coli* BL21 (DE3) pLysS cells (Invitrogen). The correct folding and solubility of the proteins at 37° C. in 1×PBS were assessed by GFP fluorescence of colonies growing on agar and by SDS-PAGE of total and soluble fractions as described above for wild type F13β2 scaffold. For in vitro library production the loop fragments were mixed in equal molar ratio (40 pmol/each)

and after extension PCR the amplification was performed with 10-fold excess of flanking primers oligo 55 and oligo 26rev. T7TMV transcription sequence was introduced at the 5' end and PEG6-linker annealing sequence (GCATCCGCTATTTAA) (SEQ ID NO:1) and polyA were introduced at the 3' end of the libraries. Additionally, Flag-tag sequence (DYKDDDDK) (SEQ ID NO:2) was introduced at the C-terminus for affinity purification of mRNA fusion molecules and proteins via M2 agarose. Oligo 661, containing unique linker sequence in 5' non-translated region, was used for amplification of Aext-NNS library, and extended 3' end oligo 73revl for Aext-NNS and A-50% FGext libraries. G4S sequence (SEQ ID NO: 32) was introduced at the C-terminus of Ct A-NNS library with oligo 85revl. DNA sequencing of approximately 100 library members confirmed the intended mutation rate. C-NNS, A-NNS, A-50% NNS and Aext-NNS libraries contained $2.41\times10^{13}$ to $9.64\times10^{13}$ members. C-NNS, A-NNS, A-50% NNS and Aext-NNS libraries were used in the myostatin selections, Aext-NNS library in the selection against human FcεRI and A-50% NNS library in the selection against human β-NGF.

C-NNS BC Loop F13β2 Library.

We investigated the effect of a full loop randomization on solubility of F13β2 scaffold by introducing changes (NNS) in five residues of BC loop (P29 to T33). Clones that had not accumulated frameshift or termination mutations ("expressible clones") accounted for 70% of the population (Table 2). They were expressed at the N-terminus of GFP in *E. coli* and their folding and solubility in PBS was measured by green fluorescence of folded GFP. Almost 60% of expressed proteins were soluble at 37° C. which indicated that BC loop can tolerate substantial diversity without perturbation of the F13β2 fold and that mutations can be incorporated into the loops of F13β2 domain.

N-Terminal Loop F13 β2 Libraries: C-NNS, C+2 NNS, A-NNS, A-50%-NNS, Aext-NNS, A-50% FG Ext.

N-terminal loop libraries were constructed by randomizing three loop regions (BC, DE and FG) positioned at the N-terminus of the F13β2 scaffold. Different randomization schemes were applied for construction of F13β2 libraries for selections (FIG. 7 and FIG. 8).

The conservative C-NNS library contained only 11 residues randomized with NNS: five in BC loop (P29-T33); four in DE loop (R58-S61) and two in FG loop (D86-S87). Only flexible loop regions were changed in this library to allow the minimal disturbance of the scaffold. Indeed, 46% of the expressible clones were correctly folded (Table 2). To extend the potential binding surface in this limited library insertion of two randomized residues was applied to the FG loop in C+2-NNS library, which increased the randomization surface to 13 amino acids.

Aggressive randomization was used in the A-NNS library which contained 22 amino acids randomized with NNS: nine in BC loop (T27-T33, R35-N36); seven in DE loop (R55-E56, R58-T62) and five in FG loop (S84-R89). In this library not only loop regions, but also the loop flanking residues that are facing towards the aqueous solution were randomized in order to increase the interaction space around each loop. L34 and 157 were not changed because they are facing towards the core of the domain in crystal structure of FXIII-A. The same randomization scheme was applied in the A-50% NNS library but instead of NNS, 50% of wild type F13β2 nucleotide was introduced simultaneously with 50% of N or S at each position, which resulted in 60 to 70% of random amino acid changes in variable loops.

The solubility of the library population decreased with increased randomization, but even in the aggressive A-NNS library 17% of the expressible clones were correctly folded, which would provide enough diversity for selection (Table 2).

To further increase the binding surface of the scaffold two more libraries with loop extensions were constructed. Aext-NNS library contained 24 residues randomized with NNS: seven in BC loop (L30-T33 and 3 aminoacid extension); five in DE loop (R55-E56, R58-N61) and twelve in FG loop (S85-H90 and 6 aminoacid extension). In A-50% FGext library 28 residues were randomized with BC and DE loops changed similar to A-50% NNS library and FG loop as in Aext-NNS library. Loop extensions are predicted to provide more flexible binding surfaces compared to randomization of existing scaffold structures.

C-Terminal Loop F13β2 Libraries: Ct C-NNS, Ct C+3-NNS, Ct A-NNS Libraries.

C-terminal loop libraries were constructed by randomizing three loop regions (AB, CD and EF) on the other side of F13β2 domain. Modification of the C-terminal loops would position the potential binding site at the end of FXIII-A molecule in close proximity to the C-terminus, which is the site for attachment to the nucleic acid in RNA display. To improve the consistency of behavior between fusion proteins and free proteins, additional flexible linkers may be added to distance the RNA fusion site from the binding site. Alternatively, N-terminal fusion display strategies could be useful for these libraries.

Randomization using the NNS scheme was employed in the construction of three C-terminal loop libraries. Conservative Ct C-NNS and Ct C+3-NNS libraries contained 13 and 16 randomized residues, respectively: six in AB loop (G12-T13, V15-V16, S18-D19); two in CD loop (P44-G45 and 3 aminoacid extension in Ct C+3-NNS library); five in FG loop (R70, W72-S74, H76). Aggressive Ct A-NNS library had 22 mutated residues: eight in AB loop (G12-D19); seven in CD loop (G43-P49); seven in EF loop (R70-H76).

Non-specific binding of fusion libraries to the beads or different target proteins didn't exceed 0.6% and fusion production provided sufficient diversity for further selections (Table 2).

TABLE 2

Characterization of F13β2 libraries.

| | N-terminal loop libraries | | | | | | | C-terminal loop libraries | | |
|---|---|---|---|---|---|---|---|---|---|---|
| | C-NNS | | | | | | A50% F | | | |
| F13β2 library | BC loop | C-NNS | C + 2-NNS | A-50% NNS | A-NNS | Aext-NNS | Gext-NNS | Ct C-NNS | Ct C + 3-NNS | Ct A-NNS |
| Randomization (aminoacids) | 5 | 11 | 13 | 22 | 22 | 24 | 28 | 13 | 16 | 22 |

TABLE 2-continued

| Characterization of F13β2 libraries. | | | | | | | | | | |
|---|---|---|---|---|---|---|---|---|---|---|
| | N-terminal loop libraries | | | | | | | C-terminal loop libraries | | |
| | C-NNS | | | | | | A50% F | | | |
| F13β2 library | BC loop | C-NNS | C + 2-NNS | A-50% NNS | A-NNS | Aext-NNS | Gext-NNS | Ct C-NNS | Ct C + 3-NNS | Ct A-NNS |
| Clones tested (n) | 43 | 67 | 55 | 66 | 68 | 76 | 37 | n.d. | n.d. | 32 |
| Frameshifts (%) | 12 | 34 | 44 | 30 | 16 | 68 | 43 | n.d. | n.d. | 56 |
| Stops (%) | 19 | 27 | 56 | 24 | 49 | 18 | 24 | n.d. | n.d. | 25 |
| Expressible clones (%) | 70 | 39 | 29 | 45 | 35 | 13 | 32 | n.d. | n.d. | 19 |
| Soluble at 37° C. in 1xPBS (% of expressible) | 57 | 46 | 31 | 30 | 17 | n.d. | n.d. | n.d. | n.d. | n.d. |
| Insoluble at 37° C. in 1xPBS (% of expressible) | 43 | 54 | 69 | 70 | 83 | n.d. | n.d. | n.d. | n.d. | n.d. |
| % oligo dT (yield) | n.d. | 4.8 | — | 2.4 | 3.7 | 1.7 | 1.8 | n.d. | n.d. | 1.5 |
| % flag (yield) | n.d. | 11.8 | n.d. | 12.4 | 9.0 | 6.0 | 9.3 | n.d. | n.d. | 9.0 |
| Pmol/mL lyzate | n.d. | 3.4 | n.d. | 2.3 | 1.8 | 0.6 | 1.2 | n.d. | n.d. | 0.8 |
| Binding to beads in R0 (%) | n.d. | 0.30 | n.d. | 0.22 | 0.29 | 0.20 | 0.32 | n.d. | n.d. | 0.07 |
| Number of targets tested at 100-250 nM | n.d. | 4 | n.d. | 6 | 5 | 4 | 1 | n.d. | n.d. | 3 |
| Binding to targets in R0 (%) | n.d. | 0.33 | n.d. | 0.35 | 0.48 | 0.26 | 0.57 | n.d. | n.d. | 0.33 |

Example 5

Selection of ETBPs Against Human Myostatin

Myostatin, a member of the tumor growth factor-β family, is a potent inhibitor of skeletal muscle growth. Disruption of the myostatin gene in mice and natural mutations identified in cattle and, recently, in humans indicate that the absence of functional myostatin results in a significant increase in muscle mass. Inhibitors of the myostatin signaling pathway are being investigated for the treatment of muscle wasting diseases, such as muscular dystrophy, sarcopenic frailty of the elderly, cancer-related muscle loss, and ALS (amyotrophic lateral sclerosis), as well as metabolic diseases.

Figure 9:
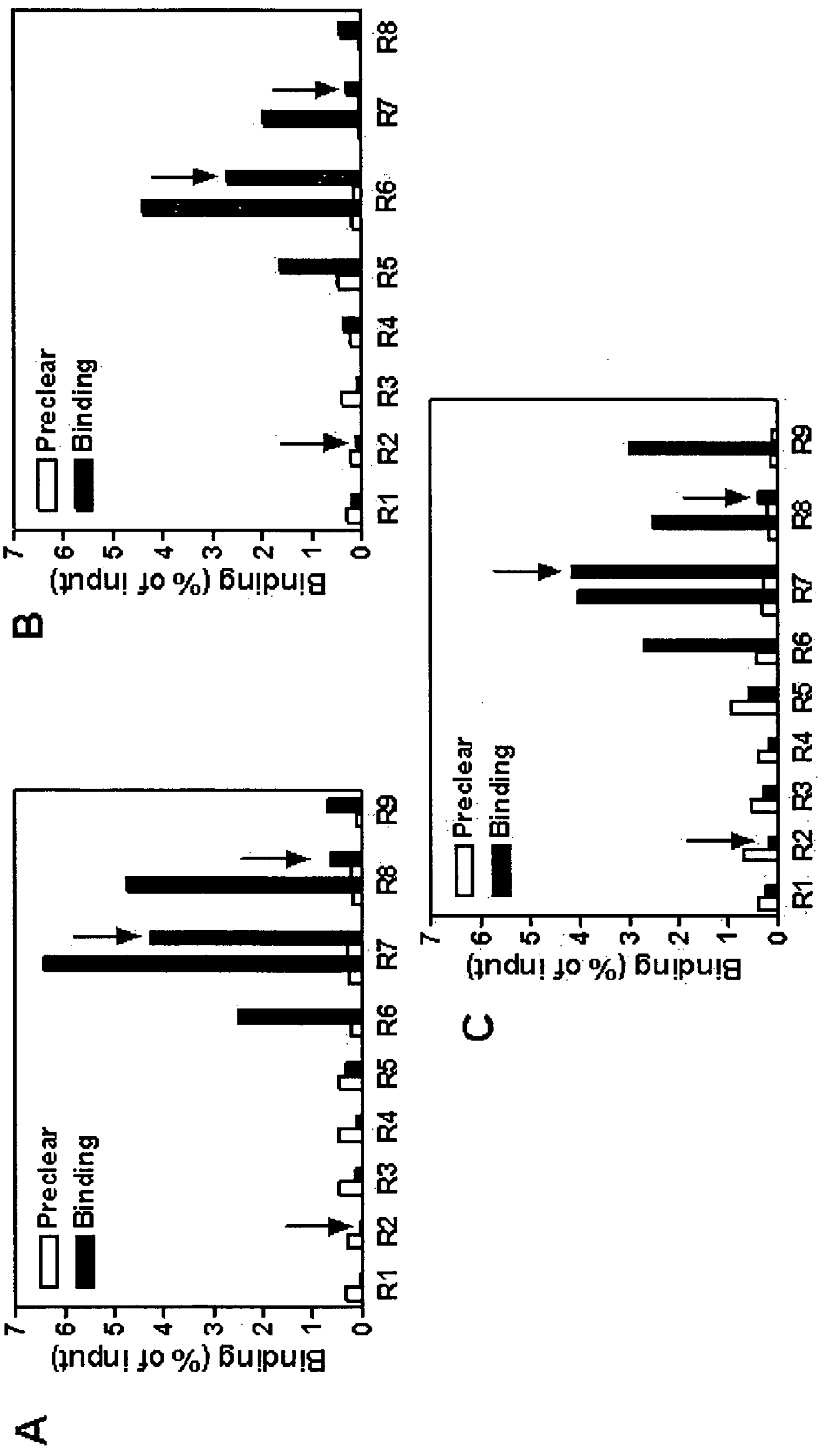
FIGS. 9A-9C are graphs showing binding of each library to beads (preclear) and target (binding) as a percent of input radioactivity.

Several F13β2 mRNA fusion libraries (C-NNS, A-50% NNS and A-NNS) were used independently for in vitro selection against biotinylated human myostatin. For each round of selection, DNA from PCR was transcribed by using the MegaScript transcription kit (Ambion). The puromycin-containing linker TEG 6/10 was synthesized and crosslinked to RNA as previously described (Kurz et al, Nucleic Acids Res. 2000, 28:E83). The crosslinked mixture was included in an in vitro translation reaction by using the rabbit reticulocyte lysate translation kit (Ambion) in the presence of $^{35}$S-labeled methionine at 30° C. for 60 min. To enhance the fusion formation, 0.5 M KCl and 0.05 M $MgCl_2$ were added to the reaction and incubated for 30 min at 4° C. Next, reactive cysteine residues were modified for 1 hr at room temperature with 10 mM N-ethylmaleimide. Fusion molecules were purified by using oligo dT cellulose chromatography. A reverse transcription reaction was conducted with SuperScript III (Invitrogen) for 1 hr at 45° C. with the primer oligo 65rev (5'-GTCGTCGTCCTTGTAGTCGCG-GCGTTGAATCTGCACGTC-3') (SEQ ID NO:3). Reactive cysteine residues were modified once more for 1 hr at room temperature with 1 mM 2-nitro-5-thiocyanatobenzoic acid or 1 mM N-ethylmaleimide at alternative rounds for the first three rounds of selection. Fusion molecules were further purified by anti-FLAG affinity chromatography on M2 agarose (Sigma) and eluted in buffer A (1×PBS, 0.02% Triton X-100, 1 mg/ml bovine serum albumin [BSA], 0.1 mg/ml salmon sperm DNA [pH 7.4]), containing 100 μg/mL Flag-peptide (DYKDDDDD (SEQ ID NO: 33)). The fusion yield was calculated based on specific activity measured by scintillation counting of $^{35}$S-methionine in the samples. Each library contained approximately $10^{13}$ variants, which significantly exceeds the diversity of phage display ($10^{9}$), or ribosome display ($10^{11}$) libraries, providing a larger pool for binder selection. The selections were performed for eight to nine rounds (FIGS. 9A-9C), and lower target concentrations and prolonged washes were utilized in later rounds of selection to favor clones with better affinities. Fusion libraries were incubated separately with 100 μl M-280 beads (Dynal) for 30 minutes at 30° C. prior to selection (preclear). The beads were washed five times with 0.5 ml of buffer A, containing 2 mM D-biotin. The supernatant was then incubated in buffer A with biotinylated human myostatin for 1 hr at 30° C. The target was captured on 100 μl M-280 beads for 10 min at 30° C., and the beads were washed five times with 0.5 ml of buffer A, containing 2 mM D-biotin. Starting from round 2, a third wash was performed for 15 minutes at 30° C. Additional stringency was added to A-50% NNS library selection in R7 and R8: both fusion incubation with the target and third wash were performed for 30 minutes at 30° C. Bound fusion molecules were eluted with 50 μl 0.1 M KOH into 25 μl 1 M Tris-HCl (pH 8.0). DNA was amplified by PCR with flanking primers oligo 55 and oligo 26rev. Primers oligo 77 and oligo 73rev were employed for amplification of Aext-NNS library. Final concentrations of biotinylated human myostatin used in the selections were as follows: R1 (250 nM), R2-R5 (100 nM), R6 (C-NNS and A-NNS: 100 nM; A-50% NNS: 100 and 10 nM); R7 (C-NNS and A-NNS: 100 nM and 10 nM; A-50% NNS: 10 and 1 nM), R8 (C-NNS and A-NNS: 10 nM and 1 nM; A-50% NNS: 1 nM), R9 (C-NNS: 1 nM; A-NNS: 1 and 0.1 nM). Binding to 100 nM of biotinylated human myostatin increased in round 5 (A-50% NNS library) or round 6 (C-NNS and A-NNS libraries). In the next round myostatin concentration was decreased to 10 nM and further to 1 nM to converge the pool for tighter binding to the target. Selections were stopped at round 8 (A-50% NNS library) and round 9 (C-NNS and A-NNS libraries), when no further significant increase in binding to the target was observed. PCR DNA of selection pools after rounds 5, 6, 7, 8 and 9 was cloned into pCR®2.1-TOPO® vector (Invitrogen), and single clones were analyzed by sequencing of 40-150 clones.

Figure 10:
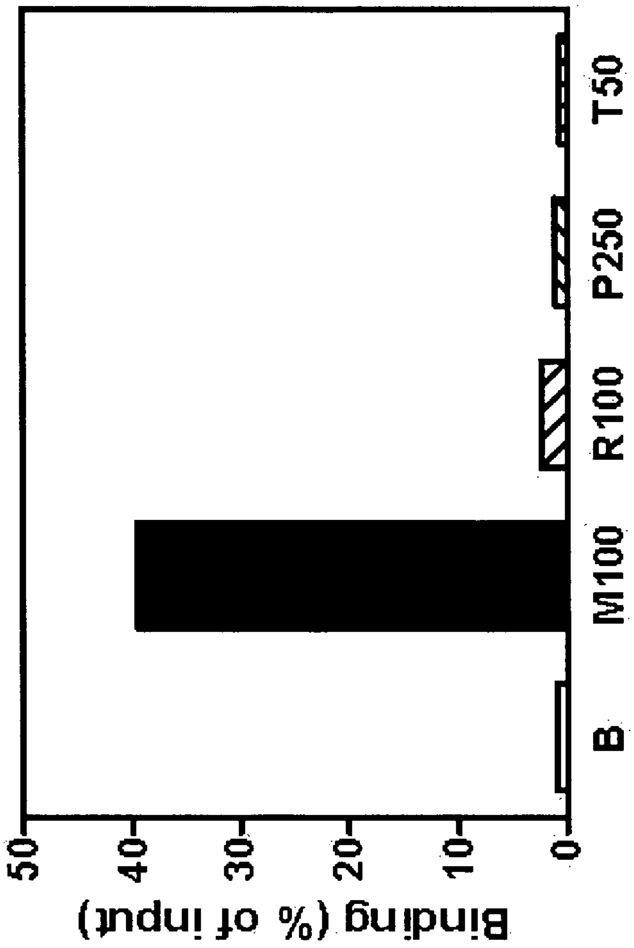
FIG. 10 is a graph showing binding of the selected binder pool to human myostastin as measured in a radioactive equilibrium assay. The bars represent the measurements from the following samples after round 6 (A-NNS library) to M-280 beads (B); human myostatin (M100; 100 nM), protein 1 (R100; 100 nM), peptide 1 (P250; 250 nM), and protein 2 (T50; 50 nM).

The selected protein pools bound to myostatin specifically since no interaction with several unrelated proteins tested at high concentration was observed (FIG. 10). Also, no binding to streptavidin beads was detected, which indicated that the negative selection (preclear) against M-280 beads and an extensive wash with 2 mM biotin were effective in suppressing streptavidin binders.

The sequences of the binding loops are shown in Table 3. Sequence analysis of selected clones revealed that several consensus motifs emerged during the selection. Three major groups could be identified in A-50% NNS library selection pools: group M1-A50 (BC loop—TNPFKETLRS (SEQ ID NO:4), DE loop—REIPPKTT (SEQ ID NO:5), FG loop—RTQYLI (SEQ ID NO:6), V91L); group M2-A50 (BC loop—SNPFKETLRN (SEQ ID NO:7); DE loop—SEIRPNST (SEQ ID NO:8), FG loop—PSLLHL (SEQ ID NO:9)) and group M3-A50 (BC loop—TNPFKETLRN (SEQ ID NO:10), DE loop—CEIRPNSI (SEQ ID NO:11); FG loop—CSLSPW (SEQ ID NO:12), ΔS82, M83R).

Only very few conservative changes were observed in BC loop: T27S, L30F, N36S. Highly hydrophobic mutation L30F was found in nearly all myostatin binding clones, suggesting that it may be beneficial for the binding to the target. The rest of BC loop residues were independently reverse selected to wild type, as indicated by different codon usages in selected clones. Remarkably, wild type BC loop was found in group M1-A binders (BC loop—TNPLKETLRN (SEQ ID NO:13); DE loop—PAIPMNHK (SEQ ID NO:14); FG loop—PQLFHI (SEQ ID NO:15)), which dominated A-NNS library selection. This could probably occur through random recombination event of a binder sequence with wild type clone and further affinity selection. Similar recombination happened when an extended F13β2 library (Aext-NNS) was subjected to selection against myostatin. Wild type BC loop is observed in major group M1-Aext with extended FG loop (BC loop—TNPLKETLRN (SEQ ID NO:16); DE loop—LKIPGC (SEQ ID NO:17); FG loop—MLGLPFSLRFIP (SEQ ID NO:18). This could indicate that the structure of BC loop tolerates only few conservative changes. In this case randomization scheme in A-50% NNS library provides the best opportunity to introduce only few mutations that do not disturb the loop structure. At the same time, it is possible that wild type BC loop is selected, because it has certain affinity to myostatin. Since we didn't observe any binding of wild type F13β2 scaffold to myostatin this is unlikely.

Upon selection DE loop was significantly changed only when NNS randomization was originally applied in A-NNS and Aext-NNS libraries, while reverse selection to wild type residues was observed in A-50% NNS selection pools. This could suggest that DE loop can tolerate many changes but only few are sufficient for binding to myostatin.

Most of the mutations were selected in FG loop: four to six residues were changed out of six randomized positions in A-NNS and A-50% NNS libraries. Several different consensus motifs were selected to bind to myostatin. High variability in FG loop suggests that this part of the scaffold is very tolerant to structural changes and positioned optimal for binding to the target. Indeed, six amino acid insertion into FG loop (group M1-Aext) and single residue deletion and mutation before FG loop (group M3-A50) also resulted in high affinity binding to myostatin. In contrast, when only two residues of FG loop were randomized in conservative (C-NNS) library, the selection yielded molecules with changed BCD β-sheets of the scaffold, as a result of frameshift mutation. These binders partially lost the F13β2 fold and resembled large peptides. This supports the importance of providing a sufficient randomization surface in FG loop, which plays the major role in target binding.

Remarkably, a similar FG loop sequence was identified independently from A-50% NNS (PSLLHL (SEQ ID NO:19)) and A-NNS libraries (PQLFHI (SEQ ID NO:20))—P(S/Q)L(L/F)H(L/I), with 3 identical residues and 3 conservative changes. This could indicate that these molecules bind to the same site on myostatin, which was confirmed later in radioactive binding assay (see below).

Additional loop exchange between clones from different sequence groups (A-50% NNS library) in selection PCR increased the diversity of the pool and allowed for the best combination to be selected (Table 3).

TABLE 3

Selected myostatin binders (grouped by FG loop sequence)

| BC loop | SEQ ID NO: | DE loop | SEQ ID NO: | FG loop | SEQ ID NO: | Scaffold mutation | In vitro clone | Kd, nM | B max, % | Solubility (37/RT/18) | Clone ID |
|---|---|---|---|---|---|---|---|---|---|---|---|
| Group M1-A50 (A-50% NNS library) | | | | | | | | | | | |
| TNPFKETLRS | 4 | REIPPKTT | 5 | RTQYLI | 6 | V91L | Typical sequence | | | | |
| TNPFKETLRS | 4 | REIPPKTT | 5 | RTQYLI | 6 | V91L | 39633-C1 | 39.90 | 74.81 | Poor/NA/ YES | M17 |
| TNPFKETLRS | 4 | REIPPKTT | 5 | RTQYLI | 6 | V91L mut | 39633-F5 I3Y, M83I) | 32.15 | 69.70 | | |
| TNPFKETLRS | 4 | REIPPKTT | 5 | RTQYLI | 6 | V91P mut | | | | | |
| TNPFKETLQS | 34 | REIPPKTT | 5 | RTQYLI | 6 | V91L | | | | | |
| TNPFKETLRG | 35 | REIPPKTT | 5 | RTQYLI | 6 | V91L mut | | | | | |
| TNPFKETLRS | 4 | RKIPPKTT | 81 | RTQYLI | 6 | V91L | | | | | |
| TNPFKETLRS | 4 | RVIPPKTT | 82 | RTQYLI | 6 | V91L | 39633-C5 | 30.84 | 93.05 | NO/NA/YES | M34 |
| TNPFKETLRS | 4 | RVIPPKTT | 82 | RTQYLI | 6 | V91L | | | | | |
| TNPYKETLRS | 36 | RVIPPKTT | 82 | RTQYLI | 6 | V91L | | | | NO/NA/YES | M83 |

TABLE 3-continued

Selected myostatin binders (grouped by FG loop sequence)

| BC loop | SEQ ID NO: | DE loop | SEQ ID NO: | FG loop | SEQ ID NO: | Scaffold mutation | In vitro clone | Kd, nM | B max, % | Solubility (37/RT/18) | Clone ID |
|---|---|---|---|---|---|---|---|---|---|---|---|
| TNPFKETLRS | 4 | REIPPETT | 83 | RTQYLI | 6 | V91L mut | 39908-F8 (K52R) | 36.58 | 45.71 | | |
| TNPFKETLRS | 4 | SEIRPNST | 8 | RTQYLI | 6 | V91L | 39633-G5 | 33.57 | 64.14 | | |
| SNPFKETLRN | 7 | SEIRPNST | 8 | RTQYLI | 6 | V91L | 40636-D2 | | | | |
| SNPFKETLRN | 7 | REIPPKTT | 5 | RTQYLI | 6 | V91L | 39633-G1 | 38.90 | 52.00 | | |
| SNPFKETLRN | 7 | RVIPPKTT | 84 | RTQYLI | 6 | V91L | | | | Poor/NA/YES | M3 |
| TNPLSQTLSA | 37 | REIPPKTT | 5 | RTQYLI | 6 | V91L | 39633-B3 | 9.93 | 6.14 | | |
| SNPFKETLRN | 7 | CEIRPNSI | 11 | RTQYLI | 6 | V91L | 39633-F4 | 26.75 | 28.47 | | |
| SNPFKETLRN | 7 | CEVRPNSV | 85 | RTQYLI | 6 | V91L | 39633-E2 | 27.28 | 20.99 | | |
| Group M2-A50 (A-50% NNS library) | | | | | | | | | | | |
| SNPFKETLRN | 7 | SEIRPNST | 8 | PSLLHL | 9 | | | Typical sequence | | | |
| SNPFKETLRN | 7 | SEIRPNST | 8 | PSLLHL | 9 | | 39908-G4 | 28.36 | 48.95 | Poor/NA/YES | M7 |
| SNPFKETLRN | 7 | SEIRPNST | 8 | PSLLHL | 9 | mut | 39633-D3 (V39M) | 26.19 | 65.77 | NO/NO/NA | |
| SNPFKETLRN | 7 | SEIRPDST | 86 | PSLLHL | 9 | | 39633-E4 | 27.75 | 59.99 | NO/NO/YES | M019 |
| SNPFKETLRN | 7 | CEIRPNSI | 11 | PSLLHL | 9 | | | | | | |
| TNPFKETLRS | 4 | SEIRPNST | 8 | PSLLHL | 9 | | 39908-G12 | 25.59 | 34.11 | Poor/NA/YES | M10 |
| TNLMKETLRN | 38 | SEIRPNST | 8 | PSLLHL | 9 | | 39633-D2 | 11.15 | 6.74 | | |
| TNPFKETLRS | 4 | REIPPKTT | 5 | PSLLHL | 9 | | 39908-H10 | 29.73 | 47.28 | Poor/NA/YES | M4 |
| TNPFKETLRS | 4 | REIPPKTT | 5 | PSLLHL | 9 | mut | 39633-H6 (M50V) | 24.83 | 61.65 | | |
| Group M3-A50 (A-50% NNS library) | | | | | | | | | | | |
| TNPFKETLRN | 10 | CEIRPNSI | 11 | CSLSPW | 12 | ΔS82, M83R | | Typical sequence | | | |
| TNPFKETLRN | 10 | CEIRPNSI | 11 | CSLSPW | 12 | ΔS82, M83R | 39633-D6 | 20.26 | 79.62 | Part/NA/NA | M020 |
| TNPFKETLRN | 10 | CEIRPNSI | 11 | CSLSPW | 12 | ΔS82, M83R mut | | | | | |
| SNPFKETLRN | 7 | CEIRPNSI | 11 | CSLSPW | 12 | ΔS82, M83R | 39908-A1 | 12.01 | 50.22 | Part/NA/NA | M02 |
| SNPFKETLRN | 7 | CEIRPNSI | 11 | CSLSPW | 12 | ΔS82, M83R mut | | | | Part/NA/NA | M013 |
| SNPFKETLRN | 7 | CEIRPNSI | 11 | CSLSPW | 12 | ΔS82, M83K | | | | | |
| SNPFKETLRN | 7 | CEIRPNST | 87 | CSLSPW | 12 | ΔS82, M83R ΔI8 | | | | | |
| SNPFKETLRN | 7 | CGIRPNSI | 88 | CSLSPW | 12 | ΔS82, M83R | | | | | |
| SNPFKETLRN | 7 | CEVRPNSI | 89 | CSLSPW | 12 | ΔS82, M83R mut | 39633-A5 (V46I) | 19.36 | 78.35 | | |
| SNPFKETLRN | 7 | CEIRPNSI | 11 | CSLPPW | 150 | ΔS82, M83R | | | | | |
| SNPFKETLRS | 39 | CEIRPNSI | 11 | CSLSPW | 12 | ΔS82, M83R mut | | | | | |
| TNPFKETLRS | 4 | CEIRPNSI | 11 | CSLSPW | 12 | ΔS82, M83R | 39908-C6 | 19.66 | 52.18 | NO/NA/YES | M05 |
| TNPFKETLRS | 4 | CEIRPNSI | 11 | CSLSPW | 12 | ΔS82, M83R mut | | | | | |
| TNPFKETLRS | 4 | CEIRPNRI | 90 | CSLSPW | 12 | ΔS82, M83R | 39908-A3 | 11.03 | 57.18 | NO/NA/Poor | M09 |
| TNPFKETLRN | 10 | SEIRPNST | 8 | CSLSPW | 12 | ΔS82, M83R mut | | | | | |
| TNPFKETLRN | 10 | SEIRTNAT | 91 | CSLSPW | 12 | ΔS82, M83R | | | | | |
| SNPFKETLRN | 7 | SEIRPNST | 8 | CSLSPW | 12 | ΔS82, M83R | 39908-E5 | 21.88 | 77.85 | YES/NA/YES | M56 |
| SNPFKETLRN | 7 | SEIRTNAT | 91 | CSLSPW | 12 | ΔS82, M83R | 39908-C11 | 16.96 | 73.74 | NO/NA/YES | M22 |
| SNPFKETLRN | 7 | SEIRPNSI | 92 | CSLSPW | 12 | ΔS82, M83R mut | | | | | |
| SNPFKETLRN | 7 | RDIRPKTK | 93 | CSLSPW | 12 | ΔS82, M83R | | | | NO/NA/YES | M58 |
| TNPFKETLRS | 4 | REIPPKTT | 5 | CSLSPW | 12 | ΔS82, M83R | 39908-D2 | 23.34 | 68.83 | Part/NA/NA | M29 |
| TNPFKETLRS | 4 | REIPPKTT | 5 | CSLSPW | 12 | ΔS82, M83R mut | | | | | |
| TNPFKETLRS | 4 | SEIRPNST | 8 | CSLSPW | 12 | ΔS82, M83R | | | | YES/NA/YES | M71 |
| TNPFKETLRS | 4 | RDIRPKTK | 93 | CSLSPW | 12 | ΔS82, M83R | | | | | |
| TNPFKETLRS | 4 | SEIRTNAT | 91 | CSLSPW | 12 | ΔS82, M83R mut | | | | | |
| TNPFKETLRS | 4 | REIPPETT | 94 | CSLSPW | 12 | ΔS82, M83R mut | | | | | |
| TNPFKGTLRS | 40 | WEIPPKTT | 95 | CSLSPW | 12 | ΔS82, M83R mut | | | | | |
| TNPFKETLRN | 10 | RDIRPKTK | 93 | CSLSPW | 12 | ΔS82, M83R | 39908-A2 | 15.21 | 68.49 | NO/NO/YES | M03 |
| TNPFKETLRN | 10 | CEIRPNSI | 11 | CQLLPW | 157 | ΔS82, M83R | 39908-F5 | 27.07 | 67.24 | YES/NA/NA | M16 |
| SNPFKETLRN | 7 | CEIRPNSI | 11 | CQLLPW | 157 | ΔS82, M83R mut | | | | | |
| SNPFKETLRN | 7 | SEIRPNST | 8 | CQLLPW | 157 | ΔS82, M83R mut | | | | | |
| SNPFKETLRN | 7 | RDIRPKTK | 93 | CQLLPW | 157 | ΔS82, M83R | 39908-H4 | 15.80 | 68.58 | NO/NO/YES | M015 |

TABLE 3-continued

Selected myostatin binders (grouped by FG loop sequence)

| BC loop | SEQ ID NO: | DE loop | SEQ ID NO: | FG loop | SEQ ID NO: | Scaffold mutation | In vitro clone | Kd, nM | B max, % | Solubility (37/RT/18) | Clone ID |
|---|---|---|---|---|---|---|---|---|---|---|---|
| SNPFKETLRN | 7 | RDIRPKTK | 93 | CQLLPW | 157 | ΔS82, M83R mut | | | | | |
| SNPFKETLRN | 7 | REIPPKTT | 5 | CQLLPW | 157 | ΔS82, M83R mut | | | | | |
| TNPFKETLRS | 4 | REIPPKTT | 5 | CQLLPW | 157 | ΔS82, M83R | 39908-B2 | 27.10 | 75.86 | Part/YES/ YES | M07 |
| TNPFKETLRS | 4 | REIPPKTT | 5 | CQLLPW | 157 | ΔS82, M83R mut | | | | | |
| TNPFKETLRS | 4 | RDIRPKTK | 93 | CQLLPW | 157 | ΔS82, M83R mut | | | | | |
| TNLMKETLRN | 41 | RDIRPKTK | 93 | CQLLPW | 157 | ΔS82, M83R | | | | | |
| TNPWAETLHN | 42 | RDIRPKTK | 93 | CQLLPW | 157 | ΔS82, M83R | | | | | |
| SNPFKETLRN | 7 | CEIRPNSI | 11 | -TLRPW | 152 | | | | | NO/Poor/NA | |
| SNPFKETLRN | 7 | CEIRPNSI | 11 | MTLRPW | 153 | ΔS82, M83R | 39908-A7 | 20.14 | 109.40 | Part/NA/NA | M24 |
| SNPFKETLRN | 7 | CEIRPNSI | 11 | -ALRPW | 154 | V69A | | | | | |
| SNPFKETLRN | 7 | REIATMST | 96 | -TLRPW | 152 | | | | | | |
| TNPFKETLRS | 4 | REIPPKTT | 5 | -TLRPW | 152 | | 39633-G6 | 19.69 | 75.13 | No exp/NA/ No exp | M18 |
| TNPFKETLRS | 4 | REIPPKTT | 5 | -TLRPW | 152 | mut | | | | | |
| TNLWKETLRN | 43 | REIATMST | 96 | -TLRPW | 152 | | | | | | |
| TNLWKETLRN | 43 | REIATMST | 96 | -TLRPW | 152 | mut | | | | | |
| TNLWKETLRN | 43 | REIATMST | 96 | -TLRPW | 152 | mut | | | | | |
| TNLWKEALRN | 44 | REIATMST | 96 | -TLRPW | 152 | V39M | 39908-E1 | 14.85 | 40.22 | No exp/NO/NA | M04 |
| TNLWKETLRN | 43 | REIPPMST | 97 | -TLRPW | 152 | mut | | | | | |
| Group M4-A50 (A-50% NNS library) | | | | | | | | | | | |
| TNPFKETLRS | 4 | REIPPKTT | 5 | CEPSLD | 155 | | 39633-D5/yes | 8.69 | 6.91 | | |
| TNPFKETLRS | 4 | REIPPKTT | 5 | YVAPLH | 156 | | | | | YES/NA/NA | M21 |
| TNPFKETLRS | 4 | REIPPKTT | 5 | GTQFPR | 157 | mut | | | | | |
| TNPFKETLRS | 4 | REIPPKTT | 5 | PSDSLP | 158 | mut | | | | | |
| TNPFKETLRS | 4 | REIPPNTT | 98 | PTHHLL | 159 | | 39633-A1 | 25.52 | 63.94 | | |
| SNPFKETLRS | 45 | EEIRQSCI | 99 | RD-ALS | 160 | mut | | | | | |
| SNPFKETLRN | 7 | CEIRPNSI | 11 | GSDCLG | 161 | mut | | | | | |
| TRPLNDRLRK | 46 | REIRPTSS | 100 | NTESIL | 162 | mut | | | | | |
| TTPQEETLIK | 47 | MKIPPASW | 101 | MSDTLR | 163 | | | | | | |
| VTPLWANLCT | 48 | WDIRHDPT | 102 | SKPPER | 164 | mut | | | | | |
| Group M1-A (A-NNS library) | | | | | | | | | | | |
| TNPLKETLRN | 13 | PAIPMNHK | 14 | PQLFHI | 15 | | Typical sequence | | | | |
| TNPLKETLRN | 13 | PAIPMNHK | 14 | PQLFHI | 15 | | 39885-A1 | 21.76 | 67.26 | NO/NO/Part | M1-1 |
| TNPLKETLRN | 13 | PAIPMNHK | 14 | PQLFHI | 15 | mut | 39885-B5(F26V) | 25.14 | 72.16 | No exp/NA/ Poor | M2-1 |
| | | | | | | | 39885-F10(S82C) | 15.43 | 73.68 | NA/NA/No exp | |
| | | | | | | | 39888-A11(D42N) | 13.55 | 82.36 | NA/NA/Very Poor | M14-1 |
| | | | | | | | 39888-G5(S82I) | 9.988 | 83.12 | | |
| TNPMKETLRN | 49 | PAIPMNHK | 14 | PQLFHI | 15 | | | | | | |
| TNPLKEILRN | 50 | PAIPMNHK | 14 | PQLFHI | 15 | | | | | | |
| TNPLRETLRN | 51 | PAIPMNHK | 14 | PQLFHI | 15 | | | | | | |
| TNPLKETLRN | 13 | RAIPMNHK | 103 | PQLFHI | 15 | | 39885-C7 | 17.43 | 68.37 | NO/NA/Poor | M3-1 |
| TNPLKETLRN | 13 | PTIPMNHK | 104 | PQLFHI | 15 | | 39885-G8 | 30.75 | 69.21 | NA/NA/Poor | M10-3 |
| TNPLKETLRN | 13 | PTIPMNHK | 105 | PHLFHI | 165 | | 39885-F7 | 24.11 | 62.72 | | |
| TNPLKETLRN | 13 | PAIPYLSY | 106 | PQLHHL | 166 | | 39885-G5 | 28.49 | 59.43 | NA/NA/YES | M8-L |
| TNPLKETLRN | 13 | PAIPMNHK | 14 | PQLFHL | 167 | | 39885-F8 | 28.1 | 98.61 | NO/NA/YES | M7-L |
| TNPLKETLRN | 13 | PAIPMNHK | 14 | PQLFHL | 168 | mut | | | | | |
| TNPLKETLRN | 13 | PAIPMNHK | 14 | PRLFHI | 169 | V39M | | | | | |
| TNPLKETLRN | 13 | PAIPMDHK | 107 | PQLFHI | 15 | | 39885-D8(K9R) | 24.73 | 57.62 | NO/NO/Poor | M5-2 |
| TNPLKETLRN | 13 | PTISRFKR | 108 | PQLQHL | 170 | | 39973-C10 | 22.79 | 71.98 | NO/NO/No exp | |
| TNPLKETLRN | 13 | ATIPPYLP | 109 | PQLIHL | 171 | | 39973-F10 | 28.65 | 68.02 | NO/NA/NO | |
| TNPLKETLRN | 13 | SLICVNRA | 110 | PQLFHI | 15 | | | | | | |
| Group M2-A (A-NNS library) | | | | | | | | | | | |
| TNPLKETLRN | 13 | PAIPMNHK | 14 | INYFYK | 172 | | | | | | |
| TNPLKETLRN | 13 | PAIPMNHK | 14 | INYFYK | 172 | | 39885-C11 | 41.59 | 18.77 | | |
| TNPLKETLRN | 13 | PAIPMNHK | 14 | INYFYK | 172 | mut | | | | NO/NO/NA | |
| TDPLKETLRN | 52 | PAIPTNHK | 111 | INYFYK | 172 | mut | | | | | |
| TNPLKETLRN | 13 | PAIPMNHK | 14 | INHFYK | 173 | | 39885-D11 | 41.03 | 22.26 | | |
| TNPLKETLRN | 13 | PAIPMNHK | 14 | INYFYN | 174 | | 39885-H9 | 14.14 | 24.06 | | |

TABLE 3-continued

Selected myostatin binders (grouped by FG loop sequence)

| BC loop | SEQ ID NO: | DE loop | SEQ ID NO: | FG loop | SEQ ID NO: | Scaffold mutation | In vitro clone | Kd, nM | B max, % | Solubility (37/RT/18) | Clone ID |
|---|---|---|---|---|---|---|---|---|---|---|---|
| TNPLKETLRN | 13 | PAIPMKHK | 112 | LNHFYK | 175 | H76Y, E94G | | | | | |
| TNPLKETLRN | 13 | PAIPMNHK | 14 | LNHFYK | 176 | | 39885-C1 | 140 | 33.34 | | |
| Group M3-A (A-NNS library) | | | | | | | | | | | |
| HSMSSGILNY | 53 | DLIRNSHV | 113 | HHGSYP | 177 | | | | | | |
| YFSPGARLAT | 54 | HSIYVPFW | 114 | TTTVQG | 178 | | 39973-D2 | 32.89 | 7.656 | | |
| KHDRYRYLQQ | 55 | KLIIFSYP | 115 | RFMCPS | 179 | | 39973-B12 | 34.54 | 7.77 | | |
| AATLYHALFS | 56 | LNISAQTM | 116 | CHAMTS | 180 | | | | | | |
| RSLPAAWLEN | 57 | TRIKCASS | 117 | KVLTEH | 181 | | | | | | |
| GLIGLLQLYE | 58 | CGIPPLSS | 118 | YLELLY | 182 | | | | | | |
| PCMGQYKLPL | 59 | MEITINGY | 119 | RHTDWS | 183 | | | | | | |
| LIGILCL-WY | 60 | MQILLYIL | 12 | QHSPPA | 184 | Q14R | | | | | |
| ARTIHTILTN | 61 | TMISWNLN | 121 | SAGCSF | 185 | Q64R | | | | | |
| MNIIRNMLTT | 62 | IMIDKLML | 122 | QTAEPR | 186 | E66G | | | | | |
| QTKLIQSLVT | 63 | HRIPCLT- | 123 | SLLITP | 187 | S82N | | | | | |
| FHTYRLWLGV | 64 | WLISNIDL | 124 | VYIKNG | 188 | PG (44-45)/MLADW | | | | | |
| TNPLKETLRN | 13 | EQIRESEY | 125 | LTETRP | 189 | | 39973-G3 | 21.97 | 1.806 | | |
| TNPLKETLRN | 13 | PAIPMNHK | 14 | NSSSNQ | 190 | | 39888-B7 | 7.092 | 1.189 | | |
| TNPLK---ETLRN | 16 | LKIPGCST | 126 | SMLGLPFSLRFIP | 191 | | | Typical sequence | | | |
| TNPLK---ETLRN | 16 | LKIPGCST | 127 | SMLGLPFSLRFIP | 191 | | 45927-B3 | 86.70 | 50.68 | NO/NA/YES | Mext |
| TNPLK---ETLRN | 16 | LKIPGCST | 128 | SMLGLPFSLRFIP | 191mut | | 45927-B7 (M50T) | 57.61 | 46.35 | | |
| TNPLK---EALRN | 65 | LKIPGCST | 129 | SMLGLPFSLRFIP | 191 | | | | | | |
| TNPLE---ETLRN | 66 | LKIPGCST | 130 | SMLGLPFSLRFIP | 191 | | | | | | |
| TNPLK---ETPRN | 67 | LKIPGCST | 131 | SMLGLPFSLRFIP | 191 | | | | | | |
| TNPLK---ETLRN | 16 | LKIPGCST | 132 | SMLGLPFSLRLIP | 192 | | | | | | |
| TNPLK---ETLRN | 16 | QKIPGCST | 133 | SMLGLPFSLRFIP | 191 | | 45927-A11 | 65.05 | 41.22 | | |
| TNPLK---ETLRN | 16 | LKILGCST | 134 | SMLGLPFSLRFIP | 191 | | 45927-A3 | 53.16 | 36.38 | | |
| TNPLK---ETLRN | 16 | TGILQWST | 135 | SPHAWWQHHGNFS | 193 | | 45927-E1 | 6.04 | 4.57 | | |
| TNPLK---ETLRN | 16 | LKIPGCST | 136 | SMRMNLLFHLMNA | 194 | | | | | | |
| TNPARGVNPSLRN | 68 | TDICKGST | 137 | SYNVCRRVLKSFI | 195 | W65G, V91E | | | | | |
| TNPFALTCRNLRN | 69 | SSINIFST | 138 | SLASAAPMMIQTW | 196 | | | | | | |
| TNPLTNWGVWLRN | 70 | NAITPVST | 139 | SCGLYGSQCCYTW | 197 | | | | | | |
| TNPNHFTRRELRN | 71 | MNIAAEST | 140 | SHLFSDDLWAAPT | 198 | | | | | | |
| TNPSCSSHCSLRN | 72 | TWIWLYST | 141 | SLLGWPMNVTLKR | 199 | | | | | | |
| TNPTDGSRPWLRN | 73 | FLIRTDST | 142 | SYGRCMVNLVRPL | 200 | | | | | | |
| TNLTNTHYSRLRN | 74 | QAITSCST | 143 | STSDSGWASNIVP | 201 | P29L | | | | | |
| TNPARGKTMNLRN | 75 | MIIYTNST | 144 | SCKLDQNCSALNL | 202 | Δ11-13 Δ44-45 | | | | | |
| TNPGSECNLSLRN | 76 | LYITPGST | 145 | SRYKLVVLARKVG | 203 | | | | | | |
| TNPDAWAKCVLRN | 77 | SGIASLST | 146 | SSLICRVKDFWMD | 204 | | | | | | |
| TNPKRDTSVWLRN | 78 | FTIGYPST | 147 | SPSILSKGNIGLG | 205 | H76R | 45927-A10 | 16.05 | 8.07 | | |
| TNPLRVSEQTLRN | 79 | GGIRVHST | 148 | SYVAEYGEWTHYS | 206 | P47L | 45927-A12 | 1.47 | 3.08 | | |
| TNPSNYRPCILRN | 80 | KMIVYHST | 149 | SKFELSGTSSRGR | 207 | | 45927-E5 | 64.07 | 8.36 | | |

Amino acids mutated from wild type after selection are underlined and marked in bold.

Example 6

Measurement of Affinity of Selected Myostatin ETBPs In Vitro

Affinities of selected F13β2 binders to biotinylated myostatin were determined in radioactive equilibrium binding assay (FIGS. 11A and 11B; Table 3). $^{35}$S-labeled binder proteins from selection pools and single clones were produced in vitro in a rabbit reticulocyte lysate translation kit (Ambion) and purified on M2-agarose (Sigma). Varying concentrations of biotinylated human myostatin (0-100 nM) or other proteins (protein 1: 100 nM; peptide 1: 250 nM; protein 2: 50 nM) were incubated with a constant concentration of the purified binder protein (1 or 2 nM) at 30° C. for 30 min in buffer B (1×PBS, 0.02% Triton X-100 [pH 7.4]). The receptor-binder complexes were captured by using 25 μl of M280 or Protein A (Dynal) (protein 2) magnetic beads for 10 min at room temperature on a Kingfisher instrument (Thermo Fisher Scientific). The beads were washed five times with 100 μl buffer B, and the amount of $^{35}$S-methionine remained on the beads was measured by scintillation counting. Data were analyzed by using the GraphPad Prism software (GraphPad Software, Inc., San Diego, Calif.), fitted with a one-site, nonlinear binding equation. For inhibition assay the binding of $^{35}$S-labeled proteins to 20 or 25 nM of biotinylated human myostatin was performed in the presence of varying concentrations of inhibitor (human activin receptor IIB/Fc chimera (R&D Systems, Minneapolis, Minn.) (0-250 nM); protein 1 (100 nM), peptide 1 (250 nM), protein 2 (50 nM); proteins, produced in *E. coli*, M17, M7, M29, M21, M1-1, WT F13β2 (500 nM)).

Moderate affinity binders from group M1-A50 and group M2-A50 interacted with myostatin with Kd of 31-40 nM and 25-30 nM, respectively. Conservative scaffold mutations in selected clones (ex., F26V, V39M, V46I, M50V, M83I) did not affect the binding affinity of the proteins. Also, no change in binding was observed when the wild type residue persisting in the DE loop was mutated (E56V), supporting the idea that the reverse selected wild type residues do not participate in binding to the target. In contrast, mutation of the consensus lysine residue in the DE loop (K60E) results in a decrease of binding activity, indicating that this position affects interaction with the target. Proteins from group M3-A50 and group M1-A bind myostatin with higher affinities (Kd of 11-27 nM and 10-31 nM, respectively). Some variability in the FG loop does not affect the binding: neither deletion of C84 and mutations C84M, S85Q/T and S87UR in the group M3-A50 proteins, nor mutations Q85H/R, F87H/Q/I, 189L in the group M1-A binders change the interaction with myostatin. On the other hand, exchange of selected FG loop sequences (but not DE loop sequences, group M1-A) to unrelated sequences significantly decreases the binding, indicating a major role for FG loop residues in interaction with the target (group M2-A, group M3-A). Conservative residues that are present in the FG loop of all highly potent binders (L86, P88, W89 in group M3-A50, and P84, L86, H88 in group M1-A) potentially form the binding site with myostatin. The conserved phenylalanine in the BC loop of the binders selected from A-50% NNS library appears necessary for interaction with myostatin, since even modest changes to this residue abolish (F20L/M) or reduce (F20W) the binding to the target (FIGS. 11A and 11B). Remarkably, the BC and DE loops of ETBPs from group M1-A50, group M2-A50 and group M3-A50 can be interchanged without significant alteration in the binding activity, which suggests that they may bind to the same site on the myostatin molecule. Binders selected from Aext-NNS library showed lower affinity (Kd=53-86 nM) for the target, which was also correlated with a decreased B max (Table 3). Binders from this group have an extended highly hydrophobic FG loop (MLGLPFSLRFIP (SEQ ID NO:21)), and it is possible that the observed decreased affinity is related to poor biophysical properties of the proteins.

Figure 12:
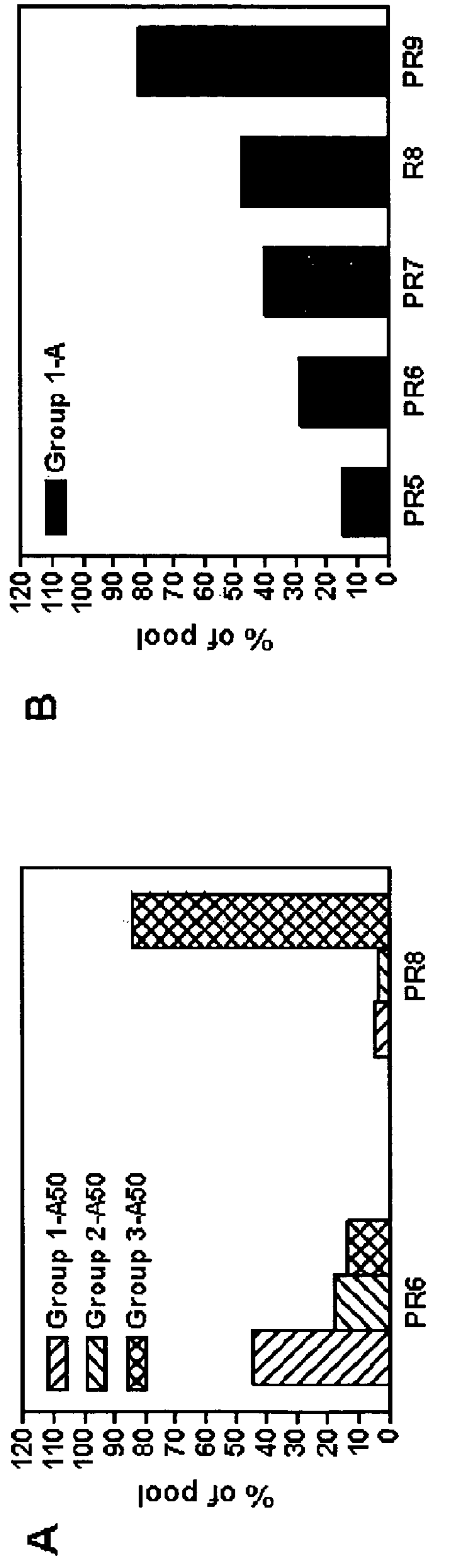
FIGS. 12A and 12B are graphs showing sample binding to myostatin under stringent conditions.

Highly potent binders from group M3-A50 and group 1-A were observed among sequenced isolates from selection under stringent conditions (FIGS. 12A and 12B): in earlier rounds low affinity binders were found to dominate the selection pool, but by the last round of selection the high affinity binders constituted more than 80% of all proteins.

Figure 13:
FIG. 13A is a graph showing percentage of binding between myostatin and in vitro-produced myostatin binders. *E. coli-produced* myostatin binder proteins disrupt the interaction between mysostatin and in vitro-produced myostatin binders. A radioactive equilibrium binding assay was performed with clones from group M1-A50 (M17), group M2-A50 (M7), and group M3-A50 (M020) (0.1 pmol) with myostatin (2 pmol) in the presence of *E. coli*-produced proteins from groups M1-A50 (M17), M2-A50 (M7), M3-A50 (M29), M1-A (M1-1) or wild type F13β2 domain (50 pmol). Binding was measured as a percentage of input binder material and binding in the absence of inhibiter was assigned as 100%.
FIG. 13B is a graph showing percentage of binding as a function of activin receptor IIB (ARIIB) concentration. A radioactive equilibrium binding assay was performed with clones from group M1-A50 (M17), group M2-50 (M7), group M3-50 (M29), and group M1-A (M1-1) (0.1 pmol) with myostatin (2 or 2.5 pmol) in the presence of different concentrations of ARIIB. Binding was measured as a percentage of input binder material and binding in the absence of ARIIB was assigned as 100%.

Myostatin binder proteins produced in *E. coli* could efficiently inhibit the interaction between myostatin and various in vitro-produced myostatin binders (FIG. 13A). Wild type F13β2 domain did not compete for binding. These data indicate that selected proteins from the four major groups bind to similar sites on the myostatin molecule.

The best binders from different sequence groups were subsequently tested for binding to myostatin in the presence of human activin receptor IIB (ARIIB) (FIG. 13B). Activin receptor efficiently inhibited target binding of the proteins with moderate affinities to myostatin—M17 (group M1-A50) and M7 (group M2-A50), suggesting that these binders may interfere with the natural ARIIB-myostatin interaction. Only a modest inhibition (20%) of target binding of high affinity proteins from group M3-A50 (M29) and group M1-A (M1-1) was observed at the highest concentration of activin receptor (250 nM). Since the selected binders bind to similar sites on myostatin (see above), it is possible that in vitro binding assay conditions are more favorable to binding of highly potent F13β2 proteins than activin receptor, and higher inhibitor concentrations would be needed to efficiently displace the binder from myostatin surface.

Example 7

Production and Purification of Selected Myostatin ETBPs from *E. Coli*

DNA from myostatin binder clones was amplified by PCR with primers oligo 53 and oligo 28rev to introduce NdeI at 5' end, and His6-tag-Stop ("His6" disclosed as SEQ ID NO: 29) sequence and Barn HI site at 3' end, respectively. To generate proteins, containing PSM-His6-Stop ("His6" disclosed as SEQ ID NO: 29) (Barn HI site) and PSM-Stop (XhoI site) sequences oligo AKx198 and oligo AKx299 were used for 3' end in PCR. To construct F13β2-GFP fusions a primer oligo 18rev (Barn HI) was used for 3' end in PCR which allowed introduce the binder proteins at the N-terminus of GFP. The binder proteins were expressed in *E. coli* by using a modified pet28(a+) vector. Protein expression was induced with 0.25-1 mM IPTG for 3 hours at 37° C. or overnight at room temperature or 18° C. Cell pellets were collected, and after freeze/thaw disruption, resuspended in 1×PBS (pH 7.4), containing Lysonase™ Bioprocessing Reagent (EMD Chemicals Inc., San Diego, Calif.). After incubation at room temperature for 20 minutes CHAPS was added to 0.4% final concentration. The solution was rotated for 20 minutes at 4° C., and the soluble fraction was separated by centrifugation. Aliquots of total and soluble fractions were collected before and after centrifugation for SDS-PAGE analysis. When F13□2-GFP fusion proteins were expressed the fluorescence was monitored under UV light in cell pellet, insoluble pellet and soluble fraction. For His-tag affinity purification the supernatant was rotated for 1 hr at 4° C. with Ni-NTA agarose (Qiagen) preequilibrated with buffer C (1×PBS [pH7.4], 0.5 M NaCl; 20 mM Imidazole, 0.3% CHAPS). The resin was washed with 50 column volumes of buffer C and 30 column volumes of buffer D (1×PBS [pH7.4], 20 mM Imidazole). Protein was eluted with 1×PBS, 200 mM Imidazole (pH 7.4) and was dialyzed against 1×PBS at 4° C.

The solubility in physiological conditions (1×PBS, pH 7.4) varied between different binders (Table 3, FIG. 14A) when expressed at 37° C. and RT, but all binders were soluble to some extent when expressed at 18° C. The best solubility profile was observed for binders from group M3-A50, for which the majority of the proteins were soluble in PBS after expression at 37° C. We purified a number of myostatin binders from the soluble fraction by affinity chromatography via a His6 tag (SEQ ID NO: 29) yielding 5-20 mg of each protein from one liter culture. *E. coli*-produced binders were able to compete for binding to myostatin in a radioactive equilibrium binding assay in vitro (see above), and their activity was further tested in a cell proliferation assay.

Figure 14:
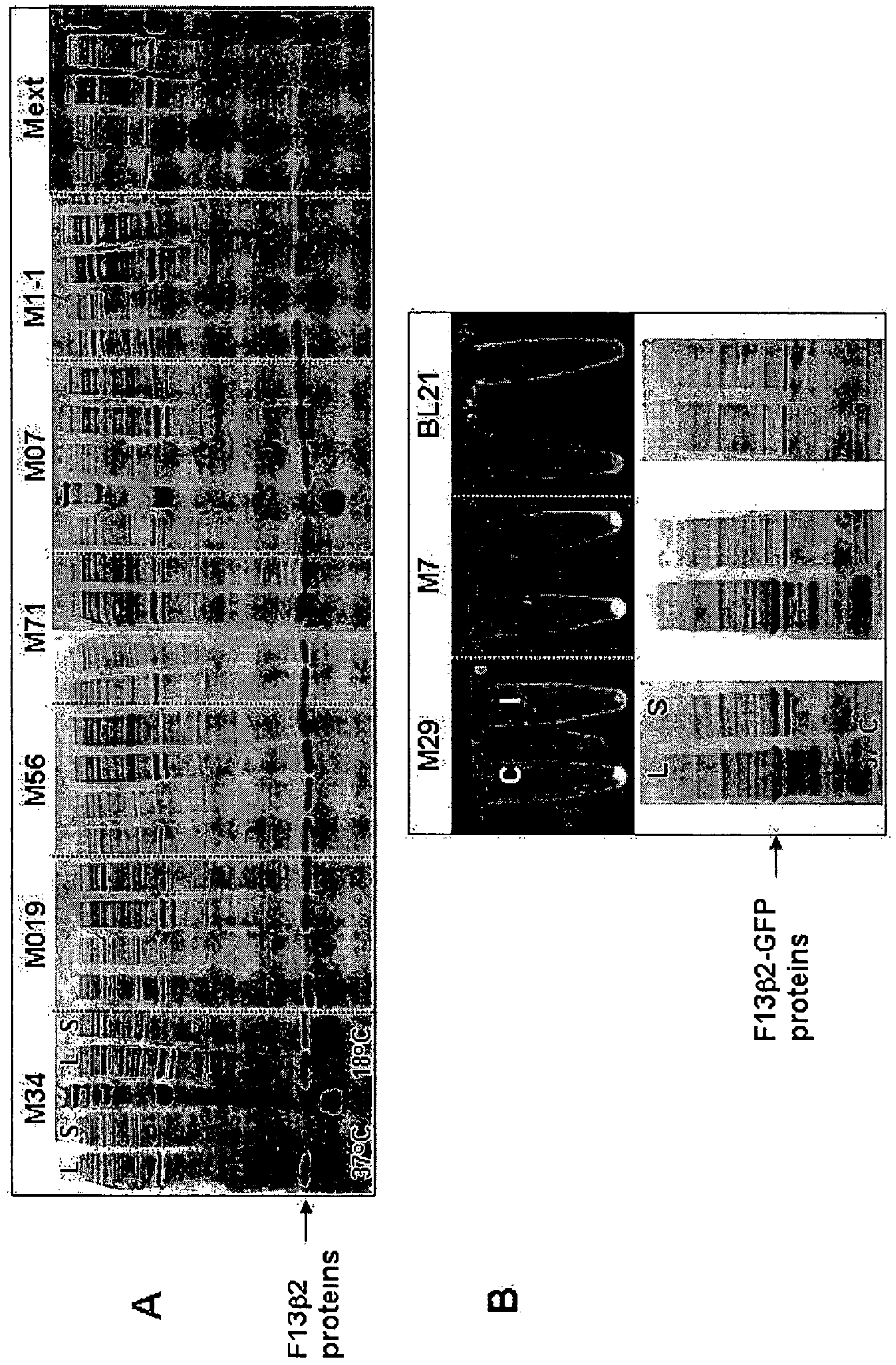
FIG. 14A is an image of an SDS-PAGE showing proteins expressed by the indicated clones in *E. coli* under different temperature conditions as total (L) and soluble in 1×PBS, pH 7.4 (S) fractions.
FIG. 14B upper panels are images showing fluorescence of the indicated clones of cell (C) and insoluble (I) pellets under UV light. Lower panels are images of SDS-PAGE gels showing total (L) and soluble (S) fractions of the indicated clones. Non-induced BL21 cells were used as a control.

To analyze the folding pattern of different myostatin binders we expressed them as N-terminal fusions with GFP as a "folding reporter". Since folding and formation of the GFP chromophore has been reported to depend on the correct folding of the upstream protein we could assess the folding of the myostatin binders by GFP fluorescence and compare it with the solubility profile in PBS (FIG. 14B). Myostatin binder M29 from group M3-A50 was soluble in PBS, as shown by SDS-PAGE. We could monitor the disappearance of green fluorescence in the insoluble pellet after solubilization, which indicated that the majority of correctly folded M29-GFP protein was in the soluble fraction. The M7 binder from group M2-A50 remained in the insoluble pellet, but was correctly folded, as indicated by a strong GFP signal. Since the majority of the *E. coli* proteins are found in the soluble fraction (FIG. 14B); the pellet is 80 to 90% enriched with a binder protein.

Figure 15:
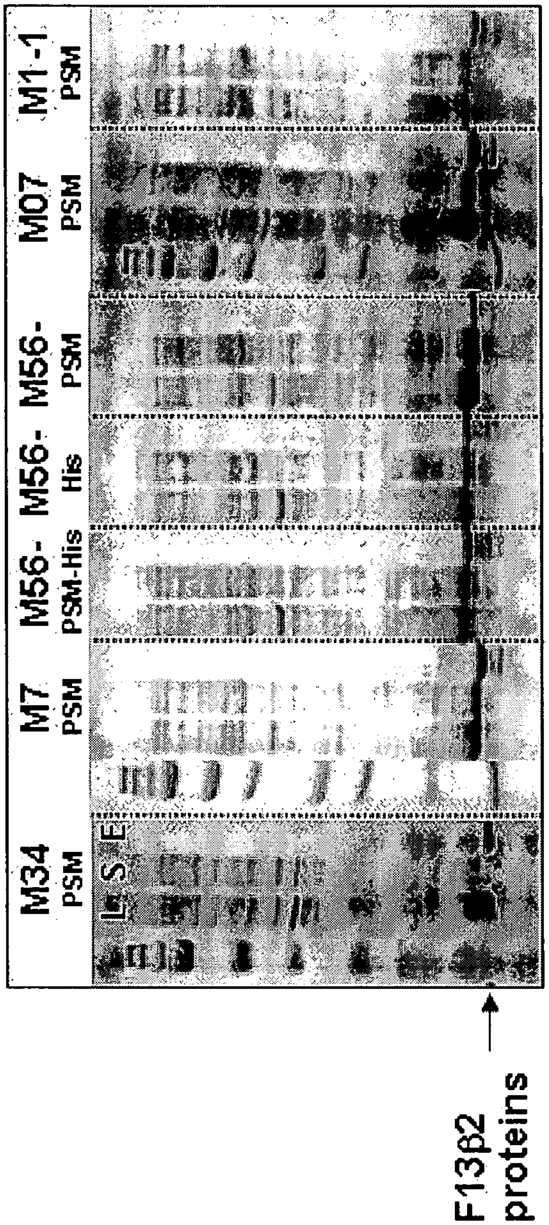
FIG. 15 is an image of SDS-PAGE gels of proteins of the indicated groups as extracted from *E. coli* grown at 37° C. and extracted from the insoluble fraction. Lanes were loaded with total (L), soluble in 1×PBS pH 7.4 diluted with water (S), and extraction (E) fractions.

To apply this finding for the purification of the binder proteins we expressed various myostatin binders at 37° C. to achieve the highest expression. Cell pellet was resuspended in PBS diluted (1:5) with water and incubated with Lysonase™ Bioprocessing Reagent at room temperature for 20 minutes. Following incubation with 0.33% CHAPS the soluble fraction was separated by centrifugation. Since F13β2 proteins that remained in the pellet are correctly folded no re-folding procedure was necessary. After testing a number of different conditions we found that 36 mM HCl was optimal for solubilization of the correctly folded proteins. Any remaining insoluble material was removed by centrifugation and the supernatant was dialyzed against water. The myostatin binders were analyzed by SDS-PAGE (FIG. 15). Presence of His6 tag (SEQ ID NO: 29) or PSM sequence on the C-terminus of the myostatin binder protein (M56-His6 ("His6" disclosed as SEQ ID NO: 29), M56-PSM-His6 ("His6" disclosed as SEQ ID NO: 29), M56-PSM) (FIG. 15) didn't change the extraction behavior although production and solubility of protein which contained only PSM sequence on the C-terminus was higher. The enrichment of F13β2 proteins achieved in a single extraction step ranged from 80 to 90% and was successfully applied for purification of tagless myostatin binders. This simple purification procedure of F13β2 binders can be utilized for high throughput screening of a large number of nearly pure proteins and ultimately gives a great advantage for therapeutic applications.

The thermostability of the myostatin binding proteins derived from F13β2 scaffold differed from binder to binder, and Tm values ranged from 55° C. to 70° C. at neutral pH.

Example 8

Measurement of Biological Activity of Selected Myostatin ETBPs

The biological activity of F13β2 myostatin binders was tested by an MPC-11 cell proliferation assay. Mouse myeloma MPC-11 cells (ATCC#CCL-167, American Type Culture Collection, Manassas, Va.) were grown in Dulbecco's modified Eagle's medium (DMEM; Invitrogen), supplemented with 10% (v/v) horse serum, and 0.05 mg/ml gentamicin. For cell proliferation assay, serial dilutions of human activin A (Peprotech (Rocky Hill, N.J.)) (0-100 ng/ml), GDF-11 (Peprotech (Rocky Hill, N.J.)) or myostatin (Peprotech (Rocky Hill, N.J.)) (0-1000 ng/ml) (100 μl) were incubated in growth medium with 2000-4000 cells/well in 96-well tissue culture plate. For inhibition assay, the cells were resuspended in growth medium, containing 10 ng/ml of activin A, or 125-250 ng/ml of GDF-11 or myostatin, and 170 μl containing 2000-4000 cells were added per well to a 96-well tissue culture plate. Serial dilutions of F13β2 proteins in 1×PBS (pH 7.4) (30 μl) were added to each well, and the cells were incubated for 72 hours at 37° C. Cell proliferation was measured by the addition of 10 μl CCK-8 solution (Cell Counting Kit-8; Dojindo Molecular Technologies, Inc., Gaithersburg, Md.) to each well, followed by incubation for 8 hr at 37° C., and measurement of the absorbance at 450 nm with a microtiter plate reader (Molecular Dynamics).

Figure 16:
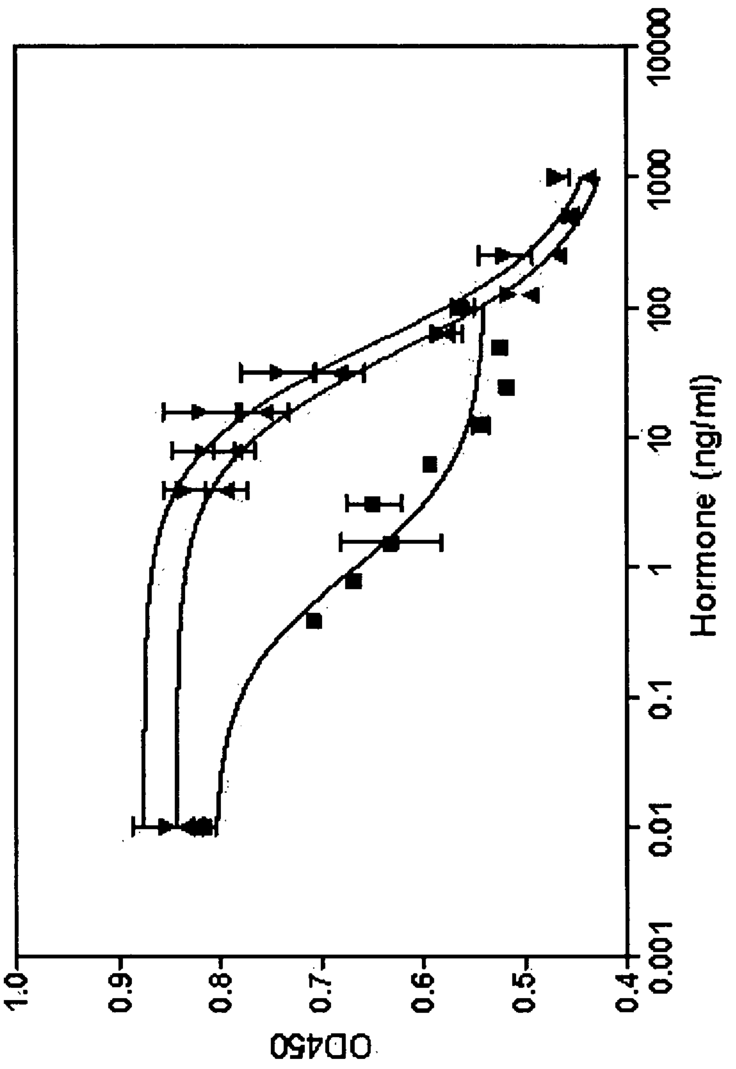
FIG. 16 is a graph of proliferation of MPC-11 cells as a function of hormone concentration as measured by absorbance at 450 nM using a CCK-8 kit. Squares=human activin A; triangles=human GDF-11; upside-down triangles=human myostatin.
Figure 17:
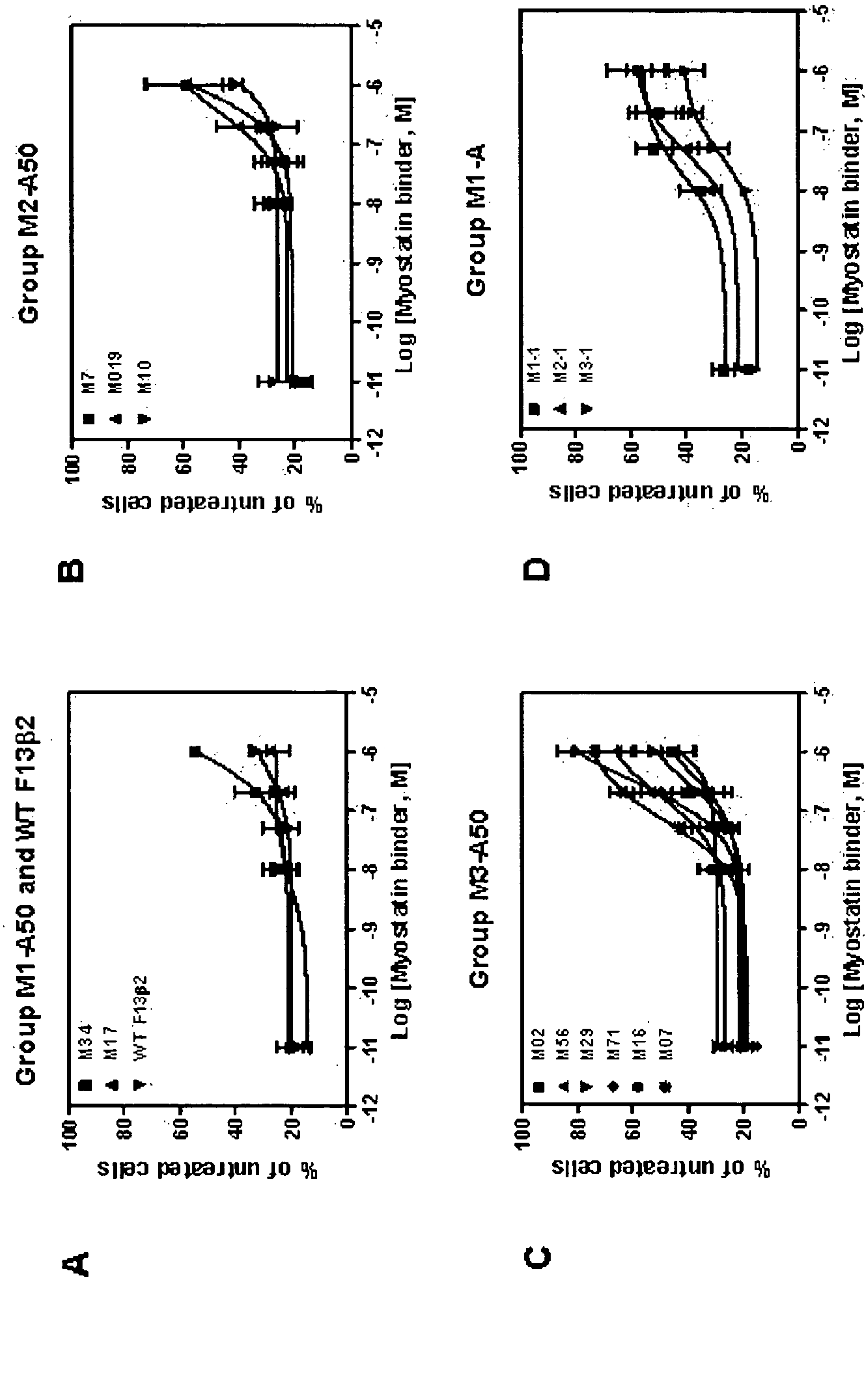
FIG. 17A-17D are graphs showing inhibition of cell proliferation as a function of indicated myostatin binding protein concentration. Blocking of myostatin-induced inhibition of cell proliferation was measured by absorbance at 450 nM using CCK-8 kit, with absorbance of growth media subtracted, and absorbance of cells untreated with myostatin assigned as 100%. Myostatin, used at a concentration of 125 ng/mL inhibited cell proliferation to approximately 20% of untreated cells. Values are means+/−S.D., n=3 replicates.

Recombinant human activin A, GDF11 and myostatin inhibit cell proliferation of mouse myeloma cells (MPC-11) in a dose-dependent manner (FIG. 16). F13β2 myostatin binding proteins from different sequence groups were found in the MPC-11 cell assay to antagonize the biological function of myostatin (FIGS. 17A-17D). Several binders from group M1-A50 (M3, M34), group M2-A50 (M7, M019, and M10) and group M1-A (M1-1, M2-1, and M3-1) showed inhibition activity at high concentrations. The binders from group M3-A50 (M56, M71, and M07) neutralized the myostatin activity in a dose-dependent fashion with better affinities (IC50s as low as 150-200 nM). The potency of inhibition appeared to be ten times lower than that of activin receptor IIB. The difference in potency in biological assay correlated with the affinity to the target and biophysical properties of the proteins: binders from group M3-A50 are highly potent against myostatin and have good biophysical properties as shown by their solubility profile. The presence of a cysteine residue in DE loop of group M3-A50 binders (M020, M02, M05, and M16) decreased their biological activity. It is possible that additional cysteine destabilized the proteins during the assay (conducted at 37° C. over 3 days) and/or formed nonspecific complexes with other proteins in the reaction media. The activity of tagless F13β2 proteins purified by acidic conditions was tested in the MPC-11 proliferation assay in which they also showed inhibition activity towards myostatin. This indicates that the acidic extraction procedure allows us to obtain fully functional F13β2 binder proteins. Additionally, the selected myostatin binders antagonized the activity of GDF11, another member of TGFβ family, which has high sequence identity to myostatin (89.9%). However, no inhibition of activin A biological action on MPC-11 cells was observed with myostatin binders. Activin A is distantly related to myostatin (sequence identity of 33.3%) and binds to the same receptors—activin receptor IIA and activin receptor IIB. This indicates that the binders are selective for myostatin and closely related proteins, but do not recognize distant members of the same family.

Example 9

Characterization of Pegylated Myostatin ETBP

For application in vivo, fusions of therapeutic proteins with other proteins, peptides or polyethylene glycol are widely used to produce molecules with longer half-life; in addition PEG-substituted proteins are known to exhibit reduced immunogenicity. One advantage of using a small scaffold protein that does not have a structural requirement for free cysteines is the possibility of introducing one or more surface-exposed cysteines to facilitate substitution with prosthetic groups, crosslinking to other proteins, or substitution with polymers such as linear or branched polyalkylene glycols.

To introduce a single cysteine into the C-terminus of myostatin binder DNA from myostatin binding clone F10 was amplified by PCR with primers oligo 53 and oligo AKx226 to introduce NdeI site at 5' end, and PCM-Stop sequence and XhoI site at 3' end, respectively. The binder protein was expressed in *E. coli* by using a modified pet28(a+) vector. Protein expression was induced with 0.25 mM IPTG for 3 hours at 37° C. and the insoluble pellet was dissolved using acidic conditions as described above for tagless myostatin binding proteins. The protein was pegylated with Y-MAL-40K (Y-Shape PEG Maleimide, JenKem Technology USA Inc., Allen, Tex.) (FIG. 18A). The pegylation reaction was performed at 4° C. under argon in 1×PBS, 2 mM EDTA using protein concentration of 1.5 mg/ml and 4:1 molar ratio of Y-MAL-40K and protein. After 20 hours the protein was dialyzed into 1×PBS, pH 7.4, and analyzed by SDS-PAGE (FIG. 18B). The activity of the pegylated F10 binder in MPC-11 cell bioassay was similar to the free protein.

Example 10

Production of ETBP Dimers in *E. Coli*

Dimerization or multimerization of binder molecules separated by various linker sequences can potentially increase binding activity towards a target protein by increases in avidity. Dimerized or multimerized molecules may also have more favorable serum persistence characteristics by virtue of their ability to escape renal filtration. To explore these possibilities we constructed a homodimer of selected myostatin binder E3.

DNA from myostatin binder clone E3 was amplified by PCR with primers oligo 53 and AKx169 to introduce NdeI at 5' end, and PSM-His6-tag-Stop sequence ("His6" disclosed as SEQ ID NO: 29) and XhoI site at 3' end, respectively. PCR product was cloned into modified pet28(a+) vector. To introduce a second E3 domain into expression vector, DNA from myostatin binder clone E3 was amplified by PCR with primers AKx202 and AKx203 to introduce XbaI site, an initiator methionine codon and glycine codon at 5' end, and NNSNNSNNSNNSNNSNNS linker (SEQ ID NO: 208) sequence and NdeI site at 3' end, respectively. The PCR product was cloned into XbaI and NdeI sites of modified pet28(a+) vector containing E3 clone, described above. The configuration of the dimer molecule is shown in FIG. 19A.

Approximately 100 independent clones were analyzed by expression in *E. coli* BL21 (DE3) pLysS cells (Invitrogen). Protein expression was induced with 0.25 mM IPTG for 3 hours at 37° C. and the protein was solubilized at acid pH from the insoluble pellet as described above for tagless myostatin binding proteins. Total, soluble and extraction fraction were analyzed by SDS-PAGE (FIG. 19B). Approximately 0.1 mg of protein was produced from 1 ml of culture for different E3 homodimers. When the activity of high-producing E3 homodimer proteins was analyzed in MPC-11 cell proliferation assay they exhibited improved biological activity compared to the single domain.

Example 11

Selection of ETBPs Against Human Nerve Growth Factor (β-NGF)

Nerve growth factor, the founding and best-characterized member of the neurotrophin family, plays a central role in the development, maintenance and survival of the peripheral and central nervous system. It has been proposed as a therapeutic target molecule in many pathological states such as Alzheimer's disease, nervous system injuries, inflammatory or neuropathic pain states, several human malignancies and asthma.

Figure 20:
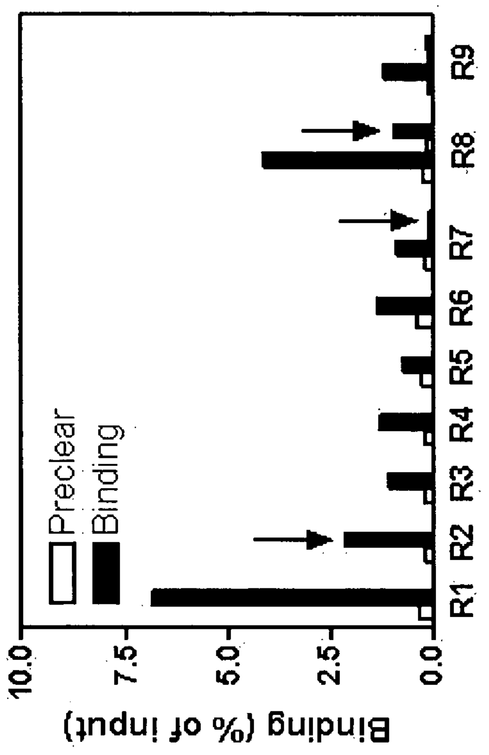
FIG. 20 is a graph showing binding of A-50% NNS library to human β-NGF. Binding to the beads (preclear) and to the target (binding) was measured as a percentage of input radioactivity. Human β-NGF concentrations used in the selections were as follows: R1 (250 nM), R2-R6 (100 nM), R7-R8 (10 nM), R9 (1 nM). Selection pools used for further fusion production after target concentration drop are marked with an arrow.

F13β2 mRNA A-50% NNS fusion library was used in in vitro selection against biotinylated human β-NGF. Fusion production and selection procedure was performed as described above for myostatin selections. The selection was performed for nine rounds (FIG. 20), and lower target concentrations and prolonged washes were utilized in later rounds of selection to favor clones with better affinities. Starting from round 2 third wash was performed for 15 minutes at 30° C. From round 3 fusion incubation with the target and third wash were performed for 30 and 45 minutes at 30° C., respectively. Final concentrations of biotinylated human β-NGF used in the selections were as follows: R1 (250 nM), R2-R8 (100 nM), R7-9 (10 nM); R9 (1 nM). After the NGF concentration was decreased to 10 nM in round 7 the specific binding to 100 nM of the target increased in round 8. Selection was stopped at round 9 following target decrease to 1 nM. PCR DNA of selection pools after rounds 6, 8 and 9 was cloned into pCR®2.1-TOPO® vector (Invitrogen), and single clones were analyzed by sequencing of 32-96 clones.

The sequences of the binding loops are shown in Table 4. Several consensus motifs were selected under stringent conditions in rounds 8 and 9: group N1 (BC loop—TNPL NEPLLF (SEQ ID NO:22), DE loop—RIISPHAT (SEQ ID NO:23), FG loop—SIGFQA (SEQ ID NO:24)); group N2 (BC loop—INTSNETLPS (SEQ ID NO:25); DE loop—PEI PPNSS (SEQ ID NO:26), FG loop—IRDSSR (SEQ ID NO:27), Δ67-70, P71A) and group N3 (BC loop—TN LSNETLGT (SEQ ID NO:28), DE loop—PHIRPKVT (SEQ ID NO:30); FG loop—LIASLR (SEQ ID NO:31)). Group N2 binders have a four amino acid deletion at the end of E β-sheet and the beginning of EF loop. Additional mutation of proline to alanine (P71A) in this region probably adds more flexibility to the EF loop and this part of the scaffold. This change could possibly shift the DE loop and expose the BC loop binding site. Indeed, BC loop in this group of binders carriers majority of mutations (6 out 9 residues are changed) compare to the other two loops (in both DE and FG loops 6 amino acids are mutated) and may play the major role in binding to the target.

TABLE 4

Selected β-NGF binders (grouped by FG loop sequence)

| BC loop | SEQ ID NO: | DE loop | SEQ ID NO: | FG loop | SEQ ID NO: | Scaffold mutation | In vitro clone | Kd, nM | B max, % |
|---|---|---|---|---|---|---|---|---|---|
| Group N1 | | | | | | | | | |
| TNPLNEPLLF | 22 | RIISPHAT | 23 | SIGFQA | 24 | | Typical sequence | | |
| TNPLNEPLLF | 22 | RIISPHAT | 23 | SIGFQA | 24 | | 61362-C6 | 24.0 | 5.5 |
| TNPLNEPLLF | 22 | RIISPHAT | 23 | SIGFQA | 24 | mut | | | |
| TNPLNEPLLF | 22 | RIISPHAT | 23 | SVGFQA | 288 | mut | | | |
| TNPLSEPLLF | 209 | RIISPHAT | 23 | SIGFQA | 24 | mut | | | |
| TNPLNDPLLF | 210 | RIISPHAT | 23 | SIGFQA | 24 | mut | | | |
| TNPLNEPLFF | 211 | RIISPHAT | 23 | SIGFQA | 24 | | | | |
| TNPLNEPLLF | 22 | PIISPHAT | 253 | SIGFQA | 24 | | | | |
| TNPLNEPLLF | 22 | RIITPHAT | 254 | SIGFQA | 24 | mut | | | |
| FNAQTEALRD | 212 | RIISPHAT | 23 | SIGFQA | 24 | mut | | | |
| INTSNETLPS | 25 | PEIPPNSS | 26 | IRDSSR | 27 | Δ67-70, P71A | Typical sequence | | |
| INTSNETLPS | 25 | PEIPPNSS | 26 | IRDSSR | 27 | Δ67-70, P71A | 61362-F2 | 62.0 | 35.4 |

TABLE 4-continued

Selected β-NGF binders (grouped by FG loop sequence)

| BC loop | SEQ ID NO: | DE loop | SEQ ID NO: | FG loop | SEQ ID NO: | Scaffold mutation | In vitro clone | Kd, nM | B max, % |
|---|---|---|---|---|---|---|---|---|---|
| INTSNETLPS | 25 | PEIPPNSS | 26 | IRDSSR | 27 | Δ67-70, P71A, mut | | | |
| INTSNETLPS | 25 | PEIPPNSS | 26 | IRDSSR | 27 | Δ67-70, P71T, mut | | | |
| INTSNETLPS | 25 | PEIPPNSS | 26 | IRDSSR | 27 | Δ67-70, P71S, mut | | | |
| INTSNETLPS | 25 | PEIPPNSS | 26 | IRDSSR | 27 | Δ67-70, P71V, mut | | | |
| TNTSNETLPS | 213 | PEIPPNSS | 26 | IRDSSR | 27 | Δ67-70, P71A, mut | | | |
| TNLSNETLPS | 214 | PEIPPNSS | 26 | IRDSSR | 27 | Δ67-70, P71A, mut | | | |
| TNTTNETLPS | 215 | PEIPPNSS | 26 | IRDSSR | 27 | Δ67-70, P71A, mut | | | |
| INTSDETLPS | 216 | PEIPPNSS | 26 | IRDSSR | 27 | Δ67-70, P71A | | | |
| INTSNKTLPS | 217 | PEIPPNSS | 26 | IRDSSR | 27 | Δ67-70, P71A, mut | | | |
| INTSNEALPS | 218 | PEIPPNSS | 26 | IRDSSR | 27 | Δ67-70, P71A, mut | | | |
| INTSNETLPR | 219 | PEIPPNSS | 26 | IRDSSR | 27 | Δ67-70, P71A, mut | | | |
| INTSNETLPS | 25 | PKIPPNSS | 255 | IRDSSR | 27 | Δ67-70, P71A, | | | |
| INTSNETLPS | 25 | PEIPPKSS | 256 | IRDSSR | 27 | Δ67-70, P71A, mut | | | |
| INTSNETLPS | 25 | PEIPPNFS | 257 | IRDSSR | 27 | Δ67-70, P71A | | | |
| INTSNETLPS | 25 | PEIPPNSS | 26 | IQDSSR | 289 | Δ67-70, P71A | | | |
| INTSNETLPS | 25 | PEIPPNSS | 26 | IRDSPR | 290 | Δ67-70, P71A | | | |
| TPAVKDKLPK | 220 | PEIPPNSS | 26 | IRDSSR | 27 | Δ67-70, P71A, mut | | | |
| TNPLNEPLLF | 22 | PEIPPNSS | 26 | IQDSSR | 291 | Δ67-70, P71A, mut | | | |
| STHLVPTLRN | 221 | PEIPPNSS | 26 | IRDPSR | 292 | Δ67-70, P71A, mut | | | |
| TIPCQSTLNS | 222 | NDIHLYSS | 258 | IRDSSR | 27 | mut | | | |
| | | | | Group N3 | | | | | |
| TNLSNETLGT | 28 | PHIRPKVT | 30 | LIASLR | 31 | | Typical sequence | | |
| TNLSNETLGT | 28 | PHIRPKVT | 30 | LIASLR | 31 | | | | |
| TNLSNETLGT | 28 | PHIRPKVT | 30 | LIASLR | 31 | mut | | | |
| TDTVLEILRT | 223 | PHIRPKVT | 30 | LIASLR | 31 | mut | 61363-C1 (G17D) | 2.8 | 1.8 |
| INTSNETLPS | 25 | PEIPPNSS | 26 | LIASLR | 31 | Δ67-70, P71A, mut | | | |
| TNPMNITLHH | 224 | SQIRPKVT | 259 | IIASLR | 293 | mut | | | |
| | | | | Group N4 | | | | | |
| TNPLEENLYN | 225 | YQISTNIP | 260 | GAHTKD | 294 | mut | 61363-C12 (G45E) | 36.0 | 33.6 |
| TNLSEENLGT | 226 | PHIRPKVP | 261 | GAHTKD | 295 | mut | | | |
| INHKEGTLPQ | 227 | GDIHPKFT | 262 | IVAYLY | 296 | mut | | | |
| INTSNETLPS | 25 | PEIPPNSS | 26 | INDPLL | 297 | Δ67-70, P71A | | | |
| INTSNETLPS | 25 | PEIPPNSS | 26 | IIATLR | 298 | Δ67-70, P71A, mut | | | |
| TTPLKERLRK | 228 | LEISPKSK | 263 | ISVSLH | 299 | | | | |
| TNALKDTLII | 229 | REISPNSS | 264 | TSYSRG | 300 | mut | | | |
| TNPLKETLYN | 230 | WEIRTNHP | 265 | SSNSRD | 301 | mut | 61363-H1 (V15A) | 22.9 | 8.4 |
| TIPLQDIL-N | 231 | FSIRMTPA | 266 | SFHTHR | 302 | mut | 61362-B8 (I23L) | 3.8 | 2.1 |
| TNTLLETLGT | 232 | SAISRRSI | 267 | STESLR | 303 | mut | | | |
| TKALKGTLGN | 233 | WNITQHQT | 268 | SSDSPR | 304 | | | | |
| SGTLSGTLLT | 234 | LDIHPNPT | 269 | NSNSLW | 305 | | | | |
| TNTRKDILGT | 235 | HGIHANTS | 270 | NSDFLR | 306 | mut | | | |
| SNHLKHTLVD | 236 | RVIRPVST | 271 | RSVYIH | 307 | | | | |
| TNAHNTTLLH | 237 | RAIGQKSE | 272 | SWHFDR | 308 | | | | |
| NYPLQETLPK | 238 | LWIFPNAP | 273 | SSHSHF | 309 | mut | | | |
| TTRPHAALLN | 239 | SVIQTDPT | 274 | SYATTR | 310 | mut | | | |
| TLPLKESLGT | 240 | HTIRRTPN | 275 | SLDTHR | 311 | | | | |
| ASPMKLTLRY | 241 | CEIRQYCS | 276 | RRNPMA | 312 | | | | |
| TNPLRDTLDT | 242 | RQIRPIAT | 277 | WAVAPC | 313 | mut | | | |
| TYRHWGTLCK | 243 | LDIRPDST | 278 | NTCSLL | 314 | | | | |
| SSTLSGRLQH | 244 | QEIRQNST | 279 | CTYSPW | 315 | mut | | | |
| AQPVKLTLRR | 245 | CEIRLYSM | 280 | IIGGTL | 316 | | | | |
| TNRPNEKLRK | 246 | REIRARST | 281 | RYDGYC | 317 | mut | | | |
| TYTRKEMLHN | 247 | RDIHENFC | 282 | RSDNLL | 318 | mut | | | |

TABLE 4-continued

| Selected β-NGF binders (grouped by FG loop sequence) | | | | | | | | | | |
|---|---|---|---|---|---|---|---|---|---|---|
| BC loop | SEQ ID NO: | DE loop | SEQ ID NO: | FG loop | SEQ ID NO: | Scaffold mutation | In vitro clone | Kd, nM | B max, % |
| TSLVQEPLCH | 248 | SGIRPYST | 283 | GRQTLH | 319 | mut | | | |
| NCTLKETLIN | 249 | DEIWTNLI | 284 | CSNRLL | 320 | | | | |
| CHTQISTLRY | 250 | PEIREPCD | 285 | NSHFLR | 321 | mut | | | |
| TRHMTEPLRI | 251 | RVICIDFI | 286 | RSYSRR | 322 | mut | | | |
| SNGLNGTLRE | 252 | REILPEST | 287 | STVSQI | 323 | mut | | | |

Amino acids mutated from wild type after selection are underlined and marked in bold.

Example 12

Measurement of Affinity of Selected NGF ETBPs In Vitro

Figure 21:
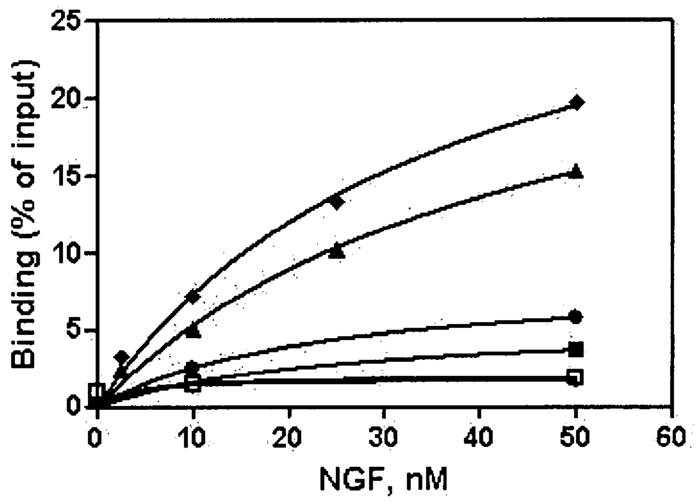
FIG. 21A is a table showing characterization of binding affinities of selected molecules to human β-NGF. Binding affinities were measured in a radioactive equilibrium binding assay.
FIG. 21B is a graph showing binding as a percentage of input of the indicated construct to the indicated concentration of NGF.

Selected F13β2 binders were tested for binding to biotinylated β-NGF in radioactive equilibrium binding assay (FIGS. 21A and 21B; Table 4) according to the procedure described for myostatin binders. NGF at concentrations up to 100 nM was incubated with a constant concentration of the purified binder protein (1 or 2 nM) at 30° C. for 1 hour. Affinities to human β-NGF differed greatly between various binders. Proteins from groups N1 and N3 bound NGF only with low affinities: binding to 50 nM of NGF did not exceed 5% of input. Binders from groups N2 and N4 interacted with β-NGF with Kd less than 100 nM. No binding to M-280 beads was observed indicating that the selected molecules interact specifically with human β-NGF.

Example 13

Selection of ETBPs Against Human IgE Receptor FcϵRI

The immunoglobulin IgE signaling cascade plays a central role in mediating allergic reactions. Blockade of this pathway has been considered a strategy for treating allergic diseases, including asthma, Crohn's disease, allergic rhinitis and peanut allergy. Upon cross linking by IgE, the high affinity IgE receptor FcϵRI initiates the signaling through its cytoplasmic immunoreceptor tyrosine-based activation motif (ITAM). The interaction between IgE and FcϵRI involves the two CH3 domains of IgE engaging the extracellular domain of FcϵRI (reviewed in Kraft & Kinet, 2007). In principle, the displacement of the interaction partners by competitive molecules should lead to inhibition of this signaling process. The only therapy based on this principle has been the anti IgE antibody (Xolair, Genentech). As another example of ETBP, we have selected binding molecules to the extracellular domain of human FcϵRI.

Figure 22:
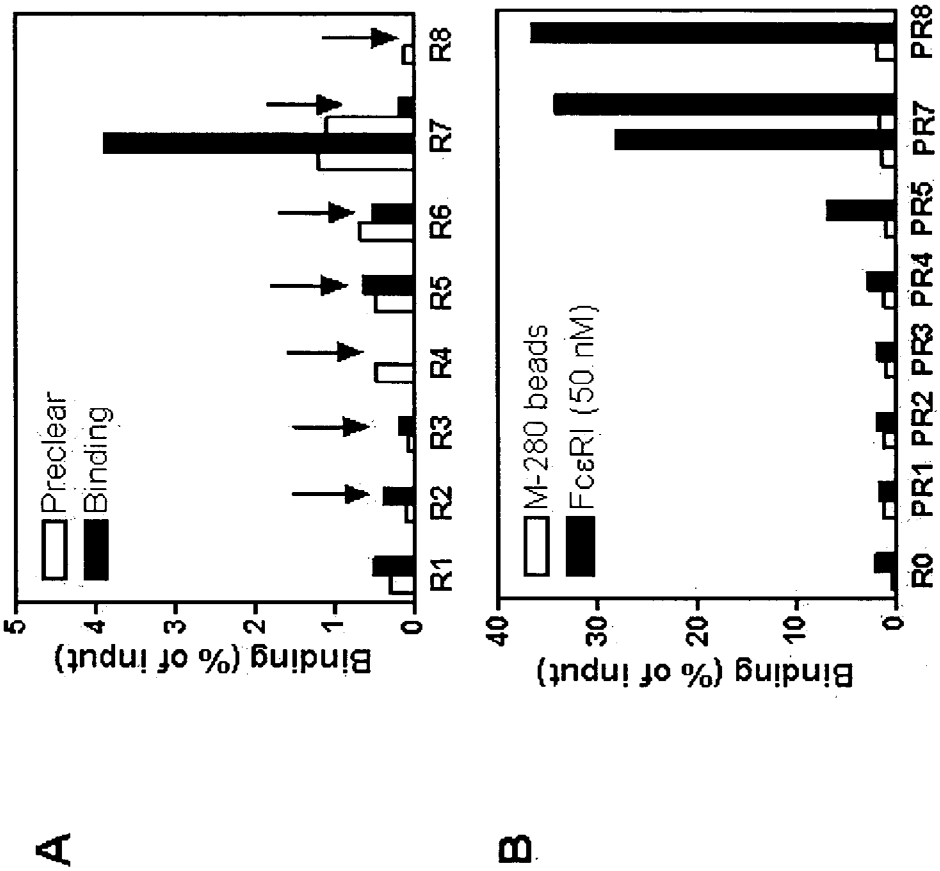
FIG. 22A is a graph showing binding of Aext-NNS library as a percentage of input to beads (Preclear) and target (Binding). Human FcεRI concentrations used in the selections were as follows: R1 (100 nM), R2 (50 nM), R3 (25 nM), R4 (12.5 nM), R5 (6.25 nM), R6 3.125 nM), R7 (16 and 1.6 nM), R8 (0.1 nM). Selections pools used for further fusion production after target concentration drop are marked with arrows.
FIG. 22B is a graph showing binding of the library (R0) and of free protein as a percentage of input after each rond (PR1-5, 7, 8) to the beads and to the target (50 nM) as measured in a radioactive equilibrium binding assay.
Figure 23:
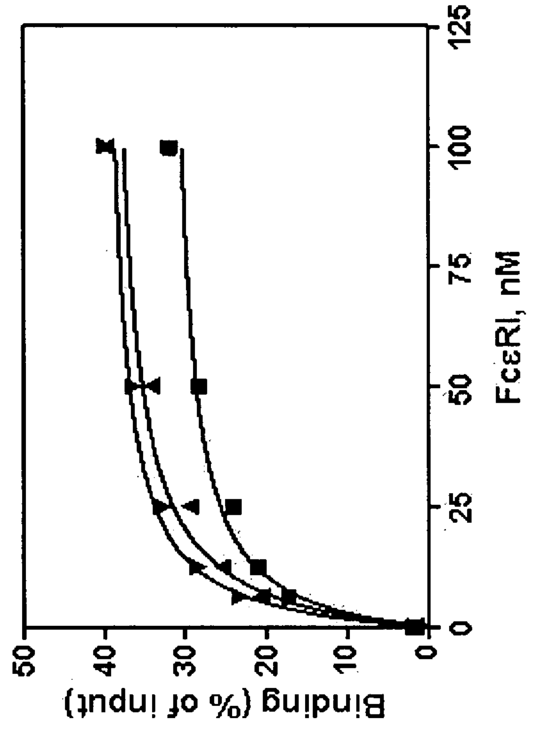
FIG. 23 is a graph and table showing binding as a percentage of input of indicated binding pools to human FcεRI.

F13β2 mRNA Aext-NNS fusion library was used in in vitro selection against biotinylated human FcϵRI. Fusion production and selection procedure was performed similar to myostatin selections. The selection was continued for eight rounds (FIGS. 22A and 22B). To achieve a rapid selection of the binders with high affinities to the target the concentration of FcϵRI was dropped twice in each round. Final concentrations of biotinylated human FcϵRI used in the selections were as follows: R1 (100 nM), R2 (50 nM), R3 (25 nM), R4 (12.5 nM), R5 (6.25 nM), R6 (3.125 nM), R7 (16 and 1.6 nM), R8 (0.1 nM). Specific binding of selection pool to the target increased after round 5, which is seen in free protein binding profile (FIG. 22B). PCR DNA of PR5 selection pool was cloned into pCR®2.1-TOPO® vector (Invitrogen), and single clones were analyzed by sequencing of 48 clones. The sequences of the binding loops are shown in Table 5. The loop sequences are very different and no sequence motif was selected after round 5 although the protein pool showed specific binding to the target. In the next rounds the pool binding increased significantly (FIG. 22B). The selection was stopped at round 8 following target decrease to 0.1 nM. The binding affinities of selected protein pools after round 7 and 8 were measured in a radioactive binding assay (FIGS. 23A and 23B). The proteins interacted with human FcϵRI with very high affinities as low as 5 nM while no non-specific binding to M-280 beads was observed.

TABLE 5

| Selected FcϵRI binders | | | | | | |
|---|---|---|---|---|---|---|
| BC loop | SEQ ID NO: | DE loop | SEQ ID NO: | FG loop | SEQ ID NO: | Scaffold mutation |
| KGTGSKQ | 324 | GDIVSS | 347 | FSAQRPNLVTLL | 370 | mut |
| QSTMRLW | 325 | KMILTR | 348 | YDSGFFPTVVIT | 371 | |
| GRLELRE | 326 | LTILYP | 349 | LFVARSKMQLAR | 372 | mut |
| ELRFPLM | 327 | ERIMVI | 350 | TSSKAFDANTNE | 373 | mut |
| LLVGRAV | 328 | RLILAR | 351 | VPGWTGAPMTVN | 374 | mut |
| GSNKIIL | 329 | LYIRIN | 352 | AATKRLRYKPAA | 375 | mut |
| EDKVTHS | 330 | TFIFXF | 353 | SCPDAVXTKSTK | 376 | |
| LGHEVAE | 331 | MVIQSV | 354 | LKLLLDSSVGST | 377 | mut |
| LSNASMP | 332 | TCIWXC | 355 | LRLSGWRIFNTK | 378 | mut |
| AAKITMW | 333 | LVIVPR | 356 | NVNRVEPMGLPP | 379 | mut |
| GEYKDPT | 334 | VRIWFP | 357 | LRSMKIWTNDTS | 380 | mut |
| MVPEGAS | 335 | NSIERL | 358 | GHDESPKNRSAD | 381 | |
| DYMARAQ | 336 | QSISQG | 359 | ANADLIIHGTNL | 382 | mut |
| CSTVKIR | 337 | TQIDRP | 360 | TKRWNTADLSAR | 383 | |
| PRWEPGE | 338 | YIIFRI | 361 | VDGADVLWTLRP | 384 | |
| APKLKDD | 339 | RIIFPW | 362 | LLFARSNQGWKV | 385 | |
| RPPRRLL | 340 | GKITLQ | 363 | FLLWVHSFVSRW | 386 | mut |
| PRPIQII | 341 | GFIQAI | 364 | KDPYHCKPHDVS | 387 | mut |
| LLTTSFR | 342 | NMILLP | 365 | LPVIIKTNSNQV | 388 | mut |
| QEILSNL | 343 | NVIVMI | 366 | ISTVANVDTGTR | 389 | |

TABLE 5-continued

Selected FcεRI binders

| BC loop | SEQ ID NO: | DE loop | SEQ ID NO: | FG loop | SEQ ID NO: | Scaffold mutation |
|---|---|---|---|---|---|---|
| **RPDEDGS** | 344 | **EM**I**MER** | 367 | **LSWTKVDKTYVV** | 390 | mut |
| **VQHYLAR** | 345 | **FG**I**DDP** | 368 | **IYGPDLEVCRLW** | 391 | |
| L**MAGDSR** | 346 | **TL**I**A**P**Y** | 369 | **LSDGGIRGQWMV** | 392 | mut |

Amino acids mutated from wild type after selection are underlined and marked in bold.

Example 14

Characterization of Wild Type F13β1 Scaffold

Figure 24:
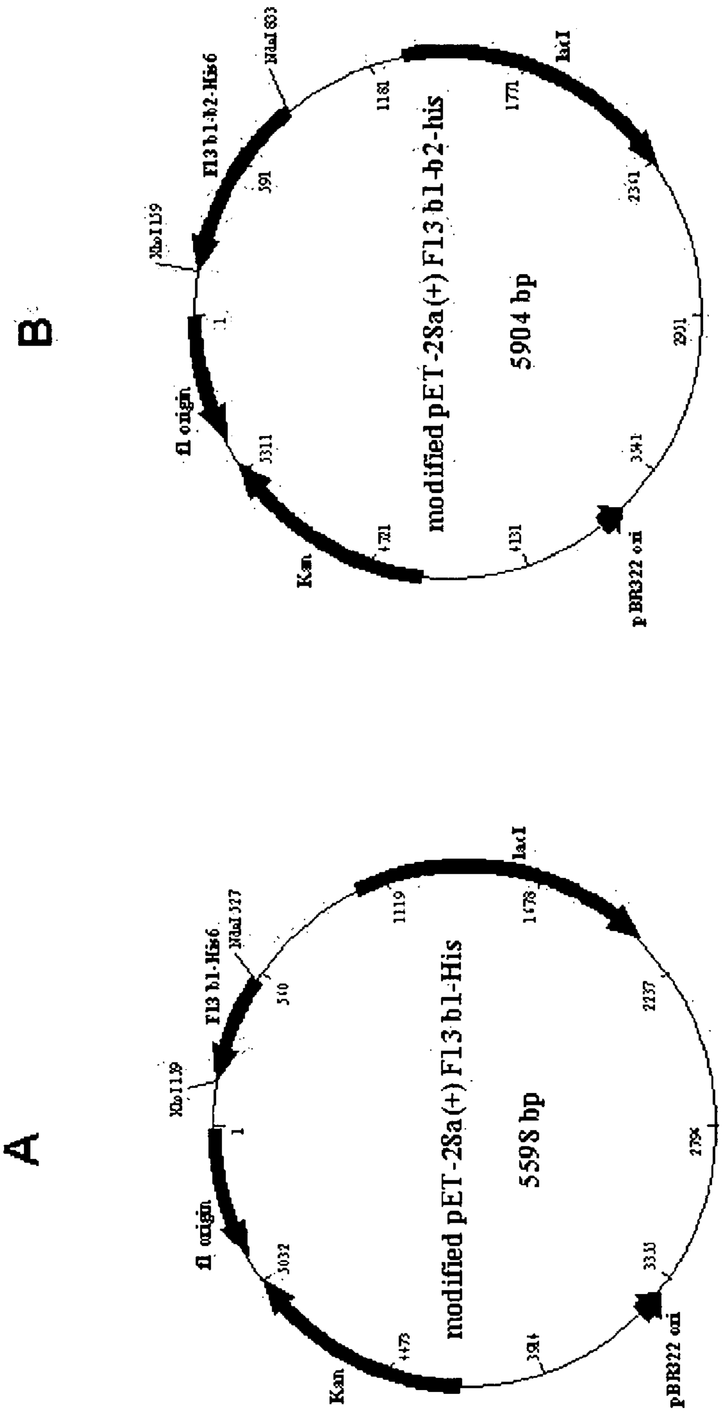
FIGS. 24A and 24B are schematics showing maps of expression plasmids for F13β1 scaffold and F13β1β2 heterodimer.

According to the crystal structure two distinct domains with a seven-stranded β-barrel fold are located at the carboxyl terminus of the FXIII-A monomer: β-barrel 1 and β-barrel. Domain β-barrel 1 contains residues S517 through L628 and is a little larger than β-barrel 2 due to its loop segments. The two barrels are structurally very similar, but there is no significant sequence similarity between them. Both of these domains were shown to be highly thermostable. To characterize the expression of an isolated barrel 1 domain in *E. coli* we amplified F13β1 sequence (S517-L628) from full length factor XIIIA cDNA clone (SC120099; OriGene Technologies, Inc., Rockville, Md.) by PCR with primers oligo 60 and oligo 62rev to introduce NdeI at 5' end, and His6-tag-Stop sequence ("His6" disclosed as SEQ ID NO: 29) and Barn HI site at 3' end, respectively. The resulting fragment was cloned into NdeI and BamHI sites of a modified pet28(a+) vector. The map of the plasmid (modified pet28(a+)-F13(1-His6 "His6" disclosed as SEQ ID NO: 29)) is shown in FIG. 24A. Tagless F13β1 domain and F13β1-GFP fusion were constructed by using primers oligo EG1rev and oligo 61rev for 3' end in PCR, respectively. The correct sequence of F13β1 scaffold was confirmed by sequencing. The sequence corresponded to the published sequence of Factor XIII-A (accession number NP_000120) (FIG. 25). The protein was expressed in *E. coli* BL21 (DE3) pLysS cells (Invitrogen) under different temperature conditions, and the solubility profile was assessed as described above for F13β2 myostatin binders. Although a small portion of F13β1 protein was soluble at 18° C. (FIG. 26A) and could be purified via affinity chromatography, the majority of the protein remained in the insoluble fraction.

Figure 26:
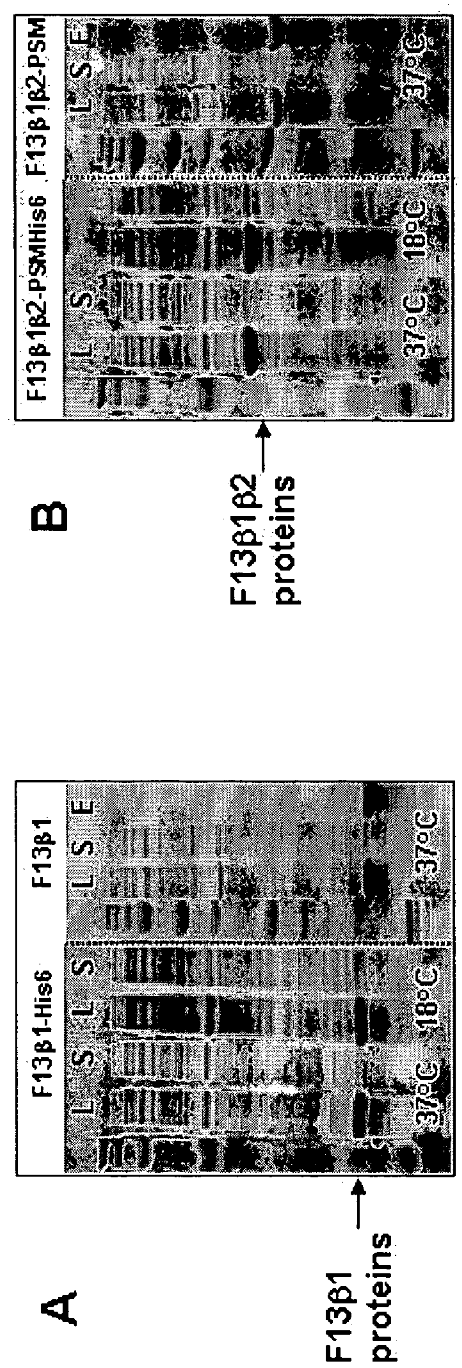
FIGS. 26A and 26B are images of SDS-PAGE gels showing expression of the indicated proteins at the indicated concentrations.

To characterize the ability of an isolated barrel 1 domain to autonomously fold in *E. coli* a fusion of the human β-barrel 1 domain joined at its C-terminus to GFP was studied for solubility in 1×PBS, pH 7.4. Although F13β1-GFP protein remained in insoluble pellet it was correctly folded, which was indicated by strong green fluorescence of GFP in the pellet. Previously, it was shown that both β-barrel domains of FXIII-A remained folded at low pH. Using the acidic condition (36 mM HCl) applied earlier for purification of F13β2 myostatin binders we were able to dissolve the F13β1 scaffold (FIG. 26A). Thus high solubility in low pH is a feature of not only isolated domains but also of proteins with more than one barrel of the Transglut_C family. As the behavior of the fusion with GFP indicates, fusions to transglutaminase barrel proteins can be used to allow the fused moiety to be purified by selective solubility at low pH.

Example 15

Diversification of F13β1 Scaffold

Figure 27:
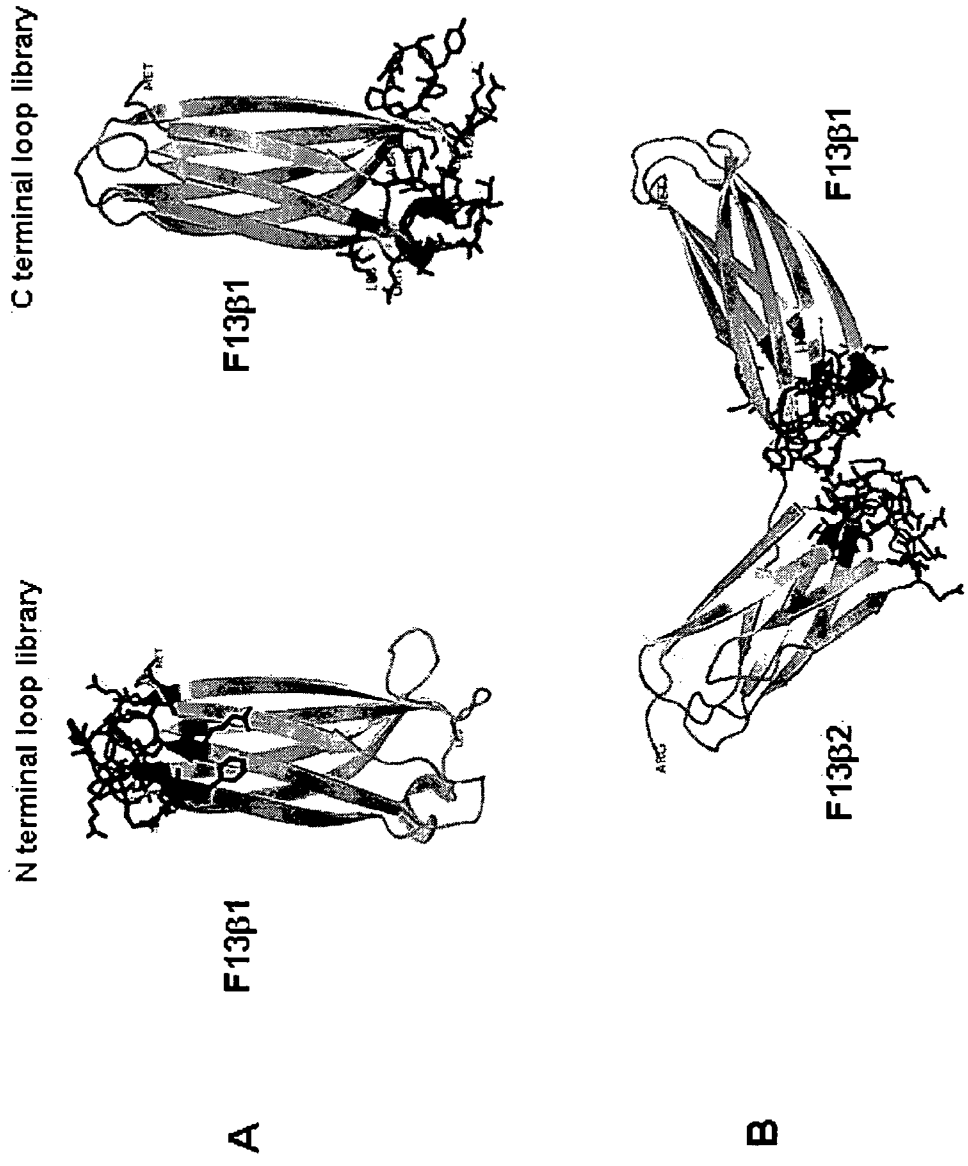
FIGS. 27A and 27B are schematics of the proposed F13β1 (27A) and F13β1β2 (27B) libraries. Potential randomization in BC, DE, FG, and AB, CD, EF loops are colored in black.
Figure 28:
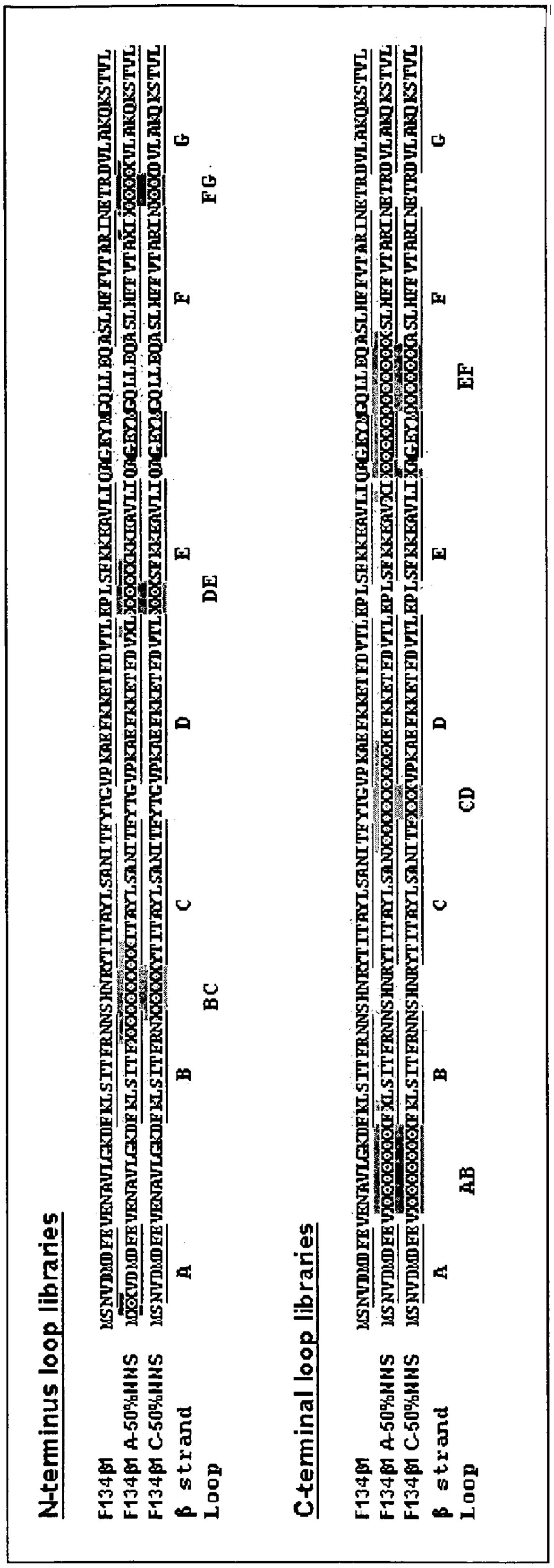
FIG. 28 is an alignment showing the protein sequences (SEQ ID NOS: 643-648, respectively, in order of appearance) of the proposed F13β1 libraries. B-strands are underlined; randomized (NNS) residues are highlighted in gray and substituted with X.

The β-barrel 1 domain of Factor XIII is also a good candidate for an alternative scaffold either in the form of a single domain or as an element of a F13β1β2 heterodimer (FIGS. 27A and 27B). Similar to the F13β2 scaffold six potential loops for randomization are present in F13β1 structure: at least 21 and 33 residues can be mutated in the N-terminal loop region and the C-terminal loop region of the domain, respectively (FIG. 28).

By utilizing F13β1β2 heterodimer as a scaffold several binding sites could be placed on one molecule: for example, six variable loops would contribute to the binding site via randomization of F13β1 C-terminal loop region and F13β2 N-terminal loop region (FIG. 27B).

Example 16

Characterization of Wild Type F13β1β2 Heterodimer

To construct a F13β1β2 heterodimer wild type optimized F13β2 domain was amplified by PCR with oligo 129 and oligo 126rev to introduce NdeI site and part of F13β1 domain (positions D617-L627) at 5' end, and PSM-His6-tag-Stop sequence ("His6" disclosed as SEQ ID NO: 29) and Barn HI site at 3' end, respectively. To insert the additional cloning site AatII two silent mutations were introduced at D618 and V619 positions of F13β1 domain. The resulting fragment was cloned into NdeI and BamHI sites of a modified pet28(a+) vector. F13β1 domain (S517-L628) was amplified from full length factor XIIIA cDNA clone (SC120099; OriGene Technologies, Inc., Rockville, Md.) by PCR with primers oligo β2 (NdeI) and oligo β6 rev (AatII) and cloned into NdeI and AatII sites of modified pet28(a+) vector, containing F13β2 domain (see above). The map of the plasmid (modified pet28(a+)-F13β1β2-His6 "His6" disclosed as SEQ ID NO: 29)) is shown in FIG. 24B. To generate proteins, containing PSM-Stop sequence or GFP fusion at the C-terminus, primers oligo AKx299 (XhoI) or oligo 52rev (Bam HI) were used for 3' end in PCR, respectively. The protein was expressed in *E. coli* BL21 (DE3) pLysS cells (Invitrogen) under different temperature conditions, and solubility profiles were assessed as described above for F13β2 myostatin binders. A small fraction of F13β1β2 heterodimer was soluble at 18° C. (FIG. 26B) and could be purified via affinity chromatography. To characterize the folding of an isolated β1β2 heterodimer in *E. coli* an F13β1β2-GFP fusion was studied for solubility in 1×PBS, pH 7.4. Correct folding was suggested by the strong GFP signal of the insoluble pellet. As for the F13β1 domain, the heterodimer of β1 and β2 barrels could be solubilized by exposure to acid (FIG. 26B).

Example 17

Display of ETBPs on Bacterial Phage

Phage display has been widely used in selecting peptides and proteins that bind desired targets with high affinity and selectivity. A translational fusion is made between the displayed peptide or protein and a phage coat protein. When the fusion protein is expressed and assembled into a phage particle in bacterial host cells, a physical linkage of phenotype (displayed protein or peptide) and genotype (DNA encoding the displayed protein or peptide) is made, which renders reiterated selections feasible. In the current invention, we have developed reagents and methods for the display of discrete or sequence-diversified ETBPs in phagemid vectors based on the filamentous bacterial phage M13. We describe construction of phage display vectors and diversified libraries of FXIIIβ barrel proteins. We demonstrate their untility for identifying ETBPs by affinity selection using phage display.

Display Vector Design

Filamentous bacterial phage M13 was employed to display ETBPs. Both phage and phagemid vectors have been used in phage display in general. Phage vectors typically encode all phage proteins as well as the displayed peptide or protein fused to a phage coat protein. A phagemid is a plasmid vector that contains an *E. coli* origin of replication and a phage origin for single stranded DNA production to allow its packaging into phage particles when other phage proteins are expressed from a helper phage genome. A number of phage coat proteins have been used as fusion partners and the product of gene III (pIII) has been the most widely used. In the absence of wild type pIII expression, five copies of fusions are expected to be displayed on a phage particle. When wild type pIII is expressed from the helper phage genome, pIII fusion copy numbers are variant depending on the display system, theoretically ranging from 0-5 copies per phage. Display copy number is an important parameter that can alter the outcome of selection. When the copy number is more than one, an avidity effect allows display phage to bind targets at an apparent affinity better than the displayed molecule's intrinsic affinity when it is uncoupled from the phage. Multivalency exerts in an avidity effect on targeting binding which renders inefficient discrimination of binders with different affinities in selections, but can be advantageous when low affinity binders are expected from a library such as short peptides. The ability to modulate display copy number is therefore preferred in a phage display system. This can be achieved through a number of strategies, including different fusion partner (pIII or pVIII, for example), different helper phage and the use of promoters that are amenable to regulation. We have employed the lacZ and pBAD promoters to display ETBPs to provide different ways to modulate fusion copy number. The pBAD promoter is known for its tight regulation. AraC positively regulates pBAD and also acts as a repressor of its own expression. pBAD has been proposed for phage display of proteins that might be toxic for the host cells. The lacZ promoter has been widely used in phage display. Basal expression from lacZ promoter is commonly used in displayed fusion protein expression. The possibility to use inducer or repressor to modulate expression makes the lacZ promoter an attractive choice for phage display. In the current invention, we provide methods and compositions using phagemid vectors to display ETBPs.

Figure 29:
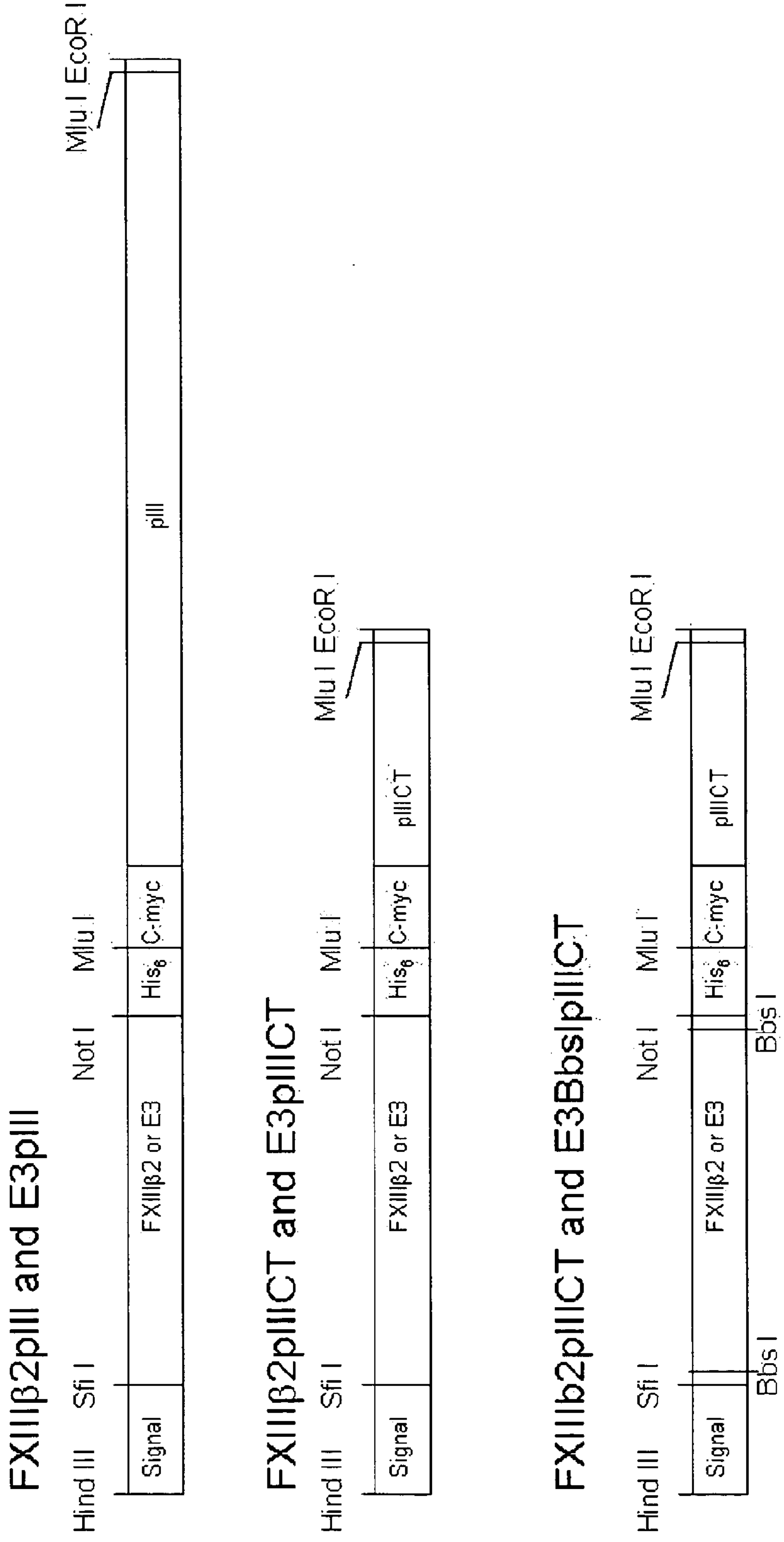
FIG. 29 is a schematic showing representations of ETBP and M13 pIII fusions under lacZ promoter control. The fusion DNA was constructed by an overlapping PCR strategy. The resulting constructs encode translational fusions of FXIIIβ2 or myostatin-binding clone E3 fused to either mature full length M13 pIII or the C-terminal domain of M13 pIII.
Figure 30:
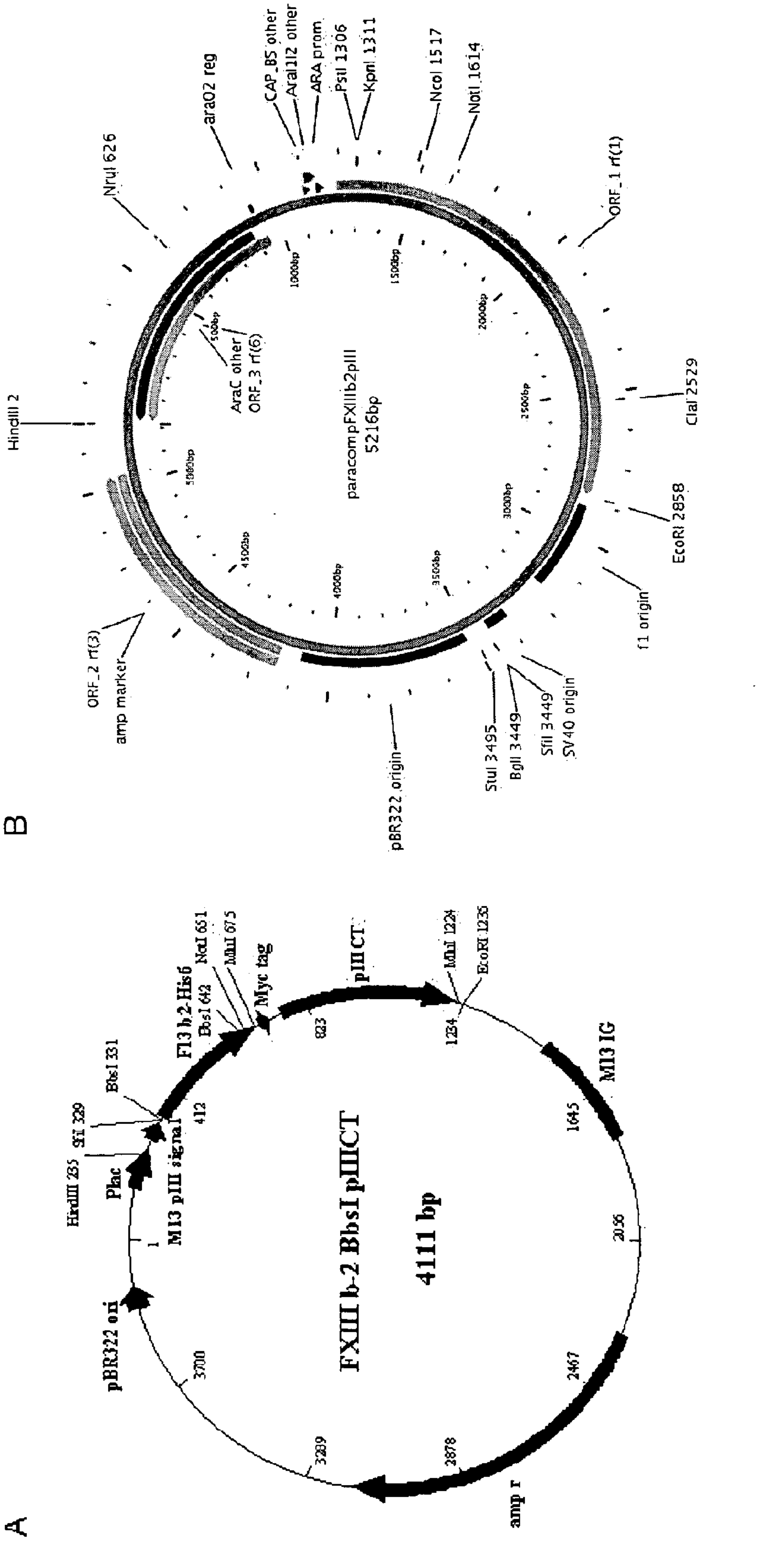
FIGS. 30A and 30B are a schematics showing DNA maps of FXIIIβ2 placed under the lacZ promoter (30A) or pBAD promoter (30B) control.

Construction of Phagemids FXIIIβ2pIII, FXIIIβ2pIIICT, E3pIII, E3pIIICT, FXIIIβ2BbsIpIIICT and E3BbsIpIIICT We have constructed a number of phagemid vectors for efficient cloning of highly diverse ETBP library DNA sequences and for functional display of discrete ETBPs as pIII fusions. FIG. 29 outlines key features of six phagemids. The myostatin binding ETBP E3 as well as the wild type FXIII barrel 2 domain (FXIIIβ2) were fused in frame to either the mature full length pIII or the C-terminal domain of pIII. FXIIIβ2pIII, FXIIIβ2pIIICT, E3pIII, and E3pIIICT were constructed by an overlapping PCR strategy where FXIIIβ2 and E3 fragments were made by PCR using primers FG2 and FG3 and their cognate plasmid DNA as template. DNA fragment encoding the mature full length pIII protein was made using primers FG4 and FG5 and helper phage M13K07 (New England Biolabs, Beverly, Mass.) as template. DNA fragment encoding the C-terminal domain of pIII was similarly made using primers FG6 and FG5. PCR reactions were carried out on a DNA engine Tetrad (MJ Research): 94° C., 3 minutes followed by 25 cycles of 94° C., 30 seconds; 55° C., 30 seconds and 72° C., 2 minutes. A further 5-minute extension was added after the last cycle. The 50 μl reactions included 200 μM dNTPs, 0.4 μM each primer, approximately 4 ng template plasmid, 5 units Herculase® Hotstart DNA Polymerase and reaction buffer (Stratagene, La Jolla). The fusion DNA fragments were assembled by annealing and extending the overlapping PCR fragments, resulting in coding sequences for translational fusions of FXIIIβ2 or myostatin binding ETBP E3 to mature full length or C-terminal domain of pIII. Overlapping PCR fragments were separated by agarose gel electrophorosis and purified using the Qiaquick Gel Extraction kit (Qiagen). Two corresponding purified overlapping DNA fragments (5μ each) were mixed with 200 uM dNTPs, 2 units Herculase® Hotstart DNA Polymerase and reaction buffer (Stratagene, La Jolla) in a total volume of 15 pl. Annealing and extension were carried out on a DNA engine Tetrad (MJ Research): 94° C., 3 minutes followed by 10 cycles of 94° C., 30 seconds; 55° C., 30 seconds and 72° C., 2 minutes. A further 5-minute extension was added after the last cycle. One ul of the assembled DNA fragments was amplified in a 50 μl reaction by PCR with primers FG1 and FG5. PCR reactions were carried out on a DNA engine Tetrad (MJ Research): 94° C., 3 minutes followed by 25 cycles of 94° C., 30 seconds; 55° C., 30 seconds and 72° C., 2 minutes. A further 5-minute extension was added after the last cycle. The 50 μl reactions included 200 uM dNTPs, 0.4 μM each primer, 5 units Herculase® Hotstart DNA Polymerase and reaction buffer (Stratagene, La Jolla). The resulting PCR products were gel-purified, digested with EcoR I and Hind III, and cloned into Hind III and EcoR I digested puc119 (Maxim Biotech, South San Francisco). FXIIIβ2BbsIpIIICT (sequence set forth in Table 15, FIGS. 30A and 30B) and E3BbsIpIIICT were constructed by a modification of E3pIIICT to include two Bbs I sites flanking FXIIIβ2 or E3. The FXIIIβ2 and E3 DNA fragments were generated by PCR using primers AKx295Y and AKx297Y with their cognate plasmid template. PCR reactions were carried out on a DNA engine Tetrad (MJ Research): 94° C., 3 minutes followed by 25 cycles of 94° C., 30 seconds; 55° C., 30 seconds and 72° C., 2 minutes. A further 5-minute extension was added after the last cycle. The 50 ul reactions included 200 uM dNTPs, 0.4 uM each primer, approximately 4 ng template plasmid, 5 units Herculase Hotstart DNA Polymerase and reaction buffer (Stratagene, La Jolla). The PCR products were purified with Qiaquick PCR purification kit (Qiagen), digested with Bgl I and Not, gel-purified with Qiaquick Gel Extraction kid (Qiagen) and cloned into Sfi I and Not I digested E3pIIICT. DNA sequences of the oligonucleotide primers used in construction are shown in Table 10. Successful constructions were confirmed by DNA sequencing of resulting bacterial clones. The resulting phagemids encode the translational fusions between FXIIIβ2 or E3 to pIII or pIIICT with a 6-his (SEQ ID NO: 29) and a myc tag for purification and detection. Two Mlu I sites were included for excision of the pIII coding sequence when expression of ETBPs as non-fusion is desired. Maps of phagemids FXIIIβ2BbsIpIIICT and paracompFXIIIβ2 are provided in FIG. 30. The complete sequence of the FXIIIβ2BbsIpIIICT phagemid is provided in Table 12.

Construction of paracompgp3 and paracompFXIIIb2pIII

The sequence of the paracompFXIIIb2pIII plasmid was generated by replacing the stuffer fragment of a phagemid vector paracompgp3 that had been constructed in three steps: (i) taking a NotI to Bsu36I fragment from pacycaracvce as the vector fragment and as the insert fragment, a NotI+Bsu361 digested PCR fragment of the M13 pIII gene using primers (#1867 & #1868 to amplify the pIII gene from M13 phage DNA); (II) inserting the phage M13 origin of replication into the above plasmid by a three part ligation consisting of: a vector fragment created by BsmBI+HindIII digestion of a PCR fragment created by amplification of the contiguous SV40 ori, pBR322 origin, beta lactamase and rrnG terminator segments of pEAK15Flpe (#1875/#1876 as primer and peak15flpe as template); Insert 1, PCR BsmB1/bsu36 M13 on fragment (#1873/#1874 as primers); and Insert 2, plasmid made from step 1, cut with HindIII and Bsu361; and finally (iii) replacing the existing insert sequences between PstI and NotI with a short synthetic DNA segment prepared from kinased oligos#1882/#1883. The complete sequence of the paracompgp3 phagemid is provided Table 13.

Functional Display of Discrete ETBPs

Figure 31:
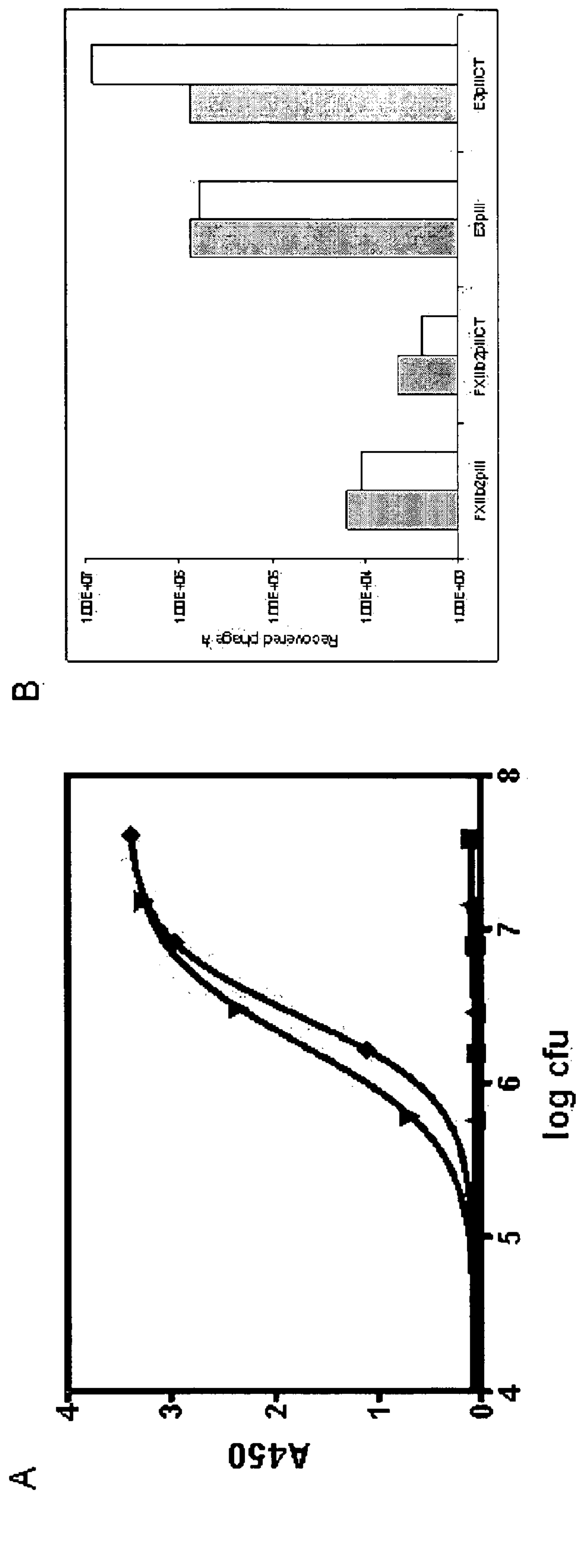
FIG. 31A is a graph showing ETBP displaying phage binding to myostatin in an ELISA assay. Four phage preparations are indicated: FXIIIβ2pIII (square), FXIIIβ2pIIICT (triangle), E3-pIII (upside-down triangle), and E3-pIIICT (diamond). Bound phage was detected with an anti-m13 pVIII antibody conjugated to HRP.
FIG. 31B is a graph showing phage recovery after binding to myostatin. Four phage preparations were bound to myostatin coated wells. Bound phage was eluted with a low pH solution (gray) or used to infect *E. coli* TG1 cells in wells directly (white). Recovered phage number were determined by ampicilin resistant colony forming units.
Figure 32:
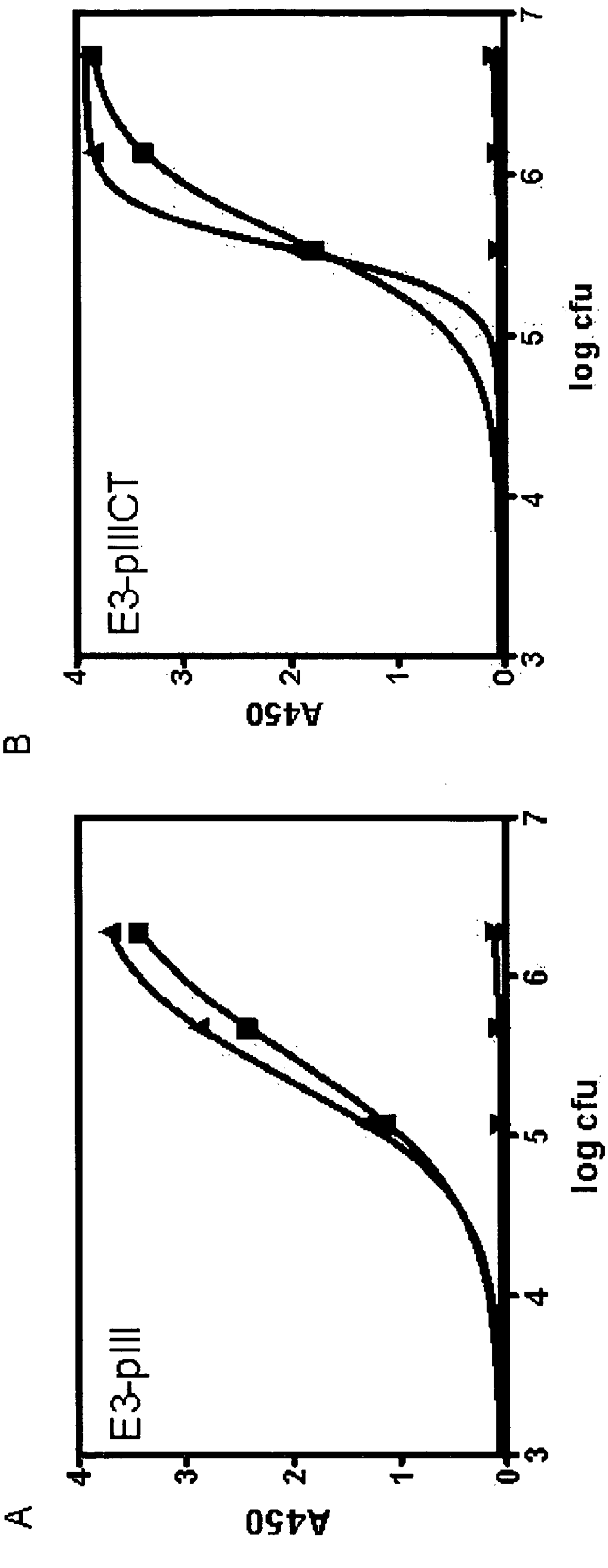
FIGS. 32A and 32B are graphs showing ETBP displaying phage binding specificity. Phage prepartions from E3-pIII (32A) and E3-pIIICT (32B) were tested for binding specificity in ELISA. The following compounds were immobilized on wells of Maxisorb plates and reacted with phage: myostatin (squares), myostatin-biotin (triangles), mbpFcεRI (upside-down triangles), and BSA (diamonds). Bound phage was detected with an anti-M13 pVIII antibody conjugated to HRP.

Functionality of displayed E3 was confirmed by E3pIII and E3pIIICT phage binding to myostatin, as shown in FIG. 31. Both E3pIII and E3pIIICT phage bound immobilized myostatin in Elisa, while FXIIIβ2pIII and FXIIIβ2pIIICT phage showed little binding (FIGS. 31A and 31B). Phage infectivity was retained after target binding, whether phage was eluted with a low pH solution or remained bound on Elisa vessel (direct infection, FIG. 31B), indicating robustness of the ETBP displaying phage. 100-1000 more phage were recovered from E3 phage than FXIIIβ2 phage, indicating efficient discrimination against the non-binding FXIIIβ2 phage. E3pIII and E3pIIICT phage binding to target was highly selective as they bound two myostatin preparations (myostatin and biotinylated myostatin) while little binding was detected when control proteins mbp-FcεRI and BSA were used in place of myostatin (FIGS. 32A and 32B). Myostatin binding Elisa was performed as described below. Wells of Maxisorb plate (Nunc) were incubated with 100μ/well with 2 μg/ml myostatin or control proteins in a bicarbonate coating buffer, pH 9.6 at room temperature for 1 hr. Wells were washed and blocked with BSA. Phage dilutions were incubated with coated and blocked wells at room temperature for 1 hr. After washes, bound phage was detected with an anti-M13 monoclonal antibody HRP conjugate (GE).

Figure 33:
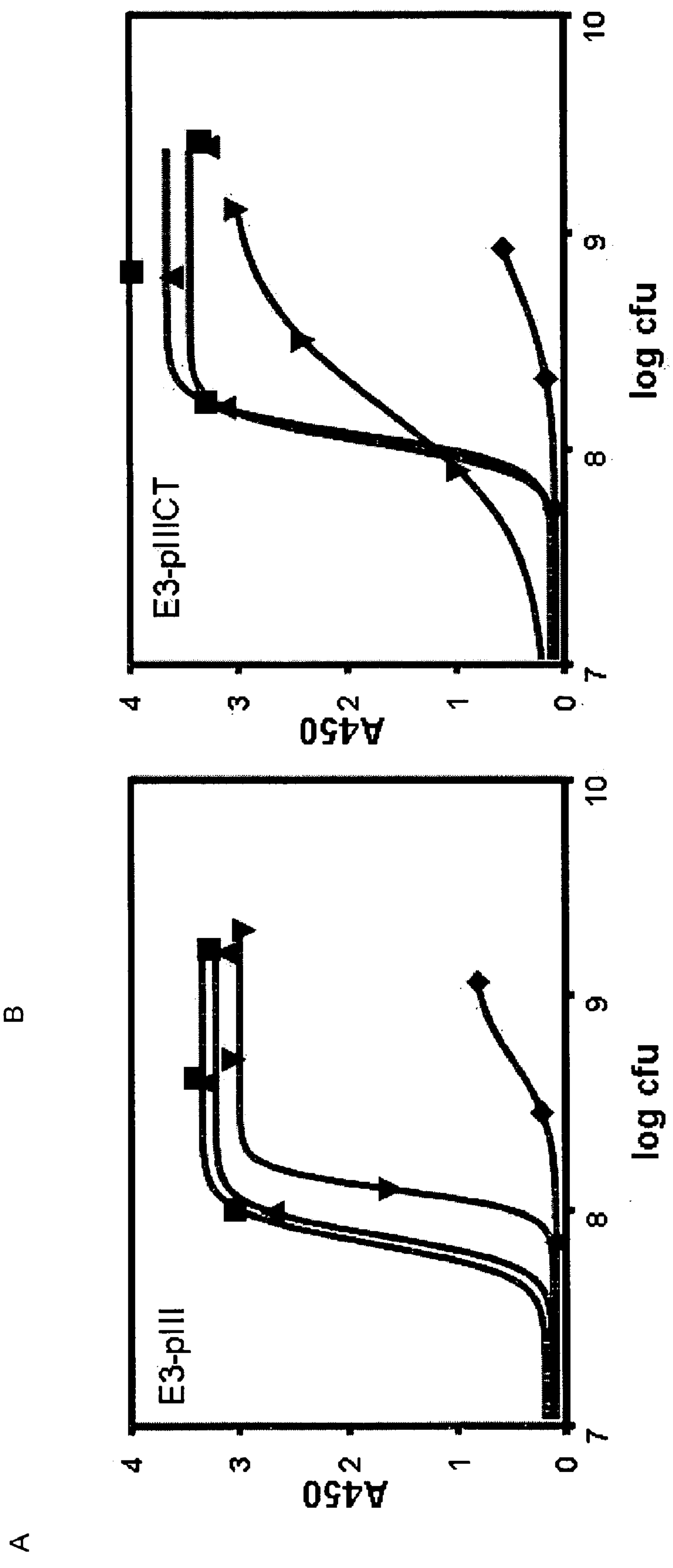
FIGS. 33A and 33B are graphs showing quantity of ETBP displaying phage propagated in the presence of glucose as measured by ELISA. E3-pIII and E3-pIIICT phage were propagated in 2XYT supplemented with different amounts of glucose: 0% (squares), 0.02% (triangles), 0.2% (upside-down triangles), and 2% (diamonds). Phage was reacted with myostatin coated wells.

Under basal expression conditions, E3pIII and E3pIIICT phage bound myostatin strongly. When high affinity binders are desired from a selection, a display copy number of no more than one is preferred. Glucose is known to decrease expression from the lacZ promoter by lowering intracellular cAMP. As shown in FIGS. 33A and 33B, phage binding to myostatin is diminished when it is propagated in culture media supplemented with increasing glucose concentrations. The dynamic range of this regulation appears broad for practical implementation in selection. For example, when binding reached near saturation with no added glucose (0%), little binding was detected with highest added glucose (2%) when phage input was similar in the binding reactions.

Figure 34:
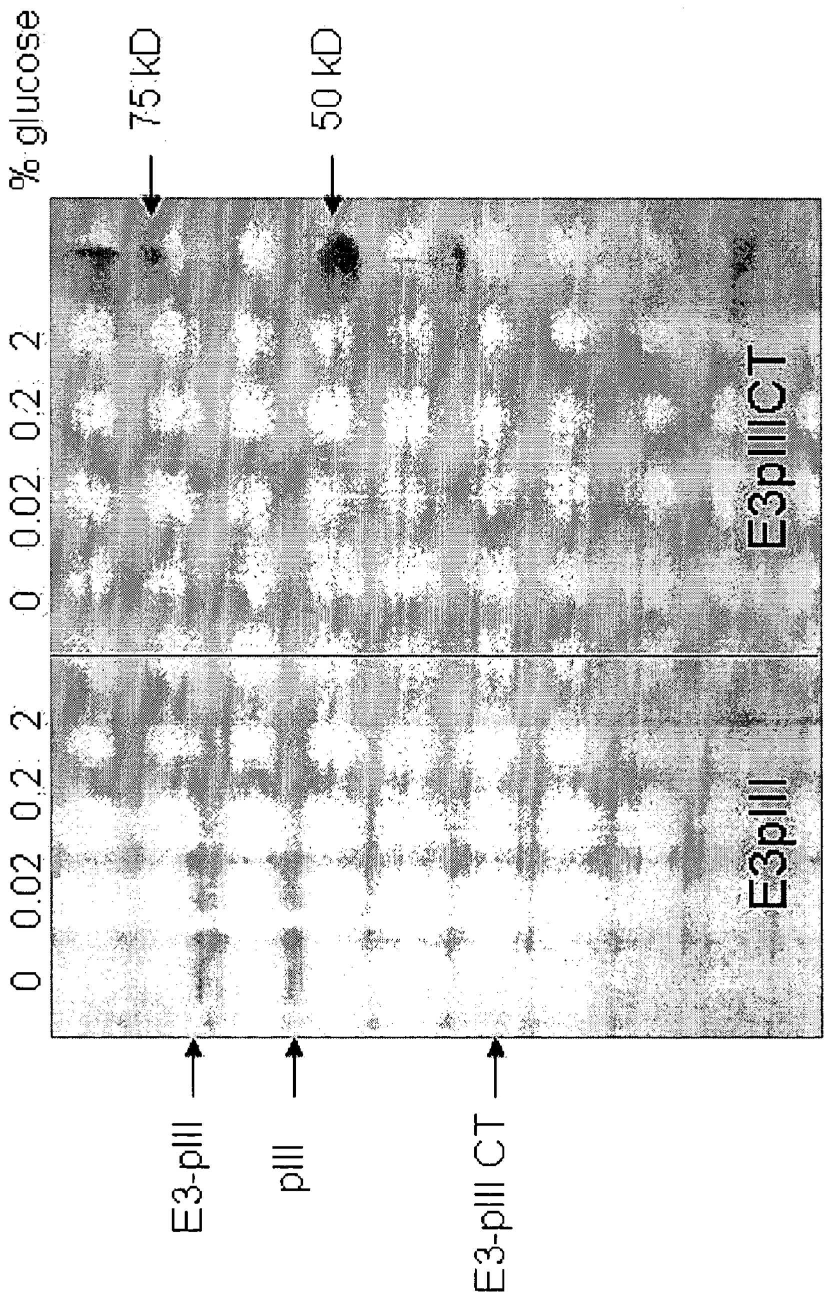
FIG. 34 is an image of a Western blot showing ETBP displaying phage. E3-pIII and E3-pIIICT phage were propagated in 2XYT supplemented with different amounts. The membrane was first probed with an anti-pIII antibody (MoTec) followed by a goat anti-mouse Fc antibody conjugated to HRP.

E3pIII and E3pIIICT protein levels also decreased in phage produced in media containing increasing concentrations of glucose, as indicated in phage Western shown in FIG. 34. This decrease is likely due to a combination of reduced copy number per phage and the number of phage containing at least one fusion copy. Phage Western was performed as described below. Phage from 500 μl culture supernatant was prepared by PEG-8000 and NaCl precipitation. Phage pellet was dissolve in 100 μl PBS pH 7.4 and 10 μl was analyzed on a 15% SDS PAGE and eletrotransferred to a PVDF membrane, which was first probed with an anti-pIII antibody (MoTec) followed by a goat anti-mouse Fc-HRP.

Figure 35:
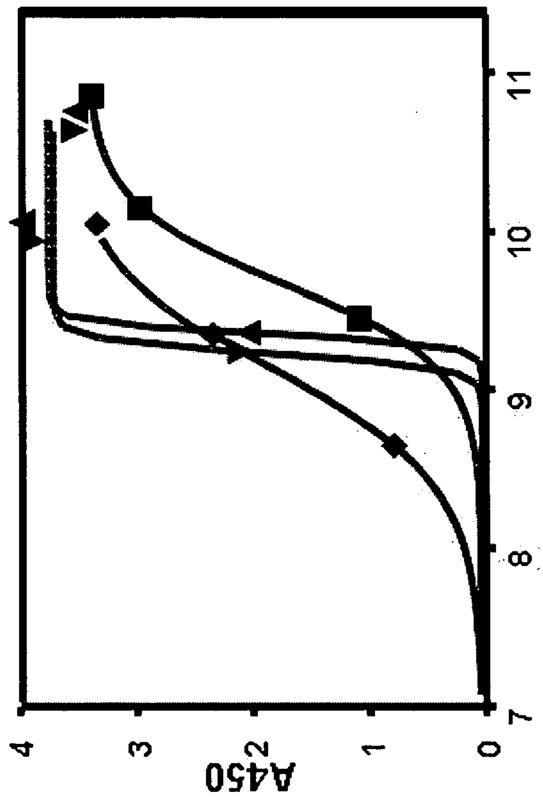
FIG. 35 is a graph showing ETBP phage propagated in the presence or absence of arabinose as measured using ELISA. paracompE3pIII phage was propagated in 2XYT supplemented with: 0 mg/mL (squares), 0.01 mg/mL (triangles), 0.1 mg/mL (upside-down triangles), or 1 mg/mL arabinose. Phage was reacted with myostatin coated wells. Bound phage was detected with an anti-M13 pVIII antibody conjugated to HRP.

FXIIIβ2 and E3 were also placed under the control of the arabinose inducible pBAD promoter in the phagemids paracompFXIIIβ2pIII and paracompE3pIII, respectively. FIG. 35 shows that phage produced from paracompE3pIII bound myostatin in Elisa. When paracompE3pIII phage was produced in growth media supplemented with arabinose, its binding to myostatin increased in an arabinose concentration dependent manner. Little binding to myostatin was detected from paracompFXIIIβ2pIII phage.

Construction of Diversified ETBP Libraries

Figure 36:
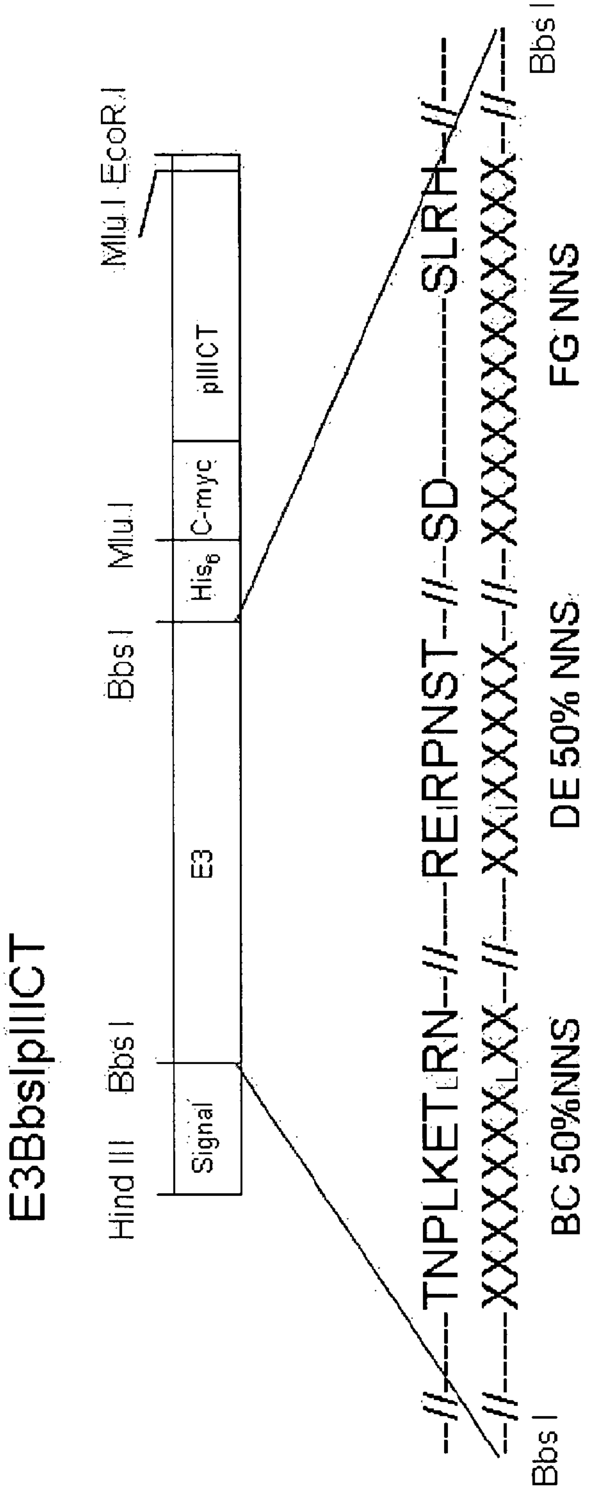
FIG. 36 is a schematic showing diversification of ETBP phage display library. The A-FGext library randomization strategy is shown. Library inserts were cloned into BbsI digested E3BbsIpIIICT. The resulting library has a sequence diversity of $5\times10^8$.

An ETBP phage display library with a sequence diversity of $5\times10^8$ was constructed based on the strategy outlined in FIG. 36. It is based on the A-50% NNSFGext library randomization strategy in which 9 positions in BC loop (50% NNS, 50% WT), 7 positions in DE loop (50% NNS, 50% WT), and 12 positions in FG loop (NNS) were randomized. Approximately 2 pmols of the A-50% NNS FGext diversifed DNA was amplified by PCR using oligonucleotide primers AKx296Y and AKx298Y in a total volume of 1 ml. PCR reactions were carried out on a DNA engine Tetrad (MJ Research): 94° C., 3 minutes followed by 25 cycles of 94° C., 30 seconds; 55° C., 30 seconds and 72° C., 2 minutes. A further 5-minute extension was added after the last cycle. The 1 ml PCR reaction included 200 uM dNTPs, 0.4 uM each primer, 100 units Herculase® Hotstart DNA Polymerase and reaction buffer (Stratagene, La Jolla). The amplified DNA was purified using Qiaquick PCR purification kit (Qiagen) and digested with Bbs I. The digested DNA was purified again using Qiaquick PCR purification kit (Qiagen). Five μg of this DNA was ligated to 20 μg of Bbs I digested E3pIIICT phagemid DNA in 2 mls using T4 DNA ligase (New England Biolabs). The reaction mixture was incubated at 16° C. overnight and precipitated with glycogen (Ambion) and ethanol. The resulting DNA dissolved in water and used to transform *E. coli* TG1 cells in 22 separate eletroporations using a Gene Pulser (Bio-Rad).

One ml of SOC media was added to cells after each electroporation. The electroporated cells were pooled (approximately 24 mls) and grew in 37° C. in a 250 ml flask with 250 rpm shaking for 40 minutes. Transformation efficiency was determined by plating serial dilutions of this culture on LB plates containing 50 μg/ml ampicilin and 1% glucose. Total number of transformants was calculated to be $5\times10^8$.

The transformed cells (24 m) were transferred to 1 L 2×YT in a 3 L baffled flask containing 50 μg/ml carbenecilin and grew in 37° C. with 250 rpm shaking for 2 hr. Cells from an aliquot of this culture (200 ml) culture were collected by centrifugation. The cells were resuspended in 2×YT. An equal volume of 30% glycerol was added to the resuspended cells and stored in −80° C. The helper phage M13K07 (amplified from New England labs) was added to the remaining culture (800 ml) to a final titer of 1×10e10 pfu/ml to produce display phage by incubation at 37° C. overnight with 250 rpm shaking. Library phage was harvested by centrifugation and precipitated by adding 1/5 volume of 20% PEG-8000 and 2.5 M NaCl. Precipitated phage was purified by centrifugation and resuspended in PBS pH 7.4, adjusted to 50% glycerol and stored in −20° C. Phage library titer was determined to be 1×10e13 cfu/ml by infecting *E.*

*coli* TG1 cells and counting ampcilin resistant colony forming units. DNA sequencing of resulting library members (96 clones from electroporation and 96 clones from infection by library phage) revealed conformity to design. No duplicates of diversified sequences were observed in the sequenced clones. A summary of library sequencing analysis is shown in Table 6.

Selections against several protein targets were carried out to validate display of sequence-diversified β barrel proteins. Library phage (200 ul, 5×10e11 cfu/ml) was added to a Maxisorp well coated with target protein and incubated at room temperature for 1 hr. Liquid was discarded and the wells were washed 10 times with 200 Elisa wash buffer (50 mM Tris-HCl, pH 8.0, 138 mM NaCl, 2.7 mM KCl, 0.05% TWEEN-20™). Bound phage was eluted with 200 μl 0.2 M glycine, 0.1 M HCl, pH 2.2 by incubating at room temperature for 10 min. Eluent was transferred to tube containing 30 μl 1M tris-HCl, pH 9.1. The eluted phage was amplified by mixing 100 μl of elution with 2 ml mid log phase TG1 cell (A600=0.7) and growing at 37° C. for 1 hr. This culture was mixed with 25 ml 2YT containing M13K07 ($1\times10^{10}$ pfu/ml) and carbenecillin (50 μg/ml) in a 250 ml flask and grown at 37° C. overnight with shaking at 250 rpm. Amplified phage was purified by PEG precipitation and used for next round of selection.

Table 8 shows a summary of DNA sequencing analysis of randomly picked clones after each round of selection. Fast sequece convergence was observed in the myostatin selection: 80%, 100% and 100% of sequenced clones share identical sequence after round 1, 2 and 3, respectively. The abundance (~1% in library by sequencing analysis) and affinity of the winning clone were likely the main reason for the observed fast enrichment. This result, however, demonstrates the possibility of functional display of ETBPs on the M13 phage. The selection process also efficiently eliminated non-displayable clones, such as those with stops codons and frameshifts. This is evident in the sequencing summary shown in Table 6.

TABLE 6

Sequencing analysis of phage display library (A50% FG-extNNS)

| | number analyzed | in frame full length | del & frame shift | in frame stop |
|---|---|---|---|---|
| 5x10e8 library ligation | 83 | 18 | 32 | 33 |
| 5x10e8 library phage | 91 | 14 | 39 | 38 |
| FcεRI PR1 | 16 | 11 | 3 | 2 |
| FcεRI PR2 | 15 | 13 | 1 | 1 |
| FcεRI PR3 | 16 | 11 | 4 | 1 |
| FcγRIIb PR1 | 16 | 6 | 6 | 4 |
| FcγRIIb PR2 | 15 | 10 | 3 | 2 |
| FcγRIIb PR3 | 14 | 6 | 5 | 3 |
| CD5-FC PR1 | 15 | 5 | 9 | 1 |
| CD5-FC PR2 | 16 | 10 | 2 | 3 |
| CD5-FC PR3 | 16 | 11 | 1 | 4 |
| CD19D2D3-FC PR1 | 16 | 11 | 3 | 2 |
| CD19D2D3-FC PR2 | 13 | 11 | 1 | 1 |
| CD19D2D3-FC PR3 | 16 | 9 | 5 | 2 |
| Myostatin PR1 | 16 | 15 | 1 | 0 |
| Myostatin PR2 | 16 | 16 | 0 | 0 |
| Myostatin PR3 | 16 | 16 | 0 | 0 |
| ActRIIb PR1 | 15 | 10 | 3 | 2 |
| ActRIIb PR2 | 13 | 13 | 0 | 0 |
| ActRIIb PR3 | 15 | 9 | 4 | 2 |

Phagemid Modifications

A number of modifications were made to the phagemid vector FXIIIβ2BbsIpIIICT, including reversing the M13 (+) origin of replication to M13 (−), creating restriction sites through silent mutations to facilitate loop shuffling, and introducing stop codons in each of BC, DE and FG loops. These modifications allow construction of highly diversed libraries by increased transformation efficiency over commonly used restriction fragment ligation.

The DNA sequence of the resulting phagemid pF13 wt-modstoppIIICT is shown in Table 16.

Construction of Phage Display Libraries with Higher Diversity

Two phage display libraries, FG6 and FG6+6, each with a sequence diversity of approximately $1\times10^{10}$, were constructed using the FXIII β barrel 2 scaffold. Targeted randomization of the BC, DE and FG loops were achieved by oligo-directed mutagenesis. The two libraries share the same BC and DE loop randomizations strategy, but differ in their FG loop randomizations. Six amino acid positions were randomized for the FG 6 library and an additional 6 randomized amino acids were inserted into the FG loop for the FG 6+6 library. FIG. 37 outlines the randomization strategy. A mixture of F13BC, F13DE plus F13FG6 or FG6+6 were phosphorylated in a reaction by T4 polynucleotide kinase. At 3 molar excess, the kinased oligos were annealed to pF13 wt-modstoppIIICT single stranded DNA containing uracil after incubating at 90° C. for 3 min, 50° C. for 5 min and 20° C. for 5 min. Following annealing, T7 DNA polymerase and T4 DNA ligase were added to complete the enzymatic synthesis of double-stranded DNA, which was then purified using the QIAquick PCR Purification Kit (Qiagen). Twenty μg of the purified DNA was used in a single electroporation of 350 μl of LC1062 *E. coli* competent cells. $1\times10^{10}$ transformants were obtained. Library phage was produced and purified by polyethlene glycol precipitation using standard protocols. DNA sequencing analysis of randomly picked clones of library members reveal that greater than 90% of clones had mutations in at least one of the targeted loops, including approximately 40% of clones had mutations in all three targeted loops. Twenty percent of the library members had mutaions in all three loops that did not include a stop codon. Table 7 shows a summary of the FG6 and FG6+6 library sequence analysis.

TABLE 7

Sequencing Analysis of FG6 and FG6+6 Libraries

| Randomization Outcome | FG6, n = 80 | FG6+6, n = 77 |
|---|---|---|
| None | 5 | 5 |
| BC | 2 | 1 |
| DE | 2 | 0 |
| FG | 0 | 2 |
| BC, DE | 7 | 2 |
| DE, FG | 1 | 1 |
| BC, FG | 4 | 3 |
| BC, DE, FG | 32 | 34 |
| BC, DE, FG no stop codon | 15 | 17 |
| Frameshift | 12 | 12 |

Selection from FG6 and FG6+6 Libraries

Figure 38:
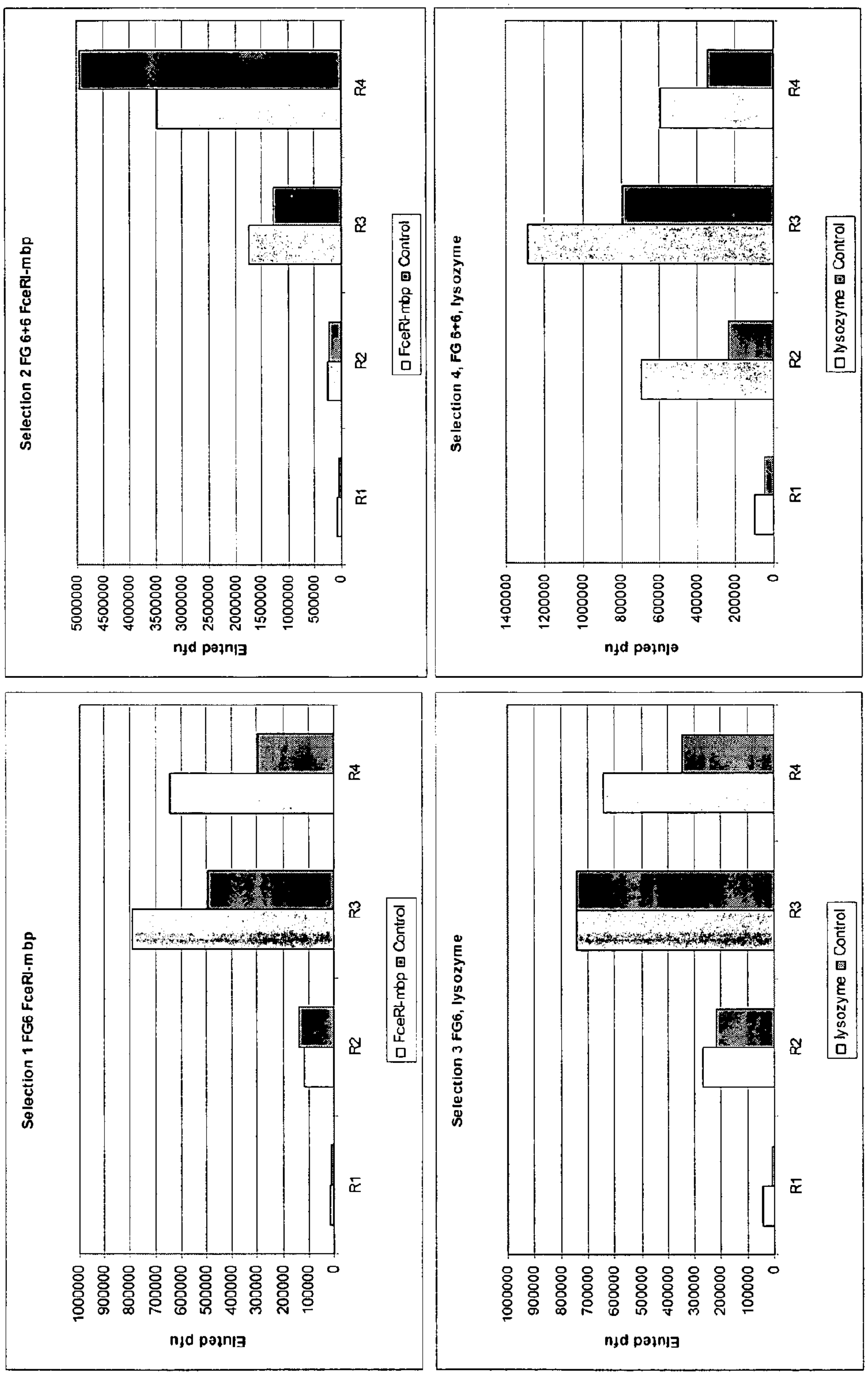
FIG. 38 is a series of graphs showing phage recovery from FG6 and FG6+6 selections to FcεRI and lysozyme. Total phage number was determined by tittering a fraction of elution from each round of selection. Elution from both target-coated and control wells were titered. Target and library used in each selection is shown in graph title.

Affinity selections to immobilized FcgRI-MBP and lysozyme were carried out from both FG6 and FG6+6 libraries. Library phage ($10^{13}$ pfu/ml in PBS pH 7.4, 0.5% w/v BSA, 0.05% TWEEN-20™) was incubated for 1 hour at room temperature with Maxisorp wells coated with FcεRI-mbp (produced in *E. coli*) and chicken lysozyme (Sigma). After removal of unbound phage and washes with PBS pH 7.4, 0.05% Tween-20, bound phage was eluted with 100 mM HCl and neutralized with 1/8 volume of 1 M Tris, pH 11. Eluted phage was titered and amplified in LC1062 cells for subsequent round of selection. Four rounds of selections were carried out using similar conditions. Phage titer from control wells without target coating was also determined to assess enrichment. FIG. 38 shows phage titers of the four selections. A general trend of increased titer was observed as selection progressed with modest specific enrichment (target vs. control) after the forth round of selection.

Figure 39:
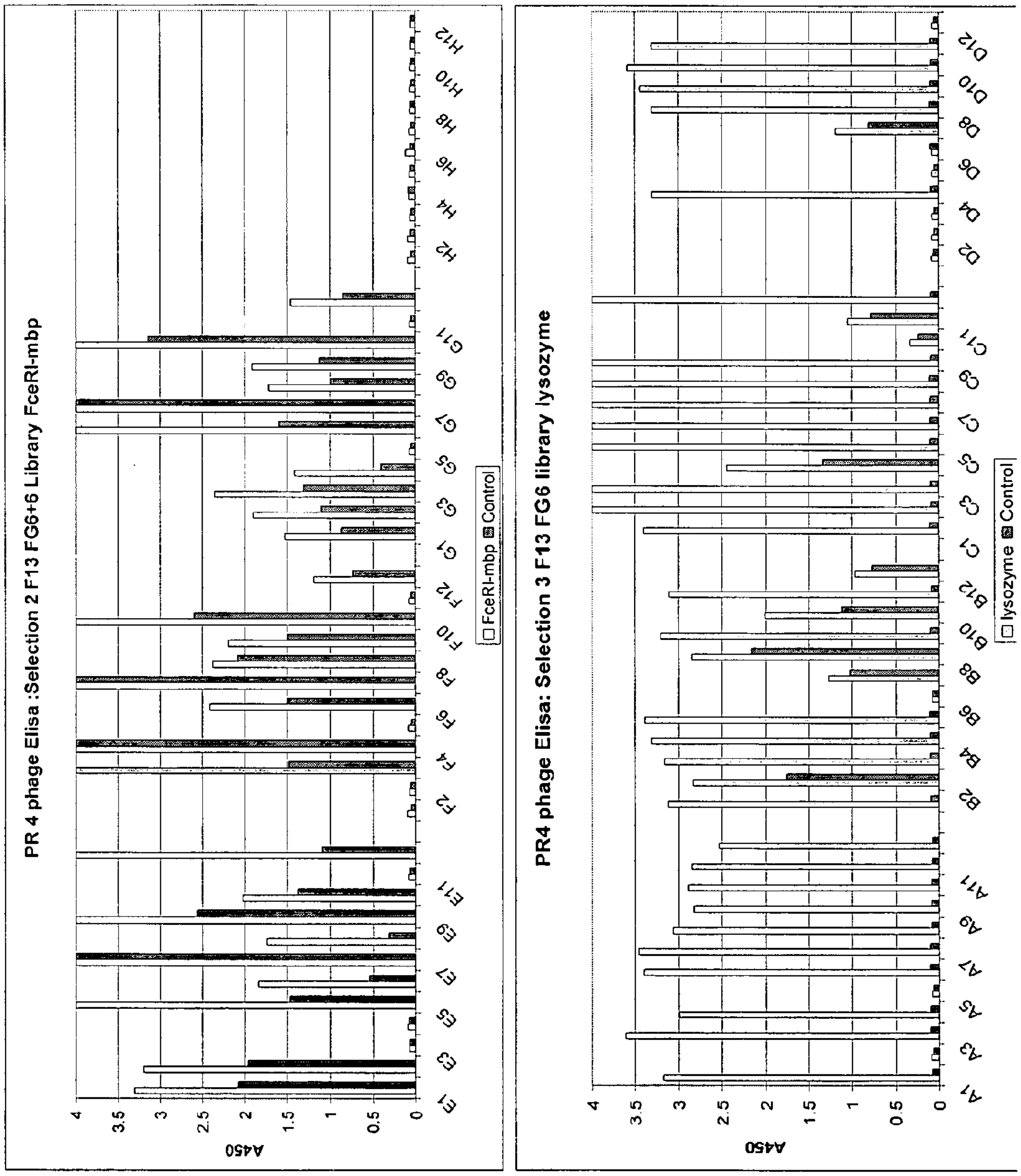
FIG. 39 is a series of graphs showing selected clones binding to targets in phage ELISA. Randomly picked clones were analyzed after the fourth round of selection. Phage was incubated with Maxisorp wells coated with or without target. Binding level was determined using an anti-M13 antibody conjugated to HRP.

An Elisa screening was performed after four rounds of selection to identify binding clones. Randomly picked phagemid clones were incubated with target-coated or buffer-coated Maxisorp wells at room temperature for 1 hour. Unbound phage was removed and the wells were washed eight times with PBS pH 7.4, 0.05% Tween-20. Binding was determined with an anti-M13 pVIII antibody-HRP conjugate (GE). FIG. 39 shows that some selected clones exhibited highly specific binding to their cognate targets. Varying levels of binding to targets and the Maxisorp surface were also observed in other clones. DNA sequencing analysis indicated clear enrichment of certain sequences, as shown in Table 8.

TABLE 8

Sequencing analysis of selected clones.
Table 8 discloses "BC loop" sequences as SEQ ID NOS 393-403, the "DE loop" sequences as SEQ ID NOS 404-414 and the "FG loop" sequences as SEQ ID NOS 415-425, all respectively, in order of appearance.

| BC loop | DE loop FG loop | n | Library | Target | Sequencing plate ID | Target Binding | Well Binding |
|---|---|---|---|---|---|---|---|
| TNPLKET | RPNSTSDSLRH | n.a. | n.a. | n.a. | n.a. | n.a | n.a |
| MNPRMEM | HPDSDRLWTLWMARWRW | 10/26 | FG6 + 6 | FcεRI-MBP | 81937 | 2.35 | 1.31 |
| SNPLSRP | RPHSNSRSLWLSIGKRH | 9/26 | FG6 + 6 | FcεRI-MBP | 81937 | 3.31 | 2.08 |
| TNPLRGT | PPNVKGLSTAGRWKRVR | 4/26 | FG6 + 6 | FcεRI-MBP | 81937 | 4.00 | 1.10 |
| GNPTKET | RPRSMYRPRRGGMRLRH | 2/26 | FG6 + 6 | FcεRI-MBP | 81937 | 4.00 | 1.47 |
| TNPRRRV | RPRSTWNSRWPAPTRRR | 1/26 | FG6 + 6 | FcεRI-MBP | 81937 | 1.73 | 0.31 |
| INPLQVS | GPSSAIYRYGL | 22/28 | FG6 | lysozyme | 81938 | 4.00 | 0.10 |
| ANPIKHM | RPTAGLGVLRR | 2/28 | FG6 | lysozyme | 81938 | 2.83 | 1.76 |
| RRPTKGN | GPGQVLGMLRR | 2/28 | FG6 | lysozyme | 81938 | 2.45 | 1.33 |
| TIPHRGR | QPNVPRAFLRH | 1/28 | FG6 | lysozyme | 81938 | 0.34 | 0.25 |
| PSPFIEN | RPECIRGWLRS | 1/28 | FG6 | lysozyme | 81938 | 1.19 | 0.80 |

Example 18

Pharmacokinetic Characterization of Pegylated ETBPs

Figure 40:
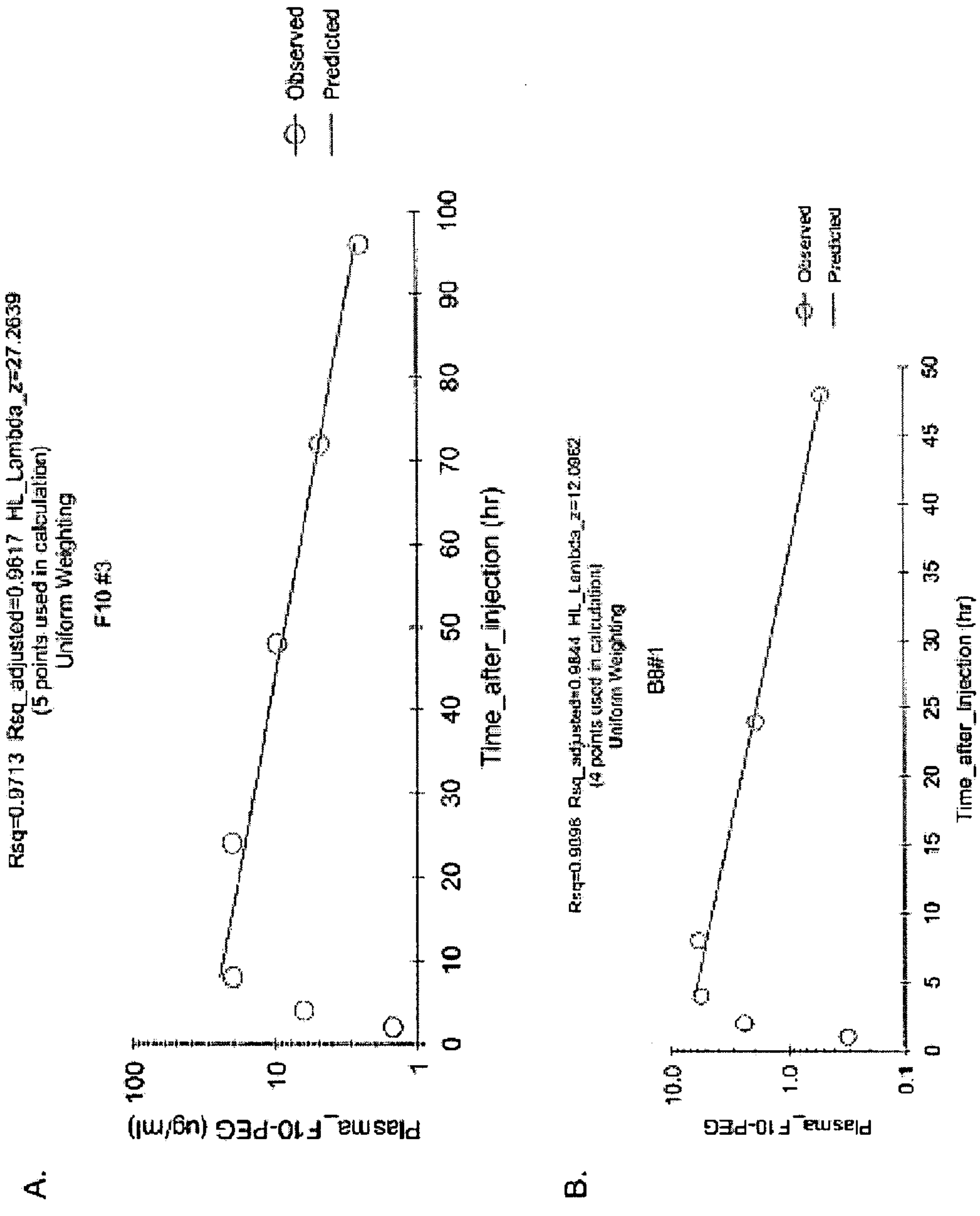
FIGS. 40A and 40B are a series of graphs showing the pharmacokinetics of PEGylated myostatin ETBPs. PEGylated monomeric (FIG. 40A) and tandem dimeric (FIG. 40B) myostatin binder were injected subcutaneously to FBV mice at 5 mg/kg. Plasma samples were collected at indicated time points post injection. Binder concentration was determined by ELISA. Pharmacokinetic modeling was performed using the WinNonLin software (Pharsight).

Conjugation of drugs to polyethylene glycol (PEG) has been shown to improve pharmacokinetic property and reduce immunogenicity of parent drug molecules. Such modifications have generally resulted in prolonged half life from minutes to hours and from hours to days. Pharmacokinetic studies were carried out to measure the in vivo half life of PEGylated ETPBs. Subject animals (FBV) were injected subcutaneously (s.c.) at 5 mg/kg PEGylated myostatin binder F10 (monomer)-PEG or B8 (tandem F10 dimer). Blood samples were collected at 0, 1, 2, 4, 8, 24, 32, 48, 56, 72 hr. after injection and placed into tubes containing 1.5 ul 0.5 M EDTA. Plasma samples were collected by centrifugation at 6000 rpm for 10 min. The F10 and B8 concentrations in plasma was determined by Elisa using an anti-PEG antibody (Epitomics) as a capture antibody and followed by biotinylated myostatin and streptavidin-HRP (Zymed) for detection. Quantitation was determined by a non-linear regression (Graphpad Prism) to F10 and B8 standards. Pharmacokinetic modeling was carried out using linear regression of log concentration (y) vs time (x) based on a non-compartmental extravascular model (200, WinNonlin). FIGS. 40A and 40B shows two examples of such modeling results. The summary in Table 9 indicated that F10 and B8 had an average in vivo half life of 25 hr. and 16 hr., respectively. These PK profiles are similar to those of a number of PEGylated drugs. F10 appears to have a better PK profile than B8: a longer half life and better bio-availability (average Cmax 22.25 vs. 5.9 ug/ml). The functionality of F10 and B8, as measured by their binding to myostatin in Elisa, did not appear to have changed during the PK study period, suggesting a favorable in vivo stability profile for these proteins.

TABLE 9

In viov Pharmacokinetic Properties of PEGylated ETBP F10 and B8

| | F10 #1 | F10 #2 | F10 #3 | F10 #4 | F10 #5 | F10 #6 |
|---|---|---|---|---|---|---|
| HL-Lambda z (hr) | 18.3 | 17.1 | 27.3 | 26 | 29.2 | 31.2 |
| Rsq | 0.98 | 0.94 | 0.97 | 0.98 | 0.99 | 0.97 |
| Cmax, ug/ml | 24.8 | 21.2 | 20.4 | 21.7 | 20.3 | 25.1 |
| Tmax, hr | 8 | 24 | 24 | 8 | 24 | 24 |
| | B8 #1 | B8 #2 | B8 #3 | B8 #4 | B8 #5 | B8 #6 |
| HL-Lambda z (hr) | 12.1 | 8.7 | 6.7 | 16.7 | 25.8 | 25.6 |
| Rsq | 0.99 | 0.99 | 0.99 | 0.96 | 0.95 | 0.96 |
| Cmax, ug/ml | 5.9 | 7.2 | 6.4 | 8.5 | 3.1 | 4.3 |
| Tmax, hr | 8 | 4 | 4 | 8 | 2 | 1 |

TABLE 10

Primers used for cloning and construction. Table 10 discloses "His6" as SEQ ID NO: 29 and "G4S" as SEQ ID NO: 32.

| Primer | Sequence | SEQ ID NO: |
|---|---|---|
| 1. Primers for wild type F13β2 scaffold. | | |
| oligo 17 (NdeI) | TAATACGACTCACTATAGGGACAATTACTATTTACAATTACATATGACCATCCCTGAGATCATCATCAAG | 426 |
| oligo 18rev (BamHI) | TTTTTTTTTTTTTTTTTTTTAAATAGCGGATGCCTTGTCGTCGTCGTCCTTGTAGTCGGATCCTCGTCTTTGAATCTGCACGTCCAG | 427 |
| 2. Primers for optimized F13β2 scaffold. | | |
| oligo 53 (NdeI) | GAAATAATTTTGTTTAACTTTAAGAAGGAGATATACATATGACCATCCCTGAGATCATCATCAAG | 428 |
| oligo 19 (or 67I) | ATGACCATCCCTGAGATCATCATCAAGGTCCGCGGCACTCAGGTCGTGGGTTCTGACATGACTGTGATCGTGGAGTTT | 429 |
| oligo 20rev (80revI) | CAGGTGCACCCAGACATTGCGCAGGGTTTCTTTCAGAGGATTGGTAAACTCCACGATCACAGTCAT | 430 |
| oligo 21 | CTGCGCAATGTCTGGGTGCACCTGGATGGTCCTGGAGTCACACGCCCAATGAAGAAGATGTTCCGCGAAATC | 431 |
| oligo 22rev (82revI) | CACTTCTTCCCACTGCACGGTGGAGTTTGGGCGGATTTCGCGGAACATCTTCTTCAT | 432 |
| oligo 23 | GTGCAGTGGGAAGAAGTGTGCCGCCCATGGGTCTCTGGGCATCGCAAGCTGATCGCCAGCATG | 433 |
| oligo 25rev | GCGGCGTTGAATCTGCACGTCCAGCTCGCCATACACATGGCGCAGGGAGTCACTGCTCATGCTGGCGATCAGCTT | 434 |
| oligo 28rev (BamHI-His6) | TAGATCATTGGATCCCTCATTAATGATGGTGATGGTGATGGCGGCGTTGAATCTGCAC | 435 |
| oligo 52rev (BamHI) | TCCTTTGCTGAATTCGCCAGAACCAGCAGCGGAGCCAGCGGATCCGCGGCGTTGAGCAC | 436 |
| oligo 48rev | GACATTGCGCAGGGTTTCTTTCAGAGGATTGGTAAACTCCACGATCACAGTCAT | 437 |
| oligo AKx198 (PSM-His6) | TAGATTATTCTCGAGCTCATTAATGATGGTGATGGTGATGCATGGACGGGCGGCGTTGAATCTGCAC | 438 |
| oligo AKx299 (PSM) | TAGATTATTCTCGAGCTCATTACATGGACGGGCGGCGTTGAATCTGCAC | 439 |
| oligo AKx226 (PCM) | TAGATTATTCTCGAGCTCATTACATGCACGGGCGGCGTTGAATCTGCAC | 440 |
| oligo AKx169 | TAGATTATTCTCGAGCTCATTAATGATGGTGATGGTGATGGCGGCGTTGAATCTGCAC | 441 |
| AKx202 | TATTATTCTAGAAATAATTTTGTTTAACTTTAAGAAGGAGATATACCATGGGGACCATCCCTGAGATCATCAT | 442 |
| AKx203 | AGTAGTAGTCATATGSNNSNNSNNSNNSNNGCGGCGTTGAATCTGCAC | 443 |
| 3. Primers for site-directed mutagenesis. | | |
| oligo 51 (C69X) | GTGCAGTGGGAAGAAGTGNNSCGCCCATGGGTCTCTGGGCATCGCAAGCTGATCGCCAGCATG | 444 |
| oligo 49 (W38X) | AAAGAAACCCTGCGCAATGTCNNSGTGCACCTGGATGGTCCTGGA | 445 |
| oligo 50rev (Y92X) | GCGGCGTTGAATCTGCACGTCCAGCTCGCCSNNCACATGGCGCAGGGAGTC | 446 |
| 4. Primers for F13β2 libraries construction. | | |
| oligo 63 (or 71I) (C69V) | GTGCAGTGGGAAGAAGTGGTGCGCCCATGGGTCTCTGGGCATCGCAAGCTGATCGCCAGCATG | 447 |
| oligo 39 | GTCTGGGTGCACCTGGATGGTCCTGGAGTCACACGCCCAATGAAGAAGATGTTC | 448 |
| oligo 55 (T7Tmv) (or 78I) | TAATACGACTCACTATAGGGACAATTACTATTTACAATTACAATGACCATCCCTGAGATCATC | 449 |
| oligo 26 rev (Flag-tag) (or 74revI) | TTTTTTTTTTTTTTTTTTTTAAATAGCGGATGCCTTGTCGTCGTCGTCCTTGTAGTCGCGGCGTTGAATCTGCACGTC | 450 |
| oligo 65rev (RT primer) (or 76revI) | GTCGTCGTCCTTGTAGTCGCGGCGTTGAATCTGCACGTC | 451 |
| N-terminal loop libraries | | |
| oligo 35 rev (BC C-NNS) | CAGGTGCACCCAGACATTGCGCAGSNNSNNSNNSNNSNNATTGGTAAACTCCACGATCACAGTCAT | 452 |
| oligo 41rev (DE C-NNS) | CACTTCTTCCCACTGCACGGTSNNSNNSNNSNNGATTTCGCGGAACATCTTCTTCATTGGGCG | 453 |
| oligo 45rev (FG C-NNS) | GCGGCGTTGAATCTGCACGTCCAGCTCGCCATACACATGGCGCAGSNNSNNACTGCTCATGCTGGCGATCAGCTT | 454 |
| oligo 46rev (FG + 2 C-NNS) | GCGGCGTTGAATCTGCACGTCCAGCTCGCCATACACATGGCGCAGSNNSNNSNNSNNACTGCTCATGCTGGCGATCAGCTT | 455 |
| oligo 34rev (BC A-NNS) | CAGGTGCACCCAGACSNNSNNCAGSNNSNNSNNSNNSNNSNNSNNAAACTCCACGATCACAGTCAT | 456 |
| oligo 40rev (DE A-NNS) | CACTTCTTCCCACTGCACSNNSNNSNNSNNSNNGATSNNSNNGAACATCTTCTTCATTGGGCG | 457 |
| oligo 44rev (FGE A-NNS) | GCGGCGTTGAATCTGCACGTCCAGCTCGCCATACACATGSNNSNNSNNSNNSNNSNNCATGCTGGCGATCAGCTT | 458 |
| oligo 55revI (BC A-50% NNS) | ACCATCCAGGTGCACCCAGAC A/S T/N T/N G/S C/N G/N CAG G/S G/N T/N T/S T/N C/N T/S T/N T/N C/S A/N G/N A/S G/N G/N A/S T/N T/N G/S G/N T/N AAACTCCACGATCACAGTCAT | 459 |
| oligo 56revI (DE A-50% NNS) | CACTTCTTCCCACTGCACG/S G/N T/N G/S G/N A/N G/S T/N T/N T/S G/N G/N G/S C/N G/N GAT T/S T/N C/N G/S C/N G/N GAACATCTTCTTCATTGGGCG | 460 |
| oligo 57revI (FG A-50% NNS) | GCGGCGTTGAATCTGCACGTCCAGCTCGCCATACACATG G/S C/N G/N C/S A/N G/N G/S G/N A/N G/S T/N C/N A/S C/N T/N G/S C/N T/N CATGCTGGCGATCAGCTT | 461 |

TABLE 10-continued

Primers used for cloning and construction. Table 10 discloses "His6" as SEQ ID NO: 29 and "G4S" as SEQ ID NO: 32.

| Primer | Sequence | SEQ ID NO: |
|---|---|---|
| oligo 68revI (BC Aext-NNS) | CAGGTGCACCCAGACATTGCGCAGSNNSNNSNNSNNSNNSNNSNNAGGATTGGTAAACTCCACGATCACAGTCATGTC | 462 |
| oligo 69I (Aext) | CTGCGCAATGTCTGGGTGCACCTGGATGGTCCTGGAGTCACACGCCCAATGAAGAAGATGTTC | 463 |
| oligo 70revI (DE Aext-NNS) | CACTTCTTCCCACTGCACGGTGGASNNSNNSNNNGATSNNSNNGAACATCTTCTTCATTGGGCG | 464 |
| oligo 72revI (FG Aext-NNS) | AATCTGCACGTCCAGCTCGCCATACACSNNSNNSNNSNNSNNSNNSNNSNNSNNSNNSNNSNNGCTCATGCTGGCGATCAGCTT | 465 |
| oligo 66I (T7Tmv Aext) | TAATACGACTCACTATAGGGACATCATCAACCATAACAATTACTATTTACAATTACAATGACCATCCCTGAGATCATC | 466 |
| oligo 73revI (Flag-tag) | TTTTTTTTTTTTTTTTTTTTAAATAGCGGATGCCTTGTCGTCGTCGTCCTTGTAGTCGCGGCGTTGAATCTGCACGTCCAGCTCGCC | 467 |
| oligo 77I (linker Aext) | TAATACGACTCACTATAGGGACATCATCAACCATA | 468 |
| C-terminal loop libraries | | |
| oligo 33 (AB C-NNS) | ATGACCATCCCTGAGATCATCATCAAGGTCCGCNNSNNSCAGNNSNNSGGTNNSNNSATGACTGTGATCGTGGAGTTT | 469 |
| oligo 37 (CD C-NNS) | CTGCGCAATGTCTGGGTGCACCTGGATGGTNNSNNSGTCACACGCCCAATGAAGAAGATGTTCCGCGAAATC | 470 |
| Oligo 43 (C69) (EF C-NNS) | GTGCAGTGGGAAGAAGTGTGCNNSCCANNSNNSNNSGGGNNSCGCAAGCTGATCGCCAGCATG | 471 |
| Oligo 38 (CD C + 3-NNS) | CTGCGCAATGTCTGGGTGCACCTGGATGGTNNSNNSNNSNNSNNSGTCACACGCCCAATGAAGAAGATGTTCCGCGAAATC | 472 |
| oligo 32 (79I) (AB A-NNS) | ATGACCATCCCTGAGATCATCATCAAGGTCCGCNNSNNSNNSNNSNNSNNSNNSNNSATGACTGTGATCGTGGAGTTT | 473 |
| oligo 36 (81I) (CD A-NNS) | CTGCGCAATGTCTGGGTGCACCTGGATNNSNNSNNSNNSNNSNNSNNSNNSATGAAGAAGATGTTCCGCGAAATC | 474 |
| oligo 83I (C69) (EF A-NNS) | GTGCAGTGGGAAGAAGTGGTGNNSNNSNNSNNSNNSNNSNNSCGCAAGCTGATCGCCAGCATGAGCAGT | 475 |
| oligo 84revI (G4S) | GGAGCCTCCGCCTCCGCGGCGTTGAATCTGCACGTCCAGCTCGCCATACACATGGCGCAGGGAGTCACTGCTCATGCTGGCGATCAG | 476 |
| oligo 85revI (G4S-Flag-tag) | TTTTTTTTTTTTTTTTTTTTAAATAGCGGATGCCTTGTCGTCGTCGTCCTTGTAGTCGGAGCCTCCGCCTCCGCGGCG | 477 |
| 5. Primers used for construction of factor XIIIA, F13β1, MBP domains | | |
| oligo129 | AATGATCTACATATGAATGATCTAGACGTCCTGGCCAAGCAAAAGTCCACCGTGCTAACCATCCCTGAGATCATCATC | 478 |
| oligo 126 rev | TAGATCATTGGATCCCTCATTAATGATGGTGATGGTGATGCATGGAAGGGCGGCGTTGAATCTGCACGTC | 479 |
| oligo 118 (NdeI) | AATGATCTACATATGTCAGAAACTTCCAGGACCGCCTTT | 480 |
| oligo 101 rev | CTGAAGAGATCCCTTCTGGGGTCATACGGACGACTGAAGTCAATCTGCAC | 481 |
| oligo 100 | GTGCAGATTGACTTCAGTCGTCCGTATGACCCCAGAAGGGATCTCTTCAG | 482 |
| oligo 103 rev | CATAGGCATAGATATTGTCCCAGGAGCCAACGAGGACACCTTCGTCATC | 483 |
| oligo 102 | GATGACGAAGGTGTCCTCGTTGGCTCCTGGGACAATATCTATGCCTATG | 484 |
| oligo 133 rev | ATCAGTAATATCCATCATGCCATCACCACCAATTTGTTTGGTCACAATTAAT | 485 |
| oligo 134 | ATTAATTGTGACCAAACAAATTGGTGGTGATGGCATGATGGATATTACTGAT | 486 |
| oligo 136 rev | CACGGTGGACTTTTGCTTGGCCAGGACGTCCCTGGTCTCATTGATGCGAGCTGT | 487 |
| oligo 127 | AATGATCTACATATGAAAATCGAAGAAGGTAAACTGGTA | 488 |
| oligo128 rev | TAGATCATTCATATGCCTTCCCTCGATCCCGAGGTTGTT | 489 |
| oligo 132 (NdeI) | AATGATCTACATATGTCCAACGTTGACATGGACTTTGAAG | 490 |
| oligo 60 (NdeI) | TAATACGACTCACTATAGGGACAATTACTATTTACAATTACATATGTCCAACGTTGACATGGACTTTGAA | 491 |
| Oligo 62rev (BamHI) | TAGATCATTGGATCCCTCATTAATGATGGTGATGGTGATGTAGCACGGTGGACTTTTGCTTGGC | 492 |
| oligo EG1rev (XhoI) | TAGATTATTCTCGAGCTCATTATAGCACGGTGGACTTTTGCTTGGCCAG | 493 |
| oligo 61rev (BamHI) | TCCTTTGCTGAATTCGCCAGAACCAGCAGCGGAGCCAGCGGATCCTAGCACGGTGGACTTTTGCTTGGC | 494 |

TABLE 11

Oligonucleotides used for ETBP phage display. Table 11 discloses SEQ ID NOS 495-515.

| Name | Sequence |
|---|---|
| FG1 | ATTACGCCAAGCTTTGGAGCCTTTTTTTTGGAGATTTTCAACGTGAAAAAATTATTATTCGCAATTCCTTTAG |
| FG2 | TTATTATTCGCAATTCCTTTAGTTGTTCCTTTCTATTCTCACTCGGCCGACGTGGCCACCATCCCTGAGATCATCATC |
| FG3 | TGAGATGAGTTTTTGTTCTGCGGCCCCAGACGCGTGATGGTGATGATGATGTGCGGCCGCGCGGCGTTGAATCTGCACG |

TABLE 11-continued

Oligonucleotides used for ETBP phage display. Table 11 discloses SEQ ID NOS 495-515.

| Name | Sequence |
|---|---|
| FG4 | GCAGAACAAAAACTCATCTCAGAAGAGGATCTGAATGGGGCAGCAGAAGCTAGTTCTGCTAGTGCCGAAACTGTTGAAAGTTG |
| FG5 | GTAAAACGACGGCCAGTGAATTCTCATCACGCGTTTCATTAAGACTCCTTATTACGCAGTATG |
| FG6 | GCAGAACAAAAACTCATCTCAGAAGAGGATCTGAATGGGGCAGCAGAAGCTAGTTCTGCTAGTGCCTCTGGTTCCGGTGATTTTG |
| FG7 | CTGAAACATGAAAGTATTAAGAGGC |
| AKx295Y | TCTATTCTCACTCGGCCGACGTGGCCGTCTTCACCATCCCTGAGATCATCATC |
| AKx296Y | TCTATTCTCACTCGAAGACACGTGGCCACCATCCCTGAGATCATCATC |
| AKx297Y | TGAGATGAGTTTGCGGCCGCGCGGCGTTGGTCTTCAATCTGCACGTCCAGCTC |
| AKx298Y | TGAGATGAGTTTGAAGACCGGCGTTGAATCTGCACGTCCAGCTCGC |
| 1867 not pI | gggatccgcggccgcaggctctaaagatatcagaactgttgaaagttgtttagcaaaacc |
| 1868 bsu36 | GGGATCCTGAGGAATTCTTATTAAGACTCCTTATTACGCAGTATGTTAGCAA |
| 1873 bgl2 b | gggagatctCCTCAGGaaccatagtacgcgccctgtag |
| 1874 bsmb1 | gggtgtacacgtctccggagattgtataagcaaatatttaaattgtaaacgtt |
| 1875 bsmb1 | ggaattccgtctccCTCCGCCCATCCCGCCCCTAACTCC |
| 1876 H3 amp | ggaattcaagcttgggACTAGTTATGCCGAAAGGCCATCCTGAC |
| 1877 F13 pst | ggaattccctgcaggtACCATCCCTGAGATCATCATCAAGGT |
| 1878 F13 not | GATGATGTGCGGCCGCGCGGCGTTGAATCTGCACGTCCAGCTCGCCA |
| 1882 pst bst | gagacgcacaacaccgtctcgc |
| 1883 pst bst | ggccgcgagacggtgttgtgcgtctctgca |

TABLE 12

Sequence of paracompgp3 phagemid vector
LOCUS paracompgp3 4930 by

| FEATURES | Location/Qualifiers |
|---|---|
| misc_binding | 1 . . . 6<br>/dbxref = "REBASE: HindIII" |
| Other Gene | 13 . . . 891<br>/gene = "AraC other" |
| ORF | 13 . . . 942<br>/sequence = "ORF_3 rf(5)" |
| misc_binding | 623 . . . 628<br>/dbxref = "REBASE: NruI" |
| Regulatory_Seq | 921 . . . 936<br>/gene = "arao2 reg" |
| Other Gene | 1120 . . . 1133<br>/gene = "CAP_BS other" |
| Other Gene | 1130 . . . 1168<br>/gene = "AraI1I2 other" |
| Promoter | 1165 . . . 1193<br>/gene = "ARA prom" |
| misc_binding | 1301 . . . 1306<br>/dbxref = "REBASE: PstI" |
| misc_binding | 1326 . . . 1333<br>/dbxref = "REBASE: NOtI" |
| ORF | 1749 . . . 2567<br>/sequence = "ORF_2 rf(3)" |
| misc_binding | 2241 . . . 2246<br>/dbxref = "REBASE: ClaI" |
| misc_binding | 2571 . . . 2576<br>/dbxref = "REBASE: EcoRI" |

TABLE 12-continued

| Sequence of paracompgp3 phagemid vector LOCUS paracompgp3 4930 by | |
|---|---|
| FEATURES | Location/Qualifiers |
| Rep_Origin | 2609 . . . 2915<br>/gene = "f1 origin" |
| Rep_Origin | 3075 . . . 3152<br>/gene = "SV40 origin" |
| misc_binding | 3155 . . . 3167<br>/dbxref = "REBASE: SfiI" |
| misc_binding | 3156 . . . 3166<br>/dbxref = "REBASE: BglI" |
| misc_binding | 3206 . . . 3211<br>/dbxref = "REBASE: StuI" |
| Rep_Origin | 3236 . . . 3818<br>/gene = "pBR322 origin" |
| Marker | 3893 . . . 4753<br>/gene = "amp marker" |
| ORF | 3893 . . . 4753<br>/sequence = "ORF_1 rf(2)" |
| BASE COUNT | 1224 a 1206 c 1214 g 1286 t 0 others |
| ORIGIN | |
| 1 | aagcttgata tcttatgaca acttgacggc tacatcattc actttttctt cacaaccggc |
| 61 | acggaactcg ctcgggctgg ccccggtgca ttttttaaat acccgcgaga aatagagttg |
| 121 | atcgtcaaaa ccaacattgc gaccgacggt ggcgataggc atccgggtgg tgctcaaaag |
| 181 | cagcttcgcc tggctgatac gttggtcctc gcgccagctt aagacgctaa tccctaactg |
| 241 | ctggcggaaa agatgtgaca gacgcgacgg cgacaagcaa acatgctgtg cgacgctggc |
| 301 | gatatcaaaa ttgctgtctg ccaggtgatc gctgatgtac tgacaagcct cgcgtacccg |
| 361 | attatccatc ggtggatgga gcgactcgtt aatcgcttcc atgcgccgca gtaacaattg |
| 421 | ctcaagcaga tttatcgcca gcagctccga atagcgccct tccccttgcc cggcgttaat |
| 481 | gatttgccca aacaggtcgc tgaaatgcgg ctggtgcgct tcatccgggc gaaagaaccc |
| 541 | cgtattggca aatattgacg gccagttaag ccattcatgc cagtaggcgc gcggacgaaa |
| 601 | gtaaacccac tggtgatacc attcgcgagc ctccggatga cgaccgtagt gatgaatctc |
| 661 | tcctggcggg aacagcaaaa tatcacccgg tcggcaaaca aattctcgtc cctgattttt |
| 721 | caccaccccc tgaccgcgaa tggtgagatt gagaatataa cctttcattc ccagcggtcg |
| 781 | gtcgataaaa aaatcgagat aaccgttggc cacaaccggc gttaaacccg ccaccagatg |
| 841 | ggcattaaac gagtatcccg gcagcagggg atcattttgc gcttcagcca tacttttcat |
| 901 | actcccgcca ttcagagaag aaaccaattg tccatattgc atcagacatt gccgtcactg |
| 961 | cgtcttttac tggctcttct cgctaaccaa accggtaacc ccgcttatta aaagcattct |
| 1021 | gtaacaaagc gggaccaaag ccatgacaaa aacgcgtaac aaaagtgtct ataatcacgg |
| 1081 | cagaaaagtc cacattgatt atttgcacgg cgtcacactt tgctatgcca tagcattttt |
| 1141 | atccataaga ttagcggatc ctacctgacg ctttttatcg caactctcta ctgtttctcc |
| 1201 | atacccgttt ttttgggcta acaggaggaa ttaatcatga tgaagcgcaa tattctggca |
| 1261 | gtgatcgtcc ctgctctgtt agtagcaggt actgcaaacg ctgcagagac gcacaacacc |
| 1321 | gtctcgcggc cgcaggctct aaagatatca gaactgttga aagttgttta gcaaaacccc |

TABLE 12-continued

Sequence of paracompgp3 phagemid vector
LOCUS paracompgp3 4930 by

| FEATURES | Location/Qualifiers |
|---|---|
| 1381 | atacagaaaa ttcatttact aacgtctgga aagacgacaa aactttagat cgttacgcta |
| 1441 | actatgaggg ttgtctgtgg aatgctacag gcgttgtagt ttgtactggt gacgaaactc |
| 1501 | agtgttacgg tacatgggtt cctattgggc ttgctatccc tgaaaatgag ggtggtggct |
| 1561 | ctgagggtgg cggttctgag ggtggcggtt ctgagggtgg cggtactaaa cctcctgagt |
| 1621 | acggtgatac acctattccg ggctatactt atatcaaccc tctcgacggc acttatccgc |
| 1681 | ctggtactga gcaaaacccc gctaatccta atccttctct tgaggagtct cagcctctta |
| 1741 | atactttcat gtttcagaat aataggttcc gaaataggca gggggcatta actgtttata |
| 1801 | cgggcactgt tactcaaggc actgaccccg ttaaaactta ttaccagtac actcctgtat |
| 1861 | catcaaaagc catgtatgac gcttactgga acggtaaatt cagagactgc gctttccatt |
| 1921 | ctggctttaa tgaggatcca ttcgtttgtg aatatcaagg ccaatcgtct gacctgcctc |
| 1981 | aacctcctgt caatgctggc ggcggctctg gtggtggttc tggtggcggc tctgagggtg |
| 2041 | gtggctctga gggtggcggt tctgagggtg gcggctctga gggaggcggt tccggtggtg |
| 2101 | gctctggttc cggtgatttt gattatgaaa agatggcaaa cgctaataag ggggctatga |
| 2161 | ccgaaaatgc cgatgaaaac gcgctacagt ctgacgctaa aggcaaactt gattctgtcg |
| 2221 | ctactgatta cggtgctgct atcgatggtt tcattggtga cgtttccggc cttgctaatg |
| 2281 | gtaatggtgc tactggtgat tttgctggct ctaattccca aatggctcaa gtcggtgacg |
| 2341 | gtgataattc acctttaatg aataatttcc gtcaatattt accttccctc cctcaatcgg |
| 2401 | ttgaatgtcg cccttttgtc tttagcgctg gtaaaccata tgaattttct attgattgtg |
| 2461 | acaaaataaa cttattccgt ggtgtctttg cgtttctttt atatgttgcc acctttatgt |
| 2521 | atgtattttc tacgtttgct aacatactgc gtaataagga gtcttaataa gaattcctca |
| 2581 | ggaaccatag tacgcgccct gtagcggcgc attaagcgcg gcgggtgtgg tggttacgcg |
| 2641 | cagcgtgacc gtaacaattg ccagcgccct agcgcccgct cctttcgctt tcttcccttc |
| 2701 | ctttctcgcc acgttcgccg gctttccccg tcaagctcta aatcgggggc tccctttagg |
| 2761 | gttccgattt agtgctttac ggcacctcga ccccaaaaaa cttgatttgg gtgatggttc |
| 2821 | acgtagtggg ccatcgccct gatagacggt ttttcgccct ttgacgttgg agtccacgtt |
| 2881 | ctttaatagt ggactcttgt tccaaactgg aacaacactc aaccctatct cgggctattc |
| 2941 | ttttgattta taagggattt tgccgatttc ggcctattgg ttaaaaaatg agctgattta |
| 3001 | acaaaaattt aacgcgaatt ttaacaaaat attaacgttt acaatttaaa tatttgctta |
| 3061 | tacaatctcc gcccatcccg cccctaactc cgcccagttc cgcccattct ccgcctcatg |
| 3121 | gctgactaat tttttttatt tatgcagagg ccgaggccgc ctcggcctct gagctattcc |
| 3181 | agaagtagtg aggaggcttt tttggaggcc taggcttttg caaaaagcta attcggcgta |
| 3241 | atctgctgct tgcaaacaaa aaaaccaccg ctaccagcgg tggtttgttt gccggatcaa |
| 3301 | gagctaccaa ctctttttcc gaaggtaact ggcttcagca gagcgcagat accaaatact |
| 3361 | gtccttctag tgtagccgta gttaggccac cacttcaaga actctgtagc accgcctaca |
| 3421 | tacctcgctc tgctgaagcc agttaccagt ggctgctgcc agtggcgata agtcgtgtct |
| 3481 | taccgggttg gactcaagag atagttaccg gataaggcgc agcggtcggg ctgaacgggg |
| 3541 | ggttcgtgca cacagcccag cttggagcga acgacctaca ccgaactgag atacctacag |
| 3601 | cgtgagctat gagaaagcgc cacgcttccc gaagggagaa aggcggacag gtatccggta |

TABLE 12-continued

| Sequence of paracompgp3 phagemid vector LOCUS paracompgp3 4930 by | |
|---|---|
| FEATURES | Location/Qualifiers |
| 3661 | agcggcaggg tcggaacagg agagcgcacg agggagcttc caggggggaaa cgcctggtat |
| 3721 | ctttatagtc ctgtcgggtt tcgccacctc tgacttgagc gtcgattttt gtgatgctcg |
| 3781 | tcaggggggc ggagcctatg gaaaaacgcc agcaacgcaa gctagagttt aaacttgaca |
| 3841 | gatgagacaa taaccctgat aaatgcttca ataatattga aaaaggaaaa gtatgagtat |
| 3901 | tcaacatttc cgtgtcgccc ttattccctt ttttgcggca ttttgccttc ctgtttttgc |
| 3961 | tcacccagaa acgctggtga aagtaaaaga tgcagaagat cacttgggtg cgcgagtggg |
| 4021 | ttacatcgaa ctggatctca acagcggtaa gatccttgag agttttcgcc ccgaagaacg |
| 4081 | tttcccaatg atgagcactt ttaaagttct gctatgtggc gcggtattat cccgtattga |
| 4141 | tgccgggcaa gagcaactcg gtcgccgcat acactattct cagaatgact tggttgaata |
| 4201 | ctcaccagtc acagaaaagc atcttacgga tggcatgaca gtaagagaat tatgcagtgc |
| 4261 | tgccataacc atgagtgata acactgcggc caacttactt ctgacaacta tcggaggacc |
| 4321 | gaaggagcta accgcttttt tgcacaacat gggggatcat gtaactcgcc ttgatcgttg |
| 4381 | ggaaccggag ctgaatgaag ccataccaaa cgacgagcgt gacaccacga tgcctgtagc |
| 4441 | aatggcaaca acgttgcgaa aactattaac tggcgaacta cttactctag cttcccggca |
| 4501 | acaactaata gactggatgg aggcggataa agttgcagga ccacttctgc gctcggcact |
| 4561 | tccggctggc tggtttattg ctgataaatc aggagccggt gagcgtgggt cacgcggtat |
| 4621 | cattgcagca ctggggccgg atggtaagcc ctcccgtatc gtagttatct acactacggg |
| 4681 | gagtcaggca actatggatg aacgaaatag acagatcgct gagataggtg cctcactgat |
| 4741 | taagcattgg taaggataaa tttctggtaa ggaggacacg tatggaagtg ggcaagttgg |
| 4801 | ggaagccgta tccgttgctg aatctggcat atgtgggagt ataagacgcg cagcgtcgca |
| 4861 | tcaggcattt ttttctgcgc caatgcaaaa aggccatccg tcaggatggc ctttcggcat |
| 4921 | aactagtccc (SEQ ID NO: 516) |
| // | |

TABLE 13

| Sequence of paracompFXIIIb2pIII phagemid vector LOCUS paracompFXIIIb2pIII 5216 bp | |
|---|---|
| FEATURES | Location/Qualifiers |
| misc_binding | 1 . . . 6<br>/dbxref = "REBASE: HindIII" |
| Other Gene | 13 . . . 891<br>/gene = "AraC other" |
| ORF | 13 . . . 942<br>/sequence = "ORF_3 rf(6)" |
| misc_binding | 623 . . . 628<br>/dbxref = "REBASE: NruI" |
| Regulatory_Seq | 921 . . . 936<br>/gene = "arao2 reg" |
| Other Gene | 1120 . . . 1133<br>/gene = "CAP_BS other" |

TABLE 13-continued

| Sequence of paracompFXIIIb2pIII phagemid vector LOCUS paracompFXIIIb2pIII 5216 bp | |
|---|---|
| FEATURES | Location/Qualifiers |
| Other Gene | 1130 . . . 1168<br>/gene = "AraI1I2 other" |
| Promoter | 1165 . . . 1193<br>/gene = "ARA prom" |
| ORF | 1237 . . . 2853<br>/sequence = "ORF_1 rf(1)" |
| misc_binding | 1301 . . . 1306<br>/dbxref = "REBASE: PstI" |
| misc_binding | 1306 . . . 1311<br>/dbxref = "REBASE: KpnI" |
| misc_binding | 1516 . . . 1521<br>/dbxref = "REBASE: NcoI" |
| misc_binding | 1612 . . . 1619<br>/dbxref = "REBASE: NotI" |
| misc_binding | 2527 . . . 2532<br>/dbxref = "REBASE: ClaI" |
| misc_binding | 2857 . . . 2862<br>/dbxref = "REBASE: EcoRI" |
| Rep_Origin | 2895 . . . 3201<br>/gene = "f1 origin" |
| Rep_Origin | 3361 . . . 3438<br>/gene = "SV40 origin" |
| misc_binding | 3441 . . . 3453<br>/dbxref = "REBASE: SfiI" |
| misc_binding | 3442 . . . 3452<br>/dbxref = "REBASE: BglI" |
| misc_binding | 3492 . . . 3497<br>/dbxref = "REBASE: StuI" |
| Rep_Origin | 3522 . . . 4104<br>/gene = "pBR322 origin" |
| Marker | 4179 . . . 5039<br>/gene = "amp marker" |
| ORF | 4179 . . . 5039<br>/sequence = "ORF-2 rf(3)" |
| BASE COUNT | 1286 a 1285 c 1298 g 1347 t 0 others |
| ORIGIN | |
| 1 | aagcttgata tcttatgaca acttgacggc tacatcattc actttttctt cacaaccggc |
| 61 | acggaactcg ctcgggctgg ccccggtgca ttttttaaat acccgcgaga aatagagttg |
| 121 | atcgtcaaaa ccaacattgc gaccgacggt ggcgataggc atccgggtgg tgctcaaaag |
| 181 | cagcttcgcc tggctgatac gttggtcctc gcgccagctt aagacgctaa tccctaactg |
| 241 | ctggcggaaa agatgtgaca gacgcgacgg cgacaagcaa acatgctgtg cgacgctggc |
| 301 | gatatcaaaa ttgctgtctg ccaggtgatc gctgatgtac tgacaagcct cgcgtacccg |
| 361 | attatccatc ggtggatgga gcgactcgtt aatcgcttcc atgcgccgca gtaacaattg |
| 421 | ctcaagcaga tttatcgcca gcagctccga atagcgccct tccccttgcc cggcgttaat |
| 481 | gatttgccca aacaggtcgc tgaaatgcgg ctggtgcgct tcatccgggc gaaagaaccc |
| 541 | cgtattggca aatattgacg gccagttaag ccattcatgc cagtaggcgc gcggacgaaa |

TABLE 13-continued

Sequence of paracompFXIIIb2pIII phagemid vector
LOCUS paracompFXIIIb2pIII 5216 bp

| FEATURES | Location/Qualifiers |
|---|---|
| 601 | gtaaacccac tggtgatacc attcgcgagc ctccggatga cgaccgtagt gatgaatctc |
| 661 | tcctggcggg aacagcaaaa tatcacccgg tcggcaaaca aattctcgtc cctgattttt |
| 721 | caccaccccc tgaccgcgaa tggtgagatt gagaatataa cctttcattc ccagcggtcg |
| 781 | gtcgataaaa aaatcgagat aaccgttggc ctcaatcggc gttaaacccg ccaccagatg |
| 841 | ggcattaaac gagtatcccg gcagcagggg atcattttgc gcttcagcca tacttttcat |
| 901 | actcccgcca ttcagagaag aaaccaattg tccatattgc atcagacatt gccgtcactg |
| 961 | cgtcttttac tggctcttct cgctaaccaa accggtaacc ccgcttatta aaagcattct |
| 1021 | gtaacaaagc gggaccaaag ccatgacaaa aacgcgtaac aaaagtgtct ataatcacgg |
| 1081 | cagaaaagtc cacattgatt atttgcacgg cgtcacactt tgctatgcca tagcattttt |
| 1141 | atccataaga ttagcggatc ctacctgacg ctttttatcg caactctcta ctgtttctcc |
| 1201 | atacccgttt ttttgggcta acaggaggaa ttaatcatga tgaagcgcaa tattctggca |
| 1261 | gtgatcgtcc ctgctctgtt agtagcaggt actgcaaacg ctgcaggtac catccctgag |
| 1321 | atcatcatca aggtccgcgg cactcaggtc gtgggttctg acatgactgt gatcgtggag |
| 1381 | tttaccaatc ctctgaaaga aaccctgcgc aatgtctggg tgcacctgga tggtcctgga |
| 1441 | gtcacacgcc caatgaagaa gatgttccgc gaaatccgcc caaactccac cgtgcagtgg |
| 1501 | gaagaagtgg tccgcccatg ggtctctggg catcgcaagc tgatcgccag catgagcagt |
| 1561 | gactccctgc gccatgtgta tggcgagctg gacgtgcaga ttcaacgccg cgcggccgca |
| 1621 | ggctctaaag atatcagaac tgttgaaagt tgtttagcaa aaccccatac agaaaattca |
| 1681 | tttactaacg tctggaaaga cgacaaaact ttagatcgtt acgctaacta tgagggttgt |
| 1741 | ctgtggaatg ctacaggcgt tgtagtttgt actggtgacg aaactcagtg ttacggtaca |
| 1801 | tgggttccta ttgggcttgc tatccctgaa aatgagggtg gtggctctga gggtggcggt |
| 1861 | tctgagggtg gcggttctga gggtggcggt actaaacctc ctgagtacgg tgatacacct |
| 1921 | attccgggct atacttatat caaccctctc gacggcactt atccgcctgg tactgagcaa |
| 1981 | aaccccgcta atcctaatcc ttctcttgag gagtctcagc ctcttaatac tttcatgttt |
| 2041 | cagaataata ggttccgaaa taggcagggg gcattaactg tttatacggg cactgttact |
| 2101 | caaggcactg accccgttaa aacttattac cagtacactc ctgtatcatc aaaagccatg |
| 2161 | tatgacgctt actggaacgg taaattcaga gactgcgctt tccattctgg ctttaatgag |
| 2221 | gatccattcg tttgtgaata tcaaggccaa tcgtctgacc tgcctcaacc tcctgtcaat |
| 2281 | gctggcggcg gctctggtgg tggttccggt ggcggctctg agggtggtgg ctctgagggt |
| 2341 | ggcggttctg agggtggcgg ctctgaggga ggcggttccg gtggtggctc tggttccggt |
| 2401 | gattttgatt atgaaaagat ggcaaacgct aataaggggg ctatgaccga aaatgccgat |
| 2461 | gaaaacgcgc tacagtctga cgctaaaggc aaacttgatt ctgtcgctac tgattacggt |
| 2521 | gctgctatcg atggtttcat tggtgacgtt tccggccttg ctaatggtaa tggtgctact |
| 2581 | ggtgattttg ctggctctaa ttcccaaatg gctcaagtcg gtgacggtga taattcacct |
| 2641 | ttaatgaata atttccgtca atatttacct tccctccctc aatcggttga atgtcgccct |
| 2701 | tttgtcttta gcgctggtaa accatatgaa ttttctattg attgtgacaa aataaactta |
| 2761 | ttccgtggtg tctttgcgtt tcttttatat gttgccacct ttatgtatgt attttctacg |

TABLE 13-continued

Sequence of paracompFXIIIb2pIII phagemid vector
LOCUS paracompFXIIIb2pIII 5216 bp

| FEATURES | Location/Qualifiers |
|---|---|
| 2821 | tttgctaaca tactgcgtaa taaggagtct taataagaat tcctcaggaa ccatagtacg |
| 2881 | cgccctgtag cggcgcatta agcgcggcgg gtgtggtggt tacgcgcagc gtgaccgcta |
| 2941 | cacttgccag cgccctagcg cccgctcctt tcgctttctt cccttccttt ctcgccacgt |
| 3001 | tcgccggctt tccccgtcaa gctctaaatc gggggctccc tttagggttc cgatttagtg |
| 3061 | ctttacggca cctcgacccc aaaaaacttg atttgggtga tggttcacgt agtgggccat |
| 3121 | cgccctgata gacggttttt cgccctttga cgttggagtc cacgttcttt aatagtggac |
| 3181 | tcttgttcca aactggaaca acactcaacc ctatctcggg ctattctttt gatttataag |
| 3241 | ggattttgcc gatttcggcc tattggttaa aaaatgagct gatttaacaa aaatttaacg |
| 3301 | cgaattttaa caaaatatta acgtttacaa tttaaatatt tgcttataca atctccgccc |
| 3361 | atcccgcccc taactccgcc cagcttcgcc cattctccgc ctcatggctg actaattttt |
| 3421 | tttatttatg cagaggccga ggccgcctcg gcctctgagc tattccagaa gtagtgagga |
| 3481 | ggcttttttg gaggcctagg cttttgcaaa aagctaattc ggcgtaatct gctgcttgca |
| 3541 | aacaaaaaaa ccaccgctac cagcggtggt ttgtttgccg gatcaagagc taccaactct |
| 3601 | ttttccgaag gtaactggct tcagcagagc gcagatacca aatactgtcc ttctagtgta |
| 3661 | gccgtagtta ggccaccact tcaagaactc tgtagcaccg cctacatacc tcgctctgct |
| 3721 | gaagccagtt accagtggct gctgccagtg gcgataagtc gtgtcttacc gggttggact |
| 3781 | caagagatag ttaccggata aggcgcagcg gtcgggctga acggggggtt cgtgcacaca |
| 3841 | gcccagcttg gagcgaacga cctacaccga actgagatac ctacagcgtg agctatgaga |
| 3901 | aagcgccacg cttcccgaag ggagaaaggc ggacaggtat ccggtaagcg gcagggtcgg |
| 3961 | aacaggagag cgcacgaggg agcttccagg gggaaacgcc tggtatcttt atagtcctgt |
| 4021 | cgggtttcgc cacctctgac ttgagcgtcg atttgggtga tgctcgtcag gggggcggag |
| 4081 | cctatggaaa aacgccagca acgcaagcta gagtttaaac ttgacagatg agacaataac |
| 4141 | cctgataaat gcttcaataa tattgaaaaa ggaaaagtat gagtattcaa catttccgtg |
| 4201 | tcgcccttat tccctttttt gcggcatttt gccttcctgt ttttgctcac ccagaaacgc |
| 4261 | tggtgaaagt aaaagatgca gaagatcact tgggtgcgcg agtgggttac atcgaactgg |
| 4321 | atctcaacag cggtaagatc cttgagagtt ttcgccccga agaacgtttc ccaatgatga |
| 4381 | gcacttttaa agttctgcta tgtggcgcgg tattatcccg tattgatgcc gggcaagagc |
| 4441 | aactcggtcg ccgcatacac tattctcaga atgacttggt tgaatactca ccagtcacag |
| 4501 | aaaagcatct tacggatggc atgacagtaa gagaattatg cagtgctgcc ataaccatga |
| 4561 | gtgataacac tgcggccaac ttacttctga caactatcgg aggaccgaag gagctaaccg |
| 4621 | cttttttgca caacatgggg gatcatgtaa ctcgccttga tcgttgggaa ccggagctga |
| 4681 | atgaagccat accaaacgac gagcgtgaca ccacgatgcc tgtagcaatg gcaacaacgt |
| 4741 | tgcgaaaact attaactggc gaactactta ctctagcttc ccggcaacaa ctaatagact |
| 4801 | ggatggaggc ggataaagtt gcaggaccac ttctgcgctc ggcacttccg gctggctggt |
| 4861 | ttattgctga taaatcagga gccggtgagc gtgggtcacg cggtatcatt gcagcactgg |
| 4921 | ggccggatgg taagccctcc cgtatcgtag ttatctacac tacggggagt caggcaacta |
| 4981 | tggatgaacg aaatagacag atcgctgaga taggtgcctc actgattaag cattggtaag |
| 5041 | gataaatttc tggtaaggag gacacgtatg gaagtgggca agttggggaa gccgtatccg |

TABLE 13-continued

| Sequence of paracompFXIIIb2pIII phagemid vector LOCUS paracompFXIIIb2pIII 5216 bp | |
|---|---|
| FEATURES | Location/Qualifiers |
| 5101 | ttgctgaatc tggcatatgt gggagtataa gacgcgcagc gtcgcatcag gcattttttt |
| 5161 | ctgcgccaat gcaaaaaggc catccgtcag gatggccttt cggcataact agtccc (SEQ ID NO: 517) |
| // | |

TABLE 14

| Sequence of pET28_wtF13-his LOCUS pET28-wtF13-his 5565 bp | |
|---|---|
| FEATURES | Location/Qualifiers |
| Terminator | 1 . . . 129<br>/gene = "T7 term" |
| misc_binding | 158 . . . 163<br>/dbxref = "REBASE: XhoI" |
| misc_binding | 161 . . . 166<br>/dbxref = "REBASE: SacI" |
| misc_binding | 403 . . . 408<br>/dbxref = "REBASE: DraI" |
| misc_binding | 492 . . . 497<br>/dbxref = "REBASE: NdeI" |
| misc_binding | 531 . . . 536<br>/dbxref = "REBASE: XbaI" |
| Regulatory_Seq | 537 . . . 564<br>/gene = "lacO reg" |
| Promoter | 564 . . . 582<br>/gene = "T7 prom" |
| misc_binding | 597 . . . 602<br>/dbxref = "REBASE: BglII" |
| misc_binding | 790 . . . 795<br>/dbxref = "REBASE: SphI" |
| Regulatory_Seq | 960 . . . 2051<br>/gene = "lacI reg" |
| ORF | 1092 . . . 2051<br>/sequence = "ORF_1 rf(3)" |
| misc_binding | 1333 . . . 1338<br>/dbxref = "REBASE: BclI" |
| misc_binding | 1526 . . . 1531<br>/dbxref = "REBASE: ApaI" |
| misc_binding | 1767 . . . 1772<br>/dbxref = "REBASE: EcoRV" |
| misc_binding | 1823 . . . 1828<br>/dbxref = "REBASE: HpaI" |
| misc_binding | 1823 . . . 1828<br>/dbxref = "REBASE: HincII" |
| misc_binding | 2377 . . . 2387<br>/dbxref = "REBASE: BglI" |
| Other Gene | 2860 . . . 3051<br>/gene = "ROP other" |

TABLE 14-continued

| Sequence of pET28_wtF13-his LOCUS pET28-wtF13-his 5565 bp | |
|---|---|
| FEATURES | Location/Qualifiers |
| misc_binding | 3189 . . . 3194<br>/dbxref = "REBASE: AccI" |
| Rep_Origin | 3466 . . . 4085<br>/gene = "pBR322 origin" |
| misc_binding | 3831 . . . 3839<br>/dbxref = "REBASE: AlwNI" |
| Marker | 4191 . . . 5006<br>/gene = "kan2 marker" |
| ORF | 4191 . . . 5006<br>/sequence = "ORF_2 rf(3)" |
| misc_binding | 4277 . . . 4282<br>/dbxref = "REBASE: NruI" |
| misc_binding | 4312 . . . 4317<br>/dbxref = "REBASE: ClaI" |
| misc_binding | 4494 . . . 4499<br>/dbxref = "REBASE: SmaI" |
| misc_binding | 4494 . . . 4499<br>/dbxref = "REBASE: XmaI" |
| Rep_Origin | 5231 . . . 5537<br>/gene = "f1 origin" |
| BASE COUNT | 1320 a 1437 c 1481 g 1327 t 0 others |
| ORIGIN | |
| 1 | atccggatat agttcctcct ttcagcaaaa aacccctcaa gacccgttta gaggccccaa |
| 61 | ggggttatgc tagttattgc tcagcggtgg cagcagccaa ctcagcttcc tttcgggctt |
| 121 | tgttagcagc cggatctcag tggtggtggt ggtggtgctc gagctcatta atgatggtga |
| 181 | tggtgatgtc gtctttgaat ctgcacgtcc agctcgccat acacatgtct cagggagtca |
| 241 | ctgctcatgc tggctatcag cttccgatgc ccagagaccc agggccggca cacttcttcc |
| 301 | cactgcacgg tggagttggg ccggatttca cggaacatct tcttcattgg tcttgttact |
| 361 | ccaggaccat ccaggtgtac ccagacattt cgcagggttt cttttaaagg attggtaaac |
| 421 | tcaactatca cagtcatgtc agaaccaact acctgagtgc cacggacctt gatgatgatc |
| 481 | tcagggatgg tcatatgtat atctccttct taaagttaaa caaaattatt tctagagggg |
| 541 | aattgttatc cgctcacaat tcccctatag tgagtcgtat taatttcgcg ggatcgagat |
| 601 | ctcgatcctc tacgccggac gcatcgtggc cggcatcacc ggcgccacag gtgcggttgc |
| 661 | tggcgcctat atcgccgaca tcaccgatgg ggaagatcgg gctcgccact tcgggctcat |
| 721 | gagcgcttgt ttcggcgtgg gtatggtggc aggccccgtg gccgggggac tgttgggcgc |
| 781 | catctccttg catgcaccat tccttgcggc ggcggtgctc aacggcctca acctactact |
| 841 | gggctgcttc ctaatgcagg agtcgcataa gggagagcgt cgagatcccg gacaccatcg |
| 901 | aatggcgcaa aacctttcgc ggtatggcat gatagcgccc ggaagagagt caattcaggg |
| 961 | tggtgaatgt gaaaccagta acgttatacg atgtcgcaga gtatgccggt gtctcttatc |
| 1021 | agaccgtttc ccgcgtggtg aaccaggcca gccacgtttc tgcgaaaacg cgggaaaaag |
| 1081 | tggaagcggc gatggcggag ctgaattaca ttcccaaccg cgtggcacaa caactggcgg |
| 1141 | gcaaacagtc gttgctgatt ggcgttgcca cctccagtct ggccctgcac gcgccgtcgc |
| 1201 | aaattgtcgc ggcgattaaa tctcgcgccg atcaactggg tgccagcgtg gtggtgtcga |

TABLE 14-continued

| Sequence of pET28_wtF13-his LOCUS pET28-wtF13-his 5565 bp | |
|---|---|
| FEATURES | Location/Qualifiers |
| 1261 | tggtagaacg aagcggcgtc gaagcctgta aagcggcggt gcacaatctt ctcgcgcaac |
| 1321 | gcgtcagtgg gctgatcatt aactatccgc tggatgacca ggatgccatt gctgtggaag |
| 1381 | ctgcctgcac taatgttccg gcgttatttc ttgatgtctc tgaccagaca cccatcaaca |
| 1441 | gtattatttt ctcccatgaa gacggtacgc gactgggcgt ggagcatctg gtcgcattgg |
| 1501 | gtcaccagca aatcgcgctg ttagcgggcc cattaagttc tgtctcggcg cgtctgcgtc |
| 1561 | tggctggctg gcataaatat ctcactcgca atcaaattca gccgatagcg gaacgggaag |
| 1621 | gcgactggag tgccatgtcc ggttttcaac aaaccatgca aatgctgaat gagggcatcg |
| 1681 | ttcccactgc gatgctggtt gccaacgatc agatggcgct gggcgcaatg cgcgccatta |
| 1741 | ccgagtccgg gctgcgcgtt ggtgcggata tctcggtagt gggatacgac gataccgaag |
| 1801 | acagctcatg ttatatcccg ccgttaacca ccatcaaaca ggattttcgc ctgctggggc |
| 1861 | aaaccagcgt ggaccgcttg ctgcaactct ctcagggcca ggcggtgaag ggcaatcagc |
| 1921 | tgttgcccgt ctcactggtg aaaagaaaaa ccaccctggc gcccaatacg caaaccgcct |
| 1981 | ctccccgcgc gttggccgat tcattaatgc agctggcacg acaggtttcc cgactggaaa |
| 2041 | gcgggcagtg agcgcaacgc aattaatgta agttagctca ctcattaggc accgggatct |
| 2101 | cgaccgatgc ccttgagagc cttcaaccca gtcagctcct tccggtgggc gcggggcatg |
| 2161 | actatcgtcg ccgcacttat gactgtcttc tttatcatgc aactcgtagg acaggtgccg |
| 2221 | gcagcgctct gggtcatttt cggcgaggac cgctttcgct ggagcgcgac gatgatcggc |
| 2281 | ctgtcgcttg cggtattcgg aatcttgcac gccctcgctc aagccttcgt cactggtccc |
| 2341 | gccaccaaac gtttcggcga gaagcaggcc attatcgccg gcatggcggc cccacgggtg |
| 2401 | cgcatgatcg tgctcctgtc gttgaggacc cggctaggct ggcggggttg ccttactggt |
| 2461 | tagcagaatg aatcaccgat acgcgagcga acgtgaagcg actgctgctg caaaacgtct |
| 2521 | gcgacctgag caacaacatg aatggtcttc ggtttccgtg tttcgtaaag tctggaaacg |
| 2581 | cggaagtcag cgccctgcac cattatgttc cggatctgca tcgcaggatg ctgctggcta |
| 2641 | ccctgtggaa cacctacatc tgtattaacg aagcgctggc attgaccctg agtgattttt |
| 2701 | ctctggtccc gccgcatcca taccgccagt tgtttaccct cacaacgttc cagtaaccgg |
| 2761 | gcatgttcat catcagtaac ccgtatcgtg agcatcctct ctcgtttcat cggtatcatt |
| 2821 | acccccatga acagaaatcc cccttacacg gaggcatcag tgaccaaaca ggaaaaaacc |
| 2881 | gcccttaaca tggcccgctt tatcagaagc cagacattaa cgcttctgga gaaactcaac |
| 2941 | gagctggacg cggatgaaca ggcagacatc tgtgaatcgc ttcacgacca cgctgatgag |
| 3001 | ctttaccgca gctgcctcgc gcgtttcggt gatgacggtg aaaacctctg acacatgcag |
| 3061 | ctcccggaga cggtcacagc ttgtctgtaa gcggatgccg ggagcagaca agcccgtcag |
| 3121 | ggcgcgtcag cgggtgttgg cgggtgtcgg ggcgcagcca tgacccagtc acgtagcgat |
| 3181 | agcggagtgt atactggctt aactatgcgg catcagagca gattgtactg agagtgcacc |
| 3241 | atatatgcgg tgtgaaatac cgcacagatg cgtaaggaga aaataccgca tcaggcgctc |
| 3301 | ttccgcttcc tcgctcactg actcgctgcg ctcggtcgtt cggctgcggc gagcggtatc |
| 3361 | agctcactca aaggcggtaa tacggttatc cacagaatca ggggataacg caggaaagaa |
| 3421 | catgtgagca aaaggccagc aaaaggccag gaaccgtaaa aaggccgcgt tgctggcgtt |

TABLE 14-continued

Sequence of pET28_wtF13-his
LOCUS pET28-wtF13-his 5565 bp

| FEATURES | Location/Qualifiers |
|---|---|
| 3481 | tttccatagg ctccgccccc ctgacgagca tcacaaaaat cgacgctcaa gtcagaggtg |
| 3541 | gcgaaacccg acaggactat aaagatacca ggcgtttccc cctggaagct ccctcgtgcg |
| 3601 | ctctcctgtt ccgaccctgc cgcttaccgg atacctgtcc gcctttctcc cttcgggaag |
| 3661 | cgtggcgctt tctcatagct cacgctgtag gtatctcagt tcggtgtagg tcgttcgctc |
| 3721 | caagctgggc tgtgtgcacg aaccccccgt tcagcccgac cgctgcgcct tatccggtaa |
| 3781 | ctatcgtctt gagtccaacc cggtaagaca cgacttatcg ccactggcag cagccactgg |
| 3841 | taacaggatt agcagagcga ggtatgtagg cggtgctaca gagttcttga agtggtggcc |
| 3901 | taactacggc tacactagaa ggacagtatt tggtatctgc gctctgctga agccagttac |
| 3961 | cttcggaaaa agagttggta gctcttgatc cggcaaacaa accaccgctg gtagcggtgg |
| 4021 | tttttttgtt tgcaagcagc agattacgcg cagaaaaaaa ggatctcaag aagatccttt |
| 4081 | gatcttttct acggggtctg acgctcagtg gaacgaaaac tcacgttaag ggattttggt |
| 4141 | catgaacaat aaaactgtct gcttacataa acagtaatac aaggggtgtt atgagccata |
| 4201 | ttcaacggga aacgtcttgc tctaggccgc gattaaattc caacatggat gctgatttat |
| 4261 | atgggtataa atgggctcgc gataatgtcg ggcaatcagg tgcgacaatc tatcgattgt |
| 4321 | atgggaagcc cgatgcgcca gagttgtttc tgaaacatgg caaaggtagc gttgccaatg |
| 4381 | atgttacaga tgagatggtc agactaaact ggctgacgga atttatgcct cttccgacca |
| 4441 | tcaagcattt tatccgtact cctgatgatg catggttact caccactgcg atccccggga |
| 4501 | aaacagcatt ccaggtatta gaagaatatc ctgattcagg tgaaaatatt gttgatgcgc |
| 4561 | tggcagtgtt cctgcgccgg ttgcattcga ttcctgtttg taattgtcct tttaacagcg |
| 4621 | atcgcgtatt tcgtctcgct caggcgcaat cacgaatgaa taacggtttg gttgatgcga |
| 4681 | gtgattttga tgacgagcgt aatggctggc ctgttgaaca agtctggaaa gaaatgcata |
| 4741 | aacttttgcc attctcaccg gattcagtcg tcactcatgg tgatttctca cttgataacc |
| 4801 | ttatttttga cgaggggaaa ttaataggtt gtattgatgt tggacgagtc ggaatcgcag |
| 4861 | accgatacca ggatcttgcc atcctatgga actgcctcgg tgagttttct ccttcattac |
| 4921 | agaaacggct ttttcaaaaa tatggtattg ataatcctga tatgaataaa ttgcagtttc |
| 4981 | atttgatgct cgatgagttt ttctaagaat taattcatga gcggatacat atttgaatgt |
| 5041 | atttagaaaa ataaacaaat aggggttccg cgcacatttc cccgaaaagt gccacctgaa |
| 5101 | attgtaaacg ttaatatttt gttaaaattc gcgttaaatt tttgttaaat cagctcattt |
| 5161 | tttaaccaat aggccgaaat cggcaaaatc ccttataaat caaaagaata gaccgagata |
| 5221 | gggttgagtg ttgttccagt ttggaacaag agtccactat taaagaacgt ggactccaac |
| 5281 | gtcaaagggc gaaaaaccgt ctatcagggc gatggcccac tacgtgaacc atcaccctaa |
| 5341 | tcaagttttt tggggtcgag gtgccgtaaa gcactaaatc ggaaccctaa agggagcccc |
| 5401 | cgatttagag cttgacgggg aaagccggcg aacgtggcga gaaaggaagg gaagaaagcg |
| 5461 | aaaggagcgg gcgctagggc gctggcaagt gtagcggtca cgctgcgcgt aaccaccaca |
| 5521 | cccgccgcgc ttaatgcgcc gctacagggc gcgtcccatt cgcca (SEQ ID NO: 518) |
| // | |

TABLE 15

Sequence of FXIIIb2BbsIpIIICT
LOCUS paracompFXIIIb2BbsIpIIICT 4111 bp

| FEATURES | Location/Qualifiers |
|---|---|
| Promoter | 143 . . . 172<br>/gene = "lac prom" |
| ORF | 217 . . . 1218<br>/sequence = "ORF_1 rf(1)" |
| misc_binding | 234 . . . 239<br>/dbxref = "REBASE: HindIII" |
| misc_binding | 321 . . . 333<br>/dbxref = "REBASE: SfiI" |
| misc_binding | 649 . . . 656<br>/dbxref = "REBASE: NotI" |
| Tag | 691 . . . 720<br>/gene = "c_myc tag" |
| misc_binding | 892 . . . 897<br>/dbxref = "REBASE: ClaI" |
| misc_binding | 1088 . . . 1093<br>/dbxref = "REBASE: NdeI" |
| misc_binding | 1234 . . . 1239<br>/dbxref = "REBASE: EcoRI" |
| Reporter | 1237 . . . 1396<br>/gene = "lacZ_a reporter" |
| misc_binding | 1395 . . . 1400<br>/dbxref = "REBASE: NarI" |
| Rep_Origin | 1486 . . . 1792<br>/gene = "f1 origin" |
| misc_binding | 1806 . . . 1811<br>/dbxref = "REBASE: AvrI" |
| misc_binding | 1806 . . . 1811<br>/dbxref = "REBASE: AvaI" |
| Promoter | 2241 . . . 2269<br>/gene = "amp prom" |
| Marker | 2311 . . . 3171<br>/gene = "amp marker" |
| ORF | 2311 . . . 3171<br>/sequence = "ORF_2 rf(1)" |
| Rep_Origin | 3326 . . . 3945<br>/gene = "pBR322 origin" |
| misc_binding | 3572 . . . 3580<br>/dbxref = "REBASE: AlwNI" |
| BASE COUNT | 999 a 1017 c 1003 g 1092 t 0 others |
| ORIGIN | |
| 1 | agcgcccaat acgcaaaccg cctctccccg cgcgttggcc gattcattaa tgcagctggc |
| 61 | acgacaggtt tcccgactgg aaagcgggca gtgagcgcaa cgcaattaat gtgagttagc |
| 121 | tcactcatta ggcaccccag gctttacact ttatgcttcc ggctcgtatg ttgtgtggaa |
| 181 | ttgtgagcgg ataacaattt cacacaggaa acagctatga ccatgattac gccaagcttt |
| 241 | ggagcctttt ttttggagat tttcaacgtg aaaaaattat tattcgcaat tcctttagtt |
| 301 | gttcctttct attctcactc ggccgacgtg gccgtcttca ccatccctga gatcatcatc |
| 361 | aaggtccgtg gcactcaggt agttggttct gacatgactg tgatagttga gtttaccaat |

TABLE 15-continued

Sequence of FXIIIb2BbsIpIIICT
LOCUS paracompFXIIIb2BbsIpIIICT 4111 bp

| FEATURES | Location/Qualifiers |
|---|---|
| 421 | cctttaaaag aaaccctgcg aaatgtctgg gtacacctgg atggtcctgg agtaacaaga |
| 481 | ccaatgaaga agatgttccg tgaaatccgg cccaactcca ccgtgcagtg ggaagaagtg |
| 541 | tgccggccct gggtctctgg gcatcggaag ctgatagcca gcatgagcag tgactccctg |
| 601 | agacatgtgt atggcgagct ggacgtgcag attgaagacc aacgccgcgc ggccgcacat |
| 661 | catcatcacc atcacgcgtc tggggccgca gaacaaaaac tcatctcaga agaggatctg |
| 721 | aatggggcag cagaagctag ttctgctagt gcctctggtt ccggtgattt tgattatgaa |
| 781 | aagatggcaa acgctaataa gggggctatg accgaaaatg ccgatgaaaa cgcgctacag |
| 841 | tctgacgcta aaggcaaact tgattctgtc gctactgatt acggtgctgc tatcgatggt |
| 901 | ttcattggtg acgtttccgg ccttgctaat ggtaatggtg ctactggtga ttttgctggc |
| 961 | tctaattccc aaatggctca agtcggtgac ggtgataatt cacctttaat gaataatttc |
| 1021 | cgtcaatatt taccttccct ccctcaatcg gttgaatgtc gcccttttgt ctttagcgct |
| 1081 | ggtaaaccat atgaattttc tattgattgt gacaaaataa acttattccg tggtgtcttt |
| 1141 | gctattcttt tatatgttgc cacctttatg tatgtatttt ctacgtttgc taacatactg |
| 1201 | cgtaataagg agtcttaatg aaacgcgtga tgagaattca ctggccgtcg ttttacaacg |
| 1261 | tcgtgactgg gaaaaccctg gcgttaccca acttaatcgc cttgcagcac atcccccttt |
| 1321 | cgccagctgg cgtaatagcg aagaggcccg caccgatcgc ccttcccaac agttgcgcag |
| 1381 | cctgaatggc gaatggcgcc tgatgcggta ttttctcctt acgcatctgt gcggtatttc |
| 1441 | acaccgcata cgtcaaagca accatagtac gcgccctgta gcggcgcatt aagcgcggcg |
| 1501 | ggtgtggtgg ttacgcgcag cgtgaccgct acacttgcca gcgccctagc gcccgctcct |
| 1561 | ttcgctttct tcccttcctt tctcgccacg ttcgccggct ttccccgtca agctctaaat |
| 1621 | cgggggctcc ctttagggtt ccgatttagt gctttacggc acctcgaccc caaaaaactt |
| 1681 | gatttgggtg atggttcacg tagtgggcca tcgccctgat agacggtttt tcgccctttg |
| 1741 | acgttggagt ccacgttctt taatagtgga ctcttgttcc aaactggaac aacactcaac |
| 1801 | cctatctcgg gctattcttt tgatttataa gggattttgc cgatttcggc ctattggtta |
| 1861 | aaaaatgagc tgatttaaca aaaatttaac gcgaatttta acaaaatatt aacgtttaca |
| 1921 | attttatggt gcactctcag tacaatctgc tctgatgccg catagttaag ccagccccga |
| 1981 | cacccgccaa cacccgctga cgcgccctga cgggcttgtc tgctcccggc atccgcttac |
| 2041 | agacaagctg tgaccgtctc cgggagctgc atgtgtcaga ggttttcacc gtcatcaccg |
| 2101 | aaacgcgcga gacgaaaggg cctcgtgata cgcctatttt tataggttaa tgtcatgata |
| 2161 | ataatggttt cttagacgtc aggtggcact tttcggggaa atgtgcgcgg aacccctatt |
| 2221 | tgtttatttt tctaaataca ttcaaatatg tatccgctca tgagacaata accctgataa |
| 2281 | atgcttcaat aatattgaaa aaggaagagt atgagtattc aacatttccg tgtcgccctt |
| 2341 | attccctttt ttgcggcatt ttgccttcct gtttttgctc acccagaaac gctggtgaaa |
| 2401 | gtaaaagatg ctgaagatca gttgggtgca cgagtgggtt acatcgaact ggatctcaac |
| 2461 | agcggtaaga tccttgagag ttttcgcccc gaagaacgtt ttccaatgat gagcactttt |
| 2521 | aaagttctgc tatgtggcgc ggtattatcc cgtattgacg ccgggcaaga gcaactcggt |
| 2581 | cgccgcatac actattctca gaatgacttg gttgagtact caccagtcac agaaaagcat |
| 2641 | cttacggatg gcatgacagt aagagaatta tgcagtgctg ccataaccat gagtgataac |

TABLE 15-continued

| Sequence of FXIIIb2BbsIpIIICT<br>LOCUS paracompFXIIIb2BbsIpIIICT 4111 bp | |
|---|---|
| FEATURES | Location/Qualifiers |
| 2701 | actgcggcca acttacttct gacaacgatc ggaggaccga aggagctaac cgcttttttg |
| 2761 | cacaacatgg gggatcatgt aactcgcctt gatcgttggg aaccggagct gaatgaagcc |
| 2821 | ataccaaacg acgagcgtga caccacgatg cctgtagcaa tggcaacaac gttgcgcaaa |
| 2881 | ctattaactg gcgaactact tactctagct tcccggcaac aattaataga ctggatggag |
| 2941 | gcggataaag ttgcaggacc acttctgcgc tcggcccttc cggctggctg gtttattgct |
| 3001 | gataaatctg gagccggtga gcgtgggtct cgcggtatca ttgcagcact ggggccagat |
| 3061 | ggtaagccct cccgtatcgt agttatctac acgacgggga gtcaggcaac tatggatgaa |
| 3121 | cgaaatagac agatcgctga gataggtgcc tcactgatta agcattggta actgtcagac |
| 3181 | caagtttact catatatact ttagattgat ttaaaacttc atttttaatt taaaaggatc |
| 3241 | taggtgaaga tcctttttga taatctcatg accaaaatcc cttaacgtga gttttcgttc |
| 3301 | cactgagcgt cagaccccgt agaaaagatc aaaggatctt cttgagatcc tttttttctg |
| 3361 | cgcgtaatct gctgcttgca aacaaaaaaa ccaccgctac cagcggtggt ttgtttgccg |
| 3421 | gatcaagagc taccaactct ttttccgaag gtaactggct tcagcagagc gcagatacca |
| 3481 | aatactgtcc ttctagtgta gccgtagtta ggccaccact tcaagaactc tgtagcaccg |
| 3541 | cctacatacc tcgctctgct aatcctgtta ccagtggctg ctgccagtgg cgataagtcg |
| 3601 | tgtcttaccg ggttggactc aagacgatag ttaccggata aggcgcagcg gtcgggctga |
| 3661 | acggggggtt cgtgcacaca gcccagcttg gagcgaacga cctacaccga actgagatac |
| 3721 | ctacagcgtg agctatgaga aagcgccacg cttcccgaag ggagaaaggc ggacaggtat |
| 3781 | ccggtaagcg gcagggtcgg aacaggagag cgcacgaggg agcttccagg gggaaacgcc |
| 3841 | tggtatcttt atagtcctgt cgggtttcgc cacctctgac ttgagcgtcg atttttgtga |
| 3901 | tgctcgtcag gggggcggag cctatggaaa aacgccagca acgcggcctt tttacggttc |
| 3961 | ctggcctttt gctggccttt tgctcacatg ttctttcctg cgttatcccc tgattctgtg |
| 4021 | gataaccgta ttaccgcctt tgagtgagct gataccgctc gccgcagccg aacgaccgag |
| 4081<br>// | cgcagcgagt cagtgagcga ggaagcggaa g (SEQ ID NO: 519) |

TABLE 16

| Sequence of pF13wt-modstoppIIICT<br>LOCUS pF13wt-modstoppIIICT 4099 bp | |
|---|---|
| FEATURES | Location/Qualifiers |
| Promoter | 143 . . . 172<br>/gene = "lac prom" |
| misc_binding | 234 . . . 239<br>/dbxref = "REBASE: HindIII" |
| misc_binding | 321 . . . 333<br>/dbxref = "REBASE: SfiI" |
| misc_binding | 541 . . . 546<br>/dbxref = "REBASE: NcoI" |
| misc_binding | 637 . . . 644<br>/dbxref = "REBASE: NotI" |

TABLE 16-continued

Sequence of pF13wt-modstoppIIICT
LOCUS pF13wt-modstoppIIICT 4099 bp

| FEATURES | Location/Qualifiers |
|---|---|
| Tag | 679 . . . 708<br>/gene = “c_myc tag” |
| misc_binding | 880 . . . 885<br>/dbxref = “REBASE: ClaI” |
| misc_binding | 1076 . . . 1081<br>/dbxref = “REBASE: NdeI” |
| misc_binding | 1222 . . . 1227<br>/dbxref = “REBASE: EcoRI” |
| Reporter | 1225 . . . 1384<br>/gene = “lacZ_a reporter” |
| misc_binding | 1383 . . . 1388<br>/dbxref = “REBASE: NarI” |
| misc_binding | 1552 . . . 1557<br>/dbxref = “REBASE: AvrI” |
| misc_binding | 1552 . . . 1557<br>/dbxref = “REBASE: AvaI” |
| Rep_Origin | 1571 . . . 1877<br>/gene = “f1 origin” |
| Promoter | 2229 . . . 2257<br>/gene = “amp prom” |
| Marker | 2299 . . . 3159<br>/gene = “amp marker” |
| ORF | 2299 . . . 3159<br>/sequence = “ORF_1 rf(1)” |
| Rep_Origin | 3314 . . . 3933<br>/gene = “pBR322 origin” |
| misc_binding | 3560 . . . 3568<br>/dbxref = “REBASE: AlwNI” |
| BASE COUNT | 1027 a 1004 c 1025 g 1043 t 0 others |
| ORIGIN | |
| 1 | agcgcccaat acgcaaaccg cctctccccg cgcgttggcc gattcattaa tgcagctggc |
| 61 | acgacaggtt tcccgactgg aaagcgggca gtgagcgcaa cgcaattaat gtgagttagc |
| 121 | tcactcatta ggcaccccag gctttacact ttatgcttcc ggctcgtatg ttgtgtggaa |
| 181 | ttgtgagcgg ataacaattt cacacaggaa acagctatga ccatgattac gccaagcttt |
| 241 | ggagcctttt ttttggagat tttcaacgtg aaaaaattat tattcgcaat tcctttagtt |
| 301 | gttcctttct attctcactc ggccgacgtg gccaccatcc ctgagatcat catcaaggtc |
| 361 | cgcgggaccc aggtcgtggg ttctgacatg actgtgatcg tggagtttac caatcctctg |
| 421 | taagaaaccc tgcgcaatgt ctgggtgcac ctggacggtc cgggggtgac ccgcccaatg |
| 481 | aagaagatgt tccgcgaaat ccgcccaaac taaaccgtgc agtgggaaga agtggtccgc |
| 541 | ccatgggtct ctggtcaccg caagctgatc gccagcatga gcagtgacta actgcgccat |
| 601 | gtgtatggcg agctggacgt gcagattcaa cgccgcgcgg ccgcacatca tcatcaccat |
| 661 | cacgcgtctg gggccgcaga acaaaaactc atctcagaag aggatctgaa tggggcagca |
| 721 | gaagctagtt ctgctagtgc ctctggttcc ggtgattttg attatgaaaa gatggcaaac |
| 781 | gctaataagg gggctatgac cgaaaatgcc gatgaaaacg cgctacagtc tgacgctaaa |
| 841 | ggcaaacttg attctgtcgc tactgattac ggtgctgcta tcgatggttt cattggtgac |

TABLE 16-continued

Sequence of pF13wt-modstoppIIICT
LOCUS pF13wt-modstoppIIICT 4099 bp

| FEATURES | Location/Qualifiers |
|---|---|
| 901 | gtttccggcc ttgctaatgg taatggtgct actggtgatt ttgctggctc taattcccaa |
| 961 | atggctcaag tcggtgacgg tgataattca cctttaatga ataatttccg tcaatattta |
| 1021 | ccttccctcc ctcaatcggt tgaatgtcgc ccttttgtct ttagcgctgg taaaccatat |
| 1081 | gaattttcta ttgattgtga caaaataaac ttattccgtg gtgtctttgc gtttctttta |
| 1141 | tatgttgcca cctttatgta tgtattttct acgtttgcta acatactgcg taataaggag |
| 1201 | tcttaatgaa acgcgtgatg agaattcact ggccgtcgtt ttacaacgtc gtgactggga |
| 1261 | aaaccctggc gttacccaac ttaatcgcct tgcagcacat ccccctttcg ccagctggcg |
| 1321 | taatagcgaa gaggcccgca ccgatcgccc ttcccaacag ttgcgcagcc tgaatggcga |
| 1381 | atggcgcctg atgcggtatt ttctccttac gcatctgtgc ggtatttcac accgcataaa |
| 1441 | attgtaaacg ttaatatttt gttaaaattc gcgttaaatt tttgttaaat cagctcattt |
| 1501 | tttaaccaat aggccgaaat cggcaaaatc ccttataaat caaaagaata gcccgagata |
| 1561 | gggttgagtg ttgttccagt ttggaacaag agtccactat taaagaacgt ggactccaac |
| 1621 | gtcaaagggc gaaaaaccgt ctatcagggc gatggcccac tacgtgaacc atcacccaaa |
| 1681 | tcaagttttt tggggtcgag gtgccgtaaa gcactaaatc ggaaccctaa agggagcccc |
| 1741 | cgatttagag cttgacgggg aaagccggcg aacgtggcga gaaaggaagg gaagaaagcg |
| 1801 | aaaggagcgg gcgctagggc gctggcaagt gtagcggtca cgctgcgcgt aaccaccaca |
| 1861 | cccgccgcgc ttaatgcgcc gctacagggc gcgtactatg gttgctttga cgtatggtgc |
| 1921 | actctcagta caatctgctc tgatgccgca tagttaagcc agccccgaca cccgccaaca |
| 1981 | cccgctgacg cgccctgacg ggcttgtctg ctcccggcat ccgcttacag acaagctgtg |
| 2041 | accgtctccg ggagctgcat gtgtcagagg ttttcaccgt catcaccgaa acgcgcgaga |
| 2101 | cgaaagggcc tcgtgatacg cctattttta taggttaatg tcatgataat aatggtttct |
| 2161 | tagacgtcag gtggcacttt tcggggaaat gtgcgcggaa cccctatttg tttatttttc |
| 2221 | taaatacatt caaatatgta tccgctcatg agacaataac cctgataaat gcttcaataa |
| 2281 | tattgaaaaa ggaagagtat gagtattcaa catttccgtg tcgcccttat tccctttttt |
| 2341 | gcggcatttt gccttcctgt ttttgctcac ccagaaacgc tggtgaaagt aaaagatgct |
| 2401 | gaagatcagt tgggtgcacg agtgggttac atcgaactgg atctcaacag cggtaagatc |
| 2461 | cttgagagtt ttcgccccga agaacgtttt ccaatgatga gcacttttaa agttctgcta |
| 2521 | tgtggcgcgg tattatcccg tattgacgcc gggcaagagc aactcggtcg ccgcatacac |
| 2581 | tattctcaga atgacttggt tgagtactca ccagtcacag aaaagcatct tacggatggc |
| 2641 | atgacagtaa gagaattatg cagtgctgcc ataaccatga gtgataacac tgcggccaac |
| 2701 | ttacttctga caacgatcgg aggaccgaag gagctaaccg cttttttgca caacatgggg |
| 2761 | gatcatgtaa ctcgccttga tcgttgggaa ccggagctga atgaagccat accaaacgac |
| 2821 | gagcgtgaca ccacgatgcc tgtagcaatg gcaacaacgt tgcgcaaact attaactggc |
| 2881 | gaactactta ctctagcttc ccggcaacaa ttaatagact ggatggaggc ggataaagtt |
| 2941 | gcaggaccac ttctgcgctc ggcccttccg gctggctggt ttattgctga taaatctgga |
| 3001 | gccggtgagc gtgggtctcg cggtatcatt gcagcactgg ggccagatgg taagccctcc |
| 3061 | cgtatcgtag ttatctacac gacggggagt caggcaacta tggatgaacg aaatagacag |

TABLE 16-continued

| Sequence of pF13wt-modstoppIIICT LOCUS pF13wt-modstoppIIICT 4099 bp | |
|---|---|
| FEATURES | Location/Qualifiers |
| 3121 | atcgctgaga taggtgcctc actgattaag cattggtaac tgtcagacca agtttactca |
| 3181 | tatatacttt agattgattt aaaacttcat ttttaattta aaaggatcta ggtgaagatc |
| 3241 | ctttttgata atctcatgac caaaatccct taacgtgagt tttcgttcca ctgagcgtca |
| 3301 | gaccccgtag aaaagatcaa aggatcttct tgagatcctt tttttctgcg cgtaatctgc |
| 3361 | tgcttgcaaa caaaaaaacc accgctacca gcggtggttt gtttgccgga tcaagagcta |
| 3421 | ccaactcttt ttccgaaggt aactggcttc agcagagcgc agataccaaa tactgtcctt |
| 3481 | ctagtgtagc cgtagttagg ccaccacttc aagaactctg tagcaccgcc tacatacctc |
| 3541 | gctctgctaa tcctgttacc agtggctgct gccagtggcg ataagtcgtg tcttaccggg |
| 3601 | ttggactcaa gacgatagtt accggataag gcgcagcggt cgggctgaac ggggggttcg |
| 3661 | tgcacacagc ccagcttgga gcgaacgacc tacaccgaac tgagatacct acagcgtgag |
| 3721 | ctatgagaaa gcgccacgct tcccgaaggg agaaaggcgg acaggtatcc ggtaagcggc |
| 3781 | agggtcggaa caggagagcg cacgagggag cttccagggg gaaacgcctg gtatctttat |
| 3841 | agtcctgtcg ggtttcgcca cctctgactt gagcgtcgat ttttgtgatg ctcgtcaggg |
| 3901 | gggcggagcc tatggaaaaa cgccagcaac gcggcctttt tacggttcct ggccttttgc |
| 3961 | tggccttttg ctcacatgtt ctttcctgcg ttatcccctg attctgtgga taaccgtatt |
| 4021 | accgcctttg agtgagctga taccgctcgc cgcagccgaa cgaccgagcg cagcgagtca |
| 4081 | gtgagcgagg aagcggaag (SEQ ID NO: 520) |
| // | |

Other Embodiments

Various modifications and variations of the described methods and compositions of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the field of medicine, immunology, pharmacology, endocrinology, or related fields are intended to be within the scope of the invention.

All publications mentioned in this specification are herein incorporated by reference to the same extent as if each independent publication was specifically and individually incorporated by reference.

What is claimed is:

1. An engineered Factor XIII barrel protein comprising a Factor XIII β2 barrel protein domain comprising:

seven scaffold regions, and six intervening regions, wherein said seven scaffold regions consist of peptides having the sequences of SEQ ID NOS: 658-664, respectively, and at least one of said intervening regions is mutated to have a loop-diversified region having less than 30% sequence identity to SEQ ID NO: 595, and wherein the protein has a beta barrel structure to increase thermostability.

2. The engineered Factor XIII barrel protein of claim 1, wherein said barrel protein is covalently linked to a polyethylene glycol (PEG).

3. The engineered Factor XIII barrel protein of claim 2, wherein said PEG is a branched PEG.

4. The engineered Factor XIII barrel protein of claim 2, wherein said barrel protein comprises a single cysteine and said cysteine is covalently bound to said PEG.

5. The engineered Factor XIII barrel protein of claim 1, wherein said engineered barrel protein is a human Factor XIII barrel protein.

6. The engineered Factor XIII barrel protein of claim 1, wherein said barrel protein is conjugated to albumin.

7. The engineered Factor XIII barrel protein of claim 1, wherein at least two of said intervening regions has an amino acid sequence of no greater than 30% identity to SEQ ID NO: 595.

8. The engineered Factor XIII barrel protein of claim 7, wherein at least three of said intervening regions has an amino acid sequence of no greater than 30% identity to SEQ ID NO: 595.

9. The engineered Factor XIII barrel protein of claim 1, which has a melting temperature (Tm) of at least 55° C.

10. An engineered Factor XIII barrel protein comprising a Factor XIII β2 barrel protein domain comprising:

seven scaffold regions, and six intervening regions, wherein said seven scaffold regions consist of peptides having the sequences of SEQ ID NOS: 658-664, respectively, and at least one of said intervening regions is mutated to have a loop-diversified region having less than 30% sequence identity to SEQ ID NO: 595, and wherein the protein has a beta barrel structure to increase thermostability to provide a melting temperature (Tm) of at least 55° C.

* * * * *

SEQUENCE LISTING

```
<160> NUMBER OF SEQ ID NOS: 664

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

gcatccgcta tttaa                                                   15


<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 2

Asp Tyr Lys Asp Asp Asp Asp Lys
1 5

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gtcgtcgtcc ttgtagtcgc ggcgttgaat ctgcacgtc 39

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Thr Asn Pro Phe Lys Glu Thr Leu Arg Ser
1 5 10

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Arg Glu Ile Pro Pro Lys Thr Thr
1 5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 6

Arg Thr Gln Tyr Leu Ile
1 5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 7

Ser Asn Pro Phe Lys Glu Thr Leu Arg Asn
1 5 10

<210> SEQ ID NO 8
<211> LENGTH: 8
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 8

Ser Glu Ile Arg Pro Asn Ser Thr
1 5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Pro Ser Leu Leu His Leu
1 5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Thr Asn Pro Phe Lys Glu Thr Leu Arg Asn
1 5 10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Cys Glu Ile Arg Pro Asn Ser Ile
1 5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Cys Ser Leu Ser Pro Trp
1 5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Thr Asn Pro Leu Lys Glu Thr Leu Arg Asn
1 5 10

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Ala Ile Pro Met Asn His Lys
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Gln Leu Phe His Ile
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Asn Pro Leu Lys Glu Thr Leu Arg Asn
1               5                   10

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Lys Ile Pro Gly Cys
1               5

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Met Leu Gly Leu Pro Phe Ser Leu Arg Phe Ile Pro
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Ser Leu Leu His Leu
1 5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Pro Gln Leu Phe His Ile
1 5

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Met Leu Gly Leu Pro Phe Ser Leu Arg Phe Ile Pro
1 5 10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Thr Asn Pro Leu Asn Glu Pro Leu Leu Phe
1 5 10

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Arg Ile Ile Ser Pro His Ala Thr
1 5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Ser Ile Gly Phe Gln Ala
1 5

<210> SEQ ID NO 25
<211> LENGTH: 10

-continued

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Ile Asn Thr Ser Asn Glu Thr Leu Pro Ser
1 5 10

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Pro Glu Ile Pro Pro Asn Ser Ser
1 5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Ile Arg Asp Ser Ser Arg
1 5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Thr Asn Leu Ser Asn Glu Thr Leu Gly Thr
1 5 10

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 29

His His His His His His
1 5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Pro His Ile Arg Pro Lys Val Thr 1 5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Leu Ile Ala Ser Leu Arg
1 5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Gly Gly Gly Gly Ser
1 5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Asp Tyr Lys Asp Asp Asp Asp Asp
1 5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 34

Thr Asn Pro Phe Lys Glu Thr Leu Gln Ser
1 5 10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Thr Asn Pro Phe Lys Glu Thr Leu Arg Gly
1 5 10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Thr Asn Pro Tyr Lys Glu Thr Leu Arg Ser
1 5 10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Thr Asn Pro Leu Ser Gln Thr Leu Ser Ala
1 5 10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Thr Asn Leu Met Lys Glu Thr Leu Arg Asn
1 5 10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Ser Asn Pro Phe Lys Glu Thr Leu Arg Ser
1 5 10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Thr Asn Pro Phe Lys Gly Thr Leu Arg Ser
1 5 10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Thr Asn Leu Met Lys Glu Thr Leu Arg Asn
1 5 10

<210> SEQ ID NO 42

<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Thr Asn Pro Trp Ala Glu Thr Leu His Asn
1 5 10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Thr Asn Leu Trp Lys Glu Thr Leu Arg Asn
1 5 10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Thr Asn Leu Trp Lys Glu Ala Leu Arg Asn
1 5 10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Ser Asn Pro Phe Lys Glu Thr Leu Arg Ser
1 5 10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Thr Arg Pro Leu Asn Asp Arg Leu Arg Lys
1 5 10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

```
Thr Thr Pro Gln Glu Glu Thr Leu Ile Lys
1               5                   10


<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Thr Pro Leu Trp Ala Asn Leu Cys Thr
1               5                   10


<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Asn Pro Met Lys Glu Thr Leu Arg Asn
1               5                   10


<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Asn Pro Leu Lys Glu Ile Leu Arg Asn
1               5                   10


<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Thr Asn Pro Leu Arg Glu Thr Leu Arg Asn
1               5                   10


<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Thr Asp Pro Leu Lys Glu Thr Leu Arg Asn
1               5                   10


<210> SEQ ID NO 53
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 53

His Ser Met Ser Ser Gly Ile Leu Asn Tyr
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Tyr Phe Ser Pro Gly Ala Arg Leu Ala Thr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys His Asp Arg Tyr Arg Tyr Leu Gln Gln
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Ala Thr Leu Tyr His Ala Leu Phe Ser
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Leu Pro Ala Ala Trp Leu Glu Asn
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Leu Ile Gly Leu Leu Gln Leu Tyr Glu
1               5                   10

-continued

```
<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Cys Met Gly Gln Tyr Lys Leu Pro Leu
1               5                   10


<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Ile Gly Ile Leu Cys Leu Trp Tyr
1               5


<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ala Arg Thr Ile His Thr Ile Leu Thr Asn
1               5                   10


<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Met Asn Ile Ile Arg Asn Met Leu Thr Thr
1               5                   10


<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Thr Lys Leu Ile Gln Ser Leu Val Thr
1               5                   10


<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64
```

-continued

Phe His Thr Tyr Arg Leu Trp Leu Gly Val
1 5 10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Thr Asn Pro Leu Lys Glu Ala Leu Arg Asn
1 5 10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Thr Asn Pro Leu Glu Glu Thr Leu Arg Asn
1 5 10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Thr Asn Pro Leu Lys Glu Thr Pro Arg Asn
1 5 10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Thr Asn Pro Ala Arg Gly Val Asn Pro Ser Leu Arg Asn
1 5 10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Thr Asn Pro Phe Ala Leu Thr Cys Arg Asn Leu Arg Asn
1 5 10

<210> SEQ ID NO 70
<211> LENGTH: 13
<212> TYPE: PRT
<213> ORGANISM: Artificial Sequence -continued
<220> FEATURE:
<223> OTHER INFORMATION: Description of Artificial Sequence: Synthetic
peptide

<400> SEQUENCE: 70

Thr Asn Pro Leu Thr Asn Trp Gly Val Trp Leu Arg Asn
1 5 10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 71

Thr Asn Pro Asn His Phe Thr Arg Arg Glu Leu Arg Asn
1 5 10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 72

Thr Asn Pro Ser Cys Ser Ser His Cys Ser Leu Arg Asn
1 5 10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

Thr Asn Pro Thr Asp Gly Ser Arg Pro Trp Leu Arg Asn
1 5 10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

Thr Asn Leu Thr Asn Thr His Tyr Ser Arg Leu Arg Asn
1 5 10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

Thr Asn Pro Ala Arg Gly Lys Thr Met Asn Leu Arg Asn
1 5 10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 76

Thr Asn Pro Gly Ser Glu Cys Asn Leu Ser Leu Arg Asn
1 5 10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 77

Thr Asn Pro Asp Ala Trp Ala Lys Cys Val Leu Arg Asn
1 5 10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Thr Asn Pro Lys Arg Asp Thr Ser Val Trp Leu Arg Asn
1 5 10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Thr Asn Pro Leu Arg Val Ser Glu Gln Thr Leu Arg Asn
1 5 10

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Thr Asn Pro Ser Asn Tyr Arg Pro Cys Ile Leu Arg Asn
1 5 10

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Arg Lys Ile Pro Pro Lys Thr Thr
1 5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Arg Val Ile Pro Pro Lys Thr Thr
1 5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Arg Glu Ile Pro Pro Glu Thr Thr
1 5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Arg Val Ile Pro Pro Lys Thr Thr
1 5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Cys Glu Val Arg Pro Asn Ser Val
1 5

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Ser Glu Ile Arg Pro Asp Ser Thr
1 5

<210> SEQ ID NO 87
<211> LENGTH: 8
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 87

Cys Glu Ile Arg Pro Asn Ser Thr
1 5

<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Cys Gly Ile Arg Pro Asn Ser Ile
1 5

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 89

Cys Glu Val Arg Pro Asn Ser Ile
1 5

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 90

Cys Glu Ile Arg Pro Asn Arg Ile
1 5

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 91

Ser Glu Ile Arg Thr Asn Ala Thr
1 5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 92

Ser Glu Ile Arg Pro Asn Ser Ile
1 5

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 93

Arg Asp Ile Arg Pro Lys Thr Lys
1 5

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 94

Arg Glu Ile Pro Pro Glu Thr Thr
1 5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Trp Glu Ile Pro Pro Lys Thr Thr
1 5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Arg Glu Ile Ala Thr Met Ser Thr
1 5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Arg Glu Ile Pro Pro Met Ser Thr
1 5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Arg Glu Ile Pro Pro Asn Thr Thr
1 5

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 99

Glu Glu Ile Arg Gln Ser Cys Ile
1 5

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Arg Glu Ile Arg Pro Thr Ser Ser
1 5

<210> SEQ ID NO 101
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Met Lys Ile Pro Pro Ala Ser Trp
1 5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Trp Asp Ile Arg His Asp Pro Thr
1 5

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Arg Ala Ile Pro Met Asn His Lys
1 5

<210> SEQ ID NO 104
<211> LENGTH: 8

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 104

Pro Thr Ile Pro Met Asn His Lys
1 5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 105

Pro Thr Ile Pro Met Asn His Lys
1 5

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 106

Pro Ala Ile Pro Tyr Leu Ser Tyr
1 5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 107

Pro Ala Ile Pro Met Asp His Lys
1 5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 108

Pro Thr Ile Ser Arg Phe Lys Arg
1 5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 109

Ala Thr Ile Pro Pro Tyr Leu Pro 1 5

<210> SEQ ID NO 110
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Ser Leu Ile Cys Val Asn Arg Ala
1 5

<210> SEQ ID NO 111
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 111

Pro Ala Ile Pro Thr Asn His Lys
1 5

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 112

Pro Ala Ile Pro Met Lys His Lys
1 5

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 113

Asp Leu Ile Arg Asn Ser His Val
1 5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 114

His Ser Ile Tyr Val Pro Phe Trp
1 5

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Lys Leu Ile Ile Phe Ser Tyr Pro
1 5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Leu Asn Ile Ser Ala Gln Thr Met
1 5

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

Thr Arg Ile Lys Cys Ala Ser Ser
1 5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 118

Cys Gly Ile Pro Pro Leu Ser Ser
1 5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Met Glu Ile Thr Ile Asn Gly Tyr
1 5

<210> SEQ ID NO 120
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

Met Gln Ile Leu Leu Tyr Ile Leu
1 5

<210> SEQ ID NO 121

<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Thr Met Ile Ser Trp Asn Leu Asn
1 5

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Ile Met Ile Asp Lys Leu Met Leu
1 5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

His Arg Ile Pro Cys Leu Thr
1 5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Trp Leu Ile Ser Asn Ile Asp Leu
1 5

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Glu Gln Ile Arg Glu Ser Glu Tyr
1 5

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Leu Lys Ile Pro Gly Cys Ser Thr
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Leu Lys Ile Pro Gly Cys Ser Thr
1               5

<210> SEQ ID NO 128
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Leu Lys Ile Pro Gly Cys Ser Thr
1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Leu Lys Ile Pro Gly Cys Ser Thr
1               5

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Leu Lys Ile Pro Gly Cys Ser Thr
1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Leu Lys Ile Pro Gly Cys Ser Thr
1               5

<210> SEQ ID NO 132
<211> LENGTH: 8
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 132

Leu Lys Ile Pro Gly Cys Ser Thr
1 5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 133

Gln Lys Ile Pro Gly Cys Ser Thr
1 5

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 134

Leu Lys Ile Leu Gly Cys Ser Thr
1 5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 135

Thr Gly Ile Leu Gln Trp Ser Thr
1 5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 136

Leu Lys Ile Pro Gly Cys Ser Thr
1 5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 137

Thr Asp Ile Cys Lys Gly Ser Thr
1 5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 138

Ser Ser Ile Asn Ile Phe Ser Thr
1 5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 139

Asn Ala Ile Thr Pro Val Ser Thr
1 5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 140

Met Asn Ile Ala Ala Glu Ser Thr
1 5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Thr Trp Ile Trp Leu Tyr Ser Thr
1 5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 142

Phe Leu Ile Arg Thr Asp Ser Thr
1 5

<210> SEQ ID NO 143
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 143

Gln Ala Ile Thr Ser Cys Ser Thr
1 5

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 144

Met Ile Ile Tyr Thr Asn Ser Thr
1 5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Leu Tyr Ile Thr Pro Gly Ser Thr
1 5

<210> SEQ ID NO 146
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Ser Gly Ile Ala Ser Leu Ser Thr
1 5

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Phe Thr Ile Gly Tyr Pro Ser Thr
1 5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Gly Gly Ile Arg Val His Ser Thr
1 5

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

Lys Met Ile Val Tyr His Ser Thr
1 5

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

Cys Ser Leu Pro Pro Trp
1 5

<210> SEQ ID NO 151
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Cys Gln Leu Leu Pro Trp
1 5

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 152

Thr Leu Arg Pro Trp
1 5

<210> SEQ ID NO 153
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 153

Met Thr Leu Arg Pro Trp
1 5

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 154

Ala Leu Arg Pro Trp
1 5

<210> SEQ ID NO 155
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 155

Cys Glu Pro Ser Leu Asp
1 5

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 156

Tyr Val Ala Pro Leu His
1 5

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 157

Gly Thr Gln Phe Pro Arg
1 5

<210> SEQ ID NO 158
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 158

Pro Ser Asp Ser Leu Pro
1 5

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 159

Pro Thr His His Leu Leu
1 5

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 160

Arg Asp Ala Leu Ser
1 5

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Gly Ser Asp Cys Leu Gly
1 5

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

Asn Thr Glu Ser Ile Leu
1 5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Met Ser Asp Thr Leu Arg
1 5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Ser Lys Pro Pro Glu Arg
1 5

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Pro His Leu Phe His Ile
1 5

<210> SEQ ID NO 166
<211> LENGTH: 6
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 166

Pro Gln Leu His His Leu
1 5

<210> SEQ ID NO 167
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 167

Pro Gln Leu Phe His Leu
1 5

<210> SEQ ID NO 168
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 168

Pro Gln Leu Phe His Leu
1 5

<210> SEQ ID NO 169
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 169

Pro Arg Leu Phe His Ile
1 5

<210> SEQ ID NO 170
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 170

Pro Gln Leu Gln His Leu
1 5

<210> SEQ ID NO 171
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 171

Pro Gln Leu Ile His Leu
1 5

<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 172

Ile Asn Tyr Phe Tyr Lys
1 5

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 173

Ile Asn His Phe Tyr Lys
1 5

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 174

Ile Asn Tyr Phe Tyr Asn
1 5

<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 175

Leu Asn His Phe Tyr Lys
1 5

<210> SEQ ID NO 176
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 176

Leu Asn His Phe Tyr Lys
1 5

<210> SEQ ID NO 177
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 177

His His Gly Ser Tyr Pro
1 5

<210> SEQ ID NO 178
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 178

Thr Thr Thr Val Gln Gly
1 5

<210> SEQ ID NO 179
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 179

Arg Phe Met Cys Pro Ser
1 5

<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 180

Cys His Ala Met Thr Ser
1 5

<210> SEQ ID NO 181
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 181

Lys Val Leu Thr Glu His
1 5

<210> SEQ ID NO 182
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 182

Tyr Leu Glu Leu Leu Tyr
1 5

<210> SEQ ID NO 183
<211> LENGTH: 6

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 183

Arg His Thr Asp Trp Ser
1 5

<210> SEQ ID NO 184
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 184

Gln His Ser Pro Pro Ala
1 5

<210> SEQ ID NO 185
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 185

Ser Ala Gly Cys Ser Phe
1 5

<210> SEQ ID NO 186
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 186

Gln Thr Ala Glu Pro Arg
1 5

<210> SEQ ID NO 187
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 187

Ser Leu Leu Ile Thr Pro
1 5

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 188

Val Tyr Ile Lys Asn Gly 1 5

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 189

Leu Thr Glu Thr Arg Pro
1 5

<210> SEQ ID NO 190
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 190

Asn Ser Ser Ser Asn Gln
1 5

<210> SEQ ID NO 191
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 191

Ser Met Leu Gly Leu Pro Phe Ser Leu Arg Phe Ile Pro
1 5 10

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 192

Ser Met Leu Gly Leu Pro Phe Ser Leu Arg Leu Ile Pro
1 5 10

<210> SEQ ID NO 193
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 193

Ser Pro His Ala Trp Trp Gln His His Gly Asn Phe Ser
1 5 10

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 194

Ser Met Arg Met Asn Leu Leu Phe His Leu Met Asn Ala
1 5 10

<210> SEQ ID NO 195
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 195

Ser Tyr Asn Val Cys Arg Arg Val Leu Lys Ser Phe Ile
1 5 10

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 196

Ser Leu Ala Ser Ala Ala Pro Met Met Ile Gln Thr Trp
1 5 10

<210> SEQ ID NO 197
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 197

Ser Cys Gly Leu Tyr Gly Ser Gln Cys Cys Tyr Thr Trp
1 5 10

<210> SEQ ID NO 198
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 198

Ser His Leu Phe Ser Asp Asp Leu Trp Ala Ala Pro Thr
1 5 10

<210> SEQ ID NO 199
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 199

Ser Leu Leu Gly Trp Pro Met Asn Val Thr Leu Lys Arg
1 5 10

<210> SEQ ID NO 200

<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 200

Ser Tyr Gly Arg Cys Met Val Asn Leu Val Arg Pro Leu
1 5 10

<210> SEQ ID NO 201
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 201

Ser Thr Ser Asp Ser Gly Trp Ala Ser Asn Ile Val Pro
1 5 10

<210> SEQ ID NO 202
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 202

Ser Cys Lys Leu Asp Gln Asn Cys Ser Ala Leu Asn Leu
1 5 10

<210> SEQ ID NO 203
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 203

Ser Arg Tyr Lys Leu Val Val Leu Ala Arg Lys Val Gly
1 5 10

<210> SEQ ID NO 204
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 204

Ser Ser Leu Ile Cys Arg Val Lys Asp Phe Trp Met Asp
1 5 10

<210> SEQ ID NO 205
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 205

```
Ser Pro Ser Ile Leu Ser Lys Gly Asn Ile Gly Leu Gly
1               5                   10


<210> SEQ ID NO 206
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ser Tyr Val Ala Glu Tyr Gly Glu Trp Thr His Tyr Ser
1               5                   10


<210> SEQ ID NO 207
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Lys Phe Glu Leu Ser Gly Thr Ser Ser Arg Gly Arg
1               5                   10


<210> SEQ ID NO 208
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: modified_base
<222> LOCATION: (13)..(14)
<223> OTHER INFORMATION: a, c, t, g, unknown or other
<220> FEATURE:
<221> NAME/KEY: misc_feature
<222> LOCATION: (13)..(14)
<223> OTHER INFORMATION: n is a, c, g, or t
```

```
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: misc_feature
<222> LOCATION: (16)..(17)
<223> OTHER INFORMATION: n is a, c, g, or t

<400> SEQUENCE: 208

nnsnnsnnsn nsnnsnns                                                18


<210> SEQ ID NO 209
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Thr Asn Pro Leu Ser Glu Pro Leu Leu Phe
1               5                   10


<210> SEQ ID NO 210
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Thr Asn Pro Leu Asn Asp Pro Leu Leu Phe
1               5                   10


<210> SEQ ID NO 211
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Thr Asn Pro Leu Asn Glu Pro Leu Phe Phe
1               5                   10


<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Phe Asn Ala Gln Thr Glu Ala Leu Arg Asp
1               5                   10


<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213
```

Thr Asn Thr Ser Asn Glu Thr Leu Pro Ser
1               5                   10

<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 214

Thr Asn Leu Ser Asn Glu Thr Leu Pro Ser
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 215

Thr Asn Thr Thr Asn Glu Thr Leu Pro Ser
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 216

Ile Asn Thr Ser Asp Glu Thr Leu Pro Ser
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 217

Ile Asn Thr Ser Asn Lys Thr Leu Pro Ser
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 218

Ile Asn Thr Ser Asn Glu Ala Leu Pro Ser
1               5                   10

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 219

Ile Asn Thr Ser Asn Glu Thr Leu Pro Arg
1 5 10

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 220

Thr Pro Ala Val Lys Asp Lys Leu Pro Lys
1 5 10

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 221

Ser Thr His Leu Val Pro Thr Leu Arg Asn
1 5 10

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 222

Thr Ile Pro Cys Gln Ser Thr Leu Asn Ser
1 5 10

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 223

Thr Asp Thr Val Leu Glu Ile Leu Arg Thr
1 5 10

<210> SEQ ID NO 224
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 224

Thr Asn Pro Met Asn Ile Thr Leu His His
1 5 10

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Thr Asn Pro Leu Glu Glu Asn Leu Tyr Asn
1               5                   10

<210> SEQ ID NO 226
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Thr Asn Leu Ser Glu Glu Asn Leu Gly Thr
1               5                   10

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ile Asn His Lys Glu Gly Thr Leu Pro Gln
1               5                   10

<210> SEQ ID NO 228
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Thr Thr Pro Leu Lys Glu Arg Leu Arg Lys
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Thr Asn Ala Leu Lys Asp Thr Leu Ile Ile
1               5                   10

<210> SEQ ID NO 230
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Thr Asn Pro Leu Lys Glu Thr Leu Tyr Asn
1 5 10

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 231

Thr Ile Pro Leu Gln Asp Ile Leu Asn
1 5

<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 232

Thr Asn Thr Leu Leu Glu Thr Leu Gly Thr
1 5 10

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

Thr Lys Ala Leu Lys Gly Thr Leu Gly Asn
1 5 10

<210> SEQ ID NO 234
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 234

Ser Gly Thr Leu Ser Gly Thr Leu Leu Thr
1 5 10

<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 235

Thr Asn Thr Arg Lys Asp Ile Leu Gly Thr
1 5 10

<210> SEQ ID NO 236
<211> LENGTH: 10
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 236

Ser Asn His Leu Lys His Thr Leu Val Asp
1               5                   10

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Thr Asn Ala His Asn Thr Thr Leu Leu His
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Asn Tyr Pro Leu Gln Glu Thr Leu Pro Lys
1               5                   10

<210> SEQ ID NO 239
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Thr Thr Arg Pro His Ala Ala Leu Leu Asn
1               5                   10

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Thr Leu Pro Leu Lys Glu Ser Leu Gly Thr
1               5                   10

<210> SEQ ID NO 241
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Ala Ser Pro Met Lys Leu Thr Leu Arg Tyr
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 242

Thr Asn Pro Leu Arg Asp Thr Leu Asp Thr
1 5 10

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 243

Thr Tyr Arg His Trp Gly Thr Leu Cys Lys
1 5 10

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 244

Ser Ser Thr Leu Ser Gly Arg Leu Gln His
1 5 10

<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 245

Ala Gln Pro Val Lys Leu Thr Leu Arg Arg
1 5 10

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 246

Thr Asn Arg Pro Asn Glu Lys Leu Arg Lys
1 5 10

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 247

Thr Tyr Thr Arg Lys Glu Met Leu His Asn
1 5 10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 248

Thr Ser Leu Val Gln Glu Pro Leu Cys His
1 5 10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 249

Asn Cys Thr Leu Lys Glu Thr Leu Ile Asn
1 5 10

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 250

Cys His Thr Gln Ile Ser Thr Leu Arg Tyr
1 5 10

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 251

Thr Arg His Met Thr Glu Pro Leu Arg Ile
1 5 10

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 252

Ser Asn Gly Leu Asn Gly Thr Leu Arg Glu
1 5 10

<210> SEQ ID NO 253
<211> LENGTH: 8

-continued

<212> TYPE: PRT
<213> ORGANISM: Artificial Sequence
<220> FEATURE:
<223> OTHER INFORMATION: Description of Artificial Sequence: Synthetic peptide

<400> SEQUENCE: 253

Pro Ile Ile Ser Pro His Ala Thr
1 5

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 254

Arg Ile Ile Thr Pro His Ala Thr
1 5

<210> SEQ ID NO 255
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 255

Pro Lys Ile Pro Pro Asn Ser Ser
1 5

<210> SEQ ID NO 256
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 256

Pro Glu Ile Pro Pro Lys Ser Ser
1 5

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 257

Pro Glu Ile Pro Pro Asn Phe Ser
1 5

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 258

Asn Asp Ile His Leu Tyr Ser Ser 1 5

<210> SEQ ID NO 259
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 259

Ser Gln Ile Arg Pro Lys Val Thr
1 5

<210> SEQ ID NO 260
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 260

Tyr Gln Ile Ser Thr Asn Ile Pro
1 5

<210> SEQ ID NO 261
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 261

Pro His Ile Arg Pro Lys Val Pro
1 5

<210> SEQ ID NO 262
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 262

Gly Asp Ile His Pro Lys Phe Thr
1 5

<210> SEQ ID NO 263
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 263

Leu Glu Ile Ser Pro Lys Ser Lys
1 5

<210> SEQ ID NO 264
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 264

Arg Glu Ile Ser Pro Asn Ser Ser
1 5

<210> SEQ ID NO 265
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 265

Trp Glu Ile Arg Thr Asn His Pro
1 5

<210> SEQ ID NO 266
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 266

Phe Ser Ile Arg Met Thr Pro Ala
1 5

<210> SEQ ID NO 267
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 267

Ser Ala Ile Ser Arg Arg Ser Ile
1 5

<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 268

Trp Asn Ile Thr Gln His Gln Thr
1 5

<210> SEQ ID NO 269
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 269

Leu Asp Ile His Pro Asn Pro Thr
1 5

<210> SEQ ID NO 270

-continued

<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

His Gly Ile His Ala Asn Thr Ser
1               5

<210> SEQ ID NO 271
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Arg Val Ile Arg Pro Val Ser Thr
1               5

<210> SEQ ID NO 272
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Arg Ala Ile Gly Gln Lys Ser Glu
1               5

<210> SEQ ID NO 273
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Leu Trp Ile Phe Pro Asn Ala Pro
1               5

<210> SEQ ID NO 274
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Ser Val Ile Gln Thr Asp Pro Thr
1               5

<210> SEQ ID NO 275
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

His Thr Ile Arg Arg Thr Pro Asn
1 5

<210> SEQ ID NO 276
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

Cys Glu Ile Arg Gln Tyr Cys Ser
1 5

<210> SEQ ID NO 277
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 277

Arg Gln Ile Arg Pro Ile Ala Thr
1 5

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 278

Leu Asp Ile Arg Pro Asp Ser Thr
1 5

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 279

Gln Glu Ile Arg Gln Asn Ser Thr
1 5

<210> SEQ ID NO 280
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 280

Cys Glu Ile Arg Leu Tyr Ser Met
1 5

<210> SEQ ID NO 281
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 281

Arg Glu Ile Arg Ala Arg Ser Thr
1               5

<210> SEQ ID NO 282
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Arg Asp Ile His Glu Asn Phe Cys
1               5

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Ser Gly Ile Arg Pro Tyr Ser Thr
1               5

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Asp Glu Ile Trp Thr Asn Leu Ile
1               5

<210> SEQ ID NO 285
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Pro Glu Ile Arg Glu Pro Cys Asp
1               5

<210> SEQ ID NO 286
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Arg Val Ile Cys Ile Asp Phe Ile
1               5

```
<210> SEQ ID NO 287
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Arg Glu Ile Leu Pro Glu Ser Thr
1               5


<210> SEQ ID NO 288
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Ser Val Gly Phe Gln Ala
1               5


<210> SEQ ID NO 289
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Ile Gln Asp Ser Ser Arg
1               5


<210> SEQ ID NO 290
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Ile Arg Asp Ser Pro Arg
1               5


<210> SEQ ID NO 291
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ile Gln Asp Ser Ser Arg
1               5


<210> SEQ ID NO 292
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292
```

Ile Arg Asp Pro Ser Arg
1 5

<210> SEQ ID NO 293
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 293

Ile Ile Ala Ser Leu Arg
1 5

<210> SEQ ID NO 294
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 294

Gly Ala His Thr Lys Asp
1 5

<210> SEQ ID NO 295
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 295

Gly Ala His Thr Lys Asp
1 5

<210> SEQ ID NO 296
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 296

Ile Val Ala Tyr Leu Tyr
1 5

<210> SEQ ID NO 297
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 297

Ile Asn Asp Pro Leu Leu
1 5

<210> SEQ ID NO 298
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 298

Ile Ile Ala Thr Leu Arg
1 5

<210> SEQ ID NO 299
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 299

Ile Ser Val Ser Leu His
1 5

<210> SEQ ID NO 300
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 300

Thr Ser Tyr Ser Arg Gly
1 5

<210> SEQ ID NO 301
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 301

Ser Ser Asn Ser Arg Asp
1 5

<210> SEQ ID NO 302
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 302

Ser Phe His Thr His Arg
1 5

<210> SEQ ID NO 303
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 303

Ser Thr Glu Ser Leu Arg
1 5

<210> SEQ ID NO 304
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ser Ser Asp Ser Pro Arg
1               5

<210> SEQ ID NO 305
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Asn Ser Asn Ser Leu Trp
1               5

<210> SEQ ID NO 306
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Asn Ser Asp Phe Leu Arg
1               5

<210> SEQ ID NO 307
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Arg Ser Val Tyr Ile His
1               5

<210> SEQ ID NO 308
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ser Trp His Phe Asp Arg
1               5

<210> SEQ ID NO 309
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ser Ser His Ser His Phe
1 5

<210> SEQ ID NO 310
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 310

Ser Tyr Ala Thr Thr Arg
1 5

<210> SEQ ID NO 311
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 311

Ser Leu Asp Thr His Arg
1 5

<210> SEQ ID NO 312
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 312

Arg Arg Asn Pro Met Ala
1 5

<210> SEQ ID NO 313
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 313

Trp Ala Val Ala Pro Cys
1 5

<210> SEQ ID NO 314
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 314

Asn Thr Cys Ser Leu Leu
1 5

<210> SEQ ID NO 315
<211> LENGTH: 6
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 315

Cys Thr Tyr Ser Pro Trp
1 5

<210> SEQ ID NO 316
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 316

Ile Ile Gly Gly Thr Leu
1 5

<210> SEQ ID NO 317
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 317

Arg Tyr Asp Gly Tyr Cys
1 5

<210> SEQ ID NO 318
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 318

Arg Ser Asp Asn Leu Leu
1 5

<210> SEQ ID NO 319
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 319

Gly Arg Gln Thr Leu His
1 5

<210> SEQ ID NO 320
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 320

Cys Ser Asn Arg Leu Leu
1 5

<210> SEQ ID NO 321
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 321

Asn Ser His Phe Leu Arg
1 5

<210> SEQ ID NO 322
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 322

Arg Ser Tyr Ser Arg Arg
1 5

<210> SEQ ID NO 323
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 323

Ser Thr Val Ser Gln Ile
1 5

<210> SEQ ID NO 324
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 324

Lys Gly Thr Gly Ser Lys Gln
1 5

<210> SEQ ID NO 325
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 325

Gln Ser Thr Met Arg Leu Trp
1 5

<210> SEQ ID NO 326
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 326

Gly Arg Leu Glu Leu Arg Glu
1 5

<210> SEQ ID NO 327
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 327

Glu Leu Arg Phe Pro Leu Met
1 5

<210> SEQ ID NO 328
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 328

Leu Leu Val Gly Arg Ala Val
1 5

<210> SEQ ID NO 329
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 329

Gly Ser Asn Lys Ile Ile Leu
1 5

<210> SEQ ID NO 330
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 330

Glu Asp Lys Val Thr His Ser
1 5

<210> SEQ ID NO 331
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 331

Leu Gly His Glu Val Ala Glu
1 5

<210> SEQ ID NO 332
<211> LENGTH: 7

-continued

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 332

Leu Ser Asn Ala Ser Met Pro
1 5

<210> SEQ ID NO 333
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 333

Ala Ala Lys Ile Thr Met Trp
1 5

<210> SEQ ID NO 334
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 334

Gly Glu Tyr Lys Asp Pro Thr
1 5

<210> SEQ ID NO 335
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 335

Met Val Pro Glu Gly Ala Ser
1 5

<210> SEQ ID NO 336
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 336

Asp Tyr Met Ala Arg Ala Gln
1 5

<210> SEQ ID NO 337
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 337

Cys Ser Thr Val Lys Ile Arg 1 5

<210> SEQ ID NO 338
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 338

Pro Arg Trp Glu Pro Gly Glu
1 5

<210> SEQ ID NO 339
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 339

Ala Pro Lys Leu Lys Asp Asp
1 5

<210> SEQ ID NO 340
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 340

Arg Pro Pro Arg Arg Leu Leu
1 5

<210> SEQ ID NO 341
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 341

Pro Arg Pro Ile Gln Ile Ile
1 5

<210> SEQ ID NO 342
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 342

Leu Leu Thr Thr Ser Phe Arg
1 5

<210> SEQ ID NO 343
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

Gln Glu Ile Leu Ser Asn Leu
1 5

<210> SEQ ID NO 344
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 344

Arg Pro Asp Glu Asp Gly Ser
1 5

<210> SEQ ID NO 345
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 345

Val Gln His Tyr Leu Ala Arg
1 5

<210> SEQ ID NO 346
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 346

Leu Met Ala Gly Asp Ser Arg
1 5

<210> SEQ ID NO 347
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 347

Gly Asp Ile Val Ser Ser
1 5

<210> SEQ ID NO 348
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 348

Lys Met Ile Leu Thr Arg
1 5

<210> SEQ ID NO 349

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Leu Thr Ile Leu Tyr Pro
1               5


<210> SEQ ID NO 350
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Glu Arg Ile Met Val Ile
1               5


<210> SEQ ID NO 351
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Arg Leu Ile Leu Ala Arg
1               5


<210> SEQ ID NO 352
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Leu Tyr Ile Arg Ile Asn
1               5


<210> SEQ ID NO 353
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 353

Thr Phe Ile Phe Xaa Phe
1               5


<210> SEQ ID NO 354
<211> LENGTH: 6
<212> TYPE: PRT
<213> ORGANISM: Artificial Sequence
<220> FEATURE:
<223> OTHER INFORMATION: Description of Artificial Sequence: Synthetic
```

peptide

<400> SEQUENCE: 354

Met Val Ile Gln Ser Val
1 5

<210> SEQ ID NO 355
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (5)..(5)
<223> OTHER INFORMATION: Any amino acid

<400> SEQUENCE: 355

Thr Cys Ile Trp Xaa Cys
1 5

<210> SEQ ID NO 356
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 356

Leu Val Ile Val Pro Arg
1 5

<210> SEQ ID NO 357
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 357

Val Arg Ile Trp Phe Pro
1 5

<210> SEQ ID NO 358
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 358

Asn Ser Ile Glu Arg Leu
1 5

<210> SEQ ID NO 359
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 359

Gln Ser Ile Ser Gln Gly 1 5

<210> SEQ ID NO 360
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 360

Thr Gln Ile Asp Arg Pro
1 5

<210> SEQ ID NO 361
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 361

Tyr Ile Ile Phe Arg Ile
1 5

<210> SEQ ID NO 362
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 362

Arg Ile Ile Phe Pro Trp
1 5

<210> SEQ ID NO 363
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 363

Gly Lys Ile Thr Leu Gln
1 5

<210> SEQ ID NO 364
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 364

Gly Phe Ile Gln Ala Ile
1 5

<210> SEQ ID NO 365
<211> LENGTH: 6
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 365

Asn Met Ile Leu Leu Pro
1 5

<210> SEQ ID NO 366
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 366

Asn Val Ile Val Met Ile
1 5

<210> SEQ ID NO 367
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 367

Glu Met Ile Met Glu Arg
1 5

<210> SEQ ID NO 368
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 368

Phe Gly Ile Asp Asp Pro
1 5

<210> SEQ ID NO 369
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 369

Thr Leu Ile Ala Pro Tyr
1 5

<210> SEQ ID NO 370
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 370

Phe Ser Ala Gln Arg Pro Asn Leu Val Thr Leu Leu
1 5 10

<210> SEQ ID NO 371

<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 371

Tyr Asp Ser Gly Phe Phe Pro Thr Val Val Ile Thr
1 5 10

<210> SEQ ID NO 372
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 372

Leu Phe Val Ala Arg Ser Lys Met Gln Leu Ala Arg
1 5 10

<210> SEQ ID NO 373
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 373

Thr Ser Ser Lys Ala Phe Asp Ala Asn Thr Asn Glu
1 5 10

<210> SEQ ID NO 374
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 374

Val Pro Gly Trp Thr Gly Ala Pro Met Thr Val Asn
1 5 10

<210> SEQ ID NO 375
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 375

Ala Ala Thr Lys Arg Leu Arg Tyr Lys Pro Ala Ala
1 5 10

<210> SEQ ID NO 376
<211> LENGTH: 12
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (7)..(7)

<223> OTHER INFORMATION: Any amino acid

<400> SEQUENCE: 376

Ser Cys Pro Asp Ala Val Xaa Thr Lys Ser Thr Lys
1 5 10

<210> SEQ ID NO 377
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 377

Leu Lys Leu Leu Leu Asp Ser Ser Val Gly Ser Thr
1 5 10

<210> SEQ ID NO 378
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 378

Leu Arg Leu Ser Gly Trp Arg Ile Phe Asn Thr Lys
1 5 10

<210> SEQ ID NO 379
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 379

Asn Val Asn Arg Val Glu Pro Met Gly Leu Pro Pro
1 5 10

<210> SEQ ID NO 380
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 380

Leu Arg Ser Met Lys Ile Trp Thr Asn Asp Thr Ser
1 5 10

<210> SEQ ID NO 381
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 381

Gly His Asp Glu Ser Pro Lys Asn Arg Ser Ala Asp
1 5 10

<210> SEQ ID NO 382

<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Ala Asn Ala Asp Leu Ile Ile His Gly Thr Asn Leu
1               5                   10

<210> SEQ ID NO 383
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Thr Lys Arg Trp Asn Thr Ala Asp Leu Ser Ala Arg
1               5                   10

<210> SEQ ID NO 384
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Val Asp Gly Ala Asp Val Leu Trp Thr Leu Arg Pro
1               5                   10

<210> SEQ ID NO 385
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Leu Leu Phe Ala Arg Ser Asn Gln Gly Trp Lys Val
1               5                   10

<210> SEQ ID NO 386
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Phe Leu Leu Trp Val His Ser Phe Val Ser Arg Trp
1               5                   10

<210> SEQ ID NO 387
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Lys Asp Pro Tyr His Cys Lys Pro His Asp Val Ser
1 5 10

<210> SEQ ID NO 388
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 388

Leu Pro Val Ile Ile Lys Thr Asn Ser Asn Gln Val
1 5 10

<210> SEQ ID NO 389
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 389

Ile Ser Thr Val Ala Asn Val Asp Thr Gly Thr Arg
1 5 10

<210> SEQ ID NO 390
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 390

Leu Ser Trp Thr Lys Val Asp Lys Thr Tyr Val Val
1 5 10

<210> SEQ ID NO 391
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 391

Ile Tyr Gly Pro Asp Leu Glu Val Cys Arg Leu Trp
1 5 10

<210> SEQ ID NO 392
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 392

Leu Ser Asp Gly Gly Ile Arg Gly Gln Trp Met Val
1 5 10

<210> SEQ ID NO 393
<211> LENGTH: 7
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 393

Thr Asn Pro Leu Lys Glu Thr
1 5

<210> SEQ ID NO 394
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 394

Met Asn Pro Arg Met Glu Met
1 5

<210> SEQ ID NO 395
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 395

Ser Asn Pro Leu Ser Arg Pro
1 5

<210> SEQ ID NO 396
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 396

Thr Asn Pro Leu Arg Gly Thr
1 5

<210> SEQ ID NO 397
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 397

Gly Asn Pro Thr Lys Glu Thr
1 5

<210> SEQ ID NO 398
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 398

Thr Asn Pro Arg Arg Arg Val
1 5

<210> SEQ ID NO 399
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 399

Ile Asn Pro Leu Gln Val Ser
1 5

<210> SEQ ID NO 400
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 400

Ala Asn Pro Ile Lys His Met
1 5

<210> SEQ ID NO 401
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 401

Arg Arg Pro Thr Lys Gly Asn
1 5

<210> SEQ ID NO 402
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 402

Thr Ile Pro His Arg Gly Arg
1 5

<210> SEQ ID NO 403
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 403

Pro Ser Pro Phe Ile Glu Asn
1 5

<210> SEQ ID NO 404
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 404

Arg Pro Asn Ser Thr
1 5

<210> SEQ ID NO 405
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 405

His Pro Asp Ser Asp
1 5

<210> SEQ ID NO 406
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 406

Arg Pro His Ser Asn
1 5

<210> SEQ ID NO 407
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 407

Pro Pro Asn Val Lys
1 5

<210> SEQ ID NO 408
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 408

Arg Pro Arg Ser Met
1 5

<210> SEQ ID NO 409
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 409

Arg Pro Arg Ser Thr
1 5

<210> SEQ ID NO 410
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 410

Gly Pro Ser Ser Ala
1 5

<210> SEQ ID NO 411
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 411

Arg Pro Thr Ala Gly
1 5

<210> SEQ ID NO 412
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 412

Gly Pro Gly Gln Val
1 5

<210> SEQ ID NO 413
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 413

Gln Pro Asn Val Pro
1 5

<210> SEQ ID NO 414
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 414

Arg Pro Glu Cys Ile
1 5

<210> SEQ ID NO 415
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 415

Ser Asp Ser Leu Arg His
1 5

<210> SEQ ID NO 416
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 416

Arg Leu Trp Thr Leu Trp Met Ala Arg Trp Arg Trp
1 5 10

<210> SEQ ID NO 417
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 417

Ser Arg Ser Leu Trp Leu Ser Ile Gly Lys Arg His
1 5 10

<210> SEQ ID NO 418
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 418

Gly Leu Ser Thr Ala Gly Arg Trp Lys Arg Val Arg
1 5 10

<210> SEQ ID NO 419
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 419

Tyr Arg Pro Arg Arg Gly Gly Met Arg Leu Arg His
1 5 10

<210> SEQ ID NO 420
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 420

Trp Asn Ser Arg Trp Pro Ala Pro Thr Arg Arg Arg
1 5 10

<210> SEQ ID NO 421
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 421

Ile Tyr Arg Tyr Gly Leu
1 5

<210> SEQ ID NO 422
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 422

Leu Gly Val Leu Arg Arg
1 5

<210> SEQ ID NO 423
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 423

Leu Gly Met Leu Arg Arg
1 5

<210> SEQ ID NO 424
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 424

Arg Ala Phe Leu Arg His
1 5

<210> SEQ ID NO 425
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 425

Arg Gly Trp Leu Arg Ser
1 5

<210> SEQ ID NO 426
<211> LENGTH: 70
<212> TYPE: DNA
<213> ORGANISM: Artificial Sequence
<220> FEATURE:
<223> OTHER INFORMATION: Description of Artificial Sequence: Synthetic
primer

<400> SEQUENCE: 426
taatacgact cactataggg acaattacta tttacaatta catatgacca tccctgagat 60
catcatcaag 70

<210> SEQ ID NO 427
<211> LENGTH: 87

-continued

<212> TYPE: DNA
<213> ORGANISM: Artificial Sequence
<220> FEATURE:
<223> OTHER INFORMATION: Description of Artificial Sequence: Synthetic
primer

<400> SEQUENCE: 427
tttttttttt tttttttttt aaatagcgga tgccttgtcg tcgtcgtcct tgtagtcgga 60
tcctcgtctt tgaatctgca cgtccag 87

<210> SEQ ID NO 428
<211> LENGTH: 65
<212> TYPE: DNA
<213> ORGANISM: Artificial Sequence
<220> FEATURE:
<223> OTHER INFORMATION: Description of Artificial Sequence: Synthetic
primer

<400> SEQUENCE: 428
gaaataattt tgtttaactt taagaaggag atatacatat gaccatccct gagatcatca 60
tcaag 65

<210> SEQ ID NO 429
<211> LENGTH: 78
<212> TYPE: DNA
<213> ORGANISM: Artificial Sequence
<220> FEATURE:
<223> OTHER INFORMATION: Description of Artificial Sequence: Synthetic
primer

<400> SEQUENCE: 429
atgaccatcc ctgagatcat catcaaggtc cgcggcactc aggtcgtggg ttctgacatg 60
actgtgatcg tggagttt 78

<210> SEQ ID NO 430
<211> LENGTH: 66
<212> TYPE: DNA
<213> ORGANISM: Artificial Sequence
<220> FEATURE:
<223> OTHER INFORMATION: Description of Artificial Sequence: Synthetic
primer

<400> SEQUENCE: 430
caggtgcacc cagacattgc gcagggtttc tttcagagga ttggtaaact ccacgatcac 60
agtcat 66

<210> SEQ ID NO 431
<211> LENGTH: 72
<212> TYPE: DNA
<213> ORGANISM: Artificial Sequence
<220> FEATURE:
<223> OTHER INFORMATION: Description of Artificial Sequence: Synthetic
primer

<400> SEQUENCE: 431
ctgcgcaatg tctgggtgca cctggatggt cctggagtca cacgcccaat gaagaagatg 60
ttccgcgaaa tc 72

<210> SEQ ID NO 432
<211> LENGTH: 57
<212> TYPE: DNA
<213> ORGANISM: Artificial Sequence
<220> FEATURE:
<223> OTHER INFORMATION: Description of Artificial Sequence: Synthetic primer

<400> SEQUENCE: 432
cacttcttcc cactgcacgg tggagtttgg gcggatttcg cggaacatct tcttcat 57

<210> SEQ ID NO 433
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 433
gtgcagtggg aagaagtgtg ccgcccatgg gtctctgggc atcgcaagct gatcgccagc 60
atg 63

<210> SEQ ID NO 434
<211> LENGTH: 75
<212> TYPE: DNA
<213> ORGANISM: Artificial Sequence
<220> FEATURE:
<223> OTHER INFORMATION: Description of Artificial Sequence: Synthetic primer

<400> SEQUENCE: 434
gcggcgttga atctgcacgt ccagctcgcc atacacatgg cgcagggagt cactgctcat 60
gctggcgatc agctt 75

<210> SEQ ID NO 435
<211> LENGTH: 58
<212> TYPE: DNA
<213> ORGANISM: Artificial Sequence
<220> FEATURE:
<223> OTHER INFORMATION: Description of Artificial Sequence: Synthetic primer

<400> SEQUENCE: 435
tagatcattg gatccctcat taatgatggt gatggtgatg gcggcgttga atctgcac 58

<210> SEQ ID NO 436
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 436
tcctttgctg aattcgccag aaccagcagc ggagccagcg gatccgcggc gttgaatctg 60
cac 63

<210> SEQ ID NO 437
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 437
gacattgcgc agggtttctt tcagaggatt ggtaaactcc acgatcacag tcat 54

<210> SEQ ID NO 438

<211> LENGTH: 67
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 438
tagattattc tcgagctcat taatgatggt gatggtgatg catggacggg cggcgttgaa     60
tctgcac                                                                67

<210> SEQ ID NO 439
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 439
tagattattc tcgagctcat tacatggacg ggcggcgttg aatctgcac                  49

<210> SEQ ID NO 440
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 440
tagattattc tcgagctcat tacatgcacg ggcggcgttg aatctgcac                  49

<210> SEQ ID NO 441
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 441
tagattattc tcgagctcat taatgatggt gatggtgatg gcggcgttga atctgcac       58

<210> SEQ ID NO 442
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 442
tattattcta gaaataattt tgtttaactt taagaaggag atataccatg gggaccatcc     60
ctgagatcat cat                                                         73

<210> SEQ ID NO 443
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(18)
<223> OTHER INFORMATION: a, c, t, g, unknown or other
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: misc_feature
<222> LOCATION: (29)..(30)
<223> OTHER INFORMATION: n is a, c, g, or t

<400> SEQUENCE: 443
agtagtagtc atatgsnnsn nsnnsnnsnn gcggcgttga atctgcac 48

<210> SEQ ID NO 444
<211> LENGTH: 63
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: misc_feature
<222> LOCATION: (19)..(20)
<223> OTHER INFORMATION: n is a, c, g, or t

<400> SEQUENCE: 444
gtgcagtggg aagaagtgnn scgcccatgg gtctctgggc atcgcaagct gatcgccagc 60
atg 63

<210> SEQ ID NO 445
<211> LENGTH: 45
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: misc_feature
<222> LOCATION: (22)..(23)

<223> OTHER INFORMATION: n is a, c, g, or t

<400> SEQUENCE: 445
aaagaaaccc tgcgcaatgt cnnsgtgcac ctggatggtc ctgga 45

<210> SEQ ID NO 446
<211> LENGTH: 51
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: misc_feature
<222> LOCATION: (32)..(33)
<223> OTHER INFORMATION: n is a, c, g, or t

<400> SEQUENCE: 446
gcggcgttga atctgcacgt ccagctcgcc snncacatgg cgcagggagt c 51

<210> SEQ ID NO 447
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 447
gtgcagtggg aagaagtggt gcgcccatgg gtctctgggc atcgcaagct gatcgccagc 60
atg 63

<210> SEQ ID NO 448
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 448
gtctgggtgc acctggatgg tcctggagtc acacgcccaa tgaagaagat gttc 54

<210> SEQ ID NO 449
<211> LENGTH: 63
<212> TYPE: DNA
<213> ORGANISM: Artificial Sequence
<220> FEATURE:
<223> OTHER INFORMATION: Description of Artificial Sequence: Synthetic primer

<400> SEQUENCE: 449
taatacgact cactataggg acaattacta tttacaatta caatgaccat ccctgagatc 60
atc 63

<210> SEQ ID NO 450
<211> LENGTH: 78
<212> TYPE: DNA
<213> ORGANISM: Artificial Sequence
<220> FEATURE:
<223> OTHER INFORMATION: Description of Artificial Sequence: Synthetic primer

<400> SEQUENCE: 450
tttttttttt tttttttttt aaatagcgga tgccttgtcg tcgtcgtcct tgtagtcgcg 60
gcgttgaatc tgcacgtc 78

<210> SEQ ID NO 451
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 451
gtcgtcgtcc ttgtagtcgc ggcgttgaat ctgcacgtc 39

<210> SEQ ID NO 452
<211> LENGTH: 66
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: misc_feature
<222> LOCATION: (38)..(39)
<223> OTHER INFORMATION: n is a, c, g, or t

<400> SEQUENCE: 452
caggtgcacc cagacattgc gcagsnnsnn snnsnnsnna ttggtaaact ccacgatcac 60
agtcat 66

<210> SEQ ID NO 453
<211> LENGTH: 63
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: misc_feature
<222> LOCATION: (32)..(33)
<223> OTHER INFORMATION: n is a, c, g, or t

<400> SEQUENCE: 453
cacttcttcc cactgcacgg tsnnsnnsnn snngatttcg cggaacatct tcttcattgg 60
gcg 63

<210> SEQ ID NO 454
<211> LENGTH: 75
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: modified_base
<222> LOCATION: (50)..(51)
<223> OTHER INFORMATION: a, c, t, g, unknown or other
<220> FEATURE:
<221> NAME/KEY: misc_feature
<222> LOCATION: (50)..(51)
<223> OTHER INFORMATION: n is a, c, g, or t

<400> SEQUENCE: 454
gcggcgttga atctgcacgt ccagctcgcc atacacatgg cgcagsnnsn nactgctcat 60
gctggcgatc agctt 75

<210> SEQ ID NO 455
<211> LENGTH: 81
<212> TYPE: DNA
<213> ORGANISM: Artificial Sequence
<220> FEATURE:

<223> OTHER INFORMATION: Description of Artificial Sequence: Synthetic primer
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: modified_base
<222> LOCATION: (50)..(51)
<223> OTHER INFORMATION: a, c, t, g, unknown or other
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: modified_base
<222> LOCATION: (56)..(57)
<223> OTHER INFORMATION: a, c, t, g, unknown or other
<220> FEATURE:
<221> NAME/KEY: misc_feature
<222> LOCATION: (56)..(57)
<223> OTHER INFORMATION: n is a, c, g, or t

<400> SEQUENCE: 455
gcggcgttga atctgcacgt ccagctcgcc atacacatgg cgcagsnnsn nsnnsnnact     60
gctcatgctg gcgatcagct t                                               81

<210> SEQ ID NO 456
<211> LENGTH: 66
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (17)..(18)
<223> OTHER INFORMATION: a, c, t, g, unknown or other
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (44)..(45)
<223> OTHER INFORMATION: n is a, c, g, or t

<400> SEQUENCE: 456
caggtgcacc cagacsnnsn ncagsnnsnn snnsnnsnns nnsnnaaact ccacgatcac 60
agtcat 66

<210> SEQ ID NO 457
<211> LENGTH: 63
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t

<400> SEQUENCE: 457
cacttcttcc cactgcacsn nsnnsnnsnn snngatsnns nngaacatct tcttcattgg 60
gcg 63

<210> SEQ ID NO 458
<211> LENGTH: 75
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: modified_base
<222> LOCATION: (50)..(51)
<223> OTHER INFORMATION: a, c, t, g, unknown or other
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: modified_base
<222> LOCATION: (56)..(57)
<223> OTHER INFORMATION: a, c, t, g, unknown or other
<220> FEATURE:
<221> NAME/KEY: misc_feature
<222> LOCATION: (56)..(57)
<223> OTHER INFORMATION: n is a, c, g, or t

<400> SEQUENCE: 458
gcggcgttga atctgcacgt ccagctcgcc atacacatgs nnsnnsnnsn nsnnsnncat 60
gctggcgatc agctt 75

<210> SEQ ID NO 459
<211> LENGTH: 72
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: modified_base
<222> LOCATION: (50)..(51)
<223> OTHER INFORMATION: a, c, t, g, unknown or other
<220> FEATURE:
<221> NAME/KEY: misc_feature
<222> LOCATION: (50)..(51)
<223> OTHER INFORMATION: n is a, c, g, or t

<400> SEQUENCE: 459
accatccagg tgcacccaga cvnnsnncag snnbnnbnns nnvnnvnnsn naaactccac 60
gatcacagtc at 72

<210> SEQ ID NO 460
<211> LENGTH: 63
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (20)..(21)
<223> OTHER INFORMATION: a, c, t, g, unknown or other
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: modified_base
<222> LOCATION: (23)..(24)
<223> OTHER INFORMATION: a, c, t, g, unknown or other
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t

<400> SEQUENCE: 460
cacttcttcc cactgcacsn nsnnsnnbnn snngatbnns nngaacatct tcttcattgg 60
gcg 63

<210> SEQ ID NO 461
<211> LENGTH: 75
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: modified_base
<222> LOCATION: (50)..(51)
<223> OTHER INFORMATION: a, c, t, g, unknown or other
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: modified_base
<222> LOCATION: (56)..(57)
<223> OTHER INFORMATION: a, c, t, g, unknown or other
<220> FEATURE:
<221> NAME/KEY: misc_feature
<222> LOCATION: (56)..(57)
<223> OTHER INFORMATION: n is a, c, g, or t

<400> SEQUENCE: 461
gcggcgttga atctgcacgt ccagctcgcc atacacatgs nnsnnsnnsn nvnnsnncat 60
gctggcgatc agctt 75

<210> SEQ ID NO 462
<211> LENGTH: 78
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (44)..(45)
<223> OTHER INFORMATION: n is a, c, g, or t

<400> SEQUENCE: 462
caggtgcacc cagacattgc gcagsnnsnn snnsnnsnns nnsnnaggat tggtaaactc 60
cacgatcaca gtcatgtc 78

<210> SEQ ID NO 463
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 463
ctgcgcaatg tctgggtgca cctggatggt cctggagtca cacgcccaat gaagaagatg     60
ttc                                                                   63

<210> SEQ ID NO 464
<211> LENGTH: 63
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t

<400> SEQUENCE: 464
cacttcttcc cactgcacgg tggasnnsnn snngatsnns nngaacatct tcttcattgg     60
gcg                                                                   63

<210> SEQ ID NO 465
<211> LENGTH: 84
<212> TYPE: DNA
<213> ORGANISM: Artificial Sequence
<220> FEATURE:
<223> OTHER INFORMATION: Description of Artificial Sequence: Synthetic
      primer <220> FEATURE:
<221> NAME/KEY: modified_base
<222> LOCATION: (29)..(30)
<223> OTHER INFORMATION: a, c, t, g, unknown or other
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: modified_base
<222> LOCATION: (32)..(33)
<223> OTHER INFORMATION: a, c, t, g, unknown or other
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: modified_base
<222> LOCATION: (38)..(39)
<223> OTHER INFORMATION: a, c, t, g, unknown or other
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: modified_base
<222> LOCATION: (41)..(42)
<223> OTHER INFORMATION: a, c, t, g, unknown or other
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: modified_base
<222> LOCATION: (44)..(45)
<223> OTHER INFORMATION: a, c, t, g, unknown or other
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: modified_base
<222> LOCATION: (47)..(48)
<223> OTHER INFORMATION: a, c, t, g, unknown or other
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: modified_base
<222> LOCATION: (50)..(51)
<223> OTHER INFORMATION: a, c, t, g, unknown or other
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: modified_base
<222> LOCATION: (53)..(54)
<223> OTHER INFORMATION: a, c, t, g, unknown or other
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: modified_base
<222> LOCATION: (56)..(57)
<223> OTHER INFORMATION: a, c, t, g, unknown or other
<220> FEATURE:
<221> NAME/KEY: misc_feature
<222> LOCATION: (56)..(57)

<223> OTHER INFORMATION: n is a, c, g, or t
<220> FEATURE:
<221> NAME/KEY: modified_base
<222> LOCATION: (59)..(60)
<223> OTHER INFORMATION: a, c, t, g, unknown or other
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: modified_base
<222> LOCATION: (62)..(63)
<223> OTHER INFORMATION: a, c, t, g, unknown or other
<220> FEATURE:
<221> NAME/KEY: misc_feature
<222> LOCATION: (62)..(63)
<223> OTHER INFORMATION: n is a, c, g, or t

<400> SEQUENCE: 465
aatctgcacg tccagctcgc catacacsnn snnsnnsnns nnsnnsnnsn nsnnsnnsnn 60
snngctcatg ctggcgatca gctt 84

<210> SEQ ID NO 466
<211> LENGTH: 78
<212> TYPE: DNA
<213> ORGANISM: Artificial Sequence
<220> FEATURE:
<223> OTHER INFORMATION: Description of Artificial Sequence: Synthetic
primer

<400> SEQUENCE: 466
taatacgact cactataggg acatcatcaa ccataacaat tactatttac aattacaatg 60
accatccctg agatcatc 78

<210> SEQ ID NO 467
<211> LENGTH: 87
<212> TYPE: DNA
<213> ORGANISM: Artificial Sequence
<220> FEATURE:
<223> OTHER INFORMATION: Description of Artificial Sequence: Synthetic
primer

<400> SEQUENCE: 467
tttttttttt tttttttttt aaatagcgga tgccttgtcg tcgtcgtcct tgtagtcgcg 60
gcgttgaatc tgcacgtcca gctcgcc 87

<210> SEQ ID NO 468
<211> LENGTH: 35
<212> TYPE: DNA
<213> ORGANISM: Artificial Sequence
<220> FEATURE:
<223> OTHER INFORMATION: Description of Artificial Sequence: Synthetic
primer

<400> SEQUENCE: 468
taatacgact cactataggg acatcatcaa ccata 35

<210> SEQ ID NO 469
<211> LENGTH: 78
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: modified_base
<222> LOCATION: (46)..(47)
<223> OTHER INFORMATION: a, c, t, g, unknown or other
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: modified_base
<222> LOCATION: (52)..(53)
<223> OTHER INFORMATION: a, c, t, g, unknown or other
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: misc_feature
<222> LOCATION: (55)..(56)
<223> OTHER INFORMATION: n is a, c, g, or t

<400> SEQUENCE: 469
atgaccatcc ctgagatcat catcaaggtc cgcnnsnnsc agnnsnnsgg tnnsnnsatg 60
actgtgatcg tggagttt 78

<210> SEQ ID NO 470
<211> LENGTH: 72
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: misc_feature
<222> LOCATION: (34)..(35)
<223> OTHER INFORMATION: n is a, c, g, or t

<400> SEQUENCE: 470
ctgcgcaatg tctgggtgca cctggatggt nnsnnsgtca cacgcccaat gaagaagatg 60
ttccgcgaaa tc 72

<210> SEQ ID NO 471
<211> LENGTH: 63
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: misc_feature
<222> LOCATION: (40)..(41)
<223> OTHER INFORMATION: n is a, c, g, or t

<400> SEQUENCE: 471
gtgcagtggg aagaagtgtg cnnsccanns nnsnnsgggn nscgcaagct gatcgccagc 60
atg 63

<210> SEQ ID NO 472
<211> LENGTH: 81
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: modified_base
<222> LOCATION: (34)..(35)
<223> OTHER INFORMATION: a, c, t, g, unknown or other
<220> FEATURE:

<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: misc_feature
<222> LOCATION: (43)..(44)
<223> OTHER INFORMATION: n is a, c, g, or t

<400> SEQUENCE: 472
ctgcgcaatg tctgggtgca cctggatggt nnsnnsnnsn nsnnsgtcac acgcccaatg 60
aagaagatgt tccgcgaaat c 81

<210> SEQ ID NO 473
<211> LENGTH: 78
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: modified_base
<222> LOCATION: (46)..(47)
<223> OTHER INFORMATION: a, c, t, g, unknown or other
<220> FEATURE:

<221> NAME/KEY: misc_feature
<222> LOCATION: (46)..(47)
<223> OTHER INFORMATION: n is a, c, g, or t
<220> FEATURE:
<221> NAME/KEY: modified_base
<222> LOCATION: (49)..(50)
<223> OTHER INFORMATION: a, c, t, g, unknown or other
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: modified_base
<222> LOCATION: (52)..(53)
<223> OTHER INFORMATION: a, c, t, g, unknown or other
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: modified_base
<222> LOCATION: (55)..(56)
<223> OTHER INFORMATION: a, c, t, g, unknown or other
<220> FEATURE:
<221> NAME/KEY: misc_feature
<222> LOCATION: (55)..(56)
<223> OTHER INFORMATION: n is a, c, g, or t

<400> SEQUENCE: 473
atgaccatcc ctgagatcat catcaaggtc cgcnnsnnsn nsnnsnnsnn snnsnnsatg 60
actgtgatcg tggagttt 78

<210> SEQ ID NO 474
<211> LENGTH: 72
<212> TYPE: DNA
<213> ORGANISM: Artificial Sequence
<220> FEATURE:
<223> OTHER INFORMATION: Description of Artificial Sequence: Synthetic
primer
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: modified_base
<222> LOCATION: (40)..(41)
<223> OTHER INFORMATION: a, c, t, g, unknown or other
<220> FEATURE:

<221> NAME/KEY: misc_feature
<222> LOCATION: (40)..(41)
<223> OTHER INFORMATION: n is a, c, g, or t
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: modified_base
<222> LOCATION: (46)..(47)
<223> OTHER INFORMATION: a, c, t, g, unknown or other
<220> FEATURE:
<221> NAME/KEY: misc_feature
<222> LOCATION: (46)..(47)
<223> OTHER INFORMATION: n is a, c, g, or t

<400> SEQUENCE: 474
ctgcgcaatg tctgggtgca cctggatnns nnsnnsnnsn nsnnsnnsat gaagaagatg 60
ttccgcgaaa tc 72

<210> SEQ ID NO 475
<211> LENGTH: 69
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: modified_base
<222> LOCATION: (28)..(29)
<223> OTHER INFORMATION: a, c, t, g, unknown or other
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (37)..(38)
<223> OTHER INFORMATION: a, c, t, g, unknown or other
<220> FEATURE:

<221> NAME/KEY: misc_feature
<222> LOCATION: (37)..(38)
<223> OTHER INFORMATION: n is a, c, g, or t
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: misc_feature
<222> LOCATION: (40)..(41)
<223> OTHER INFORMATION: n is a, c, g, or t

<400> SEQUENCE: 475
gtgcagtggg aagaagtggt gnnsnnsnns nnsnnsnnsn nscgcaagct gatcgccagc 60
atgagcagt 69

<210> SEQ ID NO 476
<211> LENGTH: 87
<212> TYPE: DNA
<213> ORGANISM: Artificial Sequence
<220> FEATURE:
<223> OTHER INFORMATION: Description of Artificial Sequence: Synthetic primer

<400> SEQUENCE: 476
ggagcctccg cctccgcggc gttgaatctg cacgtccagc tcgccataca catggcgcag 60
ggagtcactg ctcatgctgg cgatcag 87

<210> SEQ ID NO 477
<211> LENGTH: 78
<212> TYPE: DNA
<213> ORGANISM: Artificial Sequence
<220> FEATURE:
<223> OTHER INFORMATION: Description of Artificial Sequence: Synthetic primer

<400> SEQUENCE: 477
tttttttttt tttttttttt aaatagcgga tgccttgtcg tcgtcgtcct tgtagtcgga 60
gcctccgcct ccgcggcg 78

<210> SEQ ID NO 478
<211> LENGTH: 78
<212> TYPE: DNA
<213> ORGANISM: Artificial Sequence
<220> FEATURE:
<223> OTHER INFORMATION: Description of Artificial Sequence: Synthetic primer

<400> SEQUENCE: 478
aatgatctac atatgaatga tctagacgtc ctggccaagc aaaagtccac cgtgctaacc 60
atccctgaga tcatcatc 78

<210> SEQ ID NO 479
<211> LENGTH: 70
<212> TYPE: DNA
<213> ORGANISM: Artificial Sequence
<220> FEATURE:
<223> OTHER INFORMATION: Description of Artificial Sequence: Synthetic primer

<400> SEQUENCE: 479
tagatcattg gatccctcat taatgatggt gatggtgatg catggaaggg cggcgttgaa 60
tctgcacgtc 70

<210> SEQ ID NO 480
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 480
aatgatctac atatgtcaga aacttccagg accgccttt 39

<210> SEQ ID NO 481
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 481
ctgaagagat cccttctggg gtcatacgga cgactgaagt caatctgcac 50

<210> SEQ ID NO 482
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 482
gtgcagattg acttcagtcg tccgtatgac cccagaaggg atctcttcag 50

<210> SEQ ID NO 483
<211> LENGTH: 49
<212> TYPE: DNA
<213> ORGANISM: Artificial Sequence
<220> FEATURE:
<223> OTHER INFORMATION: Description of Artificial Sequence: Synthetic
primer

<400> SEQUENCE: 483
cataggcata gatattgtcc caggagccaa cgaggacacc ttcgtcatc 49

<210> SEQ ID NO 484
<211> LENGTH: 49
<212> TYPE: DNA
<213> ORGANISM: Artificial Sequence
<220> FEATURE:
<223> OTHER INFORMATION: Description of Artificial Sequence: Synthetic
primer

<400> SEQUENCE: 484
gatgacgaag gtgtcctcgt tggctcctgg gacaatatct atgcctatg 49

<210> SEQ ID NO 485
<211> LENGTH: 52
<212> TYPE: DNA
<213> ORGANISM: Artificial Sequence
<220> FEATURE:
<223> OTHER INFORMATION: Description of Artificial Sequence: Synthetic
primer

<400> SEQUENCE: 485
atcagtaata tccatcatgc catcaccacc aatttgtttg gtcacaatta at 52

<210> SEQ ID NO 486

<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 486
attaattgtg accaaacaaa ttggtggtga tggcatgatg gatattactg at 52

<210> SEQ ID NO 487
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 487
cacggtggac ttttgcttgg ccaggacgtc cctggtctca ttgatgcgag ctgt 54

<210> SEQ ID NO 488
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 488
aatgatctac atatgaaaat cgaagaaggt aaactggta 39

<210> SEQ ID NO 489
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 489
tagatcattc atatgccttc cctcgatccc gaggttgtt 39

<210> SEQ ID NO 490
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 490
aatgatctac atatgtccaa cgttgacatg gactttgaag 40

<210> SEQ ID NO 491
<211> LENGTH: 70
<212> TYPE: DNA
<213> ORGANISM: Artificial Sequence
<220> FEATURE:
<223> OTHER INFORMATION: Description of Artificial Sequence: Synthetic primer

<400> SEQUENCE: 491
taatacgact cactataggg acaattacta tttacaatta catatgtcca acgttgacat 60
ggactttgaa 70

-continued

<210> SEQ ID NO 492
<211> LENGTH: 64
<212> TYPE: DNA
<213> ORGANISM: Artificial Sequence
<220> FEATURE:
<223> OTHER INFORMATION: Description of Artificial Sequence: Synthetic primer

<400> SEQUENCE: 492
tagatcattg gatccctcat taatgatggt gatggtgatg tagcacggtg gacttttgct 60
tggc 64

<210> SEQ ID NO 493
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 493
tagattattc tcgagctcat tatagcacgg tggacttttg cttggccag 49

<210> SEQ ID NO 494
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 494
tcctttgctg aattcgccag aaccagcagc ggagccagcg gatcctagca cggtggactt 60
ttgcttggc 69

<210> SEQ ID NO 495
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 495
attacgccaa gctttggagc cttttttttg gagattttca acgtgaaaaa attattattc 60
gcaattcctt tag 73

<210> SEQ ID NO 496
<211> LENGTH: 78
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 496
ttattattcg caattccttt agttgttcct ttctattctc actcggccga cgtggccacc 60
atccctgaga tcatcatc 78

<210> SEQ ID NO 497
<211> LENGTH: 79
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 497
tgagatgagt ttttgttctg cggccccaga cgcgtgatgg tgatgatgat gtgcggccgc 60
gcggcgttga atctgcacg 79

<210> SEQ ID NO 498
<211> LENGTH: 83
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 498
gcagaacaaa aactcatctc agaagaggat ctgaatgggg cagcagaagc tagttctgct 60
agtgccgaaa ctgttgaaag ttg 83

<210> SEQ ID NO 499
<211> LENGTH: 63
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 499
gtaaaacgac ggccagtgaa ttctcatcac gcgtttcatt aagactcctt attacgcagt 60
atg 63

<210> SEQ ID NO 500
<211> LENGTH: 85
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 500
gcagaacaaa aactcatctc agaagaggat ctgaatgggg cagcagaagc tagttctgct 60
agtgcctctg gttccggtga ttttg 85

<210> SEQ ID NO 501
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 501
ctgaaacatg aaagtattaa gaggc 25

<210> SEQ ID NO 502
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 502
tctattctca ctcggccgac gtggccgtct tcaccatccc tgagatcatc atc 53

-continued

<210> SEQ ID NO 503
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 503
tctattctca ctcgaagaca cgtggccacc atccctgaga tcatcatc 48

<210> SEQ ID NO 504
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 504
tgagatgagt ttgcggccgc gcggcgttgg tcttcaatct gcacgtccag ctc 53

<210> SEQ ID NO 505
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 505
tgagatgagt ttgaagaccg gcgttgaatc tgcacgtcca gctcgc 46

<210> SEQ ID NO 506
<211> LENGTH: 60
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 506
gggatccgcg gccgcaggct ctaaagatat cagaactgtt gaaagttgtt tagcaaaacc 60

<210> SEQ ID NO 507
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 507
gggatcctga ggaattctta ttaagactcc ttattacgca gtatgttagc aa 52

<210> SEQ ID NO 508
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 508
gggagatctc ctcaggaacc atagtacgcg ccctgtag 38

<210> SEQ ID NO 509
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 509
gggtgtacac gtctccggag attgtataag caaatattta aattgtaaac gtt 53

<210> SEQ ID NO 510
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 510
ggaattccgt ctccctccgc ccatcccgcc cctaactcc 39

<210> SEQ ID NO 511
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 511
ggaattcaag cttgggacta gttatgccga aaggccatcc tgac 44

<210> SEQ ID NO 512
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 512
ggaattccct gcaggtacca tccctgagat catcatcaag gt 42

<210> SEQ ID NO 513
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 513
gatgatgtgc ggccgcgcgg cgttgaatct gcacgtccag ctcgcca 47

<210> SEQ ID NO 514
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 514
gagacgcaca acaccgtctc gc 22

<210> SEQ ID NO 515

<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 515
ggccgcgaga cggtgttgtg cgtctctgca 30

<210> SEQ ID NO 516
<211> LENGTH: 4930
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 516
aagcttgata tcttatgaca acttgacggc tacatcattc actttttctt cacaaccggc 60
acggaactcg ctcgggctgg ccccggtgca ttttttaaat acccgcgaga aatagagttg 120
atcgtcaaaa ccaacattgc gaccgacggt ggcgataggc atccgggtgg tgctcaaaag 180
cagcttcgcc tggctgatac gttggtcctc gcgccagctt aagacgctaa tccctaactg 240
ctggcggaaa agatgtgaca gacgcgacgg cgacaagcaa acatgctgtg cgacgctggc 300
gatatcaaaa ttgctgtctg ccaggtgatc gctgatgtac tgacaagcct cgcgtacccg 360
attatccatc ggtggatgga gcgactcgtt aatcgcttcc atgcgccgca gtaacaattg 420
ctcaagcaga tttatcgcca gcagctccga atagcgccct tccccttgcc cggcgttaat 480
gatttgccca aacaggtcgc tgaaatgcgg ctggtgcgct tcatccgggc gaaagaaccc 540
cgtattggca aatattgacg gccagttaag ccattcatgc cagtaggcgc gcggacgaaa 600
gtaaacccac tggtgatacc attcgcgagc ctccggatga cgaccgtagt gatgaatctc 660
tcctggcggg aacagcaaaa tatcacccgg tcggcaaaca aattctcgtc cctgattttt 720
caccaccccc tgaccgcgaa tggtgagatt gagaatataa cctttcattc ccagcggtcg 780
gtcgataaaa aaatcgagat aaccgttggc ctcaatcggc gttaaacccg ccaccagatg 840
ggcattaaac gagtatcccg gcagcagggg atcattttgc gcttcagcca tacttttcat 900
actcccgcca ttcagagaag aaaccaattg tccatattgc atcagacatt gccgtcactg 960
cgtcttttac tggctcttct cgctaaccaa accggtaacc ccgcttatta aaagcattct 1020
gtaacaaagc gggaccaaag ccatgacaaa aacgcgtaac aaaagtgtct ataatcacgg 1080
cagaaaagtc cacattgatt atttgcacgg cgtcacactt tgctatgcca tagcattttt 1140
atccataaga ttagcggatc ctacctgacg ctttttatcg caactctcta ctgtttctcc 1200
atacccgttt ttttgggcta acaggaggaa ttaatcatga tgaagcgcaa tattctggca 1260
gtgatcgtcc ctgctctgtt agtagcaggt actgcaaacg ctgcagagac gcacaacacc 1320
gtctcgcggc cgcaggctct aaagatatca gaactgttga aagttgttta gcaaaacccc 1380
atacagaaaa ttcatttact aacgtctgga aagacgacaa aactttagat cgttacgcta 1440
actatgaggg ttgtctgtgg aatgctacag gcgttgtagt ttgtactggt gacgaaactc 1500
agtgttacgg tacatgggtt cctattgggc ttgctatccc tgaaaatgag ggtggtggct 1560
ctgagggtgg cggttctgag ggtggcggtt ctgagggtgg cggtactaaa cctcctgagt 1620
acggtgatac acctattccg ggctatactt atatcaaccc tctcgacggc acttatccgc 1680
ctggtactga gcaaaacccc gctaatccta atccttctct tgaggagtct cagcctctta 1740

-continued

```
atactttcat gtttcagaat aataggttcc gaaataggca gggggcatta actgtttata   1800
cgggcactgt tactcaaggc actgaccccg ttaaaactta ttaccagtac actcctgtat   1860
catcaaaagc catgtatgac gcttactgga acggtaaatt cagagactgc gctttccatt   1920
ctggctttaa tgaggatcca ttcgtttgtg aatatcaagg ccaatcgtct gacctgcctc   1980
aacctcctgt caatgctggc ggcggctctg gtggtggttc tggtggcggc tctgagggtg   2040
gtggctctga gggtggcggt tctgagggtg gcggctctga gggaggcggt tccggtggtg   2100
gctctggttc cggtgatttt gattatgaaa agatggcaaa cgctaataag ggggctatga   2160
ccgaaaatgc cgatgaaaac gcgctacagt ctgacgctaa aggcaaactt gattctgtcg   2220
ctactgatta cggtgctgct atcgatggtt tcattggtga cgtttccggc cttgctaatg   2280
gtaatggtgc tactggtgat tttgctggct ctaattccca aatggctcaa gtcggtgacg   2340
gtgataattc acctttaatg aataatttcc gtcaatattt accttccctc cctcaatcgg   2400
ttgaatgtcg ccc tttgtc tttagcgctg gtaaaccata tgaattttct attgattgtg   2460
acaaaataaa cttattccgt ggtgtctttg cgtttctttt atatgttgcc acctttatgt   2520
atgtattttc tacgtttgct aacatactgc gtaataagga gtcttaataa gaattcctca   2580
ggaaccatag tacgcgccct gtagcggcgc attaagcgcg gcgggtgtgg tggttacgcg   2640
cagcgtgacc gctacacttg ccagcgccct agcgcccgct cctttcgctt tcttcccttc   2700
ctttctcgcc acgttcgccg gctttccccg tcaagctcta aatcgggggc tccctttagg   2760
gttccgattt agtgctttac ggcacctcga ccccaaaaaa cttgatttgg gtgatggttc   2820
acgtagtggg ccatcgccct gatagacggt ttttcgccct ttgacgttgg agtccacgtt   2880
ctttaatagt ggactcttgt tccaaactgg aacaacactc aaccctatct cgggctattc   2940
ttttgattta taagggattt tgccgatttc ggcctattgg ttaaaaaatg agctgattta   3000
acaaaaattt aacgcgaatt ttaacaaaat attaacgttt acaatttaaa tatttgctta   3060
tacaatctcc gcccatcccg cccctaactc cgcccagttc cgcccattct ccgcctcatg   3120
gctgactaat tttttttatt tatgcagagg ccgaggccgc ctcggcctct gagctattcc   3180
agaagtagtg aggaggcttt tttggaggcc taggcttttg caaaaagcta attcggcgta   3240
atctgctgct tgcaaacaaa aaaaccaccg ctaccagcgg tggtttgttt gccggatcaa   3300
gagctaccaa ctctttttcc gaaggtaact ggcttcagca gagcgcagat accaaatact   3360
gtccttctag tgtagccgta gttaggccac cacttcaaga actctgtagc accgcctaca   3420
tacctcgctc tgctgaagcc agttaccagt ggctgctgcc agtggcgata agtcgtgtct   3480
taccgggttg gactcaagag atagttaccg gataaggcgc agcggtcggg ctgaacgggg   3540
ggttcgtgca cacagcccag cttggagcga acgacctaca ccgaactgag atacctacag   3600
cgtgagctat gagaaagcgc cacgcttccc gaagggagaa aggcggacag gtatccggta   3660
agcggcaggg tcggaacagg agagcgcacg agggagcttc caggggggaaa cgcctggtat   3720
ctttatagtc ctgtcgggtt tcgccacctc tgacttgagc gtcgattttt gtgatgctcg   3780
tcaggggggc ggagcctatg gaaaaacgcc agcaacgcaa gctagagttt aaacttgaca   3840
gatgagacaa taaccctgat aaatgcttca ataatattga aaaaggaaaa gtatgagtat   3900
tcaacatttc cgtgtcgccc ttattccctt ttttgcggca ttttgccttc ctgtttttgc   3960
tcacccagaa acgctggtga aagtaaaaga tgcagaagat cacttgggtg cgcgagtggg   4020
ttacatcgaa ctggatctca acagcggtaa gatccttgag agttttcgcc ccgaagaacg   4080
```

tttcccaatg atgagcactt ttaaagttct gctatgtggc gcggtattat cccgtattga 4140
tgccgggcaa gagcaactcg gtcgccgcat acactattct cagaatgact tggttgaata 4200
ctcaccagtc acagaaaagc atcttacgga tggcatgaca gtaagagaat tatgcagtgc 4260
tgccataacc atgagtgata acactgcggc caacttactt ctgacaacta tcggaggacc 4320
gaaggagcta accgcttttt tgcacaacat gggggatcat gtaactcgcc ttgatcgttg 4380
ggaaccggag ctgaatgaag ccataccaaa cgacgagcgt gacaccacga tgcctgtagc 4440
aatggcaaca acgttgcgaa aactattaac tggcgaacta cttactctag cttcccggca 4500
acaactaata gactggatgg aggcggataa agttgcagga ccacttctgc gctcggcact 4560
tccggctggc tggtttattg ctgataaatc aggagccggt gagcgtgggt cacgcggtat 4620
cattgcagca ctggggccgg atggtaagcc ctcccgtatc gtagttatct acactacggg 4680
gagtcaggca actatggatg aacgaaatag acagatcgct gagataggtg cctcactgat 4740
taagcattgg taaggataaa tttctggtaa ggaggacacg tatggaagtg ggcaagttgg 4800
ggaagccgta tccgttgctg aatctggcat atgtgggagt ataagacgcg cagcgtcgca 4860
tcaggcattt ttttctgcgc caatgcaaaa aggccatccg tcaggatggc ctttcggcat 4920
aactagtccc 4930

<210> SEQ ID NO 517
<211> LENGTH: 5216
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 517
aagcttgata tcttatgaca acttgacggc tacatcattc actttttctt cacaaccggc 60
acggaactcg ctcgggctgg ccccggtgca ttttttaaat acccgcgaga aatagagttg 120
atcgtcaaaa ccaacattgc gaccgacggt ggcgataggc atccgggtgg tgctcaaaag 180
cagcttcgcc tggctgatac gttggtcctc gcgccagctt aagacgctaa tccctaactg 240
ctggcggaaa agatgtgaca gacgcgacgg cgacaagcaa acatgctgtg cgacgctggc 300
gatatcaaaa ttgctgtctg ccaggtgatc gctgatgtac tgacaagcct cgcgtacccg 360
attatccatc ggtggatgga gcgactcgtt aatcgcttcc atgcgccgca gtaacaattg 420
ctcaagcaga tttatcgcca gcagctccga atagcgccct tccccttgcc cggcgttaat 480
gatttgccca aacaggtcgc tgaaatgcgg ctggtgcgct tcatccgggc gaaagaaccc 540
cgtattggca aatattgacg gccagttaag ccattcatgc cagtaggcgc gcggacgaaa 600
gtaaacccac tggtgatacc attcgcgagc ctccggatga cgaccgtagt gatgaatctc 660
tcctggcggg aacagcaaaa tatcacccgg tcggcaaaca aattctcgtc cctgattttt 720
caccaccccc tgaccgcgaa tggtgagatt gagaatataa cctttcattc ccagcggtcg 780
gtcgataaaa aaatcgagat aaccgttggc ctcaatcggc gttaaacccg ccaccagatg 840
ggcattaaac gagtatcccg gcagcagggg atcattttgc gcttcagcca tacttttcat 900
actcccgcca ttcagagaag aaaccaattg tccatattgc atcagacatt gccgtcactg 960
cgtcttttac tggctcttct cgctaaccaa accggtaacc ccgcttatta aaagcattct 1020
gtaacaaagc gggaccaaag ccatgacaaa aacgcgtaac aaaagtgtct ataatcacgg 1080
cagaaaagtc cacattgatt atttgcacgg cgtcacactt tgctatgcca tagcattttt 1140

-continued

```
atccataaga ttagcggatc ctacctgacg ctttttatcg caactctcta ctgtttctcc   1200
atacccgttt ttttgggcta acaggaggaa ttaatcatga tgaagcgcaa tattctggca   1260
gtgatcgtcc ctgctctgtt agtagcaggt actgcaaacg ctgcaggtac catccctgag   1320
atcatcatca aggtccgcgg cactcaggtc gtgggttctg acatgactgt gatcgtggag   1380
tttaccaatc ctctgaaaga aaccctgcgc aatgtctggg tgcacctgga tggtcctgga   1440
gtcacacgcc caatgaagaa gatgttccgc gaaatccgcc caaactccac cgtgcagtgg   1500
gaagaagtgg tccgcccatg ggtctctggg catcgcaagc tgatcgccag catgagcagt   1560
gactccctgc gccatgtgta tggcgagctg gacgtgcaga ttcaacgccg cgcggccgca   1620
ggctctaaag atatcagaac tgttgaaagt tgtttagcaa aaccccatac agaaaattca   1680
tttactaacg tctggaaaga cgacaaaact ttagatcgtt acgctaacta tgagggttgt   1740
ctgtggaatg ctacaggcgt tgtagtttgt actggtgacg aaactcagtg ttacggtaca   1800
tgggttccta ttgggcttgc tatccctgaa aatgagggtg gtggctctga gggtggcggt   1860
tctgagggtg gcggttctga gggtggcggt actaaacctc ctgagtacgg tgatacacct   1920
attccgggct atacttatat caaccctctc gacggcactt atccgcctgg tactgagcaa   1980
aaccccgcta atcctaatcc ttctcttgag gagtctcagc ctcttaatac tttcatgttt   2040
cagaataata ggttccgaaa taggcagggg gcattaactg tttatacggg cactgttact   2100
caaggcactg accccgttaa aacttattac cagtacactc ctgtatcatc aaaagccatg   2160
tatgacgctt actggaacgg taaattcaga gactgcgctt tccattctgg ctttaatgag   2220
gatccattcg tttgtgaata tcaaggccaa tcgtctgacc tgcctcaacc tcctgtcaat   2280
gctggcggcg gctctggtgg tggttctggt ggcggctctg agggtggtgg ctctgagggt   2340
ggcggttctg agggtggcgg ctctgaggga ggcggttccg gtggtggctc tggttccggt   2400
gattttgatt atgaaaagat ggcaaacgct aataaggggg ctatgaccga aaatgccgat   2460
gaaaacgcgc tacagtctga cgctaaaggc aaacttgatt ctgtcgctac tgattacggt   2520
gctgctatcg atggtttcat tggtgacgtt tccggccttg ctaatggtaa tggtgctact   2580
ggtgattttg ctggctctaa ttcccaaatg gctcaagtcg gtgacggtga taattcacct   2640
ttaatgaata atttccgtca atatttacct tccctccctc aatcggttga atgtcgccct   2700
tttgtcttta gcgctggtaa accatatgaa ttttctattg attgtgacaa aataaactta   2760
ttccgtggtg tctttgcgtt tcttttatat gttgccacct ttatgtatgt attttctacg   2820
tttgctaaca tactgcgtaa taaggagtct taataagaat tcctcaggaa ccatagtacg   2880
cgccctgtag cggcgcatta agcgcggcgg gtgtggtggt tacgcgcagc gtgaccgcta   2940
cacttgccag cgccctagcg cccgctcctt tcgctttctt cccttccttt ctcgccacgt   3000
tcgccggctt tccccgtcaa gctctaaatc gggggctccc tttagggttc cgatttagtg   3060
ctttacggca cctcgacccc aaaaaacttg atttgggtga tggttcacgt agtgggccat   3120
cgccctgata gacggttttt cgccctttga cgttggagtc cacgttcttt aatagtggac   3180
tcttgttcca aactggaaca acactcaacc ctatctcggg ctattctttt gatttataag   3240
ggattttgcc gatttcggcc tattggttaa aaaatgagct gatttaacaa aaatttaacg   3300
cgaattttaa caaaatatta acgtttacaa tttaaatatt tgcttataca atctccgccc   3360
atcccgcccc taactccgcc cagttccgcc cattctccgc ctcatggctg actaattttt   3420
tttatttatg cagaggccga ggccgcctcg gcctctgagc tattccagaa gtagtgagga   3480
ggcttttttg gaggcctagg cttttgcaaa aagctaattc ggcgtaatct gctgcttgca   3540
```

aacaaaaaaa ccaccgctac cagcggtggt ttgtttgccg gatcaagagc taccaactct 3600
ttttccgaag gtaactggct tcagcagagc gcagatacca aatactgtcc ttctagtgta 3660
gccgtagtta ggccaccact tcaagaactc tgtagcaccg cctacatacc tcgctctgct 3720
gaagccagtt accagtggct gctgccagtg gcgataagtc gtgtcttacc gggttggact 3780
caagagatag ttaccggata aggcgcagcg gtcgggctga acggggggtt cgtgcacaca 3840
gcccagcttg gagcgaacga cctacaccga actgagatac ctacagcgtg agctatgaga 3900
aagcgccacg cttcccgaag ggagaaaggc ggacaggtat ccggtaagcg gcagggtcgg 3960
aacaggagag cgcacgaggg agcttccagg gggaaacgcc tggtatcttt atagtcctgt 4020
cgggtttcgc cacctctgac ttgagcgtcg atttttgtga tgctcgtcag gggggcggag 4080
cctatggaaa aacgccagca acgcaagcta gagtttaaac ttgacagatg agacaataac 4140
cctgataaat gcttcaataa tattgaaaaa ggaaaagtat gagtattcaa catttccgtg 4200
tcgcccttat tccctttttt gcggcatttt gccttcctgt ttttgctcac ccagaaacgc 4260
tggtgaaagt aaaagatgca gaagatcact tgggtgcgcg agtgggttac atcgaactgg 4320
atctcaacag cggtaagatc cttgagagtt ttcgccccga agaacgtttc ccaatgatga 4380
gcacttttaa agttctgcta tgtggcgcgg tattatcccg tattgatgcc gggcaagagc 4440
aactcggtcg ccgcatacac tattctcaga atgacttggt tgaatactca ccagtcacag 4500
aaaagcatct tacggatggc atgacagtaa gagaattatg cagtgctgcc ataaccatga 4560
gtgataacac tgcggccaac ttacttctga caactatcgg aggaccgaag gagctaaccg 4620 ctttttgca caacatgggg gatcatgtaa ctcgccttga tcgttgggaa ccggagctga 4680
atgaagccat accaaacgac gagcgtgaca ccacgatgcc tgtagcaatg gcaacaacgt 4740
tgcgaaaact attaactggc gaactactta ctctagcttc ccggcaacaa ctaatagact 4800
ggatggaggc ggataaagtt gcaggaccac ttctgcgctc ggcacttccg gctggctggt 4860
ttattgctga taaatcagga gccggtgagc gtgggtcacg cggtatcatt gcagcactgg 4920
ggccggatgg taagccctcc cgtatcgtag ttatctacac tacggggagt caggcaacta 4980
tggatgaacg aaatagacag atcgctgaga taggtgcctc actgattaag cattggtaag 5040
gataaatttc tggtaaggag gacacgtatg gaagtgggca agttggggaa gccgtatccg 5100
ttgctgaatc tggcatatgt gggagtataa gacgcgcagc gtcgcatcag gcattttttt 5160
ctgcgccaat gcaaaaaggc catccgtcag gatggccttt cggcataact agtccc 5216

<210> SEQ ID NO 518
<211> LENGTH: 5565
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 518
atccggatat agttcctcct ttcagcaaaa aacccctcaa gacccgttta gaggccccaa 60
ggggttatgc tagttattgc tcagcggtgg cagcagccaa ctcagcttcc tttcgggctt 120
tgttagcagc cggatctcag tggtggtggt ggtggtgctc gagctcatta atgatggtga 180
tggtgatgtc gtctttgaat ctgcacgtcc agctcgccat acacatgtct cagggagtca 240
ctgctcatgc tggctatcag cttccgatgc ccagagaccc agggccggca cacttcttcc 300
cactgcacgg tggagttggg ccggatttca cggaacatct tcttcattgg tcttgttact 360

```
ccaggaccat ccaggtgtac ccagacattt cgcagggttt cttttaaagg attggtaaac    420
tcaactatca cagtcatgtc agaaccaact acctgagtgc cacggacctt gatgatgatc    480
tcagggatgg tcatatgtat atctccttct taaagttaaa caaaattatt tctagagggg    540
aattgttatc cgctcacaat tcccctatag tgagtcgtat taatttcgcg ggatcgagat    600
ctcgatcctc tacgccggac gcatcgtggc cggcatcacc ggcgccacag gtgcggttgc    660
tggcgcctat atcgccgaca tcaccgatgg ggaagatcgg gctcgccact tcgggctcat    720
gagcgcttgt ttcggcgtgg gtatggtggc aggccccgtg gccgggggac tgttgggcgc    780
catctccttg catgcaccat tccttgcggc ggcggtgctc aacggcctca acctactact    840
gggctgcttc ctaatgcagg agtcgcataa gggagagcgt cgagatcccg gacaccatcg    900
aatggcgcaa aacctttcgc ggtatggcat gatagcgccc ggaagagagt caattcaggg    960
tggtgaatgt gaaaccagta acgttatacg atgtcgcaga gtatgccggt gtctcttatc   1020
agaccgtttc ccgcgtggtg aaccaggcca gccacgtttc tgcgaaaacg cgggaaaaag   1080
tggaagcggc gatggcggag ctgaattaca ttcccaaccg cgtggcacaa caactggcgg   1140
gcaaacagtc gttgctgatt ggcgttgcca cctccagtct ggccctgcac gcgccgtcgc   1200
aaattgtcgc ggcgattaaa tctcgcgccg atcaactggg tgccagcgtg gtggtgtcga   1260
tggtagaacg aagcggcgtc gaagcctgta aagcggcggt gcacaatctt ctcgcgcaac   1320
gcgtcagtgg gctgatcatt aactatccgc tggatgacca ggatgccatt gctgtggaag   1380
ctgcctgcac taatgttccg gcgttatttc ttgatgtctc tgaccagaca cccatcaaca   1440
gtattatttt ctcccatgaa gacggtacgc gactgggcgt ggagcatctg gtcgcattgg   1500
gtcaccagca aatcgcgctg ttagcgggcc cattaagttc tgtctcggcg cgtctgcgtc   1560
tggctggctg gcataaatat ctcactcgca atcaaattca gccgatagcg gaacgggaag   1620
gcgactggag tgccatgtcc ggttttcaac aaaccatgca aatgctgaat gagggcatcg   1680
ttcccactgc gatgctggtt gccaacgatc agatggcgct gggcgcaatg cgcgccatta   1740
ccgagtccgg gctgcgcgtt ggtgcggata tctcggtagt gggatacgac gataccgaag   1800
acagctcatg ttatatcccg ccgttaacca ccatcaaaca ggattttcgc ctgctggggc   1860
aaaccagcgt ggaccgcttg ctgcaactct ctcagggcca ggcggtgaag ggcaatcagc   1920
tgttgcccgt ctcactggtg aaaagaaaaa ccaccctggc gcccaatacg caaaccgcct   1980
ctccccgcgc gttggccgat tcattaatgc agctggcacg acaggtttcc cgactggaaa   2040
gcgggcagtg agcgcaacgc aattaatgta agttagctca ctcattaggc accgggatct   2100
cgaccgatgc ccttgagagc cttcaaccca gtcagctcct tccggtgggc gcggggcatg   2160
actatcgtcg ccgcacttat gactgtcttc tttatcatgc aactcgtagg acaggtgccg   2220
gcagcgctct gggtcatttt cggcgaggac cgctttcgct ggagcgcgac gatgatcggc   2280
ctgtcgcttg cggtattcgg aatcttgcac gccctcgctc aagccttcgt cactggtccc   2340
gccaccaaac gtttcggcga gaagcaggcc attatcgccg gcatggcggc cccacgggtg   2400
cgcatgatcg tgctcctgtc gttgaggacc cggctaggct ggcggggttg ccttactggt   2460
tagcagaatg aatcaccgat acgcgagcga acgtgaagcg actgctgctg caaaacgtct   2520
gcgacctgag caacaacatg aatggtcttc ggtttccgtg tttcgtaaag tctggaaacg   2580
cggaagtcag cgccctgcac cattatgttc cggatctgca tcgcaggatg ctgctggcta   2640
ccctgtggaa cacctacatc tgtattaacg aagcgctggc attgaccctg agtgattttt   2700
```

-continued

```
ctctggtccc gccgcatcca taccgccagt tgtttaccct cacaacgttc cagtaaccgg   2760
gcatgttcat catcagtaac ccgtatcgtg agcatcctct ctcgtttcat cggtatcatt   2820
acccccatga acagaaatcc cccttacacg gaggcatcag tgaccaaaca ggaaaaaacc   2880
gcccttaaca tggcccgctt tatcagaagc cagacattaa cgcttctgga gaaactcaac   2940
gagctggacg cggatgaaca ggcagacatc tgtgaatcgc ttcacgacca cgctgatgag   3000
ctttaccgca gctgcctcgc gcgtttcggt gatgacggtg aaaacctctg acacatgcag   3060
ctcccggaga cggtcacagc ttgtctgtaa gcggatgccg ggagcagaca agcccgtcag   3120
ggcgcgtcag cgggtgttgg cgggtgtcgg ggcgcagcca tgacccagtc acgtagcgat   3180
agcggagtgt atactggctt aactatgcgg catcagagca gattgtactg agagtgcacc   3240
atatatgcgg tgtgaaatac cgcacagatg cgtaaggaga aaataccgca tcaggcgctc   3300
ttccgcttcc tcgctcactg actcgctgcg ctcggtcgtt cggctgcggc gagcggtatc   3360
agctcactca aaggcggtaa tacggttatc cacagaatca ggggataacg caggaaagaa   3420
catgtgagca aaaggccagc aaaaggccag gaaccgtaaa aaggccgcgt tgctggcgtt   3480
tttccatagg ctccgccccc ctgacgagca tcacaaaaat cgacgctcaa gtcagaggtg   3540
gcgaaacccg acaggactat aaagatacca ggcgtttccc cctggaagct ccctcgtgcg   3600
ctctcctgtt ccgaccctgc cgcttaccgg atacctgtcc gcctttctcc cttcgggaag   3660
cgtggcgctt tctcatagct cacgctgtag gtatctcagt tcggtgtagg tcgttcgctc   3720
caagctgggc tgtgtgcacg aaccccccgt tcagcccgac cgctgcgcct tatccggtaa   3780
ctatcgtctt gagtccaacc cggtaagaca cgacttatcg ccactggcag cagccactgg   3840
taacaggatt agcagagcga ggtatgtagg cggtgctaca gagttcttga agtggtggcc   3900
taactacggc tacactagaa ggacagtatt tggtatctgc gctctgctga agccagttac   3960
cttcggaaaa agagttggta gctcttgatc cggcaaacaa accaccgctg gtagcggtgg   4020
tttttttgtt tgcaagcagc agattacgcg cagaaaaaaa ggatctcaag aagatccttt   4080
gatcttttct acggggtctg acgctcagtg gaacgaaaac tcacgttaag ggattttggt   4140
catgaacaat aaaactgtct gcttacataa acagtaatac aaggggtgtt atgagccata   4200
ttcaacggga aacgtcttgc tctaggccgc gattaaattc caacatggat gctgatttat   4260
atgggtataa atgggctcgc gataatgtcg ggcaatcagg tgcgacaatc tatcgattgt   4320
atgggaagcc cgatgcgcca gagttgtttc tgaaacatgg caaaggtagc gttgccaatg   4380
atgttacaga tgagatggtc agactaaact ggctgacgga atttatgcct cttccgacca   4440
tcaagcattt tatccgtact cctgatgatg catggttact caccactgcg atccccggga   4500
aaacagcatt ccaggtatta gaagaatatc ctgattcagg tgaaaatatt gttgatgcgc   4560
tggcagtgtt cctgcgccgg ttgcattcga ttcctgtttg taattgtcct tttaacagcg   4620
atcgcgtatt tcgtctcgct caggcgcaat cacgaatgaa taacggtttg gttgatgcga   4680
gtgattttga tgacgagcgt aatggctggc ctgttgaaca agtctggaaa gaaatgcata   4740
aacttttgcc attctcaccg gattcagtcg tcactcatgg tgatttctca cttgataacc   4800
ttatttttga cgaggggaaa ttaataggtt gtattgatgt tggacgagtc ggaatcgcag   4860
accgatacca ggatcttgcc atcctatgga actgcctcgg tgagttttct ccttcattac   4920
agaaacggct ttttcaaaaa tatggtattg ataatcctga tatgaataaa ttgcagtttc   4980
atttgatgct cgatgagttt ttctaagaat taattcatga gcggatacat atttgaatgt   5040
atttagaaaa ataaacaaat aggggttccg cgcacatttc cccgaaaagt gccacctgaa   5100
```

attgtaaacg ttaatatttt gttaaaattc gcgttaaatt tttgttaaat cagctcattt 5160
tttaaccaat aggccgaaat cggcaaaatc ccttataaat caaaagaata gaccgagata 5220
gggttgagtg ttgttccagt ttggaacaag agtccactat taaagaacgt ggactccaac 5280
gtcaaagggc gaaaaaccgt ctatcagggc gatggcccac tacgtgaacc atcaccctaa 5340
tcaagttttt tggggtcgag gtgccgtaaa gcactaaatc ggaaccctaa agggagcccc 5400
cgatttagag cttgacgggg aaagccggcg aacgtggcga gaaaggaagg gaagaaagcg 5460
aaaggagcgg gcgctagggc gctggcaagt gtagcggtca cgctgcgcgt aaccaccaca 5520
cccgccgcgc ttaatgcgcc gctacagggc gcgtcccatt cgcca 5565

<210> SEQ ID NO 519
<211> LENGTH: 4111
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 519
agcgcccaat acgcaaaccg cctctccccg cgcgttggcc gattcattaa tgcagctggc 60
acgacaggtt tcccgactgg aaagcgggca gtgagcgcaa cgcaattaat gtgagttagc 120
tcactcatta ggcaccccag gctttacact ttatgcttcc ggctcgtatg ttgtgtggaa 180
ttgtgagcgg ataacaattt cacacaggaa acagctatga ccatgattac gccaagcttt 240
ggagcctttt ttttggagat tttcaacgtg aaaaaattat tattcgcaat tcctttagtt 300
gttcctttct attctcactc ggccgacgtg gccgtcttca ccatccctga gatcatcatc 360
aaggtccgtg gcactcaggt agttggttct gacatgactg tgatagttga gtttaccaat 420
cctttaaaag aaaccctgcg aaatgtctgg gtacacctgg atggtcctgg agtaacaaga 480
ccaatgaaga agatgttccg tgaaatccgg cccaactcca ccgtgcagtg ggaagaagtg 540
tgccggccct gggtctctgg gcatcggaag ctgatagcca gcatgagcag tgactccctg 600
agacatgtgt atggcgagct ggacgtgcag attgaagacc aacgccgcgc ggccgcacat 660
catcatcacc atcacgcgtc tggggccgca gaacaaaaac tcatctcaga agaggatctg 720
aatggggcag cagaagctag ttctgctagt gcctctggtt ccggtgattt tgattatgaa 780
aagatggcaa acgctaataa gggggctatg accgaaaatg ccgatgaaaa cgcgctacag 840
tctgacgcta aaggcaaact tgattctgtc gctactgatt acggtgctgc tatcgatggt 900
ttcattggtg acgtttccgg ccttgctaat ggtaatggtg ctactggtga ttttgctggc 960
tctaattccc aaatggctca agtcggtgac ggtgataatt cacctttaat gaataatttc 1020
cgtcaatatt taccttccct ccctcaatcg gttgaatgtc gcccttttgt ctttagcgct 1080
ggtaaaccat atgaattttc tattgattgt gacaaaataa acttattccg tggtgtcttt 1140
gcgtttcttt tatatgttgc cacctttatg tatgtatttt ctacgtttgc taacatactg 1200
cgtaataagg agtcttaatg aaacgcgtga tgagaattca ctggccgtcg ttttacaacg 1260
tcgtgactgg gaaaaccctg gcgttaccca acttaatcgc cttgcagcac atcccccttt 1320
cgccagctgg cgtaatagcg aagaggcccg caccgatcgc ccttcccaac agttgcgcag 1380
cctgaatggc gaatggcgcc tgatgcggta ttttctcctt acgcatctgt gcggtatttc 1440
acaccgcata cgtcaaagca accatagtac gcgccctgta gcggcgcatt aagcgcggcg 1500
ggtgtggtgg ttacgcgcag cgtgaccgct acacttgcca gcgccctagc gcccgctcct 1560

-continued ttcgctttct tcccttcctt tctcgccacg ttcgccggct ttccccgtca agctctaaat 1620
cgggggctcc ctttagggtt ccgatttagt gctttacggc acctcgaccc caaaaaactt 1680
gatttgggtg atggttcacg tagtgggcca tcgccctgat agacggtttt tcgccctttg 1740
acgttggagt ccacgttctt taatagtgga ctcttgttcc aaactggaac aacactcaac 1800
cctatctcgg gctattcttt tgatttataa gggattttgc cgatttcggc ctattggtta 1860
aaaaatgagc tgatttaaca aaaatttaac gcgaatttta acaaaatatt aacgtttaca 1920
attttatggt gcactctcag tacaatctgc tctgatgccg catagttaag ccagccccga 1980
cacccgccaa cacccgctga cgcgccctga cgggcttgtc tgctcccggc atccgcttac 2040
agacaagctg tgaccgtctc cgggagctgc atgtgtcaga ggttttcacc gtcatcaccg 2100
aaacgcgcga gacgaaaggg cctcgtgata cgcctatttt tataggttaa tgtcatgata 2160
ataatggttt cttagacgtc aggtggcact tttcggggaa atgtgcgcgg aacccctatt 2220
tgtttatttt tctaaataca ttcaaatatg tatccgctca tgagacaata accctgataa 2280
atgcttcaat aatattgaaa aaggaagagt atgagtattc aacatttccg tgtcgccctt 2340
attccctttt ttgcggcatt ttgccttcct gtttttgctc acccagaaac gctggtgaaa 2400
gtaaaagatg ctgaagatca gttgggtgca cgagtgggtt acatcgaact ggatctcaac 2460
agcggtaaga tccttgagag ttttcgcccc gaagaacgtt ttccaatgat gagcactttt 2520
aaagttctgc tatgtggcgc ggtattatcc cgtattgacg ccgggcaaga gcaactcggt 2580
cgccgcatac actattctca gaatgacttg gttgagtact caccagtcac agaaaagcat 2640
cttacggatg gcatgacagt aagagaatta tgcagtgctg ccataaccat gagtgataac 2700
actgcggcca acttacttct gacaacgatc ggaggaccga aggagctaac cgcttttttg 2760
cacaacatgg gggatcatgt aactcgcctt gatcgttggg aaccggagct gaatgaagcc 2820
ataccaaacg acgagcgtga caccacgatg cctgtagcaa tggcaacaac gttgcgcaaa 2880
ctattaactg gcgaactact tactctagct tcccggcaac aattaataga ctggatggag 2940
gcggataaag ttgcaggacc acttctgcgc tcggcccttc cggctggctg gtttattgct 3000
gataaatctg gagccggtga gcgtgggtct cgcggtatca ttgcagcact ggggccagat 3060
ggtaagccct cccgtatcgt agttatctac acgacgggga gtcaggcaac tatggatgaa 3120
cgaaatagac agatcgctga gataggtgcc tcactgatta agcattggta actgtcagac 3180
caagtttact catatatact ttagattgat ttaaaacttc atttttaatt taaaaggatc 3240
taggtgaaga tcctttttga taatctcatg accaaaatcc cttaacgtga gttttcgttc 3300
cactgagcgt cagaccccgt agaaaagatc aaaggatctt cttgagatcc tttttttctg 3360
cgcgtaatct gctgcttgca aacaaaaaaa ccaccgctac cagcggtggt ttgtttgccg 3420
gatcaagagc taccaactct ttttccgaag gtaactggct tcagcagagc gcagatacca 3480
aatactgtcc ttctagtgta gccgtagtta ggccaccact tcaagaactc tgtagcaccg 3540
cctacatacc tcgctctgct aatcctgtta ccagtggctg ctgccagtgg cgataagtcg 3600
tgtcttaccg ggttggactc aagacgatag ttaccggata aggcgcagcg gtcgggctga 3660
acggggggtt cgtgcacaca gcccagcttg gagcgaacga cctacaccga actgagatac 3720
ctacagcgtg agctatgaga aagcgccacg cttcccgaag ggagaaaggc ggacaggtat 3780
ccggtaagcg gcagggtcgg aacaggagag cgcacgaggg agcttccagg gggaaacgcc 3840
tggtatcttt atagtcctgt cgggtttcgc cacctctgac ttgagcgtcg atttttgtga 3900

```
tgctcgtcag gggggcggag cctatggaaa aacgccagca acgcggcctt tttacggttc   3960

ctggcctttt gctggccttt tgctcacatg ttctttcctg cgttatcccc tgattctgtg   4020

gataaccgta ttaccgcctt tgagtgagct gataccgctc gccgcagccg aacgaccgag   4080

cgcagcgagt cagtgagcga ggaagcggaa g                                  4111
```

<210> SEQ ID NO 520
<211> LENGTH: 4099
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 520

```
agcgcccaat acgcaaaccg cctctccccg cgcgttggcc gattcattaa tgcagctggc     60

acgacaggtt tcccgactgg aaagcgggca gtgagcgcaa cgcaattaat gtgagttagc    120

tcactcatta ggcaccccag gctttacact ttatgcttcc ggctcgtatg ttgtgtggaa    180

ttgtgagcgg ataacaattt cacacaggaa acagctatga ccatgattac gccaagcttt    240

ggagcctttt ttttggagat tttcaacgtg aaaaaattat tattcgcaat tcctttagtt    300

gttcctttct attctcactc ggccgacgtg gccaccatcc ctgagatcat catcaaggtc    360

cgcgggaccc aggtcgtggg ttctgacatg actgtgatcg tggagtttac caatcctctg    420

taagaaaccc tgcgcaatgt ctgggtgcac ctggacggtc cgggggtgac ccgcccaatg    480

aagaagatgt tccgcgaaat ccgcccaaac taaaccgtgc agtgggaaga agtggtccgc    540

ccatgggtct ctggtcaccg caagctgatc gccagcatga gcagtgacta actgcgccat    600

gtgtatggcg agctggacgt gcagattcaa cgccgcgcgg ccgcacatca tcatcaccat    660

cacgcgtctg ggccgcagaa acaaaaactc atctcagaag aggatctgaa tggggcagca    720

gaagctagtt ctgctagtgc ctctggttcc ggtgattttg attatgaaaa gatggcaaac    780

gctaataagg gggctatgac cgaaaatgcc gatgaaaacg cgctacagtc tgacgctaaa    840

ggcaaacttg attctgtcgc tactgattac ggtgctgcta tcgatggttt cattggtgac    900

gtttccggcc ttgctaatgg taatggtgct actggtgatt ttgctggctc taattcccaa    960

atggctcaag tcggtgacgg tgataattca cctttaatga ataatttccg tcaatattta   1020

ccttccctcc ctcaatcggt tgaatgtcgc ccttttgtct ttagcgctgg taaaccatat   1080

gaattttcta ttgattgtga caaaataaac ttattccgtg gtgtctttgc gtttctttta   1140

tatgttgcca cctttatgta tgtattttct acgtttgcta acatactgcg taataaggag   1200

tcttaatgaa acgcgtgatg agaattcact ggccgtcgtt ttacaacgtc gtgactggga   1260

aaaccctggc gttacccaac ttaatcgcct tgcagcacat ccccctttcg ccagctggcg   1320

taatagcgaa gaggcccgca ccgatcgccc ttcccaacag ttgcgcagcc tgaatggcga   1380

atggcgcctg atgcggtatt ttctccttac gcatctgtgc ggtatttcac accgcataaa   1440

attgtaaacg ttaatatttt gttaaaattc gcgttaaatt tttgttaaat cagctcattt   1500

tttaaccaat aggccgaaat cggcaaaatc ccttataaat caaaagaata gcccgagata   1560

gggttgagtg ttgttccagt ttggaacaag agtccactat taaagaacgt ggactccaac   1620

gtcaaagggc gaaaaaccgt ctatcagggc gatggcccac tacgtgaacc atcacccaaa   1680

tcaagttttt tggggtcgag gtgccgtaaa gcactaaatc ggaaccctaa agggagcccc   1740

cgatttagag cttgacgggg aaagccggcg aacgtggcga gaaaggaagg gaagaaagcg   1800
```

-continued

```
aaaggagcgg gcgctagggc gctggcaagt gtagcggtca cgctgcgcgt aaccaccaca   1860
cccgccgcgc ttaatgcgcc gctacagggc gcgtactatg gttgctttga cgtatggtgc   1920
actctcagta caatctgctc tgatgccgca tagttaagcc agccccgaca cccgccaaca   1980
cccgctgacg cgccctgacg ggcttgtctg ctcccggcat ccgcttacag acaagctgtg   2040
accgtctccg ggagctgcat gtgtcagagg ttttcaccgt catcaccgaa acgcgcgaga   2100
cgaaagggcc tcgtgatacg cctattttta taggttaatg tcatgataat aatggtttct   2160
tagacgtcag gtggcacttt tcggggaaat gtgcgcggaa cccctatttg tttatttttc   2220
taaatacatt caaatatgta tccgctcatg agacaataac cctgataaat gcttcaataa   2280
tattgaaaaa ggaagagtat gagtattcaa catttccgtg tcgcccttat tccctttttt   2340
gcggcatttt gccttcctgt ttttgctcac ccagaaacgc tggtgaaagt aaaagatgct   2400
gaagatcagt tgggtgcacg agtgggttac atcgaactgg atctcaacag cggtaagatc   2460
cttgagagtt ttcgccccga agaacgtttt ccaatgatga gcacttttaa agttctgcta   2520
tgtggcgcgg tattatcccg tattgacgcc gggcaagagc aactcggtcg ccgcatacac   2580
tattctcaga atgacttggt tgagtactca ccagtcacag aaaagcatct tacggatggc   2640
atgacagtaa gagaattatg cagtgctgcc ataaccatga gtgataacac tgcggccaac   2700
ttacttctga caacgatcgg aggaccgaag gagctaaccg cttttttgca caacatgggg   2760
gatcatgtaa ctcgccttga tcgttgggaa ccggagctga atgaagccat accaaacgac   2820
gagcgtgaca ccacgatgcc tgtagcaatg gcaacaacgt tgcgcaaact attaactggc   2880
gaactactta ctctagcttc ccggcaacaa ttaatagact ggatggaggc ggataaagtt   2940
gcaggaccac ttctgcgctc ggcccttccg gctggctggt ttattgctga taaatctgga   3000
gccggtgagc gtgggtctcg cggtatcatt gcagcactgg ggccagatgg taagccctcc   3060
cgtatcgtag ttatctacac gacggggagt caggcaacta tggatgaacg aaatagacag   3120
atcgctgaga taggtgcctc actgattaag cattggtaac tgtcagacca agtttactca   3180
tatatacttt agattgattt aaaacttcat ttttaattta aaaggatcta ggtgaagatc   3240
ctttttgata atctcatgac caaaatccct taacgtgagt tttcgttcca ctgagcgtca   3300
gaccccgtag aaaagatcaa aggatcttct tgagatcctt tttttctgcg cgtaatctgc   3360
tgcttgcaaa caaaaaaacc accgctacca gcggtggttt gtttgccgga tcaagagcta   3420
ccaactcttt ttccgaaggt aactggcttc agcagagcgc agataccaaa tactgtcctt   3480
ctagtgtagc cgtagttagg ccaccacttc aagaactctg tagcaccgcc tacatacctc   3540
gctctgctaa tcctgttacc agtggctgct gccagtggcg ataagtcgtg tcttaccggg   3600
ttggactcaa gacgatagtt accggataag gcgcagcggt cgggctgaac ggggggttcg   3660
tgcacacagc ccagcttgga gcgaacgacc tacaccgaac tgagatacct acagcgtgag   3720
ctatgagaaa gcgccacgct tcccgaaggg agaaaggcgg acaggtatcc ggtaagcggc   3780
agggtcggaa caggagagcg cacgagggag cttccagggg gaaacgcctg gtatctttat   3840
agtcctgtcg ggtttcgcca cctctgactt gagcgtcgat ttttgtgatg ctcgtcaggg   3900
gggcggagcc tatggaaaaa cgccagcaac gcggcctttt tacggttcct ggccttttgc   3960
tggccttttg ctcacatgtt ctttcctgcg ttatcccctg attctgtgga taaccgtatt   4020
accgcctttg agtgagctga taccgctcgc cgcagccgaa cgaccgagcg cagcgagtca   4080
gtgagcgagg aagcggaag                                                 4099
```

<210> SEQ ID NO 521
<211> LENGTH: 19
<212> TYPE: PRT
<213> ORGANISM: Homo sapiens

<400> SEQUENCE: 521

Pro Asn Thr Pro Phe Ala Ala Thr Ser Ser Met Gly Leu Glu Thr Glu
1 5 10 15

Glu Gln Glu

<210> SEQ ID NO 522
<211> LENGTH: 105
<212> TYPE: PRT
<213> ORGANISM: Homo sapiens

<400> SEQUENCE: 522

Val Asp Met Asp Phe Glu Val Glu Asn Ala Val Leu Gly Lys Asp Phe
1 5 10 15

Lys Leu Ser Ile Thr Phe Arg Asn Asn Ser His Asn Arg Tyr Thr Ile
20 25 30

Thr Ala Tyr Leu Ser Ala Asn Ile Thr Phe Tyr Thr Gly Val Pro Lys
35 40 45

Ala Glu Phe Lys Lys Glu Thr Phe Asp Val Thr Leu Glu Pro Leu Ser
50 55 60

Phe Lys Lys Glu Ala Val Leu Ile Gln Ala Gly Glu Tyr Met Gly Gln
65 70 75 80

Leu Leu Glu Gln Ala Ser Leu His Phe Phe Val Thr Ala Arg Ile Asn
85 90 95

Glu Thr Arg Asp Val Leu Ala Lys Gln
100 105

<210> SEQ ID NO 523
<211> LENGTH: 107
<212> TYPE: PRT
<213> ORGANISM: Drosophila melanogaster

<400> SEQUENCE: 523

Ile Glu Phe Asp Met Glu Leu Lys Asp Asp Ile Lys Ile Gly Gln Ser
1 5 10 15

Phe Ser Val Val Leu Lys Val Ser Asn Lys Ser Glu Ser Arg Thr His
20 25 30

Met Ala Thr Gly Gln Ile Ser Cys Asp Ala Val Leu Tyr Thr Gly Val
35 40 45

Gly Ala Val Glu Val Lys Thr Leu Gly Phe Glu Leu Glu Leu Glu Pro
50 55 60

Lys Ser Ser Asp Tyr Val Arg Met Glu Val Ile Phe Glu Glu Tyr Tyr
65 70 75 80

Asp Lys Leu Ser Ser Gln Ala Ala Phe Gln Ile Ser Ala Ala Ala Lys
85 90 95

Val Lys Asp Thr Asp Tyr Asp Tyr Tyr Ala Gln
100 105

<210> SEQ ID NO 524
<211> LENGTH: 106
<212> TYPE: PRT
<213> ORGANISM: Patiria pectinifera

<400> SEQUENCE: 524

Val Asp Phe Asp Val Asp Met Ala Glu Glu Phe Pro Ile Gly Lys Asp

-continued

```
1               5                   10                  15

Ile Lys Phe Thr Ile Thr Met Val Asn Lys Ser Gln Gln Thr Arg Asn
            20                  25                  30

Val Phe Leu Gly Val Thr Gly Ser Thr Val Tyr Tyr Thr Gly Val Lys
        35                  40                  45

Lys Ala Lys Val Ser Ser Tyr Asn Gly Thr Leu Pro Leu Lys Ala Lys
    50                  55                  60

Glu Thr Arg Val Ile Pro Val Thr Val Pro Ala Ser Asp Tyr Leu Pro
65                  70                  75                  80

Gln Leu Thr Asp Tyr Ala Gly Val Thr Phe Phe Ile Met Ala Ser Val
                85                  90                  95

Lys Glu Thr Lys Gln Pro Phe Ser Arg Gln
            100                 105


<210> SEQ ID NO 525
<211> LENGTH: 106
<212> TYPE: PRT
<213> ORGANISM: Tachypleus tridentatus

<400> SEQUENCE: 525

Val Tyr Phe Asn Leu Leu Asp Ile Glu Lys Ile Lys Ile Gly Gln Pro
1               5                   10                  15

Phe His Val Thr Val Asn Ile Glu Asn Gln Ser Ser Glu Thr Arg Arg
            20                  25                  30

Val Ser Ala Val Leu Ser Ala Ser Ser Ile Tyr Tyr Thr Gly Ile Thr
        35                  40                  45

Gly Arg Lys Ile Lys Arg Glu Asn Gly Asn Phe Ser Leu Gln Pro His
    50                  55                  60

Gln Lys Glu Val Leu Ser Ile Glu Val Thr Pro Asp Glu Tyr Leu Glu
65                  70                  75                  80

Lys Leu Val Asp Tyr Ala Met Ile Lys Leu Tyr Ala Ile Ala Thr Val
                85                  90                  95

Lys Glu Thr Gln Gln Thr Trp Ser Glu Glu
            100                 105


<210> SEQ ID NO 526
<211> LENGTH: 105
<212> TYPE: PRT
<213> ORGANISM: Homo sapiens

<400> SEQUENCE: 526

Val Ala Met Gln Val Glu Ala Gln Asp Ala Val Met Gly Gln Asp Leu
1               5                   10                  15

Met Val Ser Val Met Leu Ile Asn His Ser Ser Ser Arg Arg Thr Val
            20                  25                  30

Lys Leu His Leu Tyr Leu Ser Val Thr Phe Tyr Thr Gly Val Ser Gly
        35                  40                  45

Thr Ile Phe Lys Glu Thr Lys Lys Glu Val Glu Leu Ala Pro Gly Ala
    50                  55                  60

Ser Asp Arg Val Thr Met Pro Val Ala Tyr Lys Glu Tyr Arg Pro His
65                  70                  75                  80

Leu Val Asp Gln Gly Ala Met Leu Leu Asn Val Ser Gly His Val Lys
                85                  90                  95

Glu Ser Gly Gln Val Leu Ala Lys Gln
            100                 105
```

```
<210> SEQ ID NO 527
<211> LENGTH: 105
<212> TYPE: PRT
<213> ORGANISM: Gallus gallus

<400> SEQUENCE: 527

Ile Glu Met Asp Leu Gln Val Gln Lys Val Val Leu Gly Ser Asp Phe
1               5                   10                  15

Lys Val Thr Ile Ile Leu Arg Asn Lys Ser Arg Asn Ser Tyr Thr Ala
            20                  25                  30

Thr Thr Tyr Leu Ser Gly Asn Ile Val Phe Tyr Thr Gly Val Thr Lys
        35                  40                  45

Ser Glu Phe Lys Lys His Ser Phe Ser Ala Lys Leu Glu Pro Leu Leu
    50                  55                  60

Ser Asn Thr Phe Asp Val Met Ile Thr Ser Ala Glu Tyr Leu Asn Asp
65                  70                  75                  80

Leu Leu Asp Gln Ala Ser Phe His Phe Phe Val Thr Ala Arg Ile Asn
                85                  90                  95

Glu Thr Gly Lys Val Leu Ala Met Gln
            100                 105


<210> SEQ ID NO 528
<211> LENGTH: 105
<212> TYPE: PRT
<213> ORGANISM: Rattus norvegicus

<400> SEQUENCE: 528

Val Asp Met Asn Phe Asp Val Glu Asn Ala Val Leu Gly Lys Asp Phe
1               5                   10                  15

Arg Val Thr Ile Thr Phe Gln Asn Asn Ser Ser Asn Leu Tyr Thr Ile
            20                  25                  30

Leu Ala Tyr Leu Ser Gly Asn Ile Thr Phe Tyr Thr Gly Val Ser Lys
        35                  40                  45

Lys Glu Phe Lys Thr Glu Ser Phe Glu Val Thr Leu Asp Pro Leu Ser
    50                  55                  60

Leu Glu Lys Lys Glu Val Leu Ile Arg Ala Gly Glu Tyr Met Ser Tyr
65                  70                  75                  80

Leu Leu Glu Gln Gly Leu Leu His Phe Phe Val Thr Ala Arg Ile Asn
                85                  90                  95

Glu Thr Arg Val Val Leu Ala Lys Gln
            100                 105


<210> SEQ ID NO 529
<211> LENGTH: 107
<212> TYPE: PRT
<213> ORGANISM: Schistocerca americana

<400> SEQUENCE: 529

Ile His Phe Asn Phe Glu Leu Arg Asp Asp Ile Val Ile Gly Ser Pro
1               5                   10                  15

Phe Ser Val Val Val Val Met Lys Asn Arg Ser Asn Gln Gln Asp Tyr
            20                  25                  30

Thr Val Thr Val Leu Leu Arg Val Asp Thr Val Leu Tyr Thr Gly His
        35                  40                  45

Val Lys Asp Gly Val Lys Lys Glu Lys Val Glu Arg Leu Ile Lys Ala
    50                  55                  60

Gly Ala Val Glu Glu Val Arg Ile Asp Val Ser Tyr Glu Asp Tyr Tyr
65                  70                  75                  80
```

-continued

```
Lys His Leu Val Asp Gln Cys Ala Phe Asn Ile Ala Cys Leu Ala Thr
                85                  90                  95

Val His Asp Thr Asn Tyr Glu Tyr Phe Ala Gln
            100                 105


<210> SEQ ID NO 530
<211> LENGTH: 101
<212> TYPE: PRT
<213> ORGANISM: Gallus gallus

<400> SEQUENCE: 530

Leu His Met Arg Ile Lys Leu Ser Glu Gly Ala Asn Asn Gly Ser Asp
1               5                   10                  15

Phe Asp Val Phe Ala Phe Ile Ser Asn Asp Thr Asp Lys Glu Arg Glu
            20                  25                  30

Cys Arg Leu Arg Leu Cys Ala Arg Thr Ala Ser Tyr Asn Gly Glu Val
        35                  40                  45

Gly Pro Gln Cys Gly Phe Lys Asp Leu Leu Asn Leu Ser Leu Gln Pro
    50                  55                  60

His Met Glu Gln Ser Val Pro Leu Arg Ile Leu Tyr Glu Gln Tyr Gly
65                  70                  75                  80

Pro Asn Leu Thr Gln Asp Asn Met Ile Lys Val Val Ala Leu Leu Thr
                85                  90                  95

Glu Tyr Glu Thr Gly
            100


<210> SEQ ID NO 531
<211> LENGTH: 101
<212> TYPE: PRT
<213> ORGANISM: Homo sapiens

<400> SEQUENCE: 531

Met Ala Met Arg Ile Arg Val Gly Gln Ser Met Asn Met Gly Ser Asp
1               5                   10                  15

Phe Asp Val Phe Ala His Ile Thr Asn Asn Thr Ala Glu Glu Tyr Val
            20                  25                  30

Cys Arg Leu Leu Leu Cys Ala Arg Thr Val Ser Tyr Asn Gly Ile Leu
        35                  40                  45

Gly Pro Glu Cys Gly Thr Lys Tyr Leu Leu Asn Leu Thr Leu Glu Pro
    50                  55                  60

Phe Ser Glu Lys Ser Val Pro Leu Cys Ile Leu Tyr Glu Lys Tyr Arg
65                  70                  75                  80

Asp Cys Leu Thr Glu Ser Asn Leu Ile Lys Val Arg Ala Leu Leu Val
                85                  90                  95

Glu Pro Val Ile Asn
            100


<210> SEQ ID NO 532
<211> LENGTH: 100
<212> TYPE: PRT
<213> ORGANISM: Mus musculus

<400> SEQUENCE: 532

Val Ala Met Arg Ile Arg Val Gly Asp Ser Met Ser Met Gly Asn Asp
1               5                   10                  15

Phe Asp Val Phe Ala His Ile Gly Asn Asp Thr Ser Glu Thr Arg Glu
            20                  25                  30
```

```
Cys Arg Leu Leu Leu Cys Ala Arg Thr Val Ser Tyr Asn Gly Val Leu
        35                  40                  45

Gly Pro Glu Cys Gly Thr Glu Asp Ile Asn Leu Thr Leu Asp Pro Tyr
    50                  55                  60

Ser Glu Asn Ser Ile Pro Leu Arg Ile Leu Tyr Glu Lys Tyr Ser Gly
65                  70                  75                  80

Cys Leu Thr Glu Ser Asn Leu Ile Lys Val Arg Gly Leu Leu Ile Glu
                85                  90                  95

Pro Ala Ala Asn
            100


<210> SEQ ID NO 533
<211> LENGTH: 101
<212> TYPE: PRT
<213> ORGANISM: Cavia cutleri

<400> SEQUENCE: 533

Val Ala Met Arg Ile Arg Val Gly Gln Asn Met Thr Met Gly Ser Asp
1               5                   10                  15

Phe Asp Ile Phe Ala Tyr Ile Thr Asn Gly Thr Ala Glu Ser His Glu
            20                  25                  30

Cys Gln Leu Leu Leu Cys Ala Arg Ile Val Ser Tyr Asn Gly Val Leu
        35                  40                  45

Gly Pro Val Cys Ser Thr Asn Asp Leu Leu Asn Leu Thr Leu Asp Pro
    50                  55                  60

Phe Ser Glu Asn Ser Ile Pro Leu His Ile Leu Tyr Glu Lys Tyr Gly
65                  70                  75                  80

Asp Tyr Leu Thr Glu Ser Asn Leu Ile Lys Val Arg Gly Leu Leu Ile
                85                  90                  95

Glu Pro Ala Ala Asn
            100


<210> SEQ ID NO 534
<211> LENGTH: 101
<212> TYPE: PRT
<213> ORGANISM: Danio rerio

<400> SEQUENCE: 534

Leu Asn Ile Thr Ile Lys Leu Ser Ser Gly Val Arg Lys Gly Cys Asp
1               5                   10                  15

Phe Asp Val Phe Ala Ile Val Thr Asn Gly Thr Ala Glu Glu Lys Lys
            20                  25                  30

Cys Arg Leu Val Phe Ala Ser Arg Ala Val Ser Tyr Asn Gly Val Ile
        35                  40                  45

Gly Arg Glu Cys Gly Phe Lys Asp Leu Leu Asn Val Glu Leu Pro Pro
    50                  55                  60

Gly Gly Glu Arg Lys Val Pro Leu Arg Leu Asn Tyr Ser Lys Tyr Cys
65                  70                  75                  80

Asn Asn Leu Thr Glu Asp Asn Leu Ile Arg Leu Gly Ala Leu Leu Ile
                85                  90                  95

Asp Tyr Ser Thr Arg
            100


<210> SEQ ID NO 535
<211> LENGTH: 106
<212> TYPE: PRT
<213> ORGANISM: Homo sapiens
```

<400> SEQUENCE: 535

Ile Ile Gly Lys Leu Lys Val Ala Gly Met Leu Ala Val Gly Lys Glu
1               5                   10                  15

Val Asn Leu Val Leu Leu Leu Lys Asn Leu Ser Arg Asp Thr Lys Thr
            20                  25                  30

Val Thr Val Asn Met Thr Ala Trp Thr Ile Ile Tyr Asn Gly Thr Leu
        35                  40                  45

Val His Glu Val Trp Lys Asp Ser Ala Thr Met Ser Leu Asp Pro Glu
    50                  55                  60

Glu Glu Ala Glu His Pro Ile Lys Ile Ser Tyr Ala Gln Tyr Glu Arg
65                  70                  75                  80

Tyr Leu Lys Ser Asp Asn Met Ile Arg Ile Thr Ala Val Cys Lys Val
                85                  90                  95

Pro Asp Glu Ser Glu Val Val Val Glu Arg
            100                 105

<210> SEQ ID NO 536
<211> LENGTH: 106
<212> TYPE: PRT
<213> ORGANISM: Mus musculus

<400> SEQUENCE: 536

Ile Ser Gly Lys Phe Lys Val Thr Gly Ile Leu Ala Val Gly Lys Glu
1               5                   10                  15

Val Ser Leu Ser Leu Met Leu Lys Asn Met Thr Asn Asp Arg Lys Thr
            20                  25                  30

Val Thr Met Asn Met Thr Ala Trp Thr Ile Val Tyr Asn Gly Thr Leu
        35                  40                  45

Val His Glu Val Trp Lys Asp Ser Ala Thr Ile Ser Leu Asp Pro Glu
    50                  55                  60

Glu Glu Ile Gln Tyr Pro Val Lys Ile Ala Tyr Ser Gln Tyr Glu Arg
65                  70                  75                  80

Tyr Leu Lys Ala Asp Asn Met Ile Arg Ile Ser Ala Val Cys Lys Val
                85                  90                  95

Pro Asp Glu Ala Glu Val Val Val Glu Trp
            100                 105

<210> SEQ ID NO 537
<211> LENGTH: 106
<212> TYPE: PRT
<213> ORGANISM: Homo sapiens

<400> SEQUENCE: 537

Ile Ala Gly Lys Phe Lys Val Leu Glu Pro Pro Met Leu Gly His Asp
1               5                   10                  15

Leu Arg Leu Ala Leu Cys Leu Ala Asn Leu Thr Ser Arg Ala Gln Arg
            20                  25                  30

Val Arg Val Asn Leu Ser Gly Ala Thr Ile Leu Tyr Thr Arg Lys Pro
        35                  40                  45

Val Ala Glu Ile Leu His Glu Ser His Ala Val Arg Leu Gly Pro Gln
    50                  55                  60

Glu Glu Lys Arg Ile Pro Ile Thr Ile Ser Tyr Ser Lys Tyr Lys Glu
65                  70                  75                  80

Asp Leu Thr Glu Asp Lys Lys Ile Leu Leu Ala Ala Met Cys Leu Val
                85                  90                  95

Thr Lys Gly Glu Lys Leu Leu Val Glu Lys 100 105

<210> SEQ ID NO 538
<211> LENGTH: 100
<212> TYPE: PRT
<213> ORGANISM: Homo sapiens

<400> SEQUENCE: 538

Val Ser Leu Lys Phe Lys Leu Leu Asp Pro Pro Asn Met Gly Gln Asp
1 5 10 15

Ile Cys Phe Val Leu Leu Ala Leu Asn Met Ser Ser Gln Phe Lys Asp
20 25 30

Leu Lys Val Asn Leu Ser Ala Gln Ser Leu Leu His Asp Gly Ser Pro
35 40 45

Leu Ser Pro Phe Trp Gln Asp Thr Ala Phe Ile Thr Leu Ser Pro Lys
50 55 60

Glu Ala Lys Thr Tyr Pro Cys Lys Ile Ser Tyr Ser Gln Tyr Ser Gln
65 70 75 80

Tyr Leu Ser Thr Asp Lys Leu Ile Arg Ile Ser Ala Leu Gly Glu Glu
85 90 95

Lys Ser Ser Pro
100

<210> SEQ ID NO 539
<211> LENGTH: 106
<212> TYPE: PRT
<213> ORGANISM: Homo sapiens

<400> SEQUENCE: 539

Leu Tyr Leu Leu Leu Lys Ala Pro Ser Ser Leu Pro Leu Arg Gly Asp
1 5 10 15

Ala Gln Ile Ser Val Thr Leu Val Asn His Ser Glu Gln Glu Lys Ala
20 25 30

Val Gln Leu Ala Ile Gly Val Gln Ala Val His Tyr Asn Gly Val Leu
35 40 45

Ala Ala Lys Leu Trp Arg Lys Lys Leu His Leu Thr Leu Ser Ala Asn
50 55 60

Leu Glu Lys Ile Ile Thr Ile Gly Leu Phe Phe Ser Asn Phe Glu Arg
65 70 75 80

Asn Pro Pro Glu Asn Thr Phe Leu Arg Leu Thr Ala Met Ala Thr His
85 90 95

Ser Glu Ser Asn Leu Ser Cys Phe Ala Gln
100 105

<210> SEQ ID NO 540
<211> LENGTH: 100
<212> TYPE: PRT
<213> ORGANISM: Mus musculus

<400> SEQUENCE: 540

Leu His Met Phe Phe Glu Ala Ser Ser Ser Ile Pro Leu Ser Gly Asp
1 5 10 15

Gly Gln Leu Ser Val Thr Leu Ile Asn Pro Thr Asp Glu Glu Lys Lys
20 25 30

Val His Leu Val Ile Gly Ala Gln Ala Leu Tyr Tyr Asn Gly Val Leu
35 40 45

Ala Ala Gly Leu Trp Ser Lys Lys Gln Leu Phe Met Leu Lys Pro Asn
50 55 60

```
Gln Val Met Arg Leu Ser Thr Asn Leu Ser Phe Ser Cys Phe Glu Gln
65                  70                  75                  80

Thr Pro Pro Glu Asn Ser Phe Leu Arg Val Thr Ala Met Ala Arg Tyr
                85                  90                  95

Ser His Thr Ser
            100


<210> SEQ ID NO 541
<211> LENGTH: 107
<212> TYPE: PRT
<213> ORGANISM: Pagrus major

<400> SEQUENCE: 541

Gly Arg Leu Gln Leu Ser Ile Lys His Ala Gln Pro Val Phe Gly Thr
1               5                   10                  15

Asp Phe Asp Val Ile Val Glu Val Lys Asn Glu Gly Gly Arg Asp Ala
            20                  25                  30

His Ala Gln Leu Thr Met Leu Ala Met Ala Val Thr Tyr Asn Ser Leu
        35                  40                  45

Arg Arg Gly Glu Cys Gln Arg Lys Thr Ile Ser Val Thr Val Pro Ala
    50                  55                  60

His Lys Ala His Lys Glu Val Met Arg Leu His Tyr Asp Asp Tyr Val
65                  70                  75                  80

Arg Cys Val Ser Glu His His Leu Ile Arg Val Lys Ala Leu Leu Asp
                85                  90                  95

Ala Pro Gly Glu Asn Gly Pro Ile Met Thr Val
            100                 105


<210> SEQ ID NO 542
<211> LENGTH: 107
<212> TYPE: PRT
<213> ORGANISM: Oncorhynchus keta

<400> SEQUENCE: 542

Gly Gln Leu Glu Leu Lys Ile Lys His Ala Gln Ala Ile Leu Gly Thr
1               5                   10                  15

Asp Phe Asp Val Ile Val Glu Val His Asn Val Gly Gly Glu Asp Thr
            20                  25                  30

Pro Ala Gln Leu Thr Val Thr Ser Asn Ala Val Thr Tyr Asn Ser Leu
        35                  40                  45

His Arg Gly Glu Cys His Arg Lys Thr Ala Ser Leu Thr Val Pro Ala
    50                  55                  60

Gln Lys Ala His Lys Glu Val Leu Arg Leu Arg Tyr Asp His Tyr Gly
65                  70                  75                  80

Ala Cys Val Ser Glu His Asn Leu Ile Arg Val Thr Ala Leu Leu Gln
                85                  90                  95

Val Ser Gly Gln Pro Glu Val Val Leu Gln Glu
            100                 105


<210> SEQ ID NO 543
<211> LENGTH: 98
<212> TYPE: PRT
<213> ORGANISM: Homo sapiens

<400> SEQUENCE: 543

Pro Glu Ile Ile Ile Lys Val Arg Gly Thr Gln Val Val Gly Ser Asp
1               5                   10                  15
```

-continued

Met Thr Val Thr Val Glu Phe Thr Asn Pro Leu Lys Glu Thr Leu Arg
            20                  25                  30

Asn Val Trp Val His Leu Asp Gly Pro Gly Val Thr Arg Pro Met Lys
        35                  40                  45

Lys Met Phe Arg Glu Ile Arg Pro Asn Ser Thr Val Gln Trp Glu Glu
    50                  55                  60

Val Cys Arg Pro Trp Val Ser Gly His Arg Lys Leu Ile Ala Ser Met
65                  70                  75                  80

Ser Ser Asp Ser Leu Arg His Val Tyr Gly Glu Leu Asp Val Gln Ile
                85                  90                  95

Gln Arg

<210> SEQ ID NO 544
<211> LENGTH: 98
<212> TYPE: PRT
<213> ORGANISM: Homo sapiens

<400> SEQUENCE: 544

Pro Asp Leu Ser Leu Thr Leu Leu Gly Ala Ala Val Val Gly Gln Glu
1               5                   10                  15

Cys Glu Val Gln Ile Val Phe Lys Asn Pro Leu Pro Val Thr Leu Thr
            20                  25                  30

Asn Val Val Phe Arg Leu Glu Gly Ser Gly Leu Gln Arg Pro Lys Ile
        35                  40                  45

Leu Asn Val Gly Asp Ile Gly Gly Asn Glu Thr Val Thr Leu Arg Gln
    50                  55                  60

Ser Phe Val Pro Val Arg Pro Gly Pro Arg Gln Leu Ile Ala Ser Leu
65                  70                  75                  80

Asp Ser Pro Gln Leu Ser Gln Val His Gly Val Ile Gln Val Asp Val
                85                  90                  95

Ala Pro

<210> SEQ ID NO 545
<211> LENGTH: 98
<212> TYPE: PRT
<213> ORGANISM: Gallus gallus

<400> SEQUENCE: 545

Pro Thr Leu Lys Ile Lys Thr Lys Gly Gln Met Val Val Asp Arg Glu
1               5                   10                  15

Thr Ser Val Val Val Glu Phe Thr Asn Pro Leu Lys Gln Thr Leu Glu
            20                  25                  30

Asn Ala Thr Leu Arg Leu Glu Gly Pro Gly Val Leu Arg Thr Met Lys
        35                  40                  45

Lys Glu Phe Arg Gln Ile Pro Ala Met Ser Thr Leu Ile Trp Asp Val
    50                  55                  60

Lys Cys Ile Pro Lys Arg Pro Gly Leu Arg Lys Leu Ile Ala Ser Leu
65                  70                  75                  80

Asn Cys Asp Ala Leu Arg His Val Tyr Gly Glu Leu Asn Ile Gln Val
                85                  90                  95

Gln Lys

<210> SEQ ID NO 546
<211> LENGTH: 99
<212> TYPE: PRT
<213> ORGANISM: Oncorhynchus keta

<400> SEQUENCE: 546

Pro Gln Leu His Val Lys Val Val Gly Asp Ala Val Val Ser Arg Lys
1 5 10 15

Leu Ile Ala His Ile Ser Phe Thr Asn Pro Leu Pro Ile Thr Leu Arg
20 25 30

Gly Gly Val Phe Thr Val Glu Gly Ala Gly Leu Thr Ala Ala Arg Glu
35 40 45

Ile Gln Ala Pro Asp Asp Ile Gly Pro Gly Gln Glu Val Lys Val Lys
50 55 60

Leu Ser Phe Lys Pro Thr Arg Ala Gly Leu Arg Lys Leu Met Val Asp
65 70 75 80

Phe Asp Ala Asp Arg Ile Arg Asp Val Lys Gly Ile Ala Thr Leu Ile
85 90 95

Val Arg Asn

<210> SEQ ID NO 547
<211> LENGTH: 99
<212> TYPE: PRT
<213> ORGANISM: Pagrus major

<400> SEQUENCE: 547

Pro Glu Leu Leu Val Gln Val Pro Gly Lys Ala Val Val Trp Glu Pro
1 5 10 15

Leu Thr Ala Tyr Val Ser Phe Thr Asn Pro Leu Pro Val Pro Leu Lys
20 25 30

Gly Gly Val Phe Thr Leu Glu Gly Ala Gly Leu Leu Ser Ala Thr Gln
35 40 45

Ile His Val Asn Gly Ala Val Ala Pro Ser Gly Lys Val Ser Val Lys
50 55 60

Leu Ser Phe Ser Pro Met Arg Thr Gly Val Arg Lys Leu Leu Val Asp
65 70 75 80

Phe Asp Ser Asp Arg Leu Lys Asp Val Lys Gly Val Thr Thr Val Val
85 90 95

Val His Lys

<210> SEQ ID NO 548
<211> LENGTH: 101
<212> TYPE: PRT
<213> ORGANISM: Danio rerio

<400> SEQUENCE: 548

Pro Glu Ile Lys Ile Arg Ile Leu Gly Glu Pro Lys Arg Thr Val Lys
1 5 10 15

Leu Ala Ala Glu Leu Thr Ile Gln Asn Pro Leu Pro Glu Ala Leu Gln
20 25 30

Ser Cys Cys Phe Thr Ile Glu Gly Ala Asn Leu Thr Gly Gly Asp Ser
35 40 45

Ile Thr His Thr Leu Asp Ser Ser Ile Glu Pro Gly Gln Glu Ala Lys
50 55 60

Ala Lys Ile Tyr Phe Thr Pro Thr Gln Ser Gly Leu Arg Lys Leu Leu
65 70 75 80

Val Asp Phe Asn Ser Asp Lys Leu Gly His Val Arg Gly Tyr Arg Asn
85 90 95

Val Ile Ile Gly Lys
100

<210> SEQ ID NO 549
<211> LENGTH: 100
<212> TYPE: PRT
<213> ORGANISM: Bos taurus

<400> SEQUENCE: 549

Pro Glu Ile Lys Ile Arg Ile Leu Gly Glu Pro Lys Gln Asn Arg Lys
1 5 10 15

Leu Val Ala Glu Ile Ser Leu Gln Asn Pro Leu Thr Val Ala Leu Ser
20 25 30

Gly Cys Thr Phe Thr Val Glu Gly Ala Gly Leu Ile Glu Glu Gln Lys
35 40 45

Thr Val Asp Val Pro Asp Pro Val Glu Ala Gly Glu Glu Val Lys Val
50 55 60

Arg Val Asp Leu Leu Pro Leu Tyr Val Gly Arg His Lys Leu Val Val
65 70 75 80

Asn Phe Glu Ser Asp Arg Leu Lys Ala Val Lys Gly Phe Arg Asn Val
85 90 95

Ile Val Gly Pro
100

<210> SEQ ID NO 550
<211> LENGTH: 100
<212> TYPE: PRT
<213> ORGANISM: Cavia cutleri

<400> SEQUENCE: 550

Pro Glu Ile Lys Ile Arg Val Leu Gly Glu Pro Lys Gln Asn Arg Lys
1 5 10 15

Leu Ile Ala Glu Val Ser Leu Lys Asn Pro Leu Pro Val Pro Leu Leu
20 25 30

Gly Cys Ile Phe Thr Val Glu Gly Ala Gly Leu Thr Lys Asp Gln Lys
35 40 45

Ser Val Glu Val Pro Asp Pro Val Glu Ala Gly Glu Gln Ala Lys Val
50 55 60

Arg Val Asp Leu Leu Pro Thr Glu Val Gly Leu His Lys Leu Val Val
65 70 75 80

Asn Phe Glu Cys Asp Lys Leu Lys Ala Val Lys Gly Tyr Arg Asn Val
85 90 95

Ile Ile Gly Pro
100

<210> SEQ ID NO 551
<211> LENGTH: 100
<212> TYPE: PRT
<213> ORGANISM: Gallus gallus

<400> SEQUENCE: 551

Pro Glu Ile Lys Ile Arg Ile Leu Gly Glu Pro Met Gln Glu Arg Lys
1 5 10 15

Leu Val Ala Glu Ile Arg Leu Val Asn Pro Leu Ala Glu Pro Leu Asn
20 25 30

Asn Cys Ile Phe Val Val Glu Gly Ala Gly Leu Thr Glu Gly Gln Arg
35 40 45

Ile Glu Glu Leu Glu Asp Pro Val Glu Pro Gln Ala Glu Ala Lys Phe
50 55 60

Arg Met Glu Phe Val Pro Arg Gln Ala Gly Leu His Lys Leu Met Val

```
65                  70                  75                  80

Asp Phe Glu Ser Asp Lys Leu Thr Gly Val Lys Gly Tyr Arg Asn Val
                85                  90                  95

Ile Ile Ala Pro
            100


<210> SEQ ID NO 552
<211> LENGTH: 99
<212> TYPE: PRT
<213> ORGANISM: Schistocerca americana

<400> SEQUENCE: 552

Pro Asp Ile Lys Ile Lys Leu Glu Gly Glu Pro Val Gln Gly Gln Glu
1               5                   10                  15

Met Ser Ala Val Ala Thr Leu Lys Asn Pro Leu Pro Ile Pro Val Lys
            20                  25                  30

Lys Gly Gln Phe Leu Ile Glu Gly Pro Gly Ile Ala Lys Thr Gln Lys
        35                  40                  45

Ile Lys Leu Ser Gln Asn Ile Ala Pro Gly Glu Glu Ala Ser Val Asn
    50                  55                  60

Phe Lys Phe Thr Pro Lys Tyr Asp Gly Arg Ala Thr Ile Ala Ala Lys
65                  70                  75                  80

Phe Ser Ser Lys Glu Leu Asp Asp Val Asp Gly Phe Leu Asn Phe Met
                85                  90                  95

Val Glu Pro


<210> SEQ ID NO 553
<211> LENGTH: 99
<212> TYPE: PRT
<213> ORGANISM: Drosophila melanogaster

<400> SEQUENCE: 553

Pro Asp Ile Lys Phe Gln Leu Gly Glu Ala Ala Ile Val Ala Gln Lys
1               5                   10                  15

Glu Leu Asp Val Ile Leu Arg Leu Glu Asn Pro Leu Pro Ile Pro Leu
            20                  25                  30

His Lys Gly Val Phe Thr Val Glu Gly Pro Gly Ile Glu Gln Pro Leu
        35                  40                  45

Lys Phe Lys Ile Ala Glu Ile Pro Val Gly Gly Thr Ala Ala Ala Thr
    50                  55                  60

Phe Lys Tyr Thr Pro Pro Tyr Ala Gly Arg Gly Thr Met Leu Ala Lys
65                  70                  75                  80

Phe Thr Ser Lys Glu Leu Asp Asp Val Asp Gly Tyr Arg His Tyr Glu
                85                  90                  95

Ile Glu Pro


<210> SEQ ID NO 554
<211> LENGTH: 98
<212> TYPE: PRT
<213> ORGANISM: Tachypleus tridentatus

<400> SEQUENCE: 554

Pro Asn Leu Glu Leu Glu Ile Arg Gly Asn Leu Gln Val Gly Thr Ala
1               5                   10                  15

Phe Val Leu Ala Ile Ser Leu Thr Asn Pro Leu Lys Arg Val Leu Asp
            20                  25                  30

Asn Cys Phe Phe Thr Ile Glu Ala Pro Gly Val Thr Gly Ala Phe Arg
```

```
        35                  40                  45

Val Thr Asn Arg Asp Ile Gln Pro Glu Glu Val Ala Val His Thr Val
    50                  55                  60

Arg Leu Ile Pro Gln Lys Pro Gly Pro Arg Lys Ile Val Ala Thr Phe
65                  70                  75                  80

Ser Ser Arg Gln Leu Ile Gln Val Val Gly Ser Lys Gln Val Glu Val
                85                  90                  95

Leu Asp


<210> SEQ ID NO 555
<211> LENGTH: 98
<212> TYPE: PRT
<213> ORGANISM: Patiria pectinifera

<400> SEQUENCE: 555

Pro Asp Leu Glu Val Lys Thr Glu Gly Pro Ile Val Arg Gly Lys Pro
1               5                   10                  15

Phe Thr Ala Ile Val Ser Leu Thr Asn Pro Leu Pro Tyr Pro Leu Thr
            20                  25                  30

Asp Cys Ser Leu Leu Met Glu Gly Ser Ile Ile Glu Gly Ala Lys Arg
        35                  40                  45

Val Lys Ala Pro His Val Pro Val Asn Gly Lys Met Ala Gln Arg Val
    50                  55                  60

Gln Leu Thr Pro Lys Thr Ala Gly Ser Cys Asp Leu Ile Val Ser Phe
65                  70                  75                  80

Ser Ser Pro Gln Leu Ser Gly Val Lys Ala His Val Thr Leu Asn Val
                85                  90                  95

Lys Ser


<210> SEQ ID NO 556
<211> LENGTH: 99
<212> TYPE: PRT
<213> ORGANISM: Homo sapiens

<400> SEQUENCE: 556

Pro Thr Leu Thr Leu Glu Val Leu Asn Glu Ala Arg Val Arg Lys Pro
1               5                   10                  15

Val Asn Val Gln Met Leu Phe Ser Asn Pro Leu Asp Glu Pro Val Arg
            20                  25                  30

Asp Cys Val Leu Met Val Glu Gly Ser Gly Leu Leu Leu Gly Asn Leu
        35                  40                  45

Lys Ile Asp Val Pro Thr Leu Gly Pro Lys Glu Arg Ser Arg Val Arg
    50                  55                  60

Phe Asp Ile Leu Pro Ser Arg Ser Gly Thr Lys Gln Leu Leu Ala Asp
65                  70                  75                  80

Phe Ser Cys Asn Lys Phe Pro Ala Ile Lys Ala Met Leu Ser Ile Asp
                85                  90                  95

Val Ala Glu


<210> SEQ ID NO 557
<211> LENGTH: 99
<212> TYPE: PRT
<213> ORGANISM: Mus musculus

<400> SEQUENCE: 557

Pro Ala Leu Thr Leu Glu Val Leu Glu Gln Ala His Val Arg Lys Pro
1               5                   10                  15
```

Val Asn Val Gln Met Ile Phe Ser Asn Pro Leu Asp Gln Pro Val Asn
20 25 30

Asn Cys Val Leu Leu Val Glu Gly Ser Gly Cys Ser Val Ala Ala Ser
35 40 45

Arg Leu Met Cys His Pro Cys Val Pro Lys Glu Lys Ser Arg Ile Arg
50 55 60

Phe Glu Ile Phe Pro Thr Arg Ser Gly Thr Lys Gln Leu Leu Ala Asp
65 70 75 80

Phe Ser Cys Asn Lys Phe Pro Thr Ile Lys Ala Met Leu Pro Ile Asp
85 90 95

Val Ser Glu

<210> SEQ ID NO 558
<211> LENGTH: 99
<212> TYPE: PRT
<213> ORGANISM: Mus musculus

<400> SEQUENCE: 558

Pro Gly Ile Met Ile Asn Val Leu Gly Ala Ala Phe Val Asn Gln Pro
1 5 10 15

Leu Thr Val Gln Val Val Phe Ser Asn Pro Leu Ser Glu Pro Val Glu
20 25 30

Asp Cys Val Leu Thr Leu Glu Gly Ser Gly Leu Phe Arg Lys Gln Gln
35 40 45

Arg Val Leu Ile Gly Val Leu Lys Pro His His Lys Ala Ser Ile Thr
50 55 60

Leu Lys Thr Val Pro Phe Lys Ser Gly Gln Arg Gln Ile Gln Ala Asn
65 70 75 80

Leu Arg Ser Asn Arg Phe Lys Asp Ile Lys Gly Tyr Lys Asn Val Tyr
85 90 95

Val Asp Ile

<210> SEQ ID NO 559
<211> LENGTH: 99
<212> TYPE: PRT
<213> ORGANISM: Homo sapiens

<400> SEQUENCE: 559

Pro Ser Ile Thr Ile Asn Val Leu Gly Ala Ala Val Val Asn Gln Pro
1 5 10 15

Leu Ser Ile Gln Val Ile Phe Ser Asn Pro Leu Ser Glu Gln Val Glu
20 25 30

Asp Cys Val Leu Thr Val Glu Gly Ser Gly Leu Phe Lys Lys Gln Gln
35 40 45

Lys Val Phe Leu Gly Val Leu Lys Pro Gln His Gln Ala Ser Ile Ile
50 55 60

Leu Glu Thr Val Pro Phe Lys Ser Gly Gln Arg Gln Ile Gln Ala Asn
65 70 75 80

Met Arg Ser Asn Lys Phe Lys Asp Ile Lys Gly Tyr Arg Asn Val Tyr
85 90 95

Val Asp Phe

<210> SEQ ID NO 560
<211> LENGTH: 98
<212> TYPE: PRT
<213> ORGANISM: Homo sapiens

<400> SEQUENCE: 560

Pro Glu Phe Ser Ile Glu Leu Pro Asn Thr Gly Arg Ile Gly Gln Leu
1 5 10 15

Leu Val Cys Asn Cys Ile Phe Lys Asn Thr Leu Ala Ile Pro Leu Thr
20 25 30

Asp Val Lys Phe Ser Leu Glu Ser Leu Gly Ile Ser Ser Leu Gln Thr
35 40 45

Ser Asp His Gly Thr Val Gln Pro Gly Glu Thr Ile Gln Ser Gln Ile
50 55 60

Lys Cys Thr Pro Ile Lys Thr Gly Pro Lys Lys Phe Ile Val Lys Leu
65 70 75 80

Ser Ser Lys Gln Val Lys Glu Ile Asn Ala Gln Lys Ile Val Leu Ile
85 90 95

Thr Lys

<210> SEQ ID NO 561
<211> LENGTH: 99
<212> TYPE: PRT
<213> ORGANISM: Rattus norvegicus

<400> SEQUENCE: 561

Ser Ala Phe Ser Val Glu Met Pro Ser Thr Ser Lys Val Asn Gln Pro
1 5 10 15

Leu Thr Ile Thr Cys Asn Phe Lys Asn Thr Leu Pro Ile Pro Leu Thr
20 25 30

Asn Ile Lys Phe Ser Val Glu Ser Leu Gly Leu Asn Asn Met Lys Ser
35 40 45

Trp Glu Gln Glu Thr Val Pro Pro Gly Lys Thr Ile Asn Phe Gln Ile
50 55 60

Glu Cys Thr Pro Val Lys Thr Gly Asn Pro Arg Lys Phe Ile Val Lys
65 70 75 80

Phe Ile Ser Arg Gln Val Lys Glu Val His Ala Glu Lys Val Val Leu
85 90 95

Ile Thr Lys

<210> SEQ ID NO 562
<211> LENGTH: 99
<212> TYPE: PRT
<213> ORGANISM: Mus musculus

<400> SEQUENCE: 562

Pro Asp Leu Ile Ile Glu Met Pro Lys Arg Ala Ala Gln Tyr Arg Pro
1 5 10 15

Leu Thr Val Ser Val Arg Met His Asn Ser Leu Glu Ala Pro Met Gln
20 25 30

Asn Ser Ile Ile Ser Ile Phe Gly Arg Gly Leu Ile His Arg Glu Lys
35 40 45

Arg Tyr Gly Leu Gly Ser Leu Trp Pro Gly Ser Ser Leu His Thr Gln
50 55 60

Phe Gln Phe Thr Pro Thr His Leu Gly Leu Gln Arg Leu Thr Val Glu
65 70 75 80

Val Asp Cys Asp Met Phe Gln Asn Leu Thr Gly Tyr Arg Ser Val Leu
85 90 95

Val Val Ala

<210> SEQ ID NO 563
<211> LENGTH: 99
<212> TYPE: PRT
<213> ORGANISM: Homo sapiens

<400> SEQUENCE: 563

```
Pro His Leu Ala Ile Lys Met Pro Glu Lys Ala Glu Gln Tyr Gln Pro
1               5                   10                  15

Leu Thr Ala Ser Val Ser Leu Gln Asn Ser Leu Asp Ala Pro Met Glu
            20                  25                  30

Asp Cys Val Ile Ser Ile Leu Gly Arg Gly Leu Ile His Arg Glu Arg
        35                  40                  45

Ser Tyr Arg Phe Arg Ser Val Trp Pro Glu Asn Thr Met Cys Ala Lys
    50                  55                  60

Phe Gln Phe Thr Pro Thr His Val Gly Leu Gln Arg Leu Thr Val Glu
65                  70                  75                  80

Val Asp Cys Asn Met Phe Gln Asn Leu Thr Asn Tyr Lys Ser Val Thr
                85                  90                  95

Val Val Ala
```

<210> SEQ ID NO 564
<211> LENGTH: 112
<212> TYPE: PRT
<213> ORGANISM: Homo sapiens

<400> SEQUENCE: 564

```
Ser Asn Val Asp Met Asp Phe Glu Val Glu Asn Ala Val Leu Gly Lys
1               5                   10                  15

Asp Phe Lys Leu Ser Ile Thr Phe Arg Asn Asn Ser His Asn Arg Tyr
            20                  25                  30

Thr Ile Thr Ala Tyr Leu Ser Ala Asn Ile Thr Phe Tyr Thr Gly Val
        35                  40                  45

Pro Lys Ala Glu Phe Lys Lys Glu Thr Phe Asp Val Thr Leu Glu Pro
    50                  55                  60

Leu Ser Phe Lys Lys Glu Ala Val Leu Ile Gln Ala Gly Glu Tyr Met
65                  70                  75                  80

Gly Gln Leu Leu Glu Gln Ala Ser Leu His Phe Phe Val Thr Ala Arg
                85                  90                  95

Ile Asn Glu Thr Arg Asp Val Leu Ala Lys Gln Lys Ser Thr Val Leu
            100                 105                 110
```

<210> SEQ ID NO 565
<211> LENGTH: 112
<212> TYPE: PRT
<213> ORGANISM: Pan troglodytes

<400> SEQUENCE: 565

```
Ser Asn Val Asp Met Asp Phe Glu Val Glu Asn Ala Val Leu Gly Lys
1               5                   10                  15

Asp Phe Lys Leu Ser Ile Thr Phe Arg Asn Asn Ser His Asn Arg Tyr
            20                  25                  30

Thr Ile Thr Ala Tyr Leu Ser Ala Asn Ile Thr Phe Tyr Thr Gly Val
        35                  40                  45

Pro Lys Ala Glu Phe Lys Lys Glu Thr Phe Asp Val Thr Leu Glu Pro
    50                  55                  60

Leu Ser Phe Lys Lys Glu Ala Val Leu Ile Gln Ala Gly Glu Tyr Met
65                  70                  75                  80
```

Gly Gln Leu Leu Glu Gln Ala Ser Leu His Phe Phe Val Thr Ala Arg
                85                  90                  95

Ile Asn Glu Thr Arg Asp Val Leu Ala Lys Gln Lys Ser Thr Val Leu
            100                 105                 110

<210> SEQ ID NO 566
<211> LENGTH: 112
<212> TYPE: PRT
<213> ORGANISM: Macaca mulatta

<400> SEQUENCE: 566

Ser Lys Val Asp Met Asp Phe Glu Val Glu Asn Ala Val Leu Gly Lys
1               5                   10                  15

Asp Leu Lys Leu Thr Ile Thr Phe Arg Asn Asn Ser His Asn His Tyr
            20                  25                  30

Thr Ile Thr Ala Tyr Leu Ser Ala Asn Ile Thr Phe Tyr Thr Gly Val
        35                  40                  45

Ser Lys Ala Glu Phe Lys Lys Glu Thr Phe Asp Val Thr Leu Glu Pro
    50                  55                  60

Leu Ser Phe Lys Lys Glu Ala Val Leu Ile Gln Ala Gly Glu Tyr Met
65                  70                  75                  80

Gly Gln Leu Leu Glu Gln Ala Ser Leu His Phe Phe Val Thr Ala Arg
                85                  90                  95

Ile Asn Glu Thr Arg Asp Val Leu Ala Lys Gln Lys Ser Thr Val Leu
            100                 105                 110

<210> SEQ ID NO 567
<211> LENGTH: 112
<212> TYPE: PRT
<213> ORGANISM: Equus caballus

<400> SEQUENCE: 567

Ser Asp Val Asp Met Asp Phe Glu Val Glu Asn Ala Val Leu Gly Lys
1               5                   10                  15

Asp Phe Lys Leu Thr Ile Thr Phe Arg Asn Gln Ser Pro Thr Arg Tyr
            20                  25                  30

Thr Ile Ser Ala Tyr Leu Ser Gly Asn Ile Thr Phe Tyr Thr Gly Val
        35                  40                  45

Ser His Val Glu Phe Lys Asn Glu Thr Phe Lys Val Thr Leu Glu Pro
    50                  55                  60

Leu Ser Val Lys Lys Glu Glu Val Leu Ile Arg Ala Gly Glu Tyr Met
65                  70                  75                  80

Gly Gln Leu Leu Glu Gln Ala Ser Leu His Phe Phe Val Thr Ala Arg
                85                  90                  95

Val Asn Glu Thr Lys Val Val Leu Ala Lys Gln Lys Ser Thr Val Leu
            100                 105                 110

<210> SEQ ID NO 568
<211> LENGTH: 112
<212> TYPE: PRT
<213> ORGANISM: Canis familiaris

<400> SEQUENCE: 568

Ser Asp Val Asp Met Asn Phe Asp Val Glu Asn Ala Val Leu Gly Arg
1               5                   10                  15

Asp Phe Lys Leu Thr Ile Thr Phe Gln Asn Asn Ser Pro Arg Arg Tyr
            20                  25                  30

-continued

```
Thr Leu Leu Ala Tyr Leu Ser Gly Asn Ile Val Phe Tyr Thr Gly Val
        35                  40                  45

Ser Lys Thr Glu Phe Lys Lys Glu Thr Phe Glu Val Thr Leu Glu Pro
    50                  55                  60

Leu Ser Phe Lys Arg Glu Glu Val Leu Ile Arg Ala Gly Glu Tyr Met
65                  70                  75                  80

Gly Gln Leu Leu Glu Gln Ala Tyr Leu His Phe Phe Val Thr Ala Arg
                85                  90                  95

Val Asn Glu Ser Lys Asp Ile Leu Ala Lys Gln Lys Ser Thr Val Leu
            100                 105                 110


<210> SEQ ID NO 569
<211> LENGTH: 112
<212> TYPE: PRT
<213> ORGANISM: Bos taurus

<400> SEQUENCE: 569

Ser Asp Val Arg Met Asn Phe Glu Val Glu Asn Ala Val Leu Gly Arg
1               5                   10                  15

Asp Leu Lys Val Ile Ile Thr Phe Arg Asn Asn Gly Ser Ala Arg Tyr
            20                  25                  30

Thr Val Thr Ala Tyr Leu Ser Gly Asn Ile Ser Phe Tyr Thr Gly Val
        35                  40                  45

Ser Lys Ala Glu Phe Lys Asn Lys Thr Phe Glu Val Thr Leu Glu Pro
    50                  55                  60

Leu Ser Phe Lys Arg Glu Glu Val Leu Ile Gly Ala Gly Glu Tyr Met
65                  70                  75                  80

Gly Gln Leu Leu Glu Gln Ala Phe Leu His Phe Phe Val Thr Ala Arg
                85                  90                  95

Val Asn Glu Thr Arg Asp Val Leu Ala Lys Gln Lys Ser Ile Ala Leu
            100                 105                 110


<210> SEQ ID NO 570
<211> LENGTH: 112
<212> TYPE: PRT
<213> ORGANISM: Rattus norvegicus

<400> SEQUENCE: 570

Ser Asp Val Asp Met Asn Phe Asp Val Glu Asn Ala Val Leu Gly Lys
1               5                   10                  15

Asp Phe Arg Val Thr Ile Thr Phe Gln Asn Asn Ser Ser Asn Leu Tyr
            20                  25                  30

Thr Ile Leu Ala Tyr Leu Ser Gly Asn Ile Thr Phe Tyr Thr Gly Val
        35                  40                  45

Ser Lys Lys Glu Phe Lys Thr Glu Ser Phe Glu Val Thr Leu Asp Pro
    50                  55                  60

Leu Ser Leu Glu Lys Lys Glu Val Leu Ile Arg Ala Gly Glu Tyr Met
65                  70                  75                  80

Ser Tyr Leu Leu Glu Gln Gly Leu Leu His Phe Phe Val Thr Ala Arg
                85                  90                  95

Ile Asn Glu Thr Arg Val Val Leu Ala Lys Gln Lys Ser Ile Val Leu
            100                 105                 110


<210> SEQ ID NO 571
<211> LENGTH: 112
<212> TYPE: PRT
<213> ORGANISM: Mus musculus
```

<400> SEQUENCE: 571

Ser Asp Val Thr Met Asn Phe Asp Val Glu Asn Ala Val Leu Gly Lys
1               5                   10                  15

Asp Phe Lys Val Thr Ile Thr Phe Gln Asn Asn Ser Ser Asn Leu Tyr
            20                  25                  30

Thr Ile Leu Ala Tyr Leu Ser Gly Asn Ile Thr Phe Tyr Thr Gly Val
        35                  40                  45

Ser Lys Lys Glu Phe Lys Lys Glu Ser Phe Glu Glu Thr Leu Asp Pro
    50                  55                  60

Phe Ser Ser Lys Lys Lys Glu Val Leu Val Arg Ala Gly Glu Tyr Met
65                  70                  75                  80

Ser His Leu Leu Glu Gln Gly Phe Leu His Phe Phe Val Thr Ala Arg
                85                  90                  95

Ile Asn Glu Ser Arg Asp Val Leu Ala Lys Gln Lys Ser Ile Ile Leu
            100                 105                 110

<210> SEQ ID NO 572
<211> LENGTH: 112
<212> TYPE: PRT
<213> ORGANISM: Monodelphis domestica

<400> SEQUENCE: 572

Ala Asp Ile Asp Met Asp Phe Glu Val Glu Lys Ala Ile Leu Gly Lys
1               5                   10                  15

Asp Phe Lys Val Thr Ile Thr Phe Arg Asn Ser Ser Ser Arg His Tyr
            20                  25                  30

Thr Ala Thr Ala Tyr Leu Ser Gly Asn Ile Val Phe Tyr Thr Gly Val
        35                  40                  45

Thr Lys Ser Glu Phe Lys Asn Gln Thr Phe Asn Val Lys Val Glu Pro
    50                  55                  60

Tyr Ser Phe Thr Asn Val Glu Val Gln Ile Lys Ala Gly Glu Tyr Met
65                  70                  75                  80

Gly Gln Leu Leu Glu Gln Ala Ser Leu His Phe Phe Val Ser Ala Arg
                85                  90                  95

Ile Asn Glu Thr Gly Lys Val Leu Ala Leu Gln Lys Ser Thr Val Leu
            100                 105                 110

<210> SEQ ID NO 573
<211> LENGTH: 111
<212> TYPE: PRT
<213> ORGANISM: Gallus gallus

<400> SEQUENCE: 573

Asp Ile Glu Met Asp Leu Gln Val Gln Lys Val Val Leu Gly Ser Asp
1               5                   10                  15

Phe Lys Val Thr Ile Ile Leu Arg Asn Lys Ser Arg Asn Ser Tyr Thr
            20                  25                  30

Ala Thr Thr Tyr Leu Ser Gly Asn Ile Val Phe Tyr Thr Gly Val Thr
        35                  40                  45

Lys Ser Glu Phe Lys Lys His Ser Phe Ser Ala Lys Leu Glu Pro Leu
    50                  55                  60

Leu Ser Asn Thr Phe Asp Val Met Ile Thr Ser Ala Glu Tyr Leu Asn
65                  70                  75                  80

Asp Leu Leu Asp Gln Ala Ser Phe His Phe Phe Val Thr Ala Arg Ile
                85                  90                  95

Asn Glu Thr Gly Lys Val Leu Ala Met Gln Lys Ala Val Val Leu 100 105 110

<210> SEQ ID NO 574
<211> LENGTH: 104
<212> TYPE: PRT
<213> ORGANISM: Homo sapiens

<400> SEQUENCE: 574

Thr Ile Pro Glu Ile Ile Ile Lys Val Arg Gly Thr Gln Val Val Gly
1 5 10 15

Ser Asp Met Thr Val Thr Val Gln Phe Thr Asn Pro Leu Lys Glu Thr
20 25 30

Leu Arg Asn Val Trp Val His Leu Asp Gly Pro Gly Val Thr Arg Pro
35 40 45

Met Lys Lys Met Phe Arg Glu Ile Arg Pro Asn Ser Thr Val Gln Trp
50 55 60

Glu Glu Val Cys Arg Pro Trp Val Ser Gly His Arg Lys Leu Ile Ala
65 70 75 80

Ser Met Ser Ser Asp Ser Leu Arg His Val Tyr Gly Glu Leu Asp Val
85 90 95

Gln Ile Gln Arg Arg Pro Ser Met
100

<210> SEQ ID NO 575
<211> LENGTH: 104
<212> TYPE: PRT
<213> ORGANISM: Pan troglodytes

<400> SEQUENCE: 575

Thr Ile Pro Glu Ile Ile Ile Lys Val Arg Gly Thr Gln Val Val Gly
1 5 10 15

Ser Asp Met Thr Val Thr Val Glu Phe Thr Asn Pro Leu Lys Glu Thr
20 25 30

Leu Arg Asn Val Trp Ile His Leu Asp Gly Pro Gly Ile Thr Arg Pro
35 40 45

Met Lys Lys Met Phe Arg Glu Ile Arg Pro Asn Ser Thr Val Gln Trp
50 55 60

Glu Glu Val Cys Arg Pro Trp Val Ser Gly His Arg Lys Leu Ile Ala
65 70 75 80

Ser Met Ser Ser Asp Ser Leu Arg His Val Tyr Gly Glu Leu Asp Val
85 90 95

Gln Ile Gln Arg Arg Pro Ser Met
100

<210> SEQ ID NO 576
<211> LENGTH: 104
<212> TYPE: PRT
<213> ORGANISM: Macaca mulatta

<400> SEQUENCE: 576

Thr Ile Pro Lys Leu Ile Ile Lys Val Arg Gly Ala Gln Val Val Gly
1 5 10 15

Ser Asp Met Ile Val Thr Val Glu Phe Thr Asn Pro Leu Lys Glu Thr
20 25 30

Leu Arg Asn Val Trp Ile His Leu Asp Gly Pro Gly Ile Thr Arg Pro
35 40 45

Met Arg Lys Met Phe Arg Glu Ile Arg Pro Asn Ser Thr Val Gln Trp
50 55 60

Glu Glu Val Cys Arg Pro Trp Val Ser Gly Pro Arg Lys Leu Ile Ala
65 70 75 80

Ser Met Ser Ser Asp Ser Leu Arg His Val Tyr Gly Glu Leu Asp Val
85 90 95

Gln Ile Gln Arg Arg Pro Ser Met
100

<210> SEQ ID NO 577
<211> LENGTH: 104
<212> TYPE: PRT
<213> ORGANISM: Bos taurus

<400> SEQUENCE: 577

Thr Val Pro Lys Val Val Ile Lys Val Arg Gly Ala Gln Val Val Gly
1 5 10 15

Ser Asp Met Val Val Thr Val Glu Phe Thr Asn Pro Leu Lys Glu Thr
20 25 30

Leu Arg Asn Val Trp Ile Arg Leu Asp Gly Pro Gly Val Thr Lys Pro
35 40 45

Leu Arg Lys Met Phe Arg Glu Ile Arg Pro Asn Ser Thr Val Gln Trp
50 55 60

Glu Glu Leu Cys Arg Pro Trp Val Ser Gly Pro Arg Lys Leu Ile Ala
65 70 75 80

Ser Leu Thr Ser Asp Ser Leu Arg His Val Tyr Gly Glu Leu Asp Leu
85 90 95

Gln Ile Gln Arg Arg Pro Ser Met
100

<210> SEQ ID NO 578
<211> LENGTH: 104
<212> TYPE: PRT
<213> ORGANISM: Mus musculus

<400> SEQUENCE: 578

Thr Ile Pro Lys Ile Thr Ile Lys Val Arg Gly Ala Ala Met Val Gly
1 5 10 15

Ser Asp Met Val Val Thr Val Glu Phe Thr Asn Pro Leu Lys Glu Thr
20 25 30

Leu Gln Asn Val Trp Ile His Leu Asp Gly Pro Gly Val Met Arg Pro
35 40 45

Lys Arg Lys Val Phe Arg Glu Ile Arg Pro Asn Thr Thr Val Gln Trp
50 55 60

Glu Glu Val Cys Arg Pro Trp Val Ser Gly His Arg Lys Leu Ile Ala
65 70 75 80

Ser Met Thr Ser Asp Ser Leu Arg His Val Tyr Gly Glu Leu Asp Leu
85 90 95

Gln Ile Gln Arg Arg Pro Thr Met
100

<210> SEQ ID NO 579
<211> LENGTH: 104
<212> TYPE: PRT
<213> ORGANISM: Rattus norvegicus

<400> SEQUENCE: 579

Thr Ile Pro Lys Val Thr Ile Lys Val Arg Gly Thr Ala Met Val Gly
1 5 10 15

Ser Asp Met Val Val Thr Val Glu Phe Thr Asn Pro Leu Lys Glu Thr
20 25 30

Leu Lys Asn Val Trp Leu His Leu Glu Gly Pro Gly Val Met Arg Pro
35 40 45

Lys Arg Lys Met Phe Arg Glu Ile Arg Pro Asn Ala Thr Val Gln Trp
50 55 60

Glu Glu Val Cys Gln Pro Trp Val Ser Gly His Arg Lys Leu Ile Ala
65 70 75 80

Ser Met Thr Ser Asp Ser Leu Arg His Val Tyr Gly Glu Leu Asp Leu
85 90 95

Gln Ile Arg Arg Arg Pro Thr Val
100

<210> SEQ ID NO 580
<211> LENGTH: 103
<212> TYPE: PRT
<213> ORGANISM: Canis familiaris

<400> SEQUENCE: 580

Thr Ile Pro Gln Leu Ile Ile Lys Val Arg Gly Ala Lys Met Val Gly
1 5 10 15

Ser Asp Met Val Val Thr Val Glu Phe Thr Asn Pro Leu Lys Glu Thr
20 25 30

Leu Arg Asn Val Trp Ile His Leu Asp Gly Pro Gly Val Ile Lys Pro
35 40 45

Met Arg Lys Met Phe Arg Glu Ile Gln Pro Ser Ala Thr Ile Gln Trp
50 55 60

Glu Glu Val Cys Arg Pro Trp Val Ser Gly Pro Arg Lys Leu Ile Ala
65 70 75 80

Ser Met Thr Ser Asp Ser Leu Arg His Val Tyr Gly Glu Leu Asn Leu
85 90 95

Gln Ile Gln Arg Arg Pro Ser
100

<210> SEQ ID NO 581
<211> LENGTH: 103
<212> TYPE: PRT
<213> ORGANISM: Equus caballus

<400> SEQUENCE: 581

Thr Ile Pro Lys Val Ile Ile Lys Val Arg Gly Ala Lys Val Val Gly
1 5 10 15

Ser Asp Met Val Val Thr Val Glu Phe Thr Asn Pro Leu Lys Gln Thr
20 25 30

Leu Arg Asn Val Trp Ile Tyr Leu Glu Gly Pro Gly Val Ile Lys Pro
35 40 45

Lys Arg Lys Leu Phe Arg Glu Ile Pro Pro Asn Ser Thr Val Gln Trp
50 55 60

Glu Glu Ala Ser Arg Pro Trp Val Ser Gly Arg Arg Lys Leu Ile Ala
65 70 75 80

Ser Met Thr Ser Asp Ser Leu Arg His Val Tyr Gly Glu Leu Asp Leu
85 90 95

Gln Ile Gln Arg Arg Pro Ala
100

<210> SEQ ID NO 582
<211> LENGTH: 101

<212> TYPE: PRT
<213> ORGANISM: Monodelphis domestica

<400> SEQUENCE: 582

Ile Pro Thr Leu Asn Leu Lys Val Arg Gly His Lys Val Val Gly Ser
1               5                   10                  15

Asp Met Val Val Thr Val Glu Phe Thr Asn Pro Leu Ala Glu Thr Leu
            20                  25                  30

Tyr Asn Ile Ser Ile His Leu Asp Gly Pro Gly Val Met Lys Pro Ile
        35                  40                  45

Arg Lys Lys Phe Arg Glu Leu Ala Pro Asn Ser Thr Leu Thr Trp Glu
    50                  55                  60

Glu Val Cys Arg Pro Trp Val Pro Gly Ser Arg Lys Leu Met Ala Thr
65                  70                  75                  80

Leu Asn Cys Asp Ala Leu Arg His Val Tyr Gly Glu Leu Lys Leu Glu
                85                  90                  95

Ile Gln Arg Arg Pro
            100

<210> SEQ ID NO 583
<211> LENGTH: 99
<212> TYPE: PRT
<213> ORGANISM: Gallus gallus

<400> SEQUENCE: 583

Ile Pro Thr Leu Lys Ile Lys Thr Lys Gly Gln Met Val Val Asp Arg
1               5                   10                  15

Glu Thr Ser Val Val Val Glu Phe Thr Asn Pro Leu Lys Gln Thr Leu
            20                  25                  30

Glu Asn Ala Thr Leu Arg Leu Glu Gly Pro Gly Val Leu Arg Thr Met
        35                  40                  45

Lys Lys Glu Phe Arg Gln Ile Pro Ala Met Ser Thr Leu Ile Trp Asp
    50                  55                  60

Val Lys Cys Ile Pro Lys Arg Pro Gly Leu Arg Lys Leu Ile Ala Ser
65                  70                  75                  80

Leu Asn Cys Asp Ala Leu Arg His Val Tyr Gly Glu Leu Asn Ile Gln
                85                  90                  95

Val Gln Lys

<210> SEQ ID NO 584
<211> LENGTH: 306
<212> TYPE: DNA
<213> ORGANISM: Homo sapiens
<220> FEATURE:
<221> NAME/KEY: CDS
<222> LOCATION: (1)..(306)

<400> SEQUENCE: 584 atg acc atc cct gag atc atc atc aag gtc cgt ggc act cag gta gtt       48
Met Thr Ile Pro Glu Ile Ile Ile Lys Val Arg Gly Thr Gln Val Val
1               5                   10                  15 ggt tct gac atg act gtg ata gtt gag ttt acc aat cct tta aaa gaa       96
Gly Ser Asp Met Thr Val Ile Val Glu Phe Thr Asn Pro Leu Lys Glu
            20                  25                  30 acc ctg cga aat gtc tgg gta cac ctg gat ggt cct gga gta aca aga      144
Thr Leu Arg Asn Val Trp Val His Leu Asp Gly Pro Gly Val Thr Arg
        35                  40                  45 cca atg aag aag atg ttc cgt gaa atc cgg ccc aac tcc acc gtg cag      192
Pro Met Lys Lys Met Phe Arg Glu Ile Arg Pro Asn Ser Thr Val Gln

```
    50                  55                  60

tgg gaa gaa gtg tgc cgg ccc tgg gtc tct ggg cat cgg aag ctg ata      240
Trp Glu Glu Val Cys Arg Pro Trp Val Ser Gly His Arg Lys Leu Ile
65                  70                  75                  80

gcc agc atg agc agt gac tcc ctg aga cat gtg tat ggc gag ctg gac      288
Ala Ser Met Ser Ser Asp Ser Leu Arg His Val Tyr Gly Glu Leu Asp
                85                  90                  95

gtg cag att caa aga cga                                              306
Val Gln Ile Gln Arg Arg
            100


<210> SEQ ID NO 585
<211> LENGTH: 102
<212> TYPE: PRT
<213> ORGANISM: Homo sapiens

<400> SEQUENCE: 585

Met Thr Ile Pro Glu Ile Ile Ile Lys Val Arg Gly Thr Gln Val Val
1               5                   10                  15

Gly Ser Asp Met Thr Val Ile Val Glu Phe Thr Asn Pro Leu Lys Glu
            20                  25                  30

Thr Leu Arg Asn Val Trp Val His Leu Asp Gly Pro Gly Val Thr Arg
        35                  40                  45

Pro Met Lys Lys Met Phe Arg Glu Ile Arg Pro Asn Ser Thr Val Gln
    50                  55                  60

Trp Glu Glu Val Cys Arg Pro Trp Val Ser Gly His Arg Lys Leu Ile
65                  70                  75                  80

Ala Ser Met Ser Ser Asp Ser Leu Arg His Val Tyr Gly Glu Leu Asp
                85                  90                  95

Val Gln Ile Gln Arg Arg
            100


<210> SEQ ID NO 586
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 586

atgaccatcc ctgagatcat catcaaggtc cgcggcactc aggtcgtggg ttctgacatg     60

actgtgatcg tggagtttac caatcctctg aaagaaaccc tgcgcaatgt ctgggtgcac    120

ctggatggtc ctggagtcac acgcccaatg aagaagatgt tccgcgaaat ccgcccaaac    180

tccaccgtgc agtgggaaga agtgtgccgc ccatgggtct ctgggcatcg caagctgatc    240

gccagcatga gcagtgactc cctgcgccat gtgtatggcg agctggacgt gcagattcaa    300

cgccgc                                                                306


<210> SEQ ID NO 587
<211> LENGTH: 102
<212> TYPE: PRT
<213> ORGANISM: Homo sapiens

<400> SEQUENCE: 587

Met Thr Ile Pro Glu Ile Ile Ile Lys Val Arg Gly Thr Gln Val Val
1               5                   10                  15

Gly Ser Asp Met Thr Val Ile Val Glu Phe Thr Asn Pro Leu Lys Glu
            20                  25                  30
```

```
Thr Leu Arg Asn Val Trp Val His Leu Asp Gly Pro Gly Val Thr Arg
        35                  40                  45

Pro Met Lys Lys Met Phe Arg Glu Ile Arg Pro Asn Ser Thr Val Gln
    50                  55                  60

Trp Glu Glu Val Cys Arg Pro Trp Val Ser Gly His Arg Lys Leu Ile
65                  70                  75                  80

Ala Ser Met Ser Ser Asp Ser Leu Arg His Val Tyr Gly Glu Leu Asp
                85                  90                  95

Val Gln Ile Gln Arg Arg
            100


<210> SEQ ID NO 588
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(33)
<223> OTHER INFORMATION: Any amino acid

<400> SEQUENCE: 588

Met Thr Ile Pro Glu Ile Ile Ile Lys Val Arg Gly Thr Gln Val Val
1               5                   10                  15

Gly Ser Asp Met Thr Val Ile Val Glu Phe Thr Asn Xaa Xaa Xaa Xaa
            20                  25                  30

Xaa Leu Arg Asn Val Trp Val His Leu Asp Gly Pro Gly Val Thr Arg
        35                  40                  45

Pro Met Lys Lys Met Phe Arg Glu Ile Arg Pro Asn Ser Thr Val Gln
    50                  55                  60

Trp Glu Glu Val Val Arg Pro Trp Val Ser Gly His Arg Lys Leu Ile
65                  70                  75                  80

Ala Ser Met Ser Ser Asp Ser Leu Arg His Val Tyr Gly Glu Leu Asp
                85                  90                  95

Val Gln Ile Gln Arg Arg
            100


<210> SEQ ID NO 589
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(33)
<223> OTHER INFORMATION: Any amino acid
<220> FEATURE:
<221> NAME/KEY: MOD_RES
<222> LOCATION: (58)..(61)
<223> OTHER INFORMATION: Any amino acid
<220> FEATURE:
<221> NAME/KEY: MOD_RES
<222> LOCATION: (86)..(87)
<223> OTHER INFORMATION: Any amino acid

<400> SEQUENCE: 589

Met Thr Ile Pro Glu Ile Ile Ile Lys Val Arg Gly Thr Gln Val Val
1               5                   10                  15

Gly Ser Asp Met Thr Val Ile Val Glu Phe Thr Asn Xaa Xaa Xaa Xaa
```

```
            20                  25                  30

Xaa Leu Arg Asn Val Trp Val His Leu Asp Gly Pro Gly Val Thr Arg
        35                  40                  45

Pro Met Lys Lys Met Phe Arg Glu Ile Xaa Xaa Xaa Xaa Thr Val Gln
    50                  55                  60

Trp Glu Glu Val Val Arg Pro Trp Val Ser Gly His Arg Lys Leu Ile
65                  70                  75                  80

Ala Ser Met Ser Ser Xaa Xaa Leu Arg His Val Tyr Gly Glu Leu Asp
                85                  90                  95

Val Gln Ile Gln Arg Arg
            100


<210> SEQ ID NO 590
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(33)
<223> OTHER INFORMATION: Any amino acid
<220> FEATURE:
<221> NAME/KEY: MOD_RES
<222> LOCATION: (58)..(61)
<223> OTHER INFORMATION: Any amino acid
<220> FEATURE:
<221> NAME/KEY: MOD_RES
<222> LOCATION: (86)..(89)
<223> OTHER INFORMATION: Any amino acid

<400> SEQUENCE: 590

Met Thr Ile Pro Glu Ile Ile Ile Lys Val Arg Gly Thr Gln Val Val
1               5                   10                  15

Gly Ser Asp Met Thr Val Ile Val Glu Phe Thr Asn Xaa Xaa Xaa Xaa
            20                  25                  30

Xaa Leu Arg Asn Val Trp Val His Leu Asp Gly Pro Gly Val Thr Arg
        35                  40                  45

Pro Met Lys Lys Met Phe Arg Glu Ile Xaa Xaa Xaa Xaa Thr Val Gln
    50                  55                  60

Trp Glu Glu Val Val Arg Pro Trp Val Ser Gly His Arg Lys Leu Ile
65                  70                  75                  80

Ala Ser Met Ser Ser Xaa Xaa Xaa Xaa Leu Arg His Val Tyr Gly Glu
                85                  90                  95

Leu Asp Val Gln Ile Gln Arg Arg
            100


<210> SEQ ID NO 591
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(33)
<223> OTHER INFORMATION: Any amino acid
<220> FEATURE:
<221> NAME/KEY: MOD_RES
<222> LOCATION: (35)..(36)
<223> OTHER INFORMATION: Any amino acid
<220> FEATURE:
<221> NAME/KEY: MOD_RES
```

<222> LOCATION: (55)..(56)
<223> OTHER INFORMATION: Any amino acid
<220> FEATURE:
<221> NAME/KEY: MOD_RES
<222> LOCATION: (58)..(62)
<223> OTHER INFORMATION: Any amino acid
<220> FEATURE:
<221> NAME/KEY: MOD_RES
<222> LOCATION: (84)..(89)
<223> OTHER INFORMATION: Any amino acid

<400> SEQUENCE: 591

```
Met Thr Ile Pro Glu Ile Ile Ile Lys Val Arg Gly Thr Gln Val Val
1               5                   10                  15

Gly Ser Asp Met Thr Val Ile Val Glu Phe Xaa Xaa Xaa Xaa Xaa Xaa
            20                  25                  30

Xaa Leu Xaa Xaa Val Trp Val His Leu Asp Gly Pro Gly Val Thr Arg
        35                  40                  45

Pro Met Lys Lys Met Phe Xaa Xaa Ile Xaa Xaa Xaa Xaa Xaa Val Gln
    50                  55                  60

Trp Glu Glu Val Val Arg Pro Trp Val Ser Gly His Arg Lys Leu Ile
65                  70                  75                  80

Ala Ser Met Xaa Xaa Xaa Xaa Xaa Xaa His Val Tyr Gly Glu Leu Asp
                85                  90                  95

Val Gln Ile Gln Arg Arg
            100
```

<210> SEQ ID NO 592
<211> LENGTH: 102
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (27)..(33)
<223> OTHER INFORMATION: Any amino acid
<220> FEATURE:
<221> NAME/KEY: MOD_RES
<222> LOCATION: (35)..(36)
<223> OTHER INFORMATION: Any amino acid
<220> FEATURE:
<221> NAME/KEY: MOD_RES
<222> LOCATION: (55)..(56)
<223> OTHER INFORMATION: Any amino acid
<220> FEATURE:
<221> NAME/KEY: MOD_RES
<222> LOCATION: (58)..(62)
<223> OTHER INFORMATION: Any amino acid
<220> FEATURE:
<221> NAME/KEY: MOD_RES
<222> LOCATION: (84)..(89)
<223> OTHER INFORMATION: Any amino acid

<400> SEQUENCE: 592

```
Met Thr Ile Pro Glu Ile Ile Ile Lys Val Arg Gly Thr Gln Val Val
1               5                   10                  15

Gly Ser Asp Met Thr Val Ile Val Glu Phe Xaa Xaa Xaa Xaa Xaa Xaa
            20                  25                  30

Xaa Leu Xaa Xaa Val Trp Val His Leu Asp Gly Pro Gly Val Thr Arg
        35                  40                  45

Pro Met Lys Lys Met Phe Xaa Xaa Ile Xaa Xaa Xaa Xaa Xaa Val Gln
    50                  55                  60

Trp Glu Glu Val Val Arg Pro Trp Val Ser Gly His Arg Lys Leu Ile
65                  70                  75                  80
```

```
Ala Ser Met Xaa Xaa Xaa Xaa Xaa Xaa His Val Tyr Gly Glu Leu Asp
                85                  90                  95

Val Gln Ile Gln Arg Arg
            100


<210> SEQ ID NO 593
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(36)
<223> OTHER INFORMATION: Any amino acid
<220> FEATURE:
<221> NAME/KEY: MOD_RES
<222> LOCATION: (58)..(59)
<223> OTHER INFORMATION: Any amino acid
<220> FEATURE:
<221> NAME/KEY: MOD_RES
<222> LOCATION: (61)..(63)
<223> OTHER INFORMATION: Any amino acid
<220> FEATURE:
<221> NAME/KEY: MOD_RES
<222> LOCATION: (88)..(99)
<223> OTHER INFORMATION: Any amino acid

<400> SEQUENCE: 593

Met Thr Ile Pro Glu Ile Ile Ile Lys Val Arg Gly Thr Gln Val Val
1               5                   10                  15

Gly Ser Asp Met Thr Val Ile Val Glu Phe Thr Asn Pro Xaa Xaa Xaa
            20                  25                  30

Xaa Xaa Xaa Xaa Leu Arg Asn Val Trp Val His Leu Asp Gly Pro Gly
        35                  40                  45

Val Thr Arg Pro Met Lys Lys Met Phe Xaa Xaa Ile Xaa Xaa Xaa Ser
    50                  55                  60

Thr Val Gln Trp Glu Glu Val Val Arg Pro Trp Val Ser Gly His Arg
65                  70                  75                  80

Lys Leu Ile Ala Ser Met Ser Xaa Xaa Xaa Xaa Xaa Xaa Xaa Xaa Xaa
                85                  90                  95

Xaa Xaa Xaa Val Tyr Gly Glu Leu Asp Val Gln Ile Gln Arg Arg
            100                 105                 110


<210> SEQ ID NO 594
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(33)
<223> OTHER INFORMATION: Any amino acid
<220> FEATURE:
<221> NAME/KEY: MOD_RES
<222> LOCATION: (35)..(36)
<223> OTHER INFORMATION: Any amino acid
<220> FEATURE:
<221> NAME/KEY: MOD_RES
<222> LOCATION: (55)..(56)
<223> OTHER INFORMATION: Any amino acid
<220> FEATURE:
<221> NAME/KEY: MOD_RES
<222> LOCATION: (58)..(62)
<223> OTHER INFORMATION: Any amino acid
```

<220> FEATURE:
<221> NAME/KEY: MOD_RES
<222> LOCATION: (85)..(96)
<223> OTHER INFORMATION: Any amino acid

<400> SEQUENCE: 594

Met Thr Ile Pro Glu Ile Ile Ile Lys Val Arg Gly Thr Gln Val Val
1 5 10 15

Gly Ser Asp Met Thr Val Ile Val Glu Phe Xaa Xaa Xaa Xaa Xaa Xaa
20 25 30

Xaa Leu Xaa Xaa Val Trp Val His Leu Asp Gly Pro Gly Val Thr Arg
35 40 45

Pro Met Lys Lys Met Phe Xaa Xaa Ile Xaa Xaa Xaa Xaa Xaa Val Gln
50 55 60

Trp Glu Glu Val Val Arg Pro Trp Val Ser Gly His Arg Lys Leu Ile
65 70 75 80

Ala Ser Met Ser Xaa Xaa Xaa Xaa Xaa Xaa Xaa Xaa Xaa Xaa Xaa Xaa
85 90 95

Val Tyr Gly Glu Leu Asp Val Gln Ile Gln Arg Arg
100 105

<210> SEQ ID NO 595
<211> LENGTH: 102
<212> TYPE: PRT
<213> ORGANISM: Homo sapiens

<400> SEQUENCE: 595

Met Thr Ile Pro Glu Ile Ile Ile Lys Val Arg Gly Thr Gln Val Val
1 5 10 15

Gly Ser Asp Met Thr Val Ile Val Glu Phe Thr Asn Pro Leu Lys Glu
20 25 30

Thr Leu Arg Asn Val Trp Val His Leu Asp Gly Pro Gly Val Thr Arg
35 40 45

Pro Met Lys Lys Met Phe Arg Glu Ile Arg Pro Asn Ser Thr Val Gln
50 55 60

Trp Glu Glu Val Cys Arg Pro Trp Val Ser Gly His Arg Lys Leu Ile
65 70 75 80

Ala Ser Met Ser Ser Asp Ser Leu Arg His Val Tyr Gly Glu Leu Asp
85 90 95

Val Gln Ile Gln Arg Arg
100

<210> SEQ ID NO 596
<211> LENGTH: 102
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (15)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (44)..(45)
<223> OTHER INFORMATION: Any amino acid
<220> FEATURE:
<221> NAME/KEY: MOD_RES
<222> LOCATION: (70)..(70)
<223> OTHER INFORMATION: Any amino acid
<220> FEATURE:
<221> NAME/KEY: MOD_RES
<222> LOCATION: (72)..(74)
<223> OTHER INFORMATION: Any amino acid
<220> FEATURE:
<221> NAME/KEY: MOD_RES
<222> LOCATION: (76)..(76)
<223> OTHER INFORMATION: Any amino acid

<400> SEQUENCE: 596

```
Met Thr Ile Pro Glu Ile Ile Ile Lys Val Arg Xaa Xaa Gln Xaa Xaa
1               5                   10                  15

Gly Xaa Xaa Met Thr Val Ile Val Glu Phe Thr Asn Pro Leu Lys Glu
            20                  25                  30

Thr Leu Arg Asn Val Trp Val His Leu Asp Gly Xaa Xaa Val Thr Arg
        35                  40                  45

Pro Met Lys Lys Met Phe Arg Glu Ile Arg Pro Asn Ser Thr Val Gln
    50                  55                  60

Trp Glu Glu Val Val Xaa Pro Xaa Xaa Xaa Gly Xaa Arg Lys Leu Ile
65                  70                  75                  80

Ala Ser Met Ser Ser Asp Ser Leu Arg His Val Tyr Gly Glu Leu Asp
                85                  90                  95

Val Gln Ile Gln Arg Arg
            100
```

<210> SEQ ID NO 597
<211> LENGTH: 105
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (12)..(13)
<223> OTHER INFORMATION: Any amino acid
<220> FEATURE:
<221> NAME/KEY: MOD_RES
<222> LOCATION: (15)..(16)
<223> OTHER INFORMATION: Any amino acid
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (44)..(48)
<223> OTHER INFORMATION: Any amino acid
<220> FEATURE:
<221> NAME/KEY: MOD_RES
<222> LOCATION: (73)..(73)
<223> OTHER INFORMATION: Any amino acid
<220> FEATURE:
<221> NAME/KEY: MOD_RES
<222> LOCATION: (75)..(77)
<223> OTHER INFORMATION: Any amino acid
<220> FEATURE:
<221> NAME/KEY: MOD_RES
<222> LOCATION: (79)..(79)
<223> OTHER INFORMATION: Any amino acid

<400> SEQUENCE: 597

```
Met Thr Ile Pro Glu Ile Ile Ile Lys Val Arg Xaa Xaa Gln Xaa Xaa
1               5                   10                  15
```

-continued

```
Gly Xaa Xaa Met Thr Val Ile Val Glu Phe Thr Asn Pro Leu Lys Glu
            20                  25                  30

Thr Leu Arg Asn Val Trp Val His Leu Asp Gly Xaa Xaa Xaa Xaa Xaa
        35                  40                  45

Val Thr Arg Pro Met Lys Lys Met Phe Arg Glu Ile Arg Pro Asn Ser
    50                  55                  60

Thr Val Gln Trp Glu Glu Val Val Xaa Pro Xaa Xaa Xaa Gly Xaa Arg
65                  70                  75                  80

Lys Leu Ile Ala Ser Met Ser Ser Asp Ser Leu Arg His Val Tyr Gly
                85                  90                  95

Glu Leu Asp Val Gln Ile Gln Arg Arg
            100                 105
```

```
<210> SEQ ID NO 598
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(19)
<223> OTHER INFORMATION: Any amino acid
<220> FEATURE:
<221> NAME/KEY: MOD_RES
<222> LOCATION: (43)..(49)
<223> OTHER INFORMATION: Any amino acid
<220> FEATURE:
<221> NAME/KEY: MOD_RES
<222> LOCATION: (70)..(76)
<223> OTHER INFORMATION: Any amino acid

<400> SEQUENCE: 598

Met Thr Ile Pro Glu Ile Ile Ile Lys Val Arg Xaa Xaa Xaa Xaa Xaa
1               5                   10                  15

Xaa Xaa Xaa Met Thr Val Ile Val Glu Phe Thr Asn Pro Leu Lys Glu
            20                  25                  30

Thr Leu Arg Asn Val Trp Val His Leu Asp Xaa Xaa Xaa Xaa Xaa Xaa
        35                  40                  45

Xaa Met Lys Lys Met Phe Arg Glu Ile Arg Pro Asn Ser Thr Val Gln
    50                  55                  60

Trp Glu Glu Val Val Xaa Xaa Xaa Xaa Xaa Xaa Xaa Arg Lys Leu Ile
65                  70                  75                  80

Ala Ser Met Ser Ser Asp Ser Leu Arg His Val Tyr Gly Glu Leu Asp
                85                  90                  95

Val Gln Ile Gln Arg Arg
            100
```

```
<210> SEQ ID NO 599
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599

Thr Asn Pro Phe Lys Glu Thr Leu Arg Ser
1               5                   10
```

```
<210> SEQ ID NO 600
```

<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Ser Asn Pro Phe Lys Glu Thr Leu Arg Asn
1               5                   10

<210> SEQ ID NO 601
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Thr Asn Pro Leu Ser Gln Thr Leu Ser Ala
1               5                   10

<210> SEQ ID NO 602
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 602

Thr Asn Leu Met Lys Glu Thr Leu Arg Asn
1               5                   10

<210> SEQ ID NO 603
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Thr Asn Pro Phe Lys Glu Thr Leu Arg Asn
1               5                   10

<210> SEQ ID NO 604
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 604

Thr Asn Leu Trp Lys Glu Ala Leu Arg Asn
1               5                   10

<210> SEQ ID NO 605
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Thr Asn Pro Leu Lys Glu Thr Leu Arg Asn
1 5 10

<210> SEQ ID NO 606
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 606

Arg Glu Ile Pro Pro Lys Thr Thr
1 5

<210> SEQ ID NO 607
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 607

Ser Glu Ile Arg Pro Asn Ser Thr
1 5

<210> SEQ ID NO 608
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 608

Cys Glu Ile Arg Pro Asn Ser Ile
1 5

<210> SEQ ID NO 609
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 609

Arg Glu Ile Ala Thr Met Ser Thr
1 5

<210> SEQ ID NO 610
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 610

Pro Ala Ile Pro Met Asn His Lys
1 5

<210> SEQ ID NO 611
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 611

Pro Thr Ile Ser Arg Phe Lys Arg
1               5

<210> SEQ ID NO 612
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Ala Thr Ile Pro Pro Tyr Leu Pro
1               5

<210> SEQ ID NO 613
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 613

Arg Thr Gln Tyr Leu Ile
1               5

<210> SEQ ID NO 614
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Pro Ser Leu Leu His Leu
1               5

<210> SEQ ID NO 615
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 615

Cys Ser Leu Ser Pro Trp
1               5

<210> SEQ ID NO 616
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Cys Gln Leu Leu Pro Trp
1               5

<210> SEQ ID NO 617
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 617

Thr Leu Arg Pro Trp
1 5

<210> SEQ ID NO 618
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 618

Pro Gln Leu Phe His Ile
1 5

<210> SEQ ID NO 619
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 619

Pro Gln Leu Gln His Leu
1 5

<210> SEQ ID NO 620
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 620

Pro Gln Leu Ile His Leu
1 5

<210> SEQ ID NO 621
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 621

Ile Asn Tyr Phe Tyr Lys
1 5

<210> SEQ ID NO 622
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 622

Asn Ser Ser Ser Asn Gln
1 5

<210> SEQ ID NO 623
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 623

Thr Asn Pro Leu Asn Glu Pro Leu Leu Phe
1 5 10

<210> SEQ ID NO 624
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 624

Ile Asn Thr Ser Asn Glu Thr Leu Pro Ser
1 5 10

<210> SEQ ID NO 625
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 625

Thr Asp Thr Val Leu Glu Ile Leu Arg Thr
1 5 10

<210> SEQ ID NO 626
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 626

Thr Asn Pro Leu Glu Glu Asn Leu Tyr Asn
1 5 10

<210> SEQ ID NO 627
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 627

Thr Asn Pro Leu Lys Glu Thr Leu Tyr Asn
1 5 10

<210> SEQ ID NO 628
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 628

Thr Ile Pro Leu Gln Asp Ile Leu Asn
1 5

<210> SEQ ID NO 629
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 629

Arg Ile Ile Ser Pro His Ala Thr
1 5

<210> SEQ ID NO 630
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 630

Pro Glu Ile Pro Pro Asn Ser Ser
1 5

<210> SEQ ID NO 631
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 631

Pro His Ile Arg Pro Lys Val Thr
1 5

<210> SEQ ID NO 632
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 632

Tyr Gln Ile Ser Thr Asn Ile Pro
1 5

<210> SEQ ID NO 633
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 633

Trp Glu Ile Arg Thr Asn His Pro
1 5

<210> SEQ ID NO 634
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 634

Phe Ser Ile Arg Met Thr Pro Ala
1 5

<210> SEQ ID NO 635
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 635

Ser Ile Gly Phe Gln Ala
1 5

<210> SEQ ID NO 636
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 636

Ile Arg Asp Ser Ser Arg
1 5

<210> SEQ ID NO 637
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 637

Leu Ile Ala Ser Leu Arg
1 5

<210> SEQ ID NO 638
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 638

Gly Ala His Thr Lys Asp
1 5

<210> SEQ ID NO 639
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 639

```
Ser Ser Asn Ser Arg Asp
1               5
```

<210> SEQ ID NO 640
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 640

```
Ser Phe His Thr His Arg
1               5
```

<210> SEQ ID NO 641
<211> LENGTH: 339
<212> TYPE: DNA
<213> ORGANISM: Homo sapiens
<220> FEATURE:
<221> NAME/KEY: CDS
<222> LOCATION: (1)..(339)

<400> SEQUENCE: 641

```
atg tcc aac gtt gac atg gac ttt gaa gtg gaa aat gct gtg ctg gga       48
Met Ser Asn Val Asp Met Asp Phe Glu Val Glu Asn Ala Val Leu Gly
1               5                   10                  15

aaa gac ttc aag ctc tcc atc acc ttc cgg aac aac agc cac aac cgt       96
Lys Asp Phe Lys Leu Ser Ile Thr Phe Arg Asn Asn Ser His Asn Arg
            20                  25                  30

tac acc atc aca gct tat ctc tca gcc aac atc acc ttc tac acc ggg      144
Tyr Thr Ile Thr Ala Tyr Leu Ser Ala Asn Ile Thr Phe Tyr Thr Gly
        35                  40                  45

gtc ccg aag gca gaa ttc aag aag gag acg ttc gac gtg acg ctg gag      192
Val Pro Lys Ala Glu Phe Lys Lys Glu Thr Phe Asp Val Thr Leu Glu
    50                  55                  60

ccc ttg tcc ttc aag aaa gag gcg gtg ctg atc caa gcc ggc gag tac      240
Pro Leu Ser Phe Lys Lys Glu Ala Val Leu Ile Gln Ala Gly Glu Tyr
65                  70                  75                  80

atg ggt cag ctg ctg gaa caa gcg tcc ctg cac ttc ttt gtc aca gct      288
Met Gly Gln Leu Leu Glu Gln Ala Ser Leu His Phe Phe Val Thr Ala
                85                  90                  95

cgc atc aat gag acc agg gat gtt ctg gcc aag caa aag tcc acc gtg      336
Arg Ile Asn Glu Thr Arg Asp Val Leu Ala Lys Gln Lys Ser Thr Val
            100                 105                 110

cta                                                                  339
Leu
```

<210> SEQ ID NO 642
<211> LENGTH: 113
<212> TYPE: PRT
<213> ORGANISM: Homo sapiens

<400> SEQUENCE: 642

```
Met Ser Asn Val Asp Met Asp Phe Glu Val Glu Asn Ala Val Leu Gly
1               5                   10                  15

Lys Asp Phe Lys Leu Ser Ile Thr Phe Arg Asn Asn Ser His Asn Arg
            20                  25                  30

Tyr Thr Ile Thr Ala Tyr Leu Ser Ala Asn Ile Thr Phe Tyr Thr Gly
        35                  40                  45

Val Pro Lys Ala Glu Phe Lys Lys Glu Thr Phe Asp Val Thr Leu Glu
```

```
    50                  55                  60

Pro Leu Ser Phe Lys Lys Glu Ala Val Leu Ile Gln Ala Gly Glu Tyr
65                  70                  75                  80

Met Gly Gln Leu Leu Glu Gln Ala Ser Leu His Phe Phe Val Thr Ala
                85                  90                  95

Arg Ile Asn Glu Thr Arg Asp Val Leu Ala Lys Gln Lys Ser Thr Val
            100                 105                 110

Leu


<210> SEQ ID NO 643
<211> LENGTH: 113
<212> TYPE: PRT
<213> ORGANISM: Homo sapiens

<400> SEQUENCE: 643

Met Ser Asn Val Asp Met Asp Phe Glu Val Glu Asn Ala Val Leu Gly
1               5                   10                  15

Lys Asp Phe Lys Leu Ser Ile Thr Phe Arg Asn Asn Ser His Asn Arg
            20                  25                  30

Tyr Thr Ile Thr Ala Tyr Leu Ser Ala Asn Ile Thr Phe Tyr Thr Gly
        35                  40                  45

Val Pro Lys Ala Glu Phe Lys Lys Glu Thr Phe Asp Val Thr Leu Glu
    50                  55                  60

Pro Leu Ser Phe Lys Lys Glu Ala Val Leu Ile Gln Ala Gly Glu Tyr
65                  70                  75                  80

Met Gly Gln Leu Leu Glu Gln Ala Ser Leu His Phe Phe Val Thr Ala
                85                  90                  95

Arg Ile Asn Glu Thr Arg Asp Val Leu Ala Lys Gln Lys Ser Thr Val
            100                 105                 110

Leu


<210> SEQ ID NO 644
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (26)..(34)
<223> OTHER INFORMATION: Any amino acid
<220> FEATURE:
<221> NAME/KEY: MOD_RES
<222> LOCATION: (62)..(62)
<223> OTHER INFORMATION: Any amino acid
<220> FEATURE:
<221> NAME/KEY: MOD_RES
<222> LOCATION: (64)..(68)
<223> OTHER INFORMATION: Any amino acid
<220> FEATURE:
<221> NAME/KEY: MOD_RES
<222> LOCATION: (97)..(97)
<223> OTHER INFORMATION: Any amino acid
<220> FEATURE:
<221> NAME/KEY: MOD_RES
<222> LOCATION: (99)..(103)
<223> OTHER INFORMATION: Any amino acid

<400> SEQUENCE: 644
```

Met Xaa Xaa Val Asp Met Asp Phe Glu Val Glu Asn Ala Val Leu Gly
1               5                   10                  15

Lys Asp Phe Lys Leu Ser Ile Thr Phe Xaa Xaa Xaa Xaa Xaa Xaa Xaa
            20                  25                  30

Xaa Xaa Ile Thr Ala Tyr Leu Ser Ala Asn Ile Thr Phe Tyr Thr Gly
        35                  40                  45

Val Pro Lys Ala Glu Phe Lys Lys Glu Thr Phe Asp Val Xaa Leu Xaa
    50                  55                  60

Xaa Xaa Xaa Xaa Lys Lys Glu Ala Val Leu Ile Gln Ala Gly Glu Tyr
65                  70                  75                  80

Met Gly Gln Leu Leu Glu Gln Ala Ser Leu His Phe Phe Val Thr Ala
                85                  90                  95

Xaa Ile Xaa Xaa Xaa Xaa Xaa Val Leu Ala Lys Gln Lys Ser Thr Val
            100                 105                 110

Leu

<210> SEQ ID NO 645
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(32)
<223> OTHER INFORMATION: Any amino acid
<220> FEATURE:
<221> NAME/KEY: MOD_RES
<222> LOCATION: (64)..(66)
<223> OTHER INFORMATION: Any amino acid
<220> FEATURE:
<221> NAME/KEY: MOD_RES
<222> LOCATION: (100)..(102)
<223> OTHER INFORMATION: Any amino acid

<400> SEQUENCE: 645

Met Ser Asn Val Asp Met Asp Phe Glu Val Glu Asn Ala Val Leu Gly
1               5                   10                  15

Lys Asp Phe Lys Leu Ser Ile Thr Phe Arg Asn Xaa Xaa Xaa Xaa Xaa
            20                  25                  30

Tyr Thr Ile Thr Ala Tyr Leu Ser Ala Asn Ile Thr Phe Tyr Thr Gly
        35                  40                  45

Val Pro Lys Ala Glu Phe Lys Lys Glu Thr Phe Asp Val Thr Leu Xaa
    50                  55                  60

Xaa Xaa Ser Phe Lys Lys Glu Ala Val Leu Ile Gln Ala Gly Glu Tyr
65                  70                  75                  80

Met Gly Gln Leu Leu Glu Gln Ala Ser Leu His Phe Phe Val Thr Ala
                85                  90                  95

Arg Ile Asn Xaa Xaa Xaa Asp Val Leu Ala Lys Gln Lys Ser Thr Val
            100                 105                 110

Leu

<210> SEQ ID NO 646
<211> LENGTH: 113
<212> TYPE: PRT
<213> ORGANISM: Homo sapiens

<400> SEQUENCE: 646

Met Ser Asn Val Asp Met Asp Phe Glu Val Glu Asn Ala Val Leu Gly
1               5                   10                  15

```
Lys Asp Phe Lys Leu Ser Ile Thr Phe Arg Asn Asn Ser His Asn Arg
            20                  25                  30

Tyr Thr Ile Thr Ala Tyr Leu Ser Ala Asn Ile Thr Phe Tyr Thr Gly
        35                  40                  45

Val Pro Lys Ala Glu Phe Lys Lys Glu Thr Phe Asp Val Thr Leu Glu
    50                  55                  60

Pro Leu Ser Phe Lys Lys Glu Ala Val Leu Ile Gln Ala Gly Glu Tyr
65                  70                  75                  80

Met Gly Gln Leu Leu Glu Gln Ala Ser Leu His Phe Phe Val Thr Ala
                85                  90                  95

Arg Ile Asn Glu Thr Arg Asp Val Leu Ala Lys Gln Lys Ser Thr Val
            100                 105                 110

Leu


<210> SEQ ID NO 647
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(18)
<223> OTHER INFORMATION: Any amino acid
<220> FEATURE:
<221> NAME/KEY: MOD_RES
<222> LOCATION: (20)..(20)
<223> OTHER INFORMATION: Any amino acid
<220> FEATURE:
<221> NAME/KEY: MOD_RES
<222> LOCATION: (43)..(52)
<223> OTHER INFORMATION: Any amino acid
<220> FEATURE:
<221> NAME/KEY: MOD_RES
<222> LOCATION: (74)..(74)
<223> OTHER INFORMATION: Any amino acid
<220> FEATURE:
<221> NAME/KEY: MOD_RES
<222> LOCATION: (76)..(88)
<223> OTHER INFORMATION: Any amino acid

<400> SEQUENCE: 647

Met Ser Asn Val Asp Met Asp Phe Glu Val Xaa Xaa Xaa Xaa Xaa Xaa
1               5                   10                  15

Xaa Xaa Phe Xaa Leu Ser Ile Thr Phe Arg Asn Asn Ser His Asn Arg
            20                  25                  30

Tyr Thr Ile Thr Ala Tyr Leu Ser Ala Asn Xaa Xaa Xaa Xaa Xaa Xaa
        35                  40                  45

Xaa Xaa Xaa Xaa Glu Phe Lys Lys Glu Thr Phe Asp Val Thr Leu Glu
    50                  55                  60

Pro Leu Ser Phe Lys Lys Glu Ala Val Xaa Ile Xaa Xaa Xaa Xaa Xaa
65                  70                  75                  80

Xaa Xaa Xaa Xaa Xaa Xaa Xaa Xaa Ser Leu His Phe Phe Val Thr Ala
                85                  90                  95

Arg Ile Asn Glu Thr Arg Asp Val Leu Ala Lys Gln Lys Ser Thr Val
            100                 105                 110

Leu


<210> SEQ ID NO 648
<211> LENGTH: 113
<212> TYPE: PRT
```

<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (11)..(18)
<223> OTHER INFORMATION: Any amino acid
<220> FEATURE:
<221> NAME/KEY: MOD_RES
<222> LOCATION: (46)..(48)
<223> OTHER INFORMATION: Any amino acid
<220> FEATURE:
<221> NAME/KEY: MOD_RES
<222> LOCATION: (76)..(76)
<223> OTHER INFORMATION: Any amino acid
<220> FEATURE:
<221> NAME/KEY: MOD_RES
<222> LOCATION: (82)..(87)
<223> OTHER INFORMATION: Any amino acid

<400> SEQUENCE: 648

```
Met Ser Asn Val Asp Met Asp Phe Glu Val Xaa Xaa Xaa Xaa Xaa Xaa
1               5                   10                  15

Xaa Xaa Phe Lys Leu Ser Ile Thr Phe Arg Asn Asn Ser His Asn Arg
            20                  25                  30

Tyr Thr Ile Thr Ala Tyr Leu Ser Ala Asn Ile Thr Phe Xaa Xaa Xaa
        35                  40                  45

Val Pro Lys Ala Glu Phe Lys Lys Glu Thr Phe Asp Val Thr Leu Glu
    50                  55                  60

Pro Leu Ser Phe Lys Lys Glu Ala Val Leu Ile Xaa Ala Gly Glu Tyr
65                  70                  75                  80

Met Xaa Xaa Xaa Xaa Xaa Xaa Ala Ser Leu His Phe Phe Val Thr Ala
                85                  90                  95

Arg Ile Asn Glu Thr Arg Asp Val Leu Ala Lys Gln Lys Ser Thr Val
            100                 105                 110

Leu
```

<210> SEQ ID NO 649
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 649

```
Thr Asn Pro Leu Lys Glu Thr Leu Arg Asn
1               5                   10
```

<210> SEQ ID NO 650
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 650

```
Arg Glu Ile Arg Pro Asn Ser Thr
1               5
```

<210> SEQ ID NO 651
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Ser Asp Ser Leu Arg His
1               5

<210> SEQ ID NO 652
<211> LENGTH: 306
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(306)

<400> SEQUENCE: 652 atg acc atc cct gag atc atc atc aag gtc cgc ggc act cag gtc gtg       48
Met Thr Ile Pro Glu Ile Ile Ile Lys Val Arg Gly Thr Gln Val Val
1               5                   10                  15 ggt tct gac atg act gtg atc gtg gag ttt acc aat cct ctg aaa gaa       96
Gly Ser Asp Met Thr Val Ile Val Glu Phe Thr Asn Pro Leu Lys Glu
            20                  25                  30 acc ctg cgc aat gtc tgg gtg cac ctg gat ggt cct gga gtc aca cgc      144
Thr Leu Arg Asn Val Trp Val His Leu Asp Gly Pro Gly Val Thr Arg
        35                  40                  45 cca atg aag aag atg ttc cgc gaa atc cgc cca aac tcc acc gtg cag      192
Pro Met Lys Lys Met Phe Arg Glu Ile Arg Pro Asn Ser Thr Val Gln
    50                  55                  60 tgg gaa gaa gtg gtc cgc cca tgg gtc tct ggg cat cgc aag ctg atc      240
Trp Glu Glu Val Val Arg Pro Trp Val Ser Gly His Arg Lys Leu Ile
65                  70                  75                  80 gcc agc atg agc agt gac tcc ctg cgc cat gtg tat ggc gag ctg gac      288
Ala Ser Met Ser Ser Asp Ser Leu Arg His Val Tyr Gly Glu Leu Asp
                85                  90                  95 gtg cag att caa cgc cgc                                              306
Val Gln Ile Gln Arg Arg
            100

<210> SEQ ID NO 653
<211> LENGTH: 102
<212> TYPE: PRT
<213> ORGANISM: Artificial Sequence
<220> FEATURE:
<223> OTHER INFORMATION: Synthetic Construct

<400> SEQUENCE: 653

Met Thr Ile Pro Glu Ile Ile Ile Lys Val Arg Gly Thr Gln Val Val
1               5                   10                  15

Gly Ser Asp Met Thr Val Ile Val Glu Phe Thr Asn Pro Leu Lys Glu
            20                  25                  30

Thr Leu Arg Asn Val Trp Val His Leu Asp Gly Pro Gly Val Thr Arg
        35                  40                  45

Pro Met Lys Lys Met Phe Arg Glu Ile Arg Pro Asn Ser Thr Val Gln
    50                  55                  60

Trp Glu Glu Val Val Arg Pro Trp Val Ser Gly His Arg Lys Leu Ile
65                  70                  75                  80

Ala Ser Met Ser Ser Asp Ser Leu Arg His Val Tyr Gly Glu Leu Asp
                85                  90                  95

```
Val Gln Ile Gln Arg Arg
            100


<210> SEQ ID NO 654
<211> LENGTH: 57
<212> TYPE: DNA
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: modified_base
<222> LOCATION: (19)..(24)
<223> OTHER INFORMATION: a, c, t, g, unknown or other
<220> FEATURE:
<221> NAME/KEY: misc_feature
<222> LOCATION: (19)..(24)
<223> OTHER INFORMATION: n is a, c, g, or t
<220> FEATURE:
<221> NAME/KEY: modified_base
<222> LOCATION: (28)..(39)
<223> OTHER INFORMATION: a, c, t, g, unknown or other
<220> FEATURE:
<221> NAME/KEY: misc_feature
<222> LOCATION: (28)..(39)
<223> OTHER INFORMATION: n is a, c, g, or t

<400> SEQUENCE: 654

actgtgatcg tggagtttnn nnnncctnnn nnnnnnnnnc tgcgcaatgt ctgggtg        57


<210> SEQ ID NO 655
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(21)
<223> OTHER INFORMATION: a, c, t, g, unknown or other
<220> FEATURE:
<221> NAME/KEY: misc_feature
<222> LOCATION: (19)..(21)
<223> OTHER INFORMATION: n is a, c, g, or t
<220> FEATURE:
<221> NAME/KEY: modified_base
<222> LOCATION: (25)..(33)
<223> OTHER INFORMATION: a, c, t, g, unknown or other
<220> FEATURE:
<221> NAME/KEY: misc_feature
<222> LOCATION: (25)..(33)
<223> OTHER INFORMATION: n is a, c, g, or t

<400> SEQUENCE: 655

aagatgttcc gcgaaatcnn nccannnnnn nnngtgcagt gggaagaagt g              51


<210> SEQ ID NO 656
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(36)
<223> OTHER INFORMATION: a, c, t, g, unknown or other
<220> FEATURE:
<221> NAME/KEY: misc_feature
<222> LOCATION: (19)..(36)
<223> OTHER INFORMATION: n is a, c, g, or t

<400> SEQUENCE: 656
```

ctgatcgcca gcatgagcnn nnnnnnnnnn nnnnnngtgt atggcgagct ggac 54

<210> SEQ ID NO 657
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (19)..(29)
<223> OTHER INFORMATION: a, c, t, g, unknown or other
<220> FEATURE:
<221> NAME/KEY: misc_feature
<222> LOCATION: (19)..(29)
<223> OTHER INFORMATION: n is a, c, g, or t
<220> FEATURE:
<221> NAME/KEY: modified_base
<222> LOCATION: (31)..(32)
<223> OTHER INFORMATION: a, c, t, g, unknown or other
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: modified_base
<222> LOCATION: (34)..(35)
<223> OTHER INFORMATION: a, c, t, g, unknown or other
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (37)..(38)
<223> OTHER INFORMATION: a, c, t, g, unknown or other
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: modified_base
<222> LOCATION: (40)..(41)
<223> OTHER INFORMATION: a, c, t, g, unknown or other
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: modified_base
<222> LOCATION: (43)..(44)
<223> OTHER INFORMATION: a, c, t, g, unknown or other
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: modified_base
<222> LOCATION: (46)..(54)
<223> OTHER INFORMATION: a, c, t, g, unknown or other
<220> FEATURE:
<221> NAME/KEY: misc_feature
<222> LOCATION: (46)..(54)
<223> OTHER INFORMATION: n is a, c, g, or t

<400> SEQUENCE: 657
ctgatcgcca gcatgagcnn nnnnnnnnns nnsnnsnnsn nsnnsnnnnn nnnngtgtat 60
ggcgagctgg ac 72

<210> SEQ ID NO 658
<211> LENGTH: 6
<212> TYPE: PRT
<213> ORGANISM: Artificial Sequence
<220> FEATURE:
<223> OTHER INFORMATION: Description of Artificial Sequence: Synthetic
Peptide

<400> SEQUENCE: 658

Ile Ile Ile Lys Val Arg
1 5

<210> SEQ ID NO 659
<211> LENGTH: 8
<212> TYPE: PRT
<213> ORGANISM: Artificial Sequence
<220> FEATURE:
<223> OTHER INFORMATION: Description of Artificial Sequence: Synthetic
Peptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 659

Met Thr Val Ile Val Glu Phe Xaa
1 5

<210> SEQ ID NO 660
<211> LENGTH: 9
<212> TYPE: PRT
<213> ORGANISM: Artificial Sequence
<220> FEATURE:
<223> OTHER INFORMATION: Description of Artificial Sequence: Synthetic
Peptide
<220> FEATURE:
<221> NAME/KEY: misc_feature
<222> LOCATION: (2)..(3)
<223> OTHER INFORMATION: Xaa can be any naturally occurring amino acid

<400> SEQUENCE: 660

Leu Xaa Xaa Val Trp Val His Leu Asp
1 5

<210> SEQ ID NO 661
<211> LENGTH: 8
<212> TYPE: PRT
<213> ORGANISM: Artificial Sequence
<220> FEATURE:
<223> OTHER INFORMATION: Description of Artificial Sequence: Synthetic
Peptide
<220> FEATURE:
<221> NAME/KEY: misc_feature
<222> LOCATION: (6)..(7)
<223> OTHER INFORMATION: Xaa can be any naturally occurring amino acid

<400> SEQUENCE: 661

Met Lys Lys Met Phe Xaa Xaa Ile
1 5

<210> SEQ ID NO 662
<211> LENGTH: 7
<212> TYPE: PRT
<213> ORGANISM: Artificial Sequence
<220> FEATURE:
<223> OTHER INFORMATION: Description of Artificial Sequence: Synthetic
Peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 662

Val Gln Trp Glu Glu Val Xaa

-continued

```
1               5


<210> SEQ ID NO 663
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 663

Lys Leu Ile Ala Ser Met Xaa
1               5


<210> SEQ ID NO 664
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 664

Xaa His Val Tyr Gly Glu Leu Asp
1               5
```